United States Patent
Smith et al.

(10) Patent No.: US 9,145,411 B2
(45) Date of Patent: Sep. 29, 2015

(54) SUBSTITUTED AMINO-PYRIMIDINE DERIVATIVES

(71) Applicant: Asana Biosciences, LLC, Bridgewater, NJ (US)

(72) Inventors: Roger Astbury Smith, Chester Springs, PA (US); Aranapakam Venkatesan, Chadds Ford, PA (US); Mallesham Bejugam, Parbhani (IN); Subramanya Hoshalli, Bangalore (IN); Srinivas Nanduri, Hyderabad (IN)

(73) Assignee: Asana Biosciences, LLC, Bridgewater, NJ (US)

( * ) Notice: Subject to any disclaimer, the term of this patent is extended or adjusted under 35 U.S.C. 154(b) by 0 days.

(21) Appl. No.: 13/957,470

(22) Filed: Aug. 2, 2013

(65) Prior Publication Data

US 2014/0038952 A1 Feb. 6, 2014

Related U.S. Application Data

(60) Provisional application No. 61/678,694, filed on Aug. 2, 2012.

(51) Int. Cl.
| | |
|---|---|
| *C07D 239/94* | (2006.01) |
| *C07D 401/14* | (2006.01) |
| *C07D 403/14* | (2006.01) |
| *C07D 409/14* | (2006.01) |
| *C07D 471/04* | (2006.01) |

(52) U.S. Cl.
CPC ............ *C07D 471/04* (2013.01); *C07D 239/94* (2013.01); *C07D 401/14* (2013.01); *C07D 403/14* (2013.01); *C07D 409/14* (2013.01)

(58) Field of Classification Search
None
See application file for complete search history.

(56) References Cited

U.S. PATENT DOCUMENTS

| | | | |
|---|---|---|---|
| 6,476,031 | B1 | 11/2002 | Chakravarty |
| 7,615,552 | B2 | 11/2009 | Ono |
| 8,022,205 | B2 | 9/2011 | Shimma |
| 8,440,662 | B2 | 5/2013 | Smith |
| 8,563,540 | B2 * | 10/2013 | Castanedo et al. ....... 514/210.21 |
| 2004/0146509 | A1 | 7/2004 | Li |
| 2005/0245508 | A1 | 11/2005 | Weller |
| 2009/0253694 | A1 | 10/2009 | Ono |
| 2011/0104186 | A1 | 5/2011 | Valiante |
| 2011/0207713 | A1 | 8/2011 | Castanedo |
| 2011/0224248 | A1 | 9/2011 | Allen |
| 2013/0190492 | A1 | 7/2013 | Smith |

FOREIGN PATENT DOCUMENTS

| | | |
|---|---|---|
| EP | 1277738 | 1/2003 |
| GB | 2431156 | 4/2007 |
| WO | WO-2006/089150 | 8/2006 |
| WO | WO-2008/018426 | 2/2008 |
| WO | WO-2008/070740 | 6/2008 |
| WO | WO-2008/098058 | 8/2008 |
| WO | WO-2009/042607 | 4/2009 |
| WO | WO-2009/045175 | 4/2009 |
| WO | WO-2009/066084 | 5/2009 |
| WO | WO-2010/056758 | 5/2010 |
| WO | WO-2010/119264 | 10/2010 |
| WO | WO-2010/143168 | 12/2010 |

OTHER PUBLICATIONS

International Search Report and Written Opinion dated Sep. 24, 2013 for corresponding International Patent Application No. PCT/US203/053327.

* cited by examiner

*Primary Examiner* — Alicia L Otton
(74) *Attorney, Agent, or Firm* — Lerner, David, Littenberg, Krumholz & Mentlik, LLP

(57) ABSTRACT

The present application provides novel substituted quinazoline and pyrido-pyrimidine compounds and pharmaceutically acceptable salts, prodrugs, and solvates thereof. Also provided are methods for preparing these compounds. These compounds are useful in co-regulating PI3K and/or mTOR activity by administering a therapeutically effective amount of one or more of the compounds to a patient. By doing so, these compounds are effective in treating conditions associated with the dysregulation of the PI3K/AKT/mTOR pathway. Advantageously, these compounds perform as dual PI3K/mTOR inhibitors. A variety of conditions can be treated using these compounds and include diseases which are characterized by inflammation or abnormal cellular proliferation. In one embodiment, the disease is cancer.

21 Claims, No Drawings

SUBSTITUTED AMINO-PYRIMIDINE DERIVATIVES

CROSS-REFERENCE TO RELATED APPLICATION

The present application claims the benefit of the filing date of U.S. Provisional Patent Application No. 61/678,694, filed Aug. 2, 2012.

BACKGROUND

With the onset of cancers which are refractory to most conventional treatments, there is a need for new and effective chemotherapeutics. As details emerge about the molecular etiology of various cancers, new chemotherapeutics can be designed which affect one or more vulnerable targets associated with a given cancer at a sub-cellular level.

Certain cancers (and indeed other diseases of abnormal cellular growth) include those which are due to the dysregulation of one particular molecular signaling pathway in the body. Restoring regulation of that particular pathway to normal or near-normal levels can have a positive impact in treating the patient, including a reduction in tumor size or even putting the patient into remission.

For example, perturbations of the phosphoinositide 3-kinase (PI3K)/AKT/mammalian target of rapamycin (mTOR) signaling pathway are closely associated with the etiology of most solid tumors. The PI3K/AKT/mTOR pathway can be overactivated by a number of molecular effectors, including chemokines, the loss of inositol polyphosphate-4-phosphatase type II (INPP4B) or phosphatase and tensin homolog (PTEN) expression, or by mutations in PI3K itself. Overactivation of this pathway can manifest in a number of molecular and morphological changes which are characteristic of tumorigenesis, including increased cell proliferation, survival and motility, and altered cell cycle entry. mTOR is a central regulator of cell growth which acts by controlling cellular protein translation. Several small molecules have been described as being mTOR inhibitors which are useful for treating cancers. PI3K is a heterodimeric enzyme that generates lipid second messengers, such as phosphatidylinositol-3,4,5-triphosphate (PIP3), that mediate signal transduction. PI3K enzymes regulate key signal transduction pathways controlling vital cell processes that are implicated in carcinogenesis, and include four isoforms; i.e., p110α, p110β, p110δ and p110γ. Specific mutations in p110α have been identified in various cancers. Several small molecules have been described as inhibitors of PI3K. Further, there are a number of compounds, including wortmannins and rapamycins, which have been shown to be highly potent and specific inhibitors of PI3K and mTOR, respectively.

Indeed, several recent compounds have been described as being useful in regulating the PI3K/mTOR pathway. For example, GDC-0941, PX-866, XL-147, BKM-120, and BAY 80-6946 are inhibitors of PI3K, whereas rapamycin, temsirolimus (CCI-779), everolimius (RAD001), deforolimus (AP23573), OSI-027 and AZD8055 are inhibitors of mTOR. However, intervention at a single point in a the PI3K/AKT/mTOR signaling pathway may not be as effective in treating solid tumors as targeting multiple pathway members. Administering multiple drugs to a cancer patient, each of which inhibit a certain target in the PI3K or mTOR pathway, carries its own risks in terms of increased drug load, potential toxicity, drug-drug interactions and the like. What remains in the art, therefore, is the need for single compounds which regulate the PI3K/AKT/mTOR pathway by targeting both PI3K and mTOR. Certain compounds recently described in the art, including BEZ-235, XL-765, GSK-2126458, PKI-587 (PF-05212384), PF-04691502, and GDC-0980 have been reported to target both PI3K and mTOR. However, the need remains for compounds with this type of dual activity profile to be developed and approved for clinical use.

SUMMARY OF THE INVENTION

In one aspect, the present invention provides a compound of formula (I), wherein $R^1$-$R^3$ and X are defined herein, or a pharmaceutically acceptable salt, prodrug or solvate thereof.

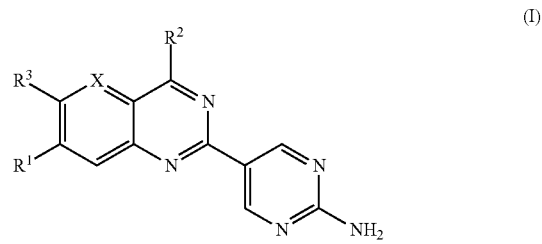

(I)

In another aspect, compounds of formulae (II)-(IV) are provided, wherein $R^1$ and X are defined herein.

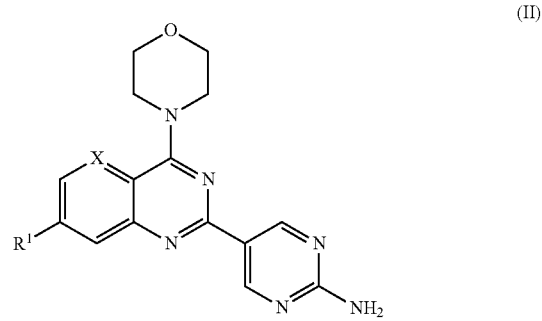

(II)

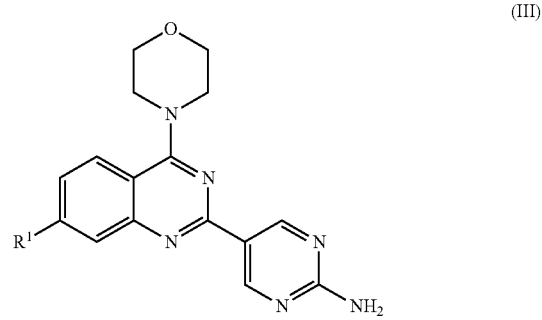

(III)

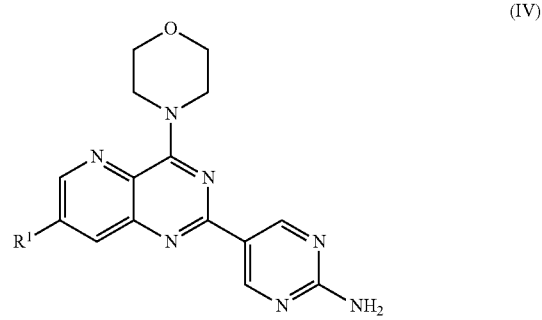

(IV)

In yet another aspect, the invention provides a pharmaceutical composition comprising a compound of formulae (I) to (IV), or a pharmaceutically acceptable salt, prodrug or solvate thereof, and a pharmaceutically acceptable carrier.

In another aspect, methods for co-regulating PI3K and mTOR are provided and include administering a therapeutically effective amount of a compound described herein to a patient in need thereof. Desirably, co-regulation includes inhibition of the PI3K/AKT/mTOR pathway.

In still a further aspect, methods for treating a disease characterized by abnormal cellular growth resulting from a dysregulated PI3K/AKT/mTOR pathway are provided. These methods include administering a therapeutically effective amount of a compound described herein to a patient in need thereof. In one embodiment, the disease is cancer. In another embodiment, the disease is characterized by the presence of at least one solid tumor. In yet another embodiment, the disease is characterized by inflammation.

Other aspects and advantages of the invention will be readily apparent from the following detailed description of the invention.

DETAILED DESCRIPTION OF THE INVENTION

The present invention provides novel compounds which have capabilities in modulating two (2) members of the PI3K/AKT/mTOR pathway, i.e., PI3K and mTOR. These compounds are can be used to treat disease affected by a dysregulation of the PI3K/AKT/mTOR pathway.

In the present invention, the compound is of formula (I), or a pharmaceutically acceptable salt, prodrug or solvate thereof.

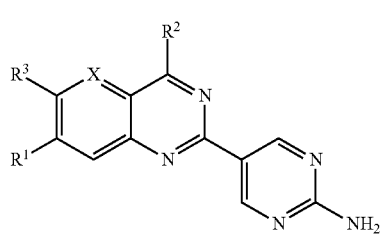

(I)

In this structure, $R^1$ is optionally substituted aryl, optionally substituted heterocycle, optionally substituted heteroaryl, optionally substituted alkyl, optionally substituted alkenyl, optionally substituted alkynyl, optionally substituted alkylamino, optionally substituted dialkylamino, optionally substituted arylamino, optionally substituted heteroarylamino, optionally substituted heterocycleamino, optionally substituted alkylcarbonylamino, optionally substituted alkylsulfonylamino, optionally substituted alkylthio, optionally substituted alkylsulfonyl, optionally substituted alkoxy, optionally substituted aryloxy, optionally substituted heteroaryloxy, optionally substituted heterocycleoxy, optionally substituted alkylaminocarbonyl, optionally substituted arylaminocarbonyl, optionally substituted heteroarylaminocarbonyl, or optionally substituted heterocycleaminocarbonyl.

In one aspect, $R^1$ is optionally substituted phenyl. In one embodiment, $R^1$ is a substituted phenyl of the following structure, wherein n is 1 to 5 and each $R^8$ is independently selected from among halogen, alkyl, aryl, alkylsulfonyl, alkylthio, alkylcarbonylamino, halogenated alkylcarbonylamino, alkylsulfonylamino, arylsulfonylamino, alkylaminocarbonyl, alkylaminocarbonylamino, alkylaminoalkylcarbonylamino, hydroxyalkylcarbonylamino, heteroarylcarbonylamino, heteroarylalkylcarbonylamino, heteroarylcarbonyl, heterocyclecarbonylamino, arylcarbonylamino, alkylsulfonylheterocyclecarbonyl, heterocyclecarbonyl, heterocycleaminocarbonyl, heteroarylalkylamino, hydroxyalkylamino, heterocyclealkylcarbonylamino, or cyanoalkylcarbonylamino. In a further embodiment, the substituted phenyl is 3- or 4-substituted. In yet another embodiment, $R^8$ in the substituted phenyl is selected from among F, $CH_3$, $C(CH_3)_2OH$, ~$NHC(O)CH_3$, ~$NHC(O)CH_2CH_3$ ~$NHC(O)CH(CH_3)_2$, ~$NHC(O)C(CH_3)_3$, ~$NHC(O)CH_2CH_2CH(CH_3)_2$, ~$N(CH_3)C(O)CH_3$, ~$NHC(O)NHCH_3$, ~$NHSO_2CH_3$, ~$NHC(O)CH_2N(CH_3)_2$, ~$NHC(O)C(CH_3)_2OH$, ~$NHC(O)CH(CH_3)OH$, ~$NHC(O)CH_2OH$, ~$NHC(O)CH(CH_3)F$, ~$NHC(O)C(CH_3)_2CN$, ~$NHC(O)CH_2CN$, ~$NHC(O)$(cyclopropyl optionally substituted with CN), ~$NHC(O)$cyclobutyl, ~$NHC(O)$(cyclopentyl), ~$NHC(O)$(cyclohexyl optionally substituted with OH), ~$NHC(O)$(adamantanyl), ~$NHC(O)$(pyridinyl), ~$NHC(O)$(furanyl optionally substituted with $CH_3$), ~$NHC(O)$(tetrahydropyranyl), ~$NHC(O)$(pyrazinyl optionally substituted with $CH_3$), ~$NHC(O)$(piperazinyl optionally substituted with $CH_3$), ~$C(O)(4-C(O)CH_3$-piperazinyl), ~$NHC(O)CH_2$(piperazinyl optionally substituted with $CH_3$), ~$C(O)(4-SO_2CH_3$-piperazinyl), ~$C(O)NHCH_3$, ~$C(O)NHCH_2CH_2N(CH_3)_2$, ~$C(O)N(CH_3)_2$, ~$C(O)NH$(thiazolyl), ~$C(O)NH$(pyridinyl optionally substituted with halogen), ~$C(O)$(piperidinyl optionally substituted with $CH_2CH_2OH$, OH or $CH_3$), ~$NHC(O)$(pyridinyl optionally substituted with F or $CF_3$), ~$NHC(O)$(thiadiazolyl), ~$C(O)NH$(cyclopropyl), ~$NHC(O)$(phenyl optionally substituted with F), ~$NHSO_2$-(phenyl optionally substituted with F), ~$NHC(O)CH_2$(morpholinyl), ~$NHC(O)CH_2$(piperidinyl optionally substituted with OH), ~$NHC(O)$(morpholinyl), ~$NHSO_2$(cyclopropyl), piperidinyl optionally substituted with $C(O)C(CH_3)_2CN$, $C(O)CH_2N(CH_3)_2$, $CH_2CH_2OH$, or $C(O)C(CH_3)_2OH$, and ~$SO_2CH_3$.

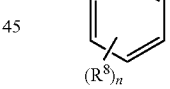

In another aspect, $R^1$ is optionally substituted heteroaryl. In one embodiment, $R^1$ is a heteroaryl substituted with 0 to 3 $R^4$ groups independently selected from among alkyl, $SO_2$(alkyl), alkylsulfonylamino, halogen, alkylcarbonylamino, alkylcarbonylheterocyclecarbonyl, heterocyclecarbonyl, and heteroarylaminocarbonyl. In a further embodiment, $R^1$ is a heteroaryl of the following structure, wherein $Z^1$ is O, S, or $NR^5$; $Z^2$ is $CR^4$ or N; $R^4$ is H, alkyl, ~$C(O)$(optionally substituted heterocycle), or ~$C(O)NH$(optionally substituted heteroaryl); $R^5$ is absent, H or alkyl; and p is 0 to 2.

In another embodiment, $R^1$ is a substituted heteroaryl selected from the group consisting of pyrazole, thiophene and furan. In still a further embodiment, $R^1$ is a heteroaryl substituted with $CH_3$, ～C(O)(optionally substituted heterocycle), or ～C(O)NH(optionally substituted heteroaryl). In yet another embodiment, $R^1$ is a heteroaryl selected from among the following structures, wherein m is 0 to 4; q is 0 to 3; and each $R^6$ is, independently, selected from among halogen, piperidinyl, 4-$CH_3$-piperidinyl, alkylsulfonyl, aminosulfonylalkyl, and alkylcarbonylamino. In a further embodiment, $R^1$ is selected from among pyridine and pyrimidine. In still another embodiment, $R^1$ is substituted with F, Cl, 4-$CH_3$-piperidinyl, ～$NHCOCH_3$, ～NHC(O)(cyclopropyl), or ～$SO_2CH_3$. In yet a further embodiment, $R^1$ is an optionally substituted benzo[b]oxazine. In another embodiment, $R^1$ is an optionally substituted benzo[b][1,3]oxazine or benzo[b][1,4]oxazine. In still a further embodiment, $R^1$ is a benzo[b]oxazinone. In yet another embodiment, $R^1$ is an optionally substituted benzo[b][1,3]oxazin-2-one, benzo[b][1,3]oxazin-4-one, benzo[b][1,4]oxazin-2-one, or benzo[b][1,4]oxazin-3-one.

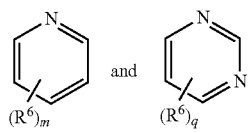

In another aspect, $R^1$ is an optionally substituted heterocycle.

In still a further aspect, $R^1$ is optionally substituted alkyl. In one embodiment, $R^1$ is ～$CH_2$-(optionally substituted heterocycle). In a further embodiment, $R^1$ is ～$CH_2$—(optionally substituted piperazinyl) or $CH_2$—(optionally substituted piperidinyl). In another embodiment, $R^1$ has the following structure, wherein Y and Y' are, independently, N or CH; and $R^7$ is H, ～C(O)(hydroxyalkyl), ～C(O)(alkyl), or ～NHC(O)(alkyl). In still a further embodiment, $R^1$ has the following structure, wherein Y and Y' are, independently, N or CH; and $R^7$ is H, ～C(O)CH($CH_3$)OH, ～C(O)C($CH_3$)$_2$OH, ～C(O)$CH_3$, or ～NHC(O)$CH_3$.

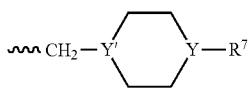

In formula (I), $R^2$ is optionally substituted morpholine or thiomorpholine. In one embodiment, $R^2$ is morpholine. In another embodiment, $R^2$ is morpholine substituted by one or more methyl groups. In a further embodiment, $R^2$ is

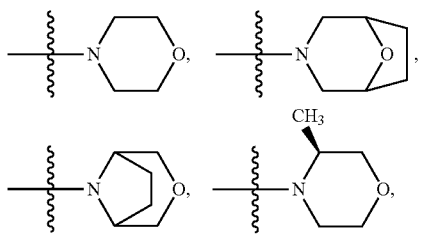

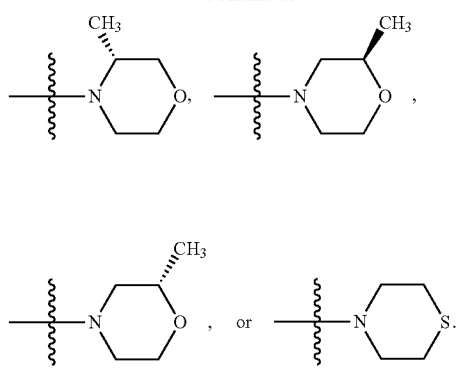

Also in formula (I), $R^3$ is H, F, Cl, $CH_3$, or $CH_3O$ and X is CH or N;

In one embodiment, the compound is of formula (I) or a pharmaceutically salt, prodrug or solvate thereof. In this structure, $R^1$ is optionally substituted aryl, optionally substituted heterocycle, optionally substituted heteroaryl, or optionally substituted alkyl; $R^2$ is optionally substituted morpholine or thiomorpholine; $R^3$ is H, F, Cl, $CH_3$, or $CH_3O$; and X is CH or N.

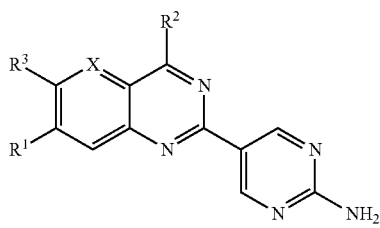

In another embodiment, the compound is of formula (I) or a pharmaceutically salt, prodrug or solvate thereof. In this structure, $R^1$ is optionally substituted aryl, optionally substituted heterocycle, optionally substituted heteroaryl, or optionally substituted alkyl; $R^2$ is optionally substituted morpholine or thiomorpholine; $R^3$ is H, F, Cl, $CH_3$, or $CH_3O$; and X is CH or N.

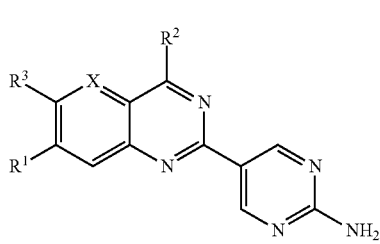

In still a further embodiment, the compound is of formula (II) or a pharmaceutically salt, prodrug or solvate thereof, wherein $R^1$ and X are defined above.

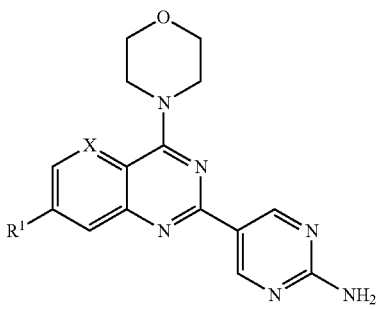

(II)

In another embodiment, the compound is of formula (III) or a pharmaceutically acceptable salt, prodrug or solvate thereof, wherein $R^1$ is defined herein.

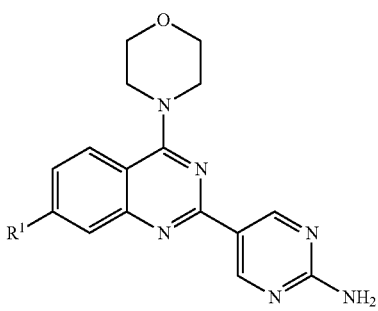

(III)

In a further embodiment, the compound is of formula (IV), or a pharmaceutically acceptable salt, prodrug or solvate thereof, wherein $R^1$ is defined herein.

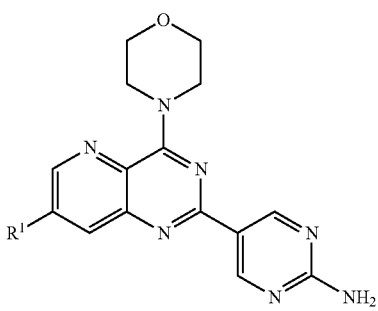

(IV)

In yet another embodiment, the compound is of formula (I-A), or a pharmaceutically acceptable salt, prodrug or solvate thereof, wherein $R^1$ and $R^3$ are defined herein.

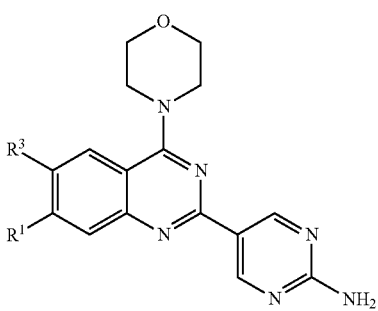

(I-A)

In still a further embodiment, the compound is of formula (I-B), or a pharmaceutically acceptable salt, prodrug or solvate thereof, wherein $R^1$ is defined herein.

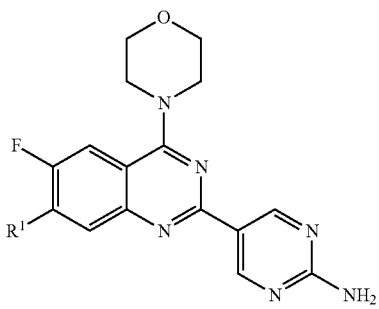

(I-B)

In another embodiment, the compound is of formula (I-C), or a pharmaceutically acceptable salt, prodrug or solvate thereof, wherein $R^1$ and $R^3$ are defined herein.

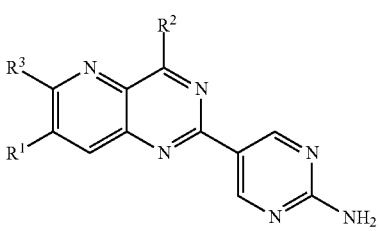

(I-C)

In yet a further embodiment, the compound is of formula (I-D), or a pharmaceutically acceptable salt, prodrug or solvate thereof, wherein $R^1$ and $R^3$ are defined herein.

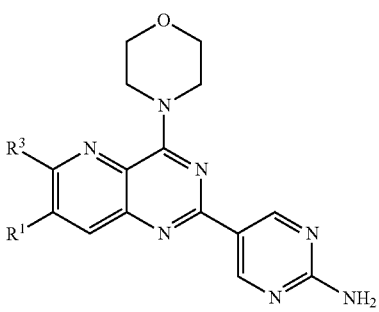

(I-D)

In another embodiment, the compound is of formula (I-E), or a pharmaceutically acceptable salt, prodrug or solvate thereof, wherein $R^2$, $R^3$, $R^8$, and $R^9$ are defined herein.

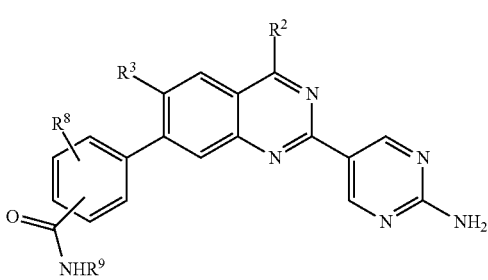

(I-E)

In still a further embodiment, the compound is of formula (I-F), or a pharmaceutically acceptable salt, prodrug or solvate thereof, wherein $R^2$, $R^3$, $R^8$, and $R^9$ are defined herein.

(I-F)

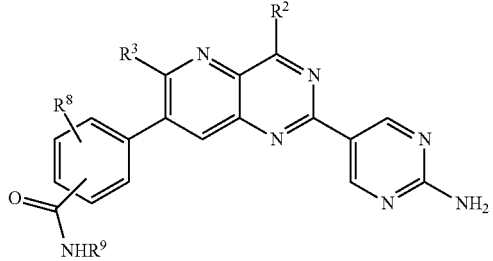

In yet another embodiment, the compound is of formula (I-G), or a pharmaceutically acceptable salt, prodrug or solvate thereof, wherein $R^3$, $R^8$, and $R^9$ are defined herein.

(I-G)

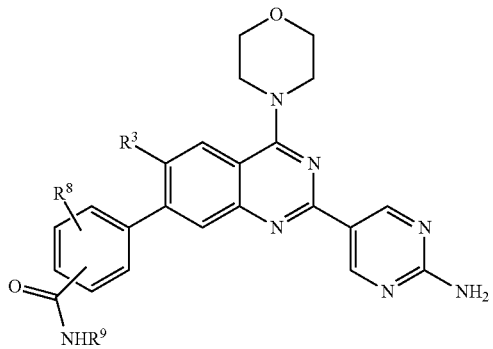

In still a further embodiment, the compound is of formula (I-H), or a pharmaceutically acceptable salt, prodrug or solvate thereof, wherein $R^3$, $R^8$, and $R^9$ are defined herein.

(I-H)

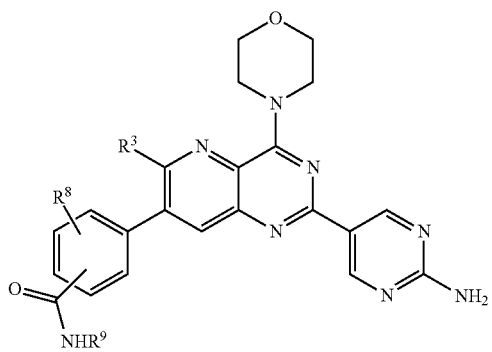

In another embodiment, the compound is of formula (I-J), or a pharmaceutically acceptable salt, prodrug or solvate thereof, wherein $R^3$, $R^8$, and $R^9$ are defined herein.

(I-J)

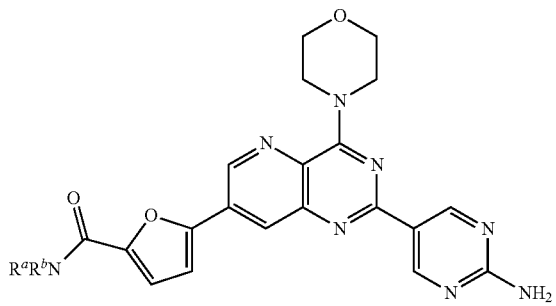

In a further embodiment, the compound is of formula (I-K), or a pharmaceutically acceptable salt, prodrug or solvate thereof, wherein $R^2$ and X are defined herein.

(I-K)

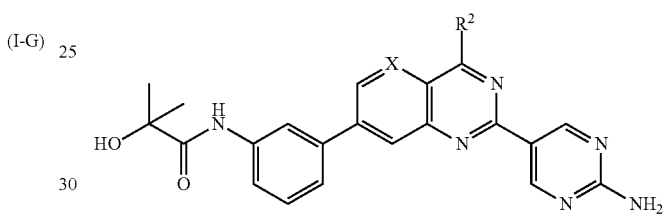

In still another embodiment, the compound is of formula (I-L), or a pharmaceutically acceptable salt, prodrug or solvate thereof, wherein $R^2$ and X are defined herein.

(I-L)

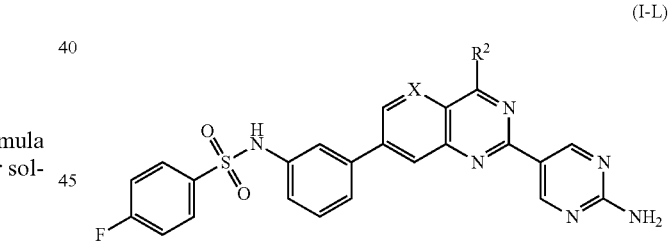

In yet a further embodiment, the compound is of formula (I-M), or a pharmaceutically acceptable salt, prodrug or solvate thereof, wherein $R^2$ and X are defined herein.

(I-M)

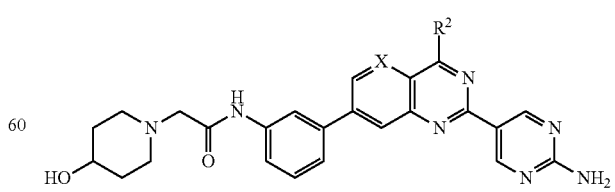

In still another embodiment, the compound is of formula (I-N), or a pharmaceutically acceptable salt, prodrug or solvate thereof, wherein $R^2$ and X are defined herein.

(I-N)

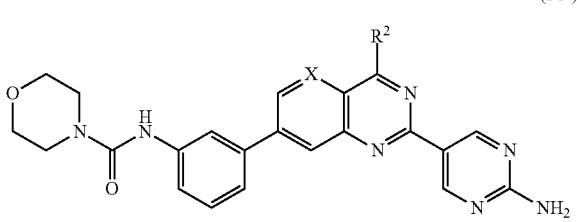

In a further embodiment, the compound is of formula (I-O), or a pharmaceutically acceptable salt, prodrug or solvate thereof, wherein $R^2$, $R^3$, $R^7$, X, and Y are defined herein.

(I-O)

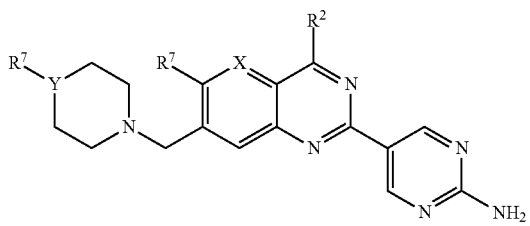

In another embodiment, the compound is of formula (I-P), or a pharmaceutically acceptable salt, prodrug or solvate thereof, wherein $R^3$, $R^7$, X, and Y are defined herein.

(I-P)

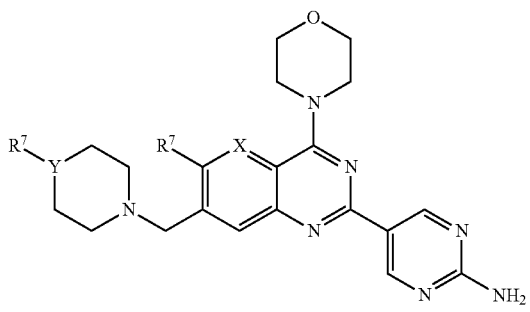

Representative "pharmaceutically acceptable salts" include but are not limited to water-soluble and water-insoluble salts. In one embodiment, the salt is of an acid or base. In another embodiment, the salt is of an acid. In a further embodiment, the salt is of an acid selected from among acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, trifluoroacetic, and camphorsulfonic. Optionally, a composition of the invention may contain both a pharmaceutically acceptable salt and the base form of a compound of the invention.

In a further embodiment, a compound of the invention may be a solvate. As used herein, a solvate does not significantly alter the physiological activity or toxicity of the compounds, and as such may function as pharmacological equivalents to non-solvate compounds of the invention. The term "solvate" as used herein is a combination, physical association and/or solvation of a compound of the present invention with a solvent molecule. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates.

Prodrugs of compounds of formula (I) may also be prepared to as a means to modulate the pharmacokinetic properties, using various methods known to those skilled in the art. See, e.g., Jarkko Rautio and coworkers in Nature Reviews Drug Discovery, 7:255-270 (2008), which is hereby incorporated by reference. In the case of drugs containing an amine moiety, a variety of prodrug approaches have been reviewed by A. L. Simplicio, Molecules, 13:519-547 (2008), which is hereby incorporated by reference. More specifically, (alkoxycarbonyloxy)alkyl carbamates, (acyloxy)alkyl carbamates, and (oxodioxolenyl)alkyl carbamates have been reported as effective prodrug strategies for amines by Zhong Li, Bioorg. Med. Chem. Lett., 7:2909-2912 (1997); J. Alexander, J. Med. Chem., 34:78-81 (1991); J. Alexander, J. Med. Chem., 31:318-322 (1988); and J. Alexander, J. Med. Chem., 39:480-486 (1996), all of which are incorporated by reference herein. (Acyloxy)alkyl carbamates have also been reported as prodrug analogs for drugs having an amide group (—CONH—). See, International Patent Publication No. WO-2005/028473 which is hereby incorporated by reference. N-Methylenephosphate disodium salt analogs have also been reported as effective prodrugs for drugs having an amide group (—CONH—) as well as other functional groups. See, e.g., International Patent Publication No. WO-2011/002999; R. Singh, "Discovery and Development of Spleen Tyrosine Kinase (SYK) Inhibitors", J. Med. Chem., online publication date: Jan. 18, 2012; Y. Ueda, Bioorg. Med. Chem. Lett., 13:3669-3372 (2003); and International Patent Publication No. WO-2007/014846; all of which are incorporated by reference herein. In one embodiment, the prodrug is a diester of formula (I). In another embodiment, the diester is ∼C(O)) ($C_1$ to $C_6$ alkyl)OC(O)($C_1$ to $C_1$ alkyl). In a further embodiment, the diester is a $C(O)OC(CH_3)OC(O)CH_3$ or $C(O)OCH_2OC(O)CH_3$ prodrug.

Some compounds within the present invention possess one or more chiral centers, and the present invention includes each separate enantiomer of such compounds as well as mixtures of the enantiomers. Where multiple chiral centers exist in compounds of the present invention, the invention includes each possible combination of chiral centers within a compound, as well as all possible enantiomeric mixtures thereof. All chiral, diastereomeric, and racemic forms of a structure are intended, unless the specific stereochemistry or isomeric form is specifically indicated. It is well known in the art how to prepare optically active forms, such as by resolution of racemic forms or by synthesis from optically active starting materials.

The following definitions are used in connection with the compounds described herein. In general, the number of carbon atoms present in a given group is designated "$C_x$ to $C_y$", where x and y are the lower and upper limits, respectively. The carbon number as used in the definitions herein refers to carbon backbone and carbon branching, but does not include carbon atoms of the substituents, such as alkoxy substitutions and the like. Unless indicated otherwise, the nomenclature of substituents that are not explicitly defined herein are determined by naming from left to right the terminal portion of the functionality followed by the adjacent functionality toward the point of attachment. As used herein, "optionally substituted" means that at least 1 hydrogen atom of the optionally substituted group has been replaced.

"Alkyl" refers to a hydrocarbon chain that may be straight or branched, or to a hydrocarbon group that consists of or contains a cyclic alkyl radical. In one embodiment, an alkyl contains 1 to 8 (inclusive) carbon atoms or integers or ranges there between. In another embodiment, an alkyl contains 1 to 7 (inclusive) carbon atoms or ranges there between. In a further embodiment, an alkyl contains 1 to 6 (inclusive) carbon atoms. In yet another embodiment, an alkyl contains 1 to 5 (inclusive) carbon atoms. In still a further embodiment, an alkyl contains 1 to 4 (inclusive) carbon atoms. Examples of alkyl groups that are hydrocarbon chains include, but are not limited to, methyl, ethyl, propyl, butyl, pentyl, hexyl, and heptyl, where all isomers of these examples are contemplated. Examples of alkyl groups that consist of or contain a cyclic alkyl radical include, but are not limited to, cyclopropyl, cyclobutyl, cyclopentyl, 3,3-dimethylcyclobutyl, (cyclopropyl)methyl, and (cyclopentyl)methyl. An alkyl can be unsubstituted or substituted with one or more groups including, without limitation, halogen, OH, $NH_2$, $N(C_1$ to $C_3$ alkyl) $C(O)(C_1$ to $C_6$ alkyl), $NHC(O)(C_1$ to $C_6$ alkyl), $NHC(O)H$, $C(O)NH_2$, $C(O)NH(C_1$ to $C_6$ alkyl), $C(O)N(C_1$ to $C_6$ alkyl)$(C_1$ to $C_6$ alkyl), CN, $C_1$ to $C_6$ alkoxy, $C(O)OH$, $C(O)O(C_1$ to $C_6$ alkyl), $C(O)(C_1$ to $C_6$ alkyl), aryl, heteroaryl, $NH(C_1$ to $C_6$ alkyl), $N(C_1$ to $C_6$ alkyl)$(C_1$ to $C_6$ alkyl), $OC(O)(C_1$ to $C_6$ alkyl), and $NO_2$. In one embodiment, the substituted alkyl is $CH_2OH$.

"Alkenyl" refers to hydrocarbon chain which is straight or branched and contains at least one degree of unsaturation (i.e., with one or more carbon-carbon double bonds), or to a hydrocarbon group that consists of or contains a cyclic alkenyl radical. Each alkenyl double bond may exist in the E or Z conformation. In one embodiment, an alkenyl contains 2 to about 8 (inclusive) carbon atoms or integers or ranges there between. In another embodiment, an alkenyl contains 2 to 7 (inclusive) carbon atoms. In a further embodiment, an alkenyl contains 2 to 6 (inclusive) carbon atoms. In yet another embodiment, an alkenyl contains 2 to 5 (inclusive) carbon atoms. In still a further embodiment, an alkenyl contains 2 to 4 (inclusive) carbon atoms. An alkenyl contains at least 1 double bond. In one embodiment, the alkenyl may contain 1 to 4 double bonds, or integers there between. Examples of alkenyl hydrocarbon chain include, but are not limited to, ethene, propene, butene, pentene, hexene, heptene, and octene. Examples of alkenyl that consist of or contain a cyclic alkenyl radical include, but are not limited to, cyclopentene, and cyclohexene. An alkenyl can be unsubstituted or substituted with one or more groups including, without limitation, halogen, OH, $NH_2$, $N(C_1$ to $C_3$ alkyl)$C(O)(C_1$ to $C_6$ alkyl), $NHC(O)(C_1$ to $C_6$ alkyl), $NHC(O)H$, $C(O)NH_2$, $C(O)NH(C_1$ to $C_6$ alkyl), $C(O)N(C_1$ to $C_6$ alkyl)$(C_1$ to $C_6$ alkyl), CN, $C_1$ to $C_6$ alkoxy, $C(O)OH$, $C(O)O(C_1$ to $C_6$ alkyl), $C(O)(C_1$ to $C_6$ alkyl), aryl, heteroaryl, $NH(C_1$ to $C_6$ alkyl), $N(C_1$ to $C_6$ alkyl)$(C_1$ to $C_6$ alkyl), $OC(O)(C_1$ to $C_6$ alkyl), and $NO_2$.

"Alkynyl" refers to a hydrocarbon chain which is straight or branched chain and contains at least one degree of unsaturation, i.e., with one or more carbon-carbon triple bond. In one embodiment, an alkynyl contains 2 to about 8 (inclusive) carbon atoms or integers or ranges there between. In another embodiment, an alkynyl contains 2 to 7 (inclusive) carbon atoms. In a further embodiment, an alkynyl contains 2 to 6 (inclusive) carbon atoms. In yet another embodiment, an alkynyl contains 2 to 5 (inclusive) carbon atoms. In still a further embodiment, an alkynyl contains 2 to 4 (inclusive) carbon atoms. An alkynyl contains at least 1 triple bond. In one embodiment, the alkynyl may contain 1 to 4 triple bonds, or integers there between. Examples of alkynyl include, but are not limited to, ethyne, propyne, butyne, pentyne, hexyne, heptyne, and octyne. An alkynyl can be unsubstituted or substituted with one or more groups including, without limitation, halogen, OH, $NH_2$, $N(C_1$ to $C_3$ alkyl)$C(O)(C_1$ to $C_6$ alkyl), $NHC(O)(C_1$ to $C_6$ alkyl), $NHC(O)H$, $C(O)NH_2$, $C(O)NH(C_1$ to $C_6$ alkyl), $C(O)N(C_1$ to $C_6$ alkyl)$(C_1$ to $C_6$ alkyl), CN, $C_1$ to $C_6$ alkoxy, $C(O)OH$, $C(O)O(C_1$ to $C_6$ alkyl), $C(O)(C_1$ to $C_6$ alkyl), aryl, heteroaryl, $NH(C_1$ to $C_6$ alkyl), $N(C_1$ to $C_6$ alkyl)$(C_1$ to $C_6$ alkyl), $OC(O)(C_1$ to $C_6$ alkyl), and $NO_2$.

"Alkoxy" refers to (alkyl)O, where the alkyl is optionally substituted and is defined above. In one embodiment, an alkoxy contains 1 to 8 (inclusive) carbon atoms or integers or ranges there between. In another embodiment, an alkoxy contains 1 to 7 (inclusive) carbon atoms or ranges there between. In a further embodiment, an alkoxy contains 1 to 6 (inclusive) carbon atoms. In yet another embodiment, an alkoxy contains 1 to 5 (inclusive) carbon atoms. In still a further embodiment, an alkoxy contains 1 to 4 (inclusive) carbon atoms. Examples of alkoxy include, but are not limited to, methoxy, ethoxy, propoxy, and butoxy. The alkyl radical of an alkoxy group can be unsubstituted or substituted as defined above for "alkyl".

"Hydroxyalkyl" refers to (alkyl)OH, where the alkyl is optionally substituted and is defined above. The OH moiety of the hydroxyalkyl may be bound to any carbon atom, for example, any one of the internal carbon atoms or the terminal carbon atom of a hydrocarbon alkyl chain. In one embodiment, a hydroxyalkyl contains 1 to 8 (inclusive) carbon atoms or integers or ranges there between. In another embodiment, a hydroxyalkyl contains 1 to 7 (inclusive) carbon atoms or ranges there between. In a further embodiment, a hydroxyalkyl contains 1 to 6 (inclusive) carbon atoms. In yet another embodiment, a hydroxyalkyl contains 1 to 5 (inclusive) carbon atoms. In still a further embodiment, a hydroxyalkyl contains 1 to 4 (inclusive) carbon atoms. Examples of a hydroxyalkyl include, but are not limited to, $CH_2OH$, $CH_2CH_2OH$, $CH(OH)CH_3$, $CH_2CH_2CH_2OH$, $CH_2CH(OH)CH_3$, $CH(OH)CH_2CH_3$, $C(OH)(CH_3)_2$, (2-hydroxy)-cyclopentyl, (3-hydroxy)-cyclobutyl, and the like.

"Cyanoalkyl" refers to (alkyl)CN, where the alkyl is optionally substituted and is defined above. The CN moiety of the cyanoalkyl may be bound to any carbon atom; for example, any one of the internal carbon atoms or the terminal carbon atom of a hydrocarbon alkyl chain. In one embodiment, a cyanoalkyl contains 1 to 8 (inclusive) carbon atoms or integers or ranges there between. In another embodiment, a cyanoalkyl contains 1 to 7 (inclusive) carbon atoms or ranges there between. In a further embodiment, a cyanoalkyl contains 1 to 6 (inclusive) carbon atoms. In yet another embodiment, a cyanoalkyl contains 1 to 5 (inclusive) carbon atoms. In still a further embodiment, a cyanoalkyl contains 1 to 4 (inclusive) carbon atoms. Examples of cyanoalkyl include, but are not limited to, $CH_2CN$, $CH_2CH_2CN$, $CH(CN)CH_3$, $CH_2CH_2CH_2CN$, $CH_2CH(CN)CH_3$, $CH(CN)CH_2CH_3$, $C(CN)(CH_3)_2$, (2-cyano)-cyclopentyl, (3-cyano)-cyclobutyl, and the like.

"Aryl" refers to an aromatic hydrocarbon group containing carbon atoms. In one embodiment, the aryl contains 6, 7 or 8 carbon atoms, and is phenyl or is an aromatic or partly aromatic bicyclic group. In a further embodiment, the aryl is a phenyl group. In another embodiment, the aryl is naphthyl (such as α-naphthyl or β-naphthyl), 1,2,3,4-tetrahydronaphthyl, or indanyl. An aryl group can be unsubstituted or substituted with one or more groups including, without limitation, halogen, OH, $NH_2$, $N(C_1$ to $C_3$ alkyl)$C(O)(C_1$ to $C_6$ alkyl), $NHC(O)(C_1$ to $C_6$ alkyl), $NHC(O)H$, $C(O)NH_2$, $C(O)NH(C_1$ to $C_6$ alkyl), $C(O)N(C_1$ to $C_6$ alkyl)$(C_1$ to $C_6$ alkyl), CN, $C_1$ to $C_6$ alkoxy, $C(O)OH$, $C(O)O(C_1$ to $C_6$ alkyl), $C(O)$ ($C_1$ to $C_6$ alkyl), aryl, heteroaryl, NH($C_1$ to $C_6$ alkyl), N($C_1$ to $C_6$ alkyl)($C_1$ to $C_6$ alkyl), OC(O)($C_1$ to $C_6$ alkyl), and $NO_2$. In one embodiment, an aryl is substituted with one or more halogen, OH, CN, $NH_2$, $C_1$ to $C_6$ alkylamino, $C_1$ to $C_6$ alkyl substituted with OH, $C_1$ to $C_6$ alkoxy, $C_1$ to $C_6$ haloalkyl, $OCF_3$, $SO_2$($C_1$ to $C_6$ alkyl), or $NHSO_2$($C_1$ to $C_6$ alkyl). In another embodiment, an aryl is substituted with one halogen, OH, CN, $NH_2$, $C_1$ to $C_6$ alkylamino, $C_1$ to $C_6$ alkyl substituted with OH, $C_1$ to $C_6$ alkoxy, $CF_3$, $OCF_3$, $SO_2CH_3$, $NHCOCH_3$, or $NHSO_2CH_3$. In a further embodiment, an aryl is substituted with one halogen, OH, CN, $N(CH_3)_2$, $CH_2OH$, $OCH_3$, $OCF_3$, $CF_3$, $SO_2CH_3$, $NHCOCH_3$, or $NHSO_2CH_3$.

"Halogen" refers to F, Cl, Br and I.

The term "heteroatom" refers to a sulfur, nitrogen, or oxygen atom.

"Heteroaryl" refers to a monocyclic aromatic 5- or 6-membered ring containing at least one ring heteroatom. In one embodiment, the heteroaryl contains 1 to 5 carbon atoms (inclusive) or integers or ranges there between. In a further embodiment, the heteroaryl contains 2 to 5 carbon atoms (inclusive). In another embodiment, the heteroaryl contains 3 to 5 carbon atoms (inclusive). In still a further embodiment, the heteroaryl contains 4 or 5 carbon atoms. "Heteroaryl" also refers to bicyclic aromatic ring systems wherein a heteroaryl group as just described is fused to at least one other cyclic moiety. In one embodiment, a phenyl radical is fused to a 5- or 6-membered monocyclic heteroaryl to form the bicyclic heteroaryl. In another embodiment, a cyclic alkyl is fused to a monocyclic heteroaryl to form the bicyclic heteroaryl. In yet a further embodiment, the bicyclic heteroaryl is a pyridine fused to a 5- or 6-membered monocyclic heteroaryl. In another embodiment, the bicyclic heteroaryl is a pyrimidine fused to a 5- or 6-membered monocyclic heteroaryl. In yet a further embodiment, the bicyclic heteroaryl is a pyridazine fused to a 5- or 6-membered monocyclic heteroaryl. In still another embodiment, the heteroaryl ring has 1 or 2 nitrogen atoms in the ring. In a further embodiment, the heteroaryl ring has 1 nitrogen atom and 1 oxygen atom. In yet another embodiment, the heteroaryl ring has 1 nitrogen atom and 1 sulfur atom. Examples of heteroaryl groups include, without limitation, furan, thiophene, indole, azaindole, oxazole, thiazole, isoxazole, isothiazole, imidazole, pyridine, pyrimidine, pyrazine, pyridazine, pyrrole, pyrazole, 1,3,4-oxadiazole, 1,2,4-triazole, tetrazole, benzoxazole, benzothiazole, benzofuran, benzisoxazole, benzimidazole, azabenzimidazole, indazole, quinazoline, quinoline, and isoquinoline. A heteroaryl may be unsubstituted or substituted with one or more groups including, without limitation, halogen, OH, $NH_2$, N($C_1$ to $C_3$ alkyl)C(O)($C_1$ to $C_6$ alkyl), NHC(O)($C_1$ to $C_6$ alkyl), NHC(O)H, C(O)$NH_2$, C(O)NH($C_1$ to $C_6$ alkyl), C(O)N($C_1$ to $C_6$ alkyl)($C_1$ to $C_6$ alkyl), CN, $C_1$ to $C_6$ alkoxy, C(O)OH, C(O)O($C_1$ to $C_6$ alkyl), C(O)($C_1$ to $C_6$ alkyl), aryl, heteroaryl, NH($C_1$ to $C_6$ alkyl), N($C_1$ to $C_6$ alkyl)($C_1$ to $C_6$ alkyl), OC(O)($C_1$ to $C_6$ alkyl), and $NO_2$. In one embodiment, a heteroaryl is substituted with one or more halogen, OH, CN, $NH_2$, $C_1$ to $C_6$ alkylamino, $C_1$ to $C_6$ alkyl substituted with OH, $C_1$ to $C_6$ alkoxy, $C_1$ to $C_6$ haloalkyl, $OCF_3$, $SO_2$($C_1$ to $C_6$ alkyl), $NHCOCH_3$, or $NHSO_2$($C_1$ to $C_6$ alkyl). In another embodiment, a heteroaryl is substituted with one halogen, OH, CN, $N(CH_3)_2$, $CH_2OH$, $OCH_3$, $OCF_3$, $CF_3$, $SO_2CH_3$, $NHCOCH_3$, or $NHSO_2CH_3$.

"Heterocycle" refers to a monocyclic or bicyclic group in which at least 1 ring atom is a heteroatom. A heterocycle may be saturated or partially saturated. In one embodiment, the heterocycle contains 3 to 7 carbon atoms (inclusive) or integers or ranges there between. In a further embodiment, the heterocycle contains 4 to 7 carbon atoms (inclusive). In another embodiment, the heterocycle contains 4 to 6 carbon atoms (inclusive). In still a further embodiment, the heterocycle contains 5 or 6 carbon atoms (inclusive). Examples of heterocycles include, but are not limited, to aziridine, oxirane, thiirane, morpholine, thiomorpholine, pyrroline, pyrrolidine, azepane, dihydrofuran, tetrahydrofuran, dihydrothiophene, tetrahydrothiophene, dithiolane, piperidine, 1,2,3,6-tetrahydropyridine-1-yl, tetrahydropyran, pyran, thiane, thiine, piperazine, homopiperazine, oxazine, azecane, tetrahydroquinoline, perhydroisoquinoline, 5,6-dihydro-4H-1,3-oxazin-2-yl, 2,5-diazabicyclo[2.2.1]heptane, 2,5-diazabicyclo[2.2.2]octane, 3,6-diazabicyclo[3.1.1]heptane, 3,8-diazabicyclo[3.2.1]octane, 6-oxa-3,8-diazabicyclo[3.2.1]octane, 7-oxa-2,5-diazabicyclo[2.2.2]octane, 2,7-dioxa-5-azabicyclo[2.2.2]octane, 2-oxa-5-azabicyclo[2.2.1]heptane-5-yl, 2-oxa-5-azabicyclo[2.2.2]octane, 3,6-dioxa-8-azabicyclo[3.2.1]octane, 3-oxa-6-azabicyclo[3.1.1]heptane, 3-oxa-8-azabicyclo[3.2.1]octan-8-yl, 5,7-dioxa-2-azabicyclo[2.2.2]octane, 6,8-dioxa-3-azabicyclo[3.2.1]octane, 6-oxa-3-azabicyclo[3.1.1]heptane, 8-oxa-3-azabicyclo[3.2.1]octan-3-yl, 2,5-diazabicyclo[2.2.1]heptane-5-yl, 6-azabicyclo[3.2.1]oct-6-yl, 8-azabicyclo[3.2.1]octan-8-yl, 3-oxa-7,9-diazabicyclo[3.3.1]nonan-9-yl, 9-oxa-3-azabicyclo[3.3.1]nonan-3-yl, 3-oxa-9-azabicyclo[3.3.1]nonan-9-yl, 3,7-dioxa-9-azabicyclo[3.3.1]nonan-9-yl, 3,4-dihydro-2H-1,4-benzoxazin-7-yl, thiazine, dithiane, and dioxane. In another embodiment, the heterocycle contains 1 or 2 nitrogen atoms. In a further embodiment, the heterocycle contains 1 or 2 nitrogen atoms and 3 to 6 carbon atoms. In yet another embodiment, the heterocycle contains 1 or 2 nitrogen atoms, 3 to 6 carbon atoms, and 1 oxygen atom. In still a further embodiment, the heterocycle is morpholine. In one embodiment, the heterocycle is morpholine and is substituted with one or more $C_1$ to $C_3$ alkyl. In another embodiment, the heterocycle is morpholine and 2 carbons of the heterocycle are joined to form a 4- or 5-membered ring. A heterocycle may be unsubstituted or substituted with one or more groups including, without limitation, halogen, OH, $NH_2$, N($C_1$ to $C_3$ alkyl)C(O)($C_1$ to $C_6$ alkyl), NHC(O)($C_1$ to $C_6$ alkyl), NHC(O)H, C(O)$NH_2$, C(O)NH($C_1$ to $C_6$ alkyl), C(O)N($C_1$ to $C_6$ alkyl)($C_1$ to $C_6$ alkyl), CN, $C_1$ to $C_6$ alkoxy, C(O)OH, C(O)O($C_1$ to $C_6$ alkyl), C(O)($C_1$ to $C_6$ alkyl), aryl, heteroaryl, NH($C_1$ to $C_6$ alkyl), N($C_1$ to $C_6$ alkyl)($C_1$ to $C_6$ alkyl), OC(O)($C_1$ to $C_6$ alkyl), and $NO_2$. In one embodiment, a heterocycle is substituted with one or more halogen, OH, CN, $NH_2$, $C_1$ to $C_6$ alkylamino, $C_1$ to $C_6$ alkyl substituted with OH, $C_1$ to $C_6$ alkoxy, $C_1$ to $C_6$ haloalkyl, $OCF_3$, $SO_2$($C_1$ to $C_6$ alkyl), $NHCOCH_3$, or $NHSO_2$($C_1$ to $C_6$ alkyl). In another embodiment, a heterocycle is substituted with one F, OH, CN, $NH_2$, $N(CH_3)_2$, $CH_2OH$, $OCH_3$, $OCF_3$, $CF_3$, $SO_2CH_3$, $NHCOCH_3$, or $NHSO_2CH_3$.

"$C_1$ to $C_6$ haloalkyl" refers to a $C_1$ to $C_6$ alkyl group, as defined above, wherein one or more of the $C_1$ to $C_6$ alkyl group's hydrogen atoms has been replaced with F, Cl, Br, or I. Each substitution can be independently selected from F, Cl, Br, or I. Representative examples of an $C_1$ to $C_6$ haloalkyl group include, but are not limited to, $CH_2F$, $CF_3$, $CH_2CF_3$, and the like.

"Alkylthio" refers to (alkyl)S⁓, where the alkyl is optionally substituted and is defined above. In one embodiment, an alkylthio contains 1 to 8 (inclusive) carbon atoms or integers or ranges there between. Examples of alkylthio include, but are not limited to, $SCH_3$, $SCH_2CH_3$, $SCH_2CH_2CH_3$, and $SCH_2CH_2CH_2CH_3$.

"Aryloxy" refers to (aryl)O⁓, where the aryl is defined above and is optionally substituted as described above. An aryloxy group is attached through the oxygen atom moiety. Examples of aryloxy include, but are not limited to, phenoxy and pentafluorophenoxy.

"Heteroaryloxy" refers to (heteroaryl)O~~~, where the heteroaryl is optionally substituted and is defined above. The heteroaryloxy moiety is bound through the oxygen atom moiety. Examples of heteroaryloxy include, but are not limited to, (3-pyridyl)oxy and (4-pyridyl)oxy.

"Heterocycle-oxy" refers to (heterocycle)O~~~, where the heterocycle is optionally substituted and is defined above. The heterocycle-oxy moiety is bound through the oxygen atom. Examples of heterocycleoxy include, but are not limited to, (4-piperidinyl)oxy.

"Alkylsulfonyl" refers to an (alkyl)$SO_2$~~~, group, which is bound through the $SO_2$ moiety. The alkyl group is defined and optionally substituted as described above. Examples of alkylsulfonyl include, but are not limited to, $CH_3SO_2$, $CH_3CH_2CH_2SO_2$, $CH_3CH(CH_3)SO_2$, $CH_3CH_2CH_2CH_2SO_2$, $CH_3CH(CH_3)CH_2SO_2$, $(CH_3)_3CSO_2$, and the like.

"Alkylsulfonylalkyl" refers to an (alkyl)$SO_2$(alkyl) group, which is bound through one of the alkyl groups. The alkyl group is defined and optionally substituted as described above. The alkyl groups may be the same or different. Examples of alkylsulfonylalkyl include, but are not limited to, 3-(methylsulfonyl)propyl and 3-(methylsulfonyl)cyclopentyl.

"Alkylamino" refers to an NH or N group, the nitrogen atom of said group being attached to 1 or 2 alkyl substituents, respectively, where alkyl is as defined above. The alkylamino is bound through the nitrogen atom of the group. In one embodiment, alkylamino refers to a (alkyl)NH~~~ group. In another embodiment, alkylamino refers to a (alkyl)(alkyl)N~~~ group, i.e., a "dialkylamino". When the nitrogen atom is bound to 2 alkyls, each alkyl group may be independently selected. In another embodiment, two alkyl groups on the nitrogen atom may be taken together with the nitrogen to which they are attached to form a 3- to 7-membered nitrogen-containing heterocycle wherein up to two of the carbon atoms of the heterocycle can be replaced with N(H), N($C_1$ to $C_6$ alkyl), N(aryl), N(heteroaryl), O, S, S(O), or $S(O)_2$. Examples of alkylamino include, but are not limited to $CH_3NH$, $CH_3CH_2NH$, $CH_3CH_2CH_2NH$, $CH_3CH_2CH_2CH_2NH$, $(CH_3)_2CHNH$, $(CH_3)_2CHCH_2NH$, $CH_3CH_2CH(CH_3)NH$, $(CH_3)_3CNH$, $N(CH_3)_2$, $N(CH_2CH_3)(CH_3)$, $N(CH_2CH_3)_2$, $N(CH_2CH_2CH_3)_2$, $N(CH_2CH_2CH_2CH_3)_2$, $N(CH(CH_3)_2)(CH_3)$, and the like.

"Aminoalkyl" refers to an alkyl group having an $NH_2$ substituent. The aminoalkyl is bound through one carbon atom of the group. That is, alkylamino refers to a $NH_2$(alkyl)~~~ group. Examples of aminoalkyl include, but are not limited to $CH_2NH_2$, $CH_2CH_2NH_2$, $CH_2CH_2CH_2NH_2$, $CH_2CH_2CH_2CH_2NH_2$, $C(CH_3)_2NH_2$, $C(CH_3)_2CH_2NH_2$, and the like.

"Alkylaminoalkyl" refers to an (alkyl)NH(alkyl)~~~ group, the nitrogen atom of being attached to 2 alkyl substituents, respectively, as defined above, and where the group is bound through one of the alkyl groups. Each of the alkyl groups may be independently selected and substituted as described above. In another embodiment, the alkyl groups may be taken together with the nitrogen to which they are attached to form a 3- to 7-membered nitrogen containing heterocycle wherein up to two of the carbon atoms of the heterocycle can be replaced with N(H), N($C_1$ to $C_6$ alkyl), N(aryl), N(heteroaryl), O, S, S(O), or $S(O)_2$. Examples of alkylaminoalkyl include, but are not limited to $CH_3NHCH_2$, $CH_3NHCH_2CH_2$, $CH_3NHCH(CH_3)$, $CH_3CH_2NHCH_2$, $CH_3CH_2NHCH_2CH_2$, $CH_3CH_2NHCH(CH_3)$, and the like.

"Dialkylaminoalkyl" refers to an (alkyl)$_2$N(alkyl)~~~ group, the nitrogen atom of being attached to 3 alkyl substituents, respectively, as defined above, and where the group is bound through one of the alkyl groups. Each of the alkyl groups may be independently selected and substituted as described above. In another embodiment, two of the alkyl groups may be taken together with the nitrogen to which they are attached to form a 3- to 7-membered nitrogen containing heterocycle wherein up to two of the carbon atoms of the heterocycle can be replaced with N(H), N($C_1$ to $C_6$ alkyl), N(aryl), N(heteroaryl), O, S, S(O), or $S(O)_2$. Examples of dialkylaminoalkyl include, but are not limited to $(CH_3)_2NCH_2$, $(CH_3)_2NCH_2CH_2$, $(CH_3)_2NCH(CH_3)$, $(CH_3CH_2)_2NCH_2$, $(CH_3CH_2)_2NCH_2CH_2$, $(CH_3CH_2)_2NCH(CH_3)$, $(CH_3)(CH_3CH_2)NCH_2$, and the like.

"Acylamino" refers to an (aryl)NH~~~ group, where aryl is optionally substituted and defined as above. The arylamino is bound through the nitrogen atom. Examples of arylamino include, but are not limited to, phenyl-amino.

"Heteroarylamino" refers to a (heteroaryl)NH~~~ group, where heteroaryl is optionally substituted and defined as above. The heteroarylamino is bound through the amino nitrogen atom. Examples of heteroarylamino include, but are not limited to (pyridin-2-yl)amino and (pyrimidin-2-yl)amino "Heterocycle-amino" refers to a (heterocycle)NH~~~ group, where heterocycle is optionally substituted and defined as above. Examples of heterocycle-amino include, but are not limited to (piperidin-4-yl)amino.

"Alkylcarbonylamino" refers to an (alkyl)C(O)NH~~~ group, which is bound through the nitrogen atom. The alkyl group is defined and optionally substituted as described above. Examples of alkylcarbonylamino include, but are not limited to, $CH_3CONH$, $CH_3CH_2CONH$, $CH_3CH_2CH_2CONH$, $CH_3CH(CH_3)CONH$, and the like.

"Alkylsulfonylamino" refers to an (alkyl)$SO_2NH$~~~ group which is bound through the nitrogen atom. The alkyl group is defined and optionally substituted as described above. Examples of alkylsulfonylamino include, but are not limited to $CH_3SO_2NH$, $CH_3CH_2SO_2NH$, $CH_3CH_2CH_2SO_2NH$, $CH_3CH(CH_3)SO_2NH$, and the like.

"Alkylaminocarbonyl" refers to an (alkyl)NHC(O)~~~ group, which is bound through the carbonyl moiety. The alkyl group is defined and optionally substituted as described above. Examples of alkylaminocarbonyl include, but are not limited to, $CH_3NHCO$, $CH_3CH_2NHCO$, $CH_3CH_2CH_2NHCO$, $CH_3CH(CH_3)NHCO$, and the like.

"Alkylaminosulfonyl" refers to an (alkyl)$NHSO_2$~~~ group, which is bound through the sulfur atom. The alkyl group is defined and optionally substituted as described above. Examples of alkylaminosulfonyl include, but are not limited to, $CH_3NHSO_2$, $CH_3CH_2NHSO_2$, $CH_3CH_2CH_2NHSO_2$, $CH_3CH(CH_3)NHSO_2$, and the like.

"Arylaminocarbonyl" refers to an (aryl)NHC(O)~~~ group, which is bound through the carbon atom of the carbonyl moiety. The aryl group is defined and optionally substituted as described above. Examples of arylaminocarbonyl include, but are not limited to phenyl-NHC(O)—.

"Heteroarylaminocarbonyl" refers to an (heteroaryl)NHC(O)~~~ group, which is bound through the carbon atom of the carbonyl moiety. The heteroaryl group is defined and optionally substituted as described above. Examples of heteroarylaminocarbonyl include, but are not limited to (pyridine-4-yl)NHC(O).

"Heterocycleaminocarbonyl" refers to an (heterocycle)N-HC(O)〰 group, which is bound through the carbonyl moiety. The heterocycle group is defined and optionally substituted as described above. Examples of heterocycleaminocarbonyl include, but are not limited to (tetrahydro-2H-pyran-4-yl)NHC(O).

A "patient" or "subject" is a mammal, e.g., a human or a veterinary patient or subject, e.g., mouse, rat, guinea pig, dog, cat, horse, cow, pig, or non-human primate, such as a monkey, chimpanzee, baboon or gorilla.

The term "treating" or "treatment" is meant to encompass administering to a subject a compound of the present invention for the purposes of amelioration of one or more symptoms of a disease or disorder, including palliative care. A "therapeutically effective amount" refers to the minimum amount of the active compound which effects treatment.

The following abbreviations are used herein and have the indicated definitions: ACN is acetonitrile; BCA is bicinchoninic acid; bid po means twice daily by mouth; conc is concentrated; DMSO is dimethylsulfoxide; DCC is dicyclohexylcarbodiimide; DCM is dichloromethane; DIPEA is diisopropylethylamine; DMF is N,N-dimethylformamide; dppf is 1,1'-bis(diphenylphosphino)ferrocene; DTT is dithiothreitol; EDC.HCl is 1-(3-dimethylaminopropyl)-3-ethylcarbodiimide hydrochloride; EDTA is ethylenediamine tetraacetic acid; EGTA is ethylene glycol tetraacetic acid; ELISA is enzyme-linked immunosorbent assay; EtOH is ethanol; ESI is electrospray ionization; EI is electron impact ionization; HATU is 2-(1H-7-azabenzotriazol-1-yl)-1,1,3,3-tetramethyl uronium hexafluorophosphate methanaminium; HEPES is (4-(2-hydroxyethyl)-1-piperazineethanesulfonic acid; HPCD is hydroxypropyl-β-cyclodextrin; HPLC is high performance liquid chromatography; Hz is hertz; HOAt is 1-hydroxy-7-azabenzotriazole; HOBt is 1-hydroxy benzotriazole; KOAc is potassium acetate; LC is liquid chromatography; MS is mass spectroscopy; MeOH is methanol; MHz is megahertz; mM is millimolar; mL is milliliter; min is minutes; mol is moles; M$^+$ is molecular ion; [M+H]$^+$ is protonated molecular ion; N is normality; NMR is nuclear magnetic resonance; PIP2 is 5-bisphosphate; PBS is phosphate buffered saline; PH is pleckstrin homology; PMSF is phenylmethanesulfonyl fluoride; PPh$_3$ is triphenylphosphine; PTSA is para-toluenesulphonic acid; psi is pound per square inch; PPM is parts per million; qd po means daily by mouth; rt is room temperature; RT is retention time; TLC is thin layer chromatography; TFA is trifluoroacetic acid; TEA is triethylamine; THF is tetrahydrofuran; TMS is tetramethylsilane; and XTT is sodium 2,3,-bis(2-methoxy-4-nitro-5-sulfophenyl)-5-[(phenylamino)-carbonyl]-2H-tetrazolium inner salt.

The words "comprise", "comprises", and "comprising" are to be interpreted inclusively rather than exclusively. The works "consist", "consisting", and its variants, are to be interpreted exclusively, rather than inclusively.

As used herein, the term "about" means a variability of 10% from the reference given, unless otherwise specified.

Methods useful for making the compounds of Formula (I) are set forth in the Examples below and generalized in Schemes I-V. One of skill in the art will recognize that Schemes I-V can be adapted to produce the other compounds of Formula (I) and pharmaceutically acceptable salts or prodrugs of compounds of Formula (I) according to the present invention.

Scheme I

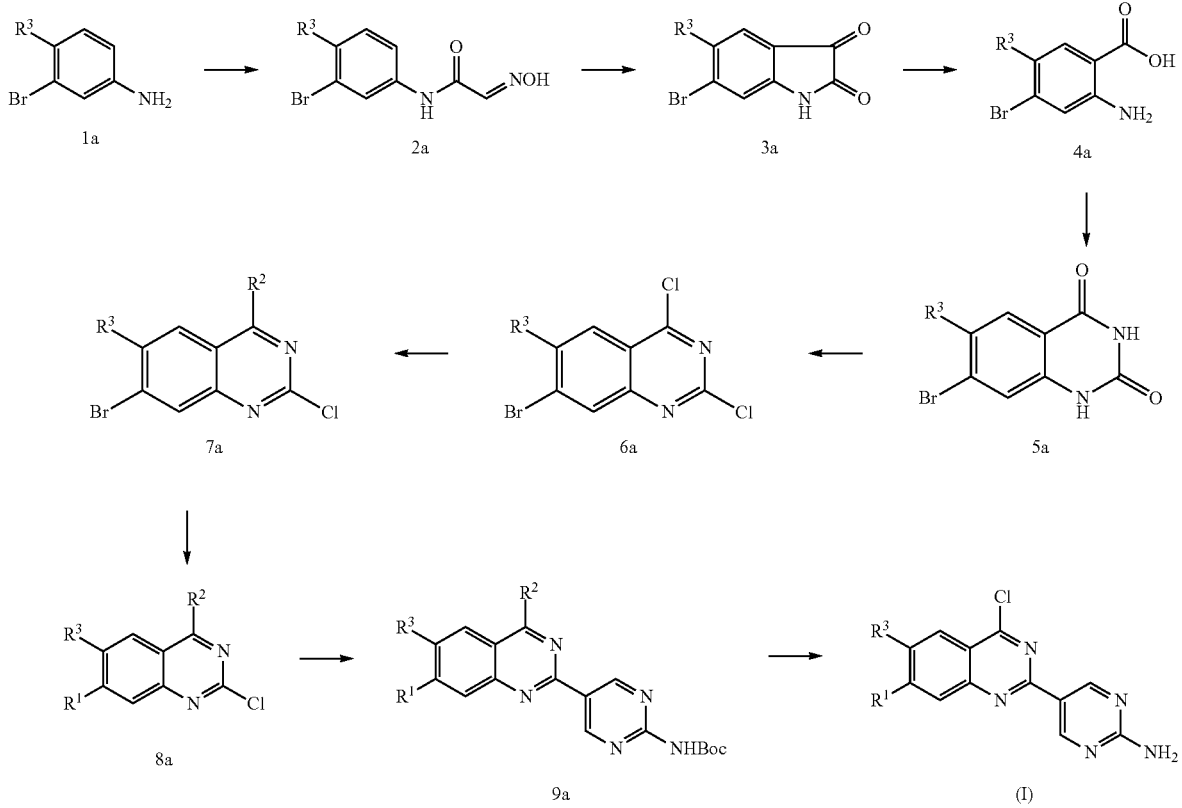

Scheme I provides the preparation of the compounds (I) of the invention. In this scheme, the noted $R^1$-substituted 3-bromo aniline 1a is reacted with chloral hydrate and hydroxylamine hydrochloride to provide compound 2a. In one embodiment, the reaction is performed in the presence of about 1 equivalent of chloral hydrate. In another embodiment, the reaction is performed in the presence of about 3 equivalents of hydroxylamine hydrochloride. In a further embodiment the reaction is performed in the presence of $Na_2SO_4$, HCl, and water. In yet another embodiment, the reaction is performed at elevated temperatures. In still a further embodiment, the reaction is performed at about 90° C. Alternatively, 1a could have a different leaving group substituent such as 3-chloro in place of the 3-bromo substituent, with some modifications to subsequent steps in the synthetic sequence. The hydroxylamine substituent of compound 2a is then cyclized to form dione compound 3a. This reaction is performed by adding compound 2a to a solution of sulfuric acid. In one embodiment, the reaction is conducted at an elevated temperature. In another embodiment, the reaction is conducted at a temperature of about 50° C. In a further embodiment, the temperature of the reaction mixture is raised above about 50° C. during the reaction. In yet another embodiment, the temperature of the reaction mixture is raised to about 90° C. The dione ring portion of compound 3a is then opened to provide carboxylic acid compound 4a. In one embodiment, the ring is opened using hydrogen peroxide. The ring opening reaction is typically performed at reduced temperatures. In one embodiment, the ring opening reaction is performed at about 0° C. In a further embodiment, the ring opening reaction is performed in the presence of sodium hydroxide. Carboxylic acid compound 4a is then cyclized to the corresponding cyclic urea 5a. In one embodiment, the cyclization is performed using urea. In another embodiment, the cyclization is performed using an excess of urea. In a further embodiment, the cyclization is performed using about 10 equivalents of urea. The cyclization is typically performed at elevated temperatures. In one embodiment, the cyclization is performed at about 200° C. The oxo groups of compound 5a are then replaced with chlorine groups to provide compound 6a. In one embodiment, compound 5a is reacted with phosphoryl chloride ($POCl_3$). In another embodiment, the reaction to form compound 6a is performed in the presence of a base such as triethylamine or DIPEA. This reaction may be performed at elevated temperatures. In one embodiment, compound 6a is formed from compound 5a at a temperature of about 130° C. The chlorine at the 4-position of compound 6a is then replaced with an optionally substituted morpholine ($R^2$) to provide compound 7a. In one embodiment, compound 6a is reacted with an optionally substituted morpholine. In another embodiment, compound 6a is reacted with morpholine. The reaction is typically performed at a reduced temperature. In one embodiment, compound 7a is formed via compound 6a at a temperature of about 0° C. Compound 7a is then $R^3$ substituted at the 7-position using reagents and conditions understood by those skilled in the art. In one embodiment, compound 7a is $R^3$-substituted by a coupling reaction using $R^3B(OH)_2$ or $R^3B(OR)_2$ to provide compound 8a. In one embodiment, the $R^3$-substitution is performed in the presence of a palladium catalyst such as $PdCl_2(PPh_3)_2$. In another embodiment, the $R^3$-substitution is performed at elevated temperatures. In a further embodiment, the $R^3$-substitution is performed at about 90-95° C. In a further embodiment, the $R^3$-substitution is carried out in the presence of $Na_2CO_3$. In one embodiment, the $R^3$-substitution is carried out in a solvent system such as DMF and water. In another embodiment, the $R^3$-substitution is carried out in a solvent system such as toluene, ethanol and water. Compound 8a is then substituted at the 2-position with a tert-butoxycarbonyl)amino-pyrimidine group to provide compound 9a. In one embodiment, the 2-position of compound 8a is substituted using 2-((tert-butoxycarbonyl)amino)pyrimidin-5-yl)boronic acid. In another embodiment, the substitution is performed in the presence of a palladium catalyst such as $Pd(PPh_3)_4$ or $PdCl_2(PPh_3)_2$. In a further embodiment, the pyrimidine substitution is performed at elevated temperatures of about 90 to about 110° C. In still another embodiment, the pyrimidine substitution is performed using $Pd(PPh_3)_4$ in the presence of $K_3PO_4$. In yet a further embodiment, the pyrimidine substitution is performed using $PdCl_2(PPh_3)_2$ in the presence of $Cs_2CO_3$. In one embodiment, the $R^3$-substitution is carried out in a solvent system such as DMF and water. In another embodiment, the $R^3$-substitution is carried out in a solvent system such as toluene, ethanol and water. Finally compound 9a is hydrolyzed to the corresponding amino compound. In one embodiment, the hydrolysis is performed using trifluoroacetic acid (TFA). In another embodiment, the hydrolysis is carried out using HCl in dioxane.

Scheme Ia

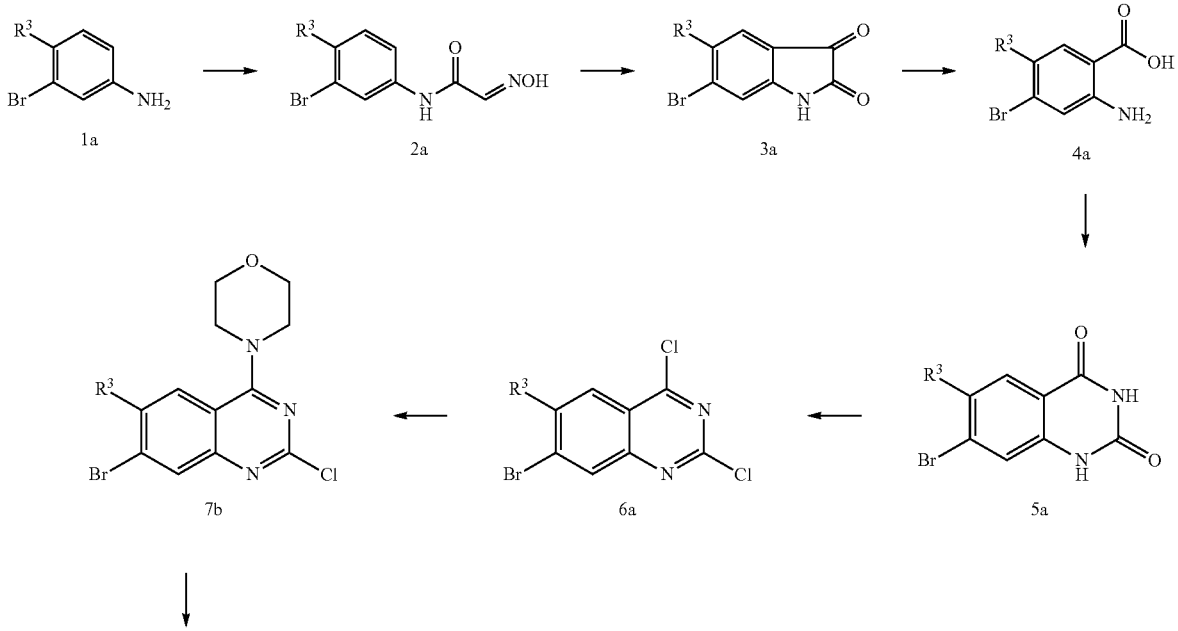

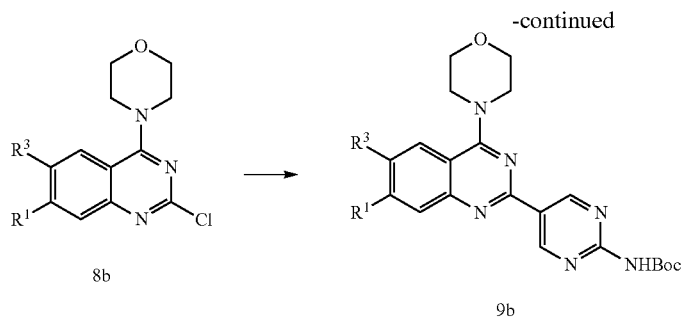
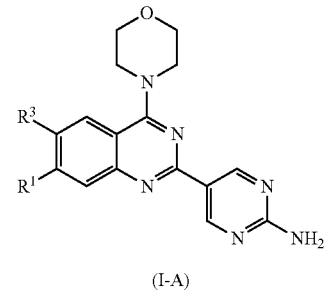

Scheme Ia provides the preparation of the compounds of the invention where $R^1$ is a substituted aryl or heteroaryl and $R^2$ is morpholine. In this scheme, compound 6a is formed as described above in Scheme I. In one embodiment, the $R^1$-substituted 3-bromoaniline 1a is reacted with chloral hydrate and $NH_2OH \cdot HCl$ in the presence of $Na_2SO_4$ and hydrochloric acid at 90° C. to provide compound 2a. In another embodiment, the $R^1$-substituted 3-bromoaniline 1a is reacted with about 1 equivalents of chloral hydrate and about 3 equivalents of $NH_2OH \cdot HCl$ in the presence of $Na_2SO_4$ and hydrochloric acid at about 90° C. to provide compound 2a. Compound 2a is then added to sulfuric acid at about 50° C., followed by a warming of the solution to about 90° C. Compound 3a is then reacted with hydrogen peroxide and 2N NaOH at about 0° C. to provide compound 4a. In one embodiment, compound 3a is reacted with about 1.5 volumes of 30% hydrogen peroxide and about 5 volumes of 2N NaOH at about 0° C. to provide compound 4a. Compound 4a is then reacted with urea at about 200° C. to provide compound 5a. In one embodiment, compound 4a is reacted with about 10 equivalents of urea at about 200° C. to provide compound 5a. Compound 5a is then reacted with phosphoryl chloride and DIPEA at about 130° C. to provide compound 6a. Compound 6a is reacted with morpholine to provide compound 7b. In one embodiment, the reaction is performed at about 0° C. In another embodiment, the reaction is performed in methylene chloride at about 0° C. Compound 7b is then $R^3$-substituted to provide compound 8b. In one embodiment, compound 7b is $R^3$-substituted using $R^3B(OR)_2$. In another embodiment, compound 7b is $R^3$ substituted using $R^3B(OR)_2$ and $PdCl_2(PPh_3)_2$ at about 90-95° C. in the presence of $Na_2CO_3$, toluene, ethanol and $H_2O$. In another embodiment, compound 7b is $R^3$-substituted using $R^3B(OR)_2$ and a catalytic amount of $PdCl_2(PPh_3)_2$ at about 90-95° C. in the presence of $Na_2CO_3$, DMF and $H_2O$ to provide compound 8b. Compound 8b is then substituted with 2-((tert-butoxycarbonyl)amino)pyrimidine using (2-((tert-butoxycarbonyl)amino)pyrimidin-5-yl)boronic acid to provide compound 9b. In one embodiment, the reaction is performed in the presence of a catalytic amount of $Pd(PPh_3)_4$ and $K_3PO_4$ at about 90-110° C. In another embodiment, the reaction is performed in the presence of about 0.05 equivalents of $PdCl_2(PPh_3)_2$ and about 2 equivalents of $Cs_2CO_3$ at about 90-95° C. Finally, compound 9b is hydrolyzed using TFA in methylene chloride of HCl in dioxane to provide compound (I-A).

Scheme Ib

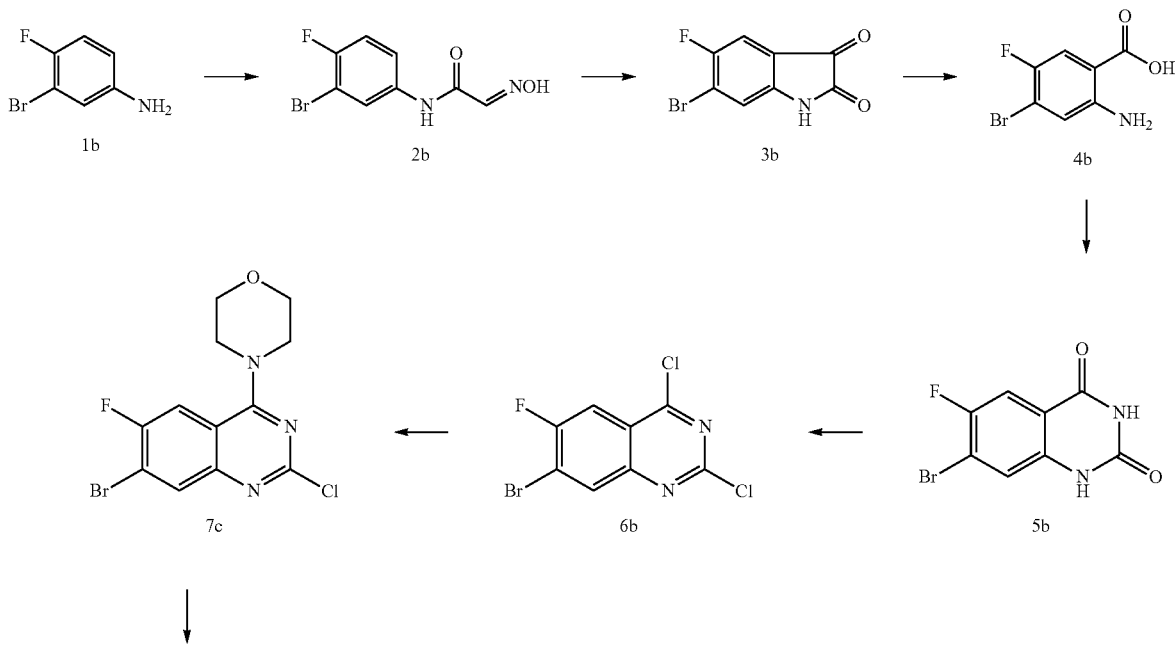

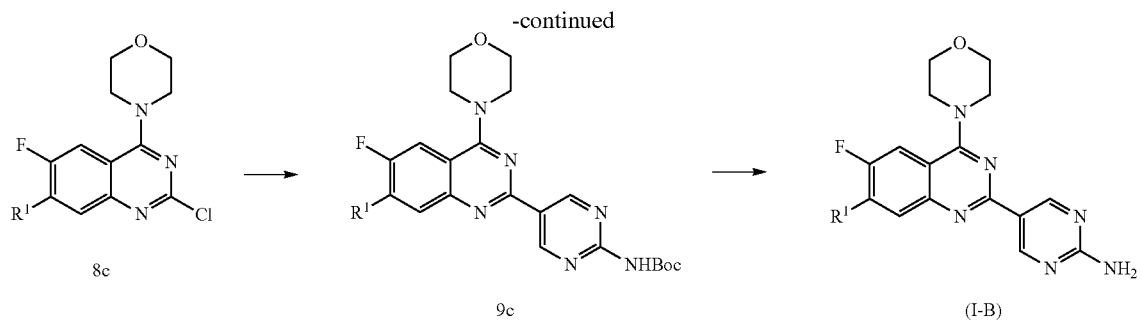

Scheme Ib provides the preparation of the compounds of the invention where $R^1$ is F and $R^2$ is morpholine following the synthetic route described in Scheme I. Specifically 3-bromo-4-fluoro-aniline 1b is reacted with chloral hydrate and hydroxylamine hydrochloride at about 90° C. to provide N-(3-bromo-4-fluoro-phenyl)-2-hydroxyimino-acetamide 2b. In one embodiment, 3-bromo-4-fluoro-aniline 1b is reacted with about 1 equivalent of chloral hydrate and about 3 equivalents of $NH_2OH \cdot HCl$ in the presence of $Na_2SO_4$ and hydrochloric acid. Addition of N-(3-bromo-4-fluoro-phenyl)-2-hydroxyimino-acetamide 2b to sulfuric acid at about 50° C., followed by raising the temperature of the solution to about 90° C. provided 5-fluoro-6-bromo-1H-indolin-2,3-dione 3b. Conversion of 5-fluoro-6-bromo-1H-indolin-2,3-dione 3b to 3-fluoro-4-bromo-6-amino-benzoic acid 4b was performed using hydrogen peroxide. In one embodiment, the reaction is performed at about 0° C. In another embodiment, 3-fluoro-4-bromo-6-amino-benzoic acid 4b is prepared using about 1.5 volumes of $H_2O_2$ at about 0° C. in the presence of NaOH, such as 2N NaOH. Conversion of 3-fluoro-4-bromo-6-amino-benzoic acid 4b to 6-fluoro-7-bromo-quinazolin-2,4-dione 5b may be performed using urea at about 200° C. In one embodiment, 3-fluoro-4-bromo-6-amino-benzoic acid 4b is converted to 6-fluoro-7-bromo-quinazolin-2,4-dione 5b using an excess, i.e., about 10 equivalents, of urea. Replacement of the oxo groups of 6-fluoro-7-bromo-quinazolin-2,4-dione 5b with chlorine groups may be performed using a chlorinating agent such as $POCl_3$. In one embodiment, the reaction is performed in the presence of DIPEA at about 130° C. The resultant 2,4-dichloro-6-fluoro-7-bromo-quinazoline 6b is then reacted with morpholine at about 0° C. to provide 2-chloro-4-morpholino-6-fluoro-7-bromo-quinazoline 7c. $R^3$-substitution of 2-chloro-4-morpholino-6-fluoro-7-bromo-quinazoline 7c may be performed using $R^3B(OR)_2$. In one embodiment, $R^3$-substitution is performed in the presence of a catalytic amount of $PdCl_2(PPh_3)_2$. In another embodiment, the reaction is performed at about 90-95° C. in the presence of $Na_2CO_3$, ethanol and $H_2O$. The 2-position of compound 8c is then substituted with a 2-(tert-butoxycarbonyl)amino)pyrimidine using (2-(tert-butoxycarbonyl)amino)pyrimidin-5-yl)boronic acid to provide compound 9c. In one embodiment, the reaction is performed in the presence of a catalytic amount of $PdCl_2(PPh_3)_2$. In another embodiment, the reaction is also performed in the presence of about 2 equivalents of $Cs_2CO_3$ and DMF at about 75° C. to provide compound 9c. Finally, deprotection of compound 9c is performed using TFA or HCl, such as 4N HCl in 1,4-dioxane at about 0° C. to room temperature.

Scheme II

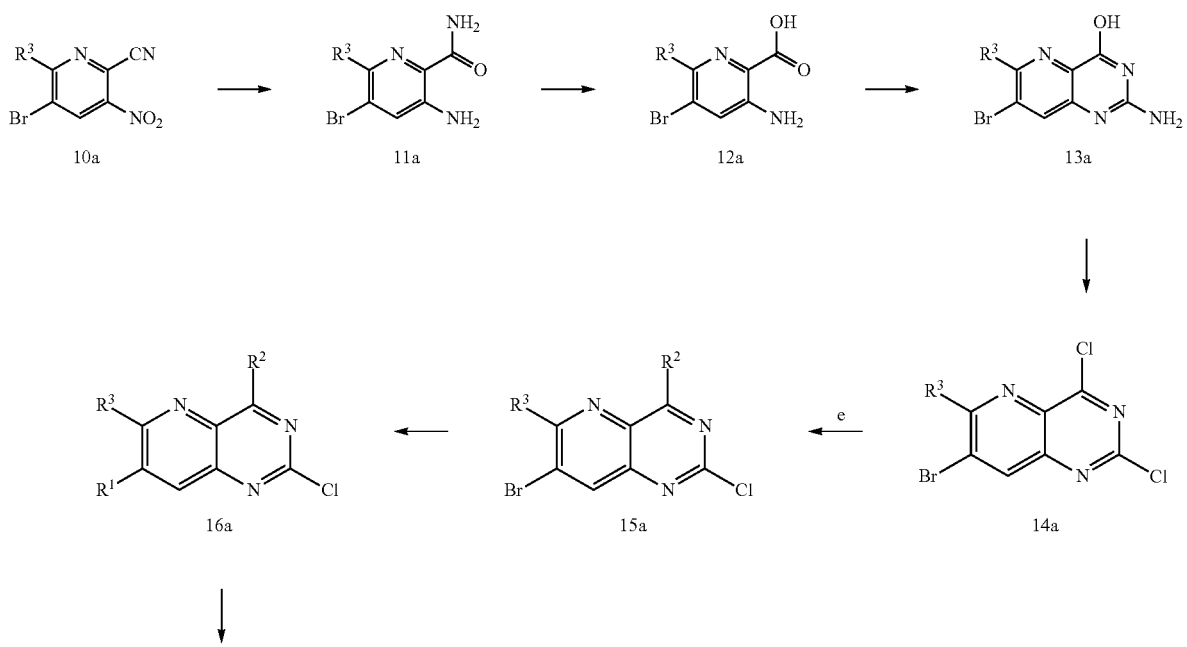

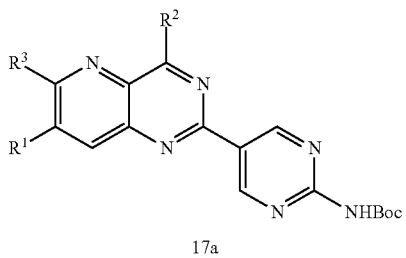

17a

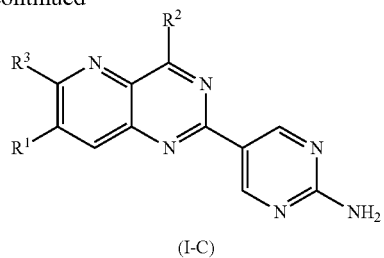

(I-C)

Scheme II provides the preparation of compounds of the invention where X is N. In this scheme, cyano-pyridine compound 10a is hydrolyzed to the corresponding amide compound 11a. In one embodiment, the hydrolysis is performed as a hydrogenolysis using hydrogen gas and a suitable catalyst in ethanol. In another embodiment, the hydrolysis is performed using hydrogen and Raney nickel in ethanol. Amide compound 11a is then converted to the corresponding acid compound 12a using reagents known to those skilled in the art. In one embodiment, compound 11a is reacted with a base such as aqueous sodium hydroxide. In another embodiment, compound 11a is reacted with aqueous sodium hydroxide at elevated temperatures such as 120° C. In a further embodiment, compound 11a is reacted with an excess, i.e., about 5 equivalents, of sodium hydroxide in water. Compound 12a is then reacted with urea to form compound 13a. In one embodiment, an excess, i.e., about 5 equivalents, of urea is utilized. In another embodiment, compound 12a is reacted with urea at elevated temperatures, e.g., about 200° C. The 2 and 4-positions of compound 13a are then chlorinated using a chlorinating agent to provide compound 14a. In one embodiment, the chlorinating agent is phosphoryl chloride. In another embodiment, compound 13a is reacted with phosphoryl chloride in the presence of DIPEA at elevated temperatures, e.g., 130° C. Compound 14a is then substituted at the 4-position with $R^2$, i.e., an optionally substituted morpholine substituent, to provide compound 15a. In one embodiment, compound 14a is reacted with an optionally substituted morpholine reagent to provide compound 15a. In another embodiment, the reaction is performed at reduced temperatures, e.g., about 0° C., for about 15-30 minutes. Compound 15a is then $R^3$-substituted at the 7-position to provide compound 16a. In one embodiment, the $R^3$-substitution is performed using $R^3B(OH)_2$ or $R^3B(OR)_2$. In another embodiment, the $R^3$-substitution is performed in the presence of a catalyst such as $PdCl_2(PPh_3)_2$ in the presence of $Na_2CO_3$ (2.0 eq), in a solvent system such as toluene, ethanol and $H_2O$, or DMF and $H_2O$. In yet another embodiment, the $R^3$-substitution is performed at elevated temperatures, such as about 90° C. to about 95° C. Compound 16a is then substituted at the 2-position with a pyrimidine substituent to provide compound 17a. In one embodiment, compound 16a is reacted with (2-((tert-butoxycarbonyl)amino)pyrimidin-5-yl)boronic acid. In another embodiment, the reaction is performed in the presence of a catalyst such as $Pd(PPh_3)_4$ or $PdCl_2(PPh_3)_2$ in the presence of $K_3PO_4$ or $Cs_2CO_3$, in a solvent system such as DMF and $H_2O$, or toluene/ethanol/$H_2O$. In a yet another embodiment, the reaction is performed at about 90° C. to about 110° C. In still a further embodiment, the reaction is performed at about 90° C. to about 95° C. or about 90° C. to about 110° C. Finally, the BOC group of compound 17a is removed to provide compound (I-C). In one embodiment, the BOC group is removed using TFA or HCl. In another embodiment, the BOC group is removed by using TFA in DCM at about 0° C. to about room temperature.

Scheme IIa

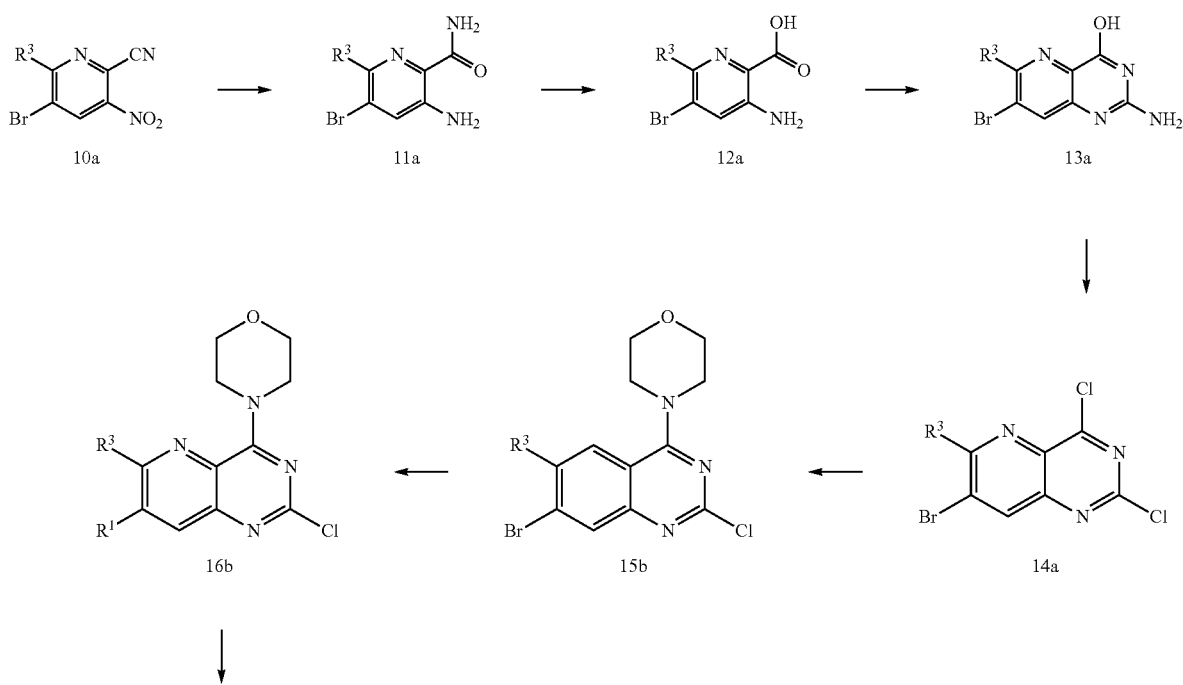

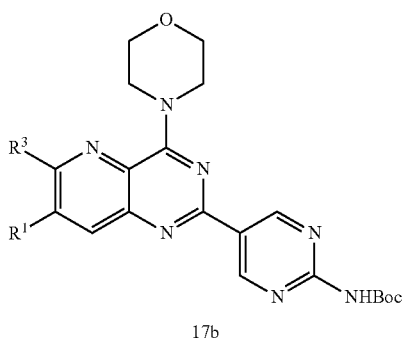

17b

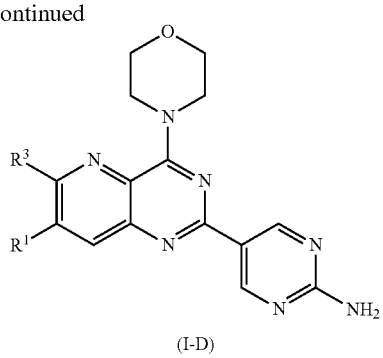

(I-D)

Scheme IIa provides the preparation of compounds (I-D), where X is N, $R^2$ is morpholine, and compound 14a is prepared as described in Scheme II. Compound 14a is then substituted at the 4-position with a morpholine substituent by its reaction with morpholine to provide compound 15b. In one embodiment, the reaction is performed at reduced temperatures, e.g., about 0° C. Compound 15b is then $R^3$-substituted at the 7-position to provide compound 16b. In one embodiment, the $R^3$-substitution is performed using $R^3B(OR)_2$. In another embodiment, the $R^3$-substitution is performed in the presence of a catalyst, such as $PdCl_2(PPh_3)_2$ in the presence of $Na_2CO_3$ (2.0 eq), in a solvent system such as toluene, ethanol and $H_2O$, or DMF and $H_2O$. In yet another embodiment, the is reacted with (2-((tert-butoxycarbonyl)amino)pyrimidin-5-yl)boronic acid. In another embodiment, the reaction is performed in the presence of a catalyst such as $Pd(PPh_3)_4$ or $PdCl_2(PPh_3)_2$ in the presence of $K_3PO_4$ or $Cs_2CO_3$, in a solvent system such as DMF and $H_2O$, or toluene/ethanol/$H_2O$. In a yet another embodiment, the reaction is performed at about 90 to about 110° C. In still a further embodiment, the reaction is performed at about 90° C. to about 95° C. Finally, the BOC group of compound 17b is removed to provide compound (I-C). In one embodiment, the BOC group is removed using TFA or HCl. In another embodiment, the BOC group is removed by using TFA in DCM at about 0° C. to about room temperature.

Scheme III

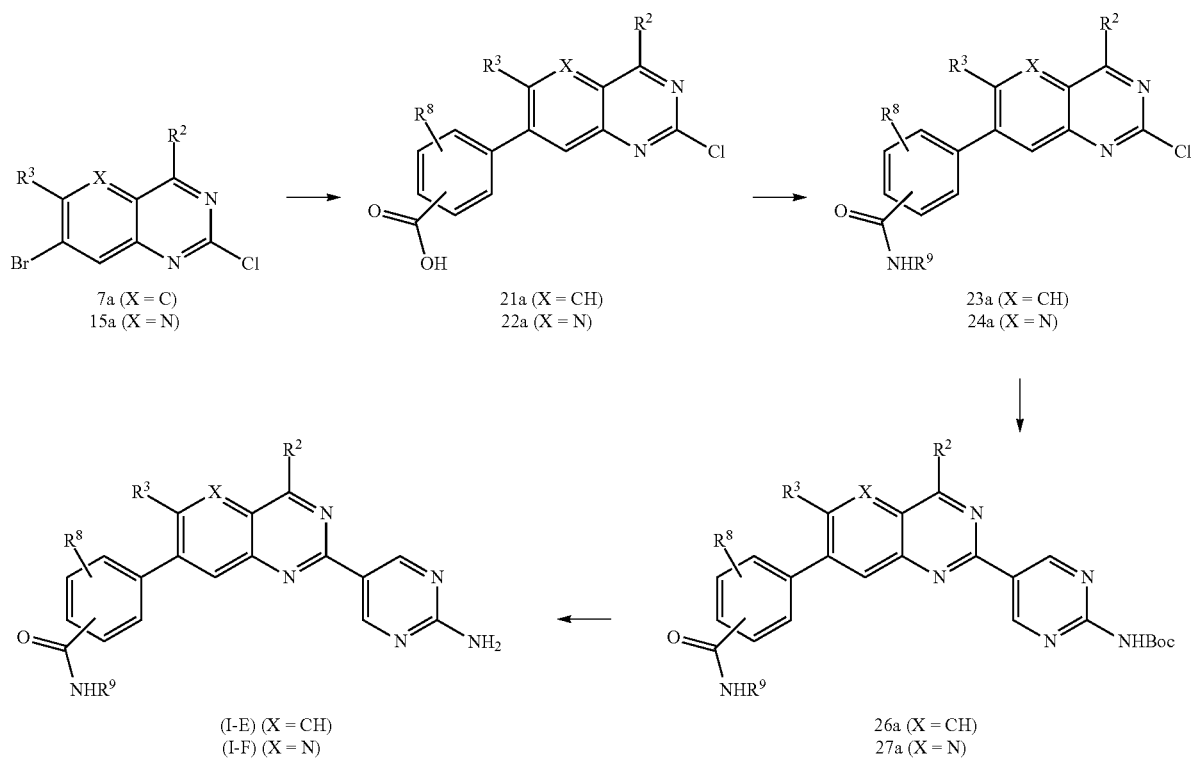

$R^3$-substitution is performed at elevated temperatures, such as about 90° C. to about 95° C. Compound 16b is then substituted at the 2-position with a pyrimidine substituent to provide compound 17b. In one embodiment, compound 16b Scheme III provides the preparation of compounds (I-E) and (I-F), which are encompassed by the compounds of formula (I). In one embodiment, $R^3$ is F or $CH_3$. In another embodiment, $R^9$ is an optionally substituted alkyl, cycloalkyl, aryl, or heteroaryl. Specifically, compound 7a may be prepared as described in Scheme I and compound 15a may be prepared as described in Scheme II. Compound 7a or 15a is then converted to carboxylic acid compounds 21a or 22a, respectively. In one embodiment, compound 7a or 15a is reacted with an optionally substituted carboxyphenyl boronic acid or carboxyphenylboronic acid pinacol ester to provide compound 21a or 22a, respectively. In another embodiment, the reaction is performed in the presence of a catalytic amount of Pd(PPh$_3$)$_4$ or PdCl$_2$(PPh$_3$)$_2$ in the presence of K$_3$PO$_4$ or Cs$_2$CO$_3$, in a solvent system such as DMF and H$_2$O, or toluene/ethanol/H$_2$O. In still a further embodiment, the reaction is performed at elevated temperatures, such as about 90 to about 110° C. Finally, compounds 26a and 27a are converted to compounds (I-E) and (I-F), respectively. In one embodiment, compounds 26a and 27a are reacted with TFA or HCl. In another embodiment, the reaction is performed by using TFA in methylene chloride at about room temperature.

Scheme IIIa

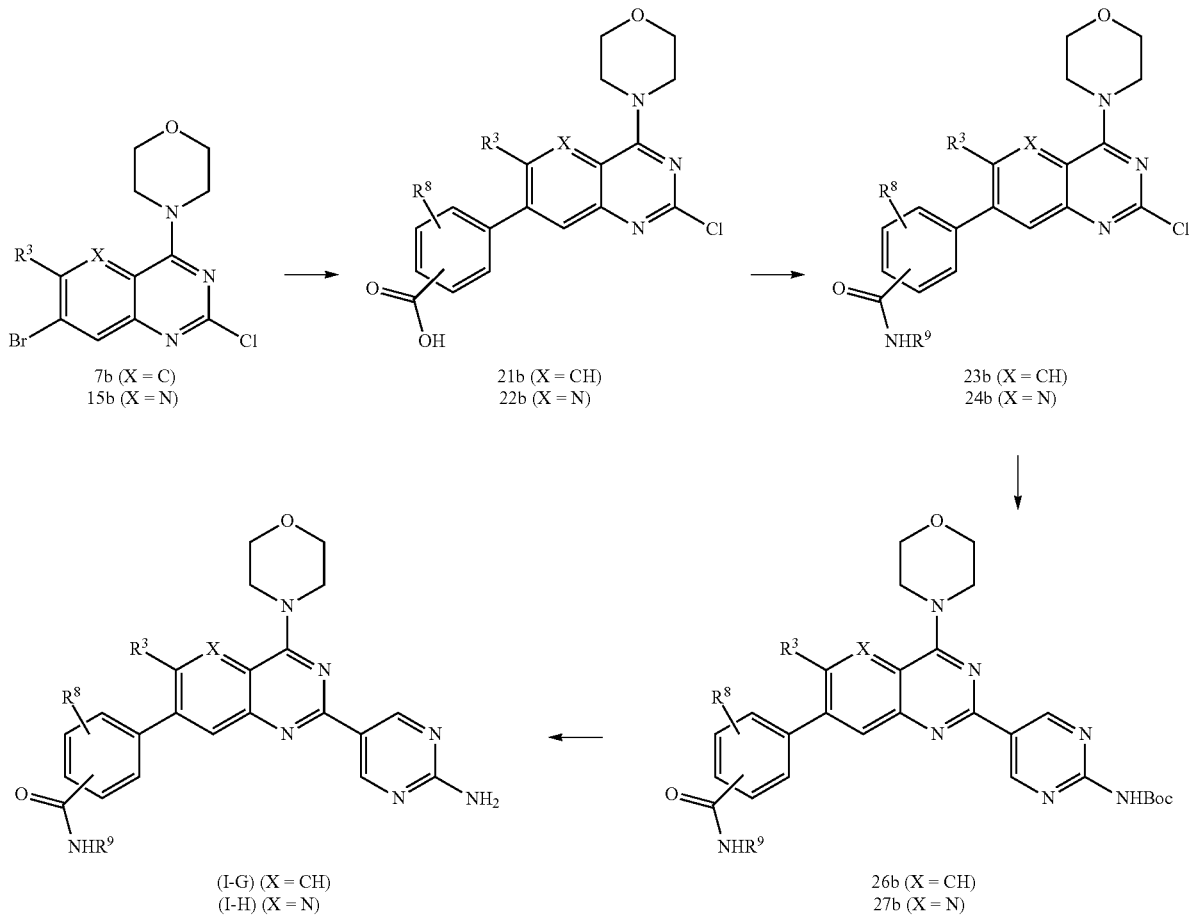

of PdCl$_2$(PPh$_3$)$_2$ in the presence of Na$_2$CO$_3$, in a solvent system such as toluene, ethanol and H$_2$O, or DMF and H$_2$O. In yet another embodiment, the reaction is performed at elevated temperatures, such as about 95° C. Carboxylic acid compounds 21a and 22a are then converted to the corresponding amide compounds 23a and 24a, respectively. In one embodiment, compound 21a or 22a is reacted with an amine such as NH$_2$R$^9$. In another embodiment, the reaction is performed in DMF in the presence of HATU and TEA. In still another embodiment, the reaction is performed at about room temperature. Compounds 23a and 24a are then substituted at the 2-position with a pyrimidine substituent to provide compound 25a and 26a, respectively. In one embodiment, the reaction is performed with an amine protected pyrimidine boronic acid such as (2-((tert-butoxycarbonyl)amino)pyrimidin-5-yl)boronic acid. In another embodiment, the reaction is performed in the presence of a catalyst. In a further embodiment, the reaction is performed in the presence of a catalytic Scheme IIIa provides the preparation of compounds (I-G) and (I-H), which are encompassed by the compounds of formula (I). In one embodiment, R$^3$ is F or CH$_3$. In another embodiment, R$^9$ is an optionally substituted alkyl, cycloalkyl, aryl, or heteroaryl. Specifically, compound 7b may be prepared as described in Scheme Ia and compound 15b may be prepared as described in Scheme IIa. Compound 7b or 15b is then converted to carboxylic acid compounds 21b or 22b, respectively. In one embodiment, compound 7b or 15b is reacted with an optionally substituted carboxyphenyl boronic acid or carboxyphenylboronic acid pinacol ester to provide compound 21b or 22b, respectively. In another embodiment, the reaction is performed in the presence of a catalytic amount of PdCl$_2$(PPh$_3$)$_2$ in the presence of Na$_2$CO$_3$, in a solvent system such as toluene, ethanol and H$_2$O, or DMF and H$_2$O. In yet another embodiment, the reaction is performed at elevated temperatures, such as about 95° C. Carboxylic acid compound 21b or 22b is then converted to the corresponding amide compound 23b and 24b, respectively. In one embodiment, compound 21b or 22b is reacted with an amine such as NH₂R⁹. In another embodiment, the reaction is performed in DMF in the presence of HATU and TEA. In still another embodiment, the reaction is performed at about room temperature. Compound 23b or 24b is then substituted at the 2-position with a pyrimidine substituent to provide compound 25b or 26b, respectively. In one embodiment, the reaction is performed with an amine protected pyrimidine boronic acid such as (2-((tert-butoxycarbonyl)amino)pyrimidin-5-yl) boronic acid. In another embodiment, the reaction is performed in the presence of a catalyst. In a further embodiment, the reaction is performed in the presence of a catalytic amount of Pd(PPh₃)₄ or PdCl₂(PPh₃)₂ in the presence of K₃PO₄ or Cs₂CO₃, in a solvent system such as DMF and H₂O, or toluene/ethanol/H₂O. In still a further embodiment, the reaction is performed at elevated temperatures, such as about 90 to about 110° C. Finally, compound 26b or 27b are converted to compound (I-E) or (I-F), respectively. In one embodiment, compound 26a or 27a is reacted with TFA or HCl. In another embodiment, the reaction is performed by using TFA in methylene chloride at about room temperature.

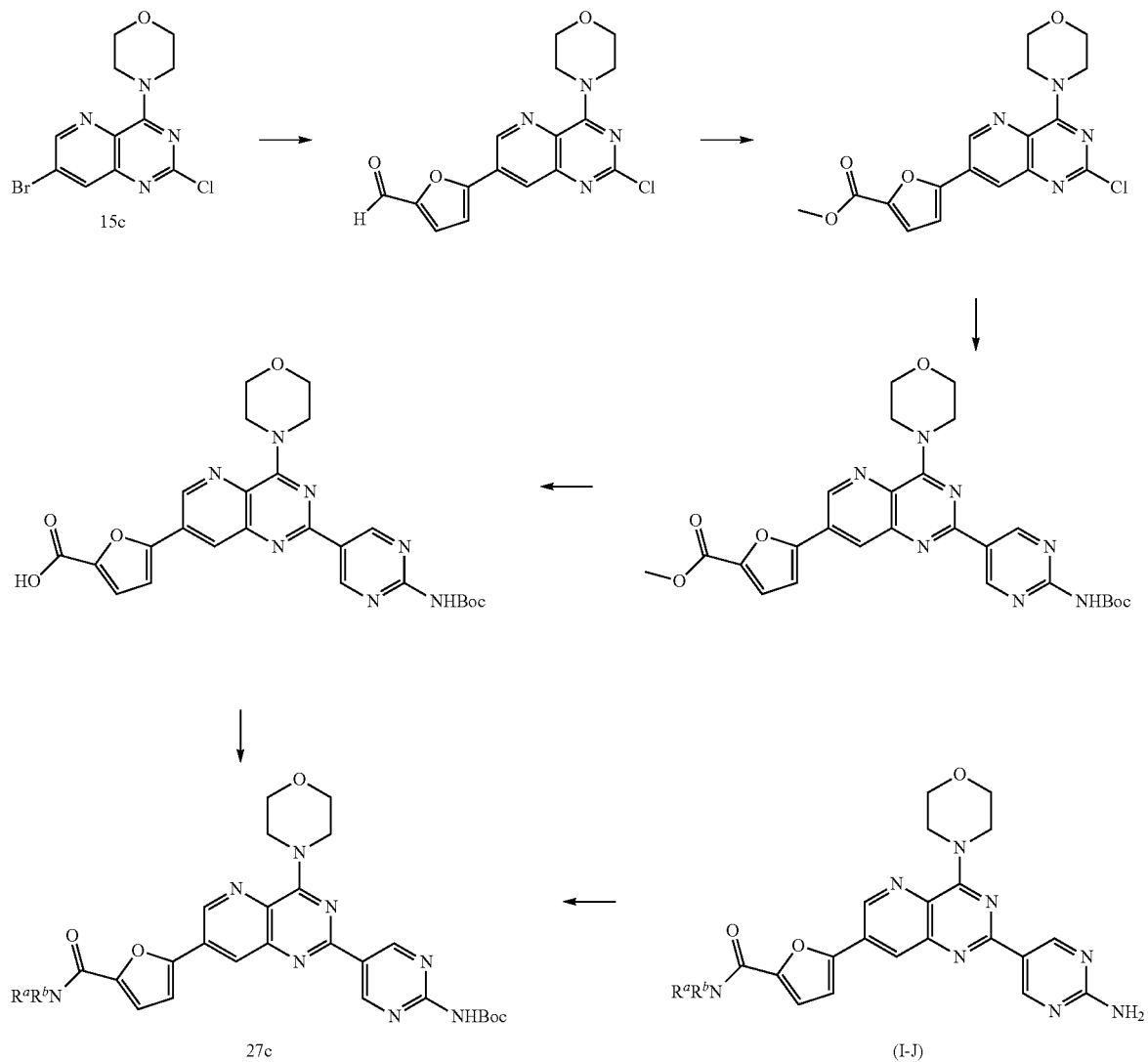

Scheme IIIb

Scheme IIIb provides the preparation of compounds encompassed by formula (I) where R¹ is an amide-substituted heteroaryl. In this scheme, compound 15c is reacted with 5-formyl-2-furanylboronic acid to provide 5-(2-chloro-4-morpholinopyrido[3,2-d]pyrimidin-7-yl)furan-2-carbaldehyde. In one embodiment, the reaction is performed in the presence of a catalyst such as PdCl₂(Ph)₃ in the presence of Na₂CO₃, in a solvent system such as toluene, ethanol and H₂O, or DMF and H₂O. In another embodiment, the reaction is performed at about 90 to about 95° C. The aldehyde substituent of 5-(2-chloro-4-morpholinopyrido[3,2-d]pyrimidin-7-yl)furan-2-carbaldehyde is then converted to the carboxylate thereby providing methyl 5-(2-chloro-4-morpholinopyrido[3,2-d]pyrimidin-7-yl)furan-2-carboxylate. In one embodiment, this conversion is performed using NaCN and MnO₂. In one embodiment, the conversion is performed in methanol at about 0° C. The 2-position of methyl 5-(2-chloro-4-morpholinopyrido[3,2-d]pyrimidin-7-yl)furan-2-carboxylate is then substituted with an amine-protected pyrimidine substituent to provide 5-(2-(2-(tert-butoxycarbonyl)amino)pyrimidin-5-yl)-4-morpholinopyrido[3,2-d]pyrimidin-7-yl)furan-2-carboxylic acid. In one embodiment, methyl 5-(2-chloro-4-morpholinopyrido[3,2-d]pyrimidin-7-yl)furan-2-carboxylate is reacted with (2-(tert-butoxycarbonyl)amino)pyrimidin-5-yl)boronic acid. In another embodiment, this reaction is performed in the presence of a catalytic amount of Pd(PPh$_3$)$_4$ or PdCl$_2$(PPh$_3$)$_2$ in the presence of K$_3$PO$_4$ or Cs$_2$CO$_3$, in a solvent system such as DMF and H$_2$O, or toluene/ethanol/H$_2$O. In a further embodiment, the reaction is performed at elevated temperatures such as about 90° C. to about 95° C. The ester group of 5-(2-(2-(tert-butoxycarbonyl)amino)pyrimidin-5-yl)-4-morpholinopyrido[3,2-d]pyrimidin-7-yl)furan-2-carboxylic acid is the converted to the corresponding acid thereby providing 5-(2-(2-(tert-butoxycarbonyl)amino)pyrimidin-5-yl)-4-morpholinopyrido[3,2-d]pyrimidin-7-yl)furan- 2-carboxylic acid. In one embodiment, the reaction is performed using lithium hydroxide in aqueous methanol and THF. In another embodiment, the reaction is performed at about room temperature. 5-(2-(2-(Tert-butoxycarbonyl)amino)pyrimidin-5-yl)-4-morpholinopyrido[3,2-d]pyrimidin-7-yl)furan-2-carboxylic acid is then reacted with an optionally substituted amine to provide compound 27c. In one embodiment, the amine is NHR$^a$R$^b$, wherein R$^a$ and R$^b$ are, independently, CH$_3$, ⌇C(O)(optionally substituted heterocycle), or ⌇C(O)NH(optionally substituted heteroaryl). In another embodiment, the reaction is performed in DMF in the presence of HATU and TEA. Finally, the amine substituent on the pyrimidine moiety of compound 27c is deprotected to provide compound (I-J). In one embodiment, the deprotection is performed using trifluoroacetic acid. In another embodiment, the deprotection is performed in DCM at about room temperature.

Scheme IV

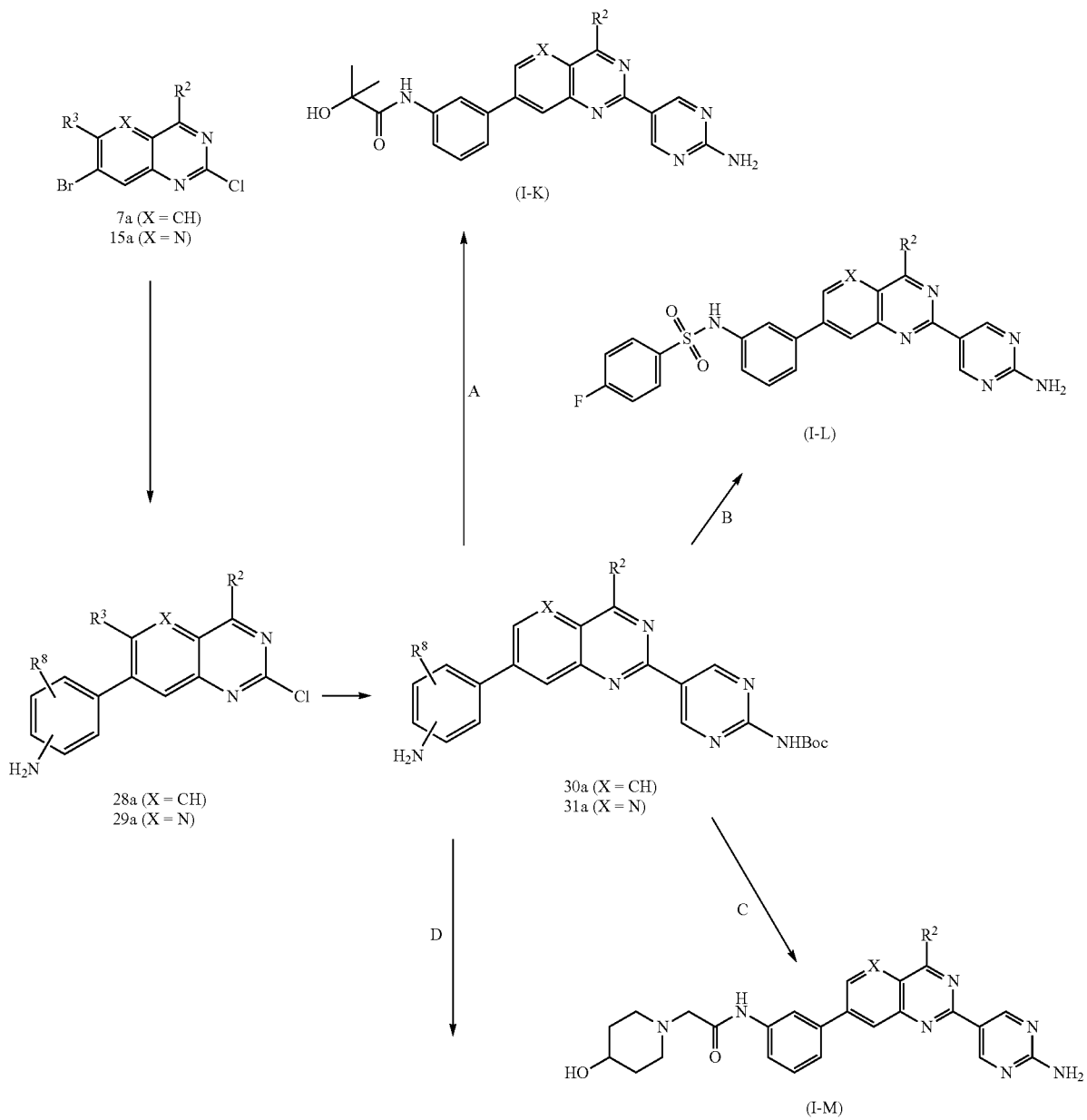

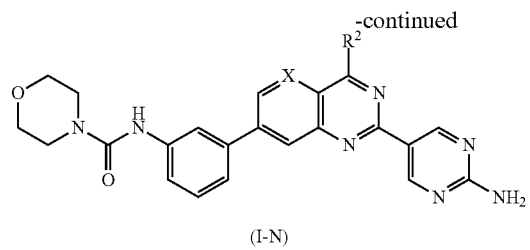

(I-N)

It will be recognized by those skilled in the art that various additional compounds of Formula (I) can be prepared by well-known methods, e.g., by derivatization of the amino moiety in compound 30a or compound 31a in Scheme IV. For example, Scheme IV provides the synthesis of compounds (I-K) to (I-N) via compound 7a (prepared as described in Scheme I) or compound 15a (prepared as described in Scheme II). Specifically, compound 7a or compound 15a is reacted with an amino(optionally-substituted phenyl)boronic acid or an amino(optionally-substituted phenyl)boronic pinacol ester to form the corresponding compounds 28a and 29a, respectively. In one embodiment, the compound 7a or 15a is reacted with $H_2N(R^8$-substituted phenyl)$B(OH)_2$ or its pinacol ester thereof. In another embodiment, the reaction is performed in the presence of a catalyst. In a further embodiment, the reaction is performed in the presence of a palladium catalyst such as $PdCl_2(PPh_3)_2$ in the presence of $Na_2CO_3$, in a solvent system such as toluene, ethanol and $H_2O$, or DMF and $H_2O$. In yet another embodiment, the reaction is performed at elevated temperatures such as about 90° C. to about 95° C. The 2-position of compound 28a or 29a is then substituted with an amino-protected pyrimidine group to provide compound 30a or 31a, respectively. In one embodiment compound 28a or 29a is reacted with (2-(tert-butoxycarbonyl)amino)pyrimidin-5-yl)boronic acid. In a further embodiment, the reaction is performed in the presence of a catalyst. In another embodiment, the reaction is performed in the presence of a palladium catalyst such as $Pd(PPh_3)_4$ or $PdCl_2$ $(PPh_3)_2$ in the presence of $K_3PO_4$ or $Cs_2CO_3$, in a solvent system such as DMF and $H_2O$, or toluene/ethanol/$H_2O$. In still a further embodiment, the reaction is performed at elevated temperatures such as about 90° C. to about 95° C. or about 90° C. to about 110° C.

Compound 30a or 31a may then be converted to compounds encompassed by formula (I). In one embodiment, compound 30a or 31a may then be converted to compound (I-K) by reaction with an optionally substituted carboxylic acid or an optionally substituted carboxylic acid chloride as the first step to form the corresponding amide intermediate compound. In one embodiment, compound 30a or 31a is reacted with an optionally substituted carboxylic acid such as ($C_1$ to $C_6$ alkyl)C(O)OH or ($C_1$ to $C_6$ hydroxyalkyl)C(O)OH. In another embodiment, the reaction is performed in DMF in the presence of HATU and TEA. In a further embodiment, the optionally substituted carboxylic acid is $HOC(CH_3)_2C(O)$OH. In another embodiment, compound 30a is reacted with an optionally substituted carboxylic acid chloride such as ($C_1$ to $C_6$ alkyl)C(O)Cl in the presence of pyridine or TEA. The BOC group of the pyrimidine substituent is then removed using reagents and conditions known to those skilled in the art. In one embodiment, the BOC-deprotection is performed using trifluoroacetic acid. In another embodiment, the deprotection is performed in DCM at about room temperature.

Compound 30a may also be converted to compound (I-L) via reaction with an optionally substituted sulfonyl chloride.

In one embodiment, the sulfonyl chloride is (optionally-substituted phenyl)$SO_2Cl$, (optionally-substituted heteroaryl) $SO_2Cl$, (optionally-substituted heterocycle)$SO_2Cl$, or (optionally-substituted alkyl)$SO_2Cl$. In one embodiment, the sulfonyl chloride is selected from among the following, wherein $R^6$-$R^8$, $Z^1$, $Z^2$, m, n, and q are defined above:

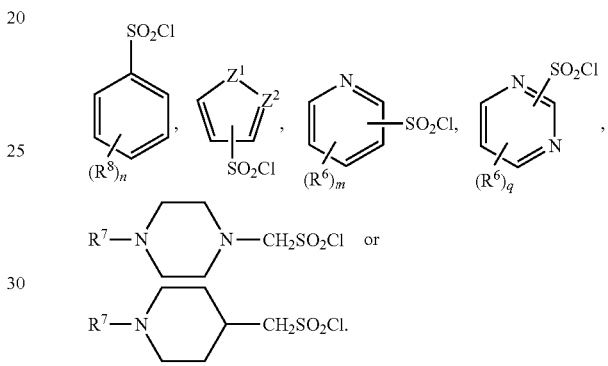

In another embodiment, the reaction with the optionally substituted sulfonyl chloride is carried out in pyridine. The BOC group of the pyrimidine substituent is then removed using reagents and conditions known to those skilled in the art. In one embodiment, the BOC group is removed using TFA. In another embodiment, the deprotection is performed in DCM at about room temperature.

Compound 30a or 31a may also be converted to compound (I-M) via reaction with chloroacetyl chloride to provide the following intermediate:

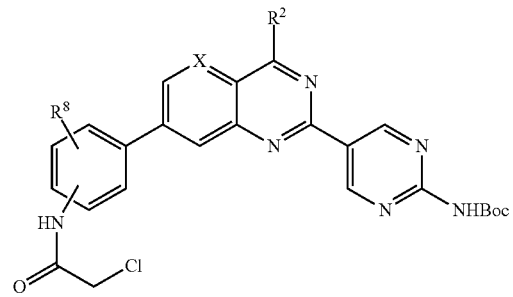

In one embodiment, the reaction is performed in DCM in the presences of TEA. In another embodiment, the reaction is performed at about 10° C. to about room temperature. This chloroacetyl intermediate is then reacted with an optionally substituted amine, for example in DMF in the presence of potassium carbonate at 0° C. to about room temperature. In one embodiment, the optionally substituted amine is a primary amine. In another embodiment, the optionally substituted amine is a secondary amine. In a further embodiment,

Scheme V

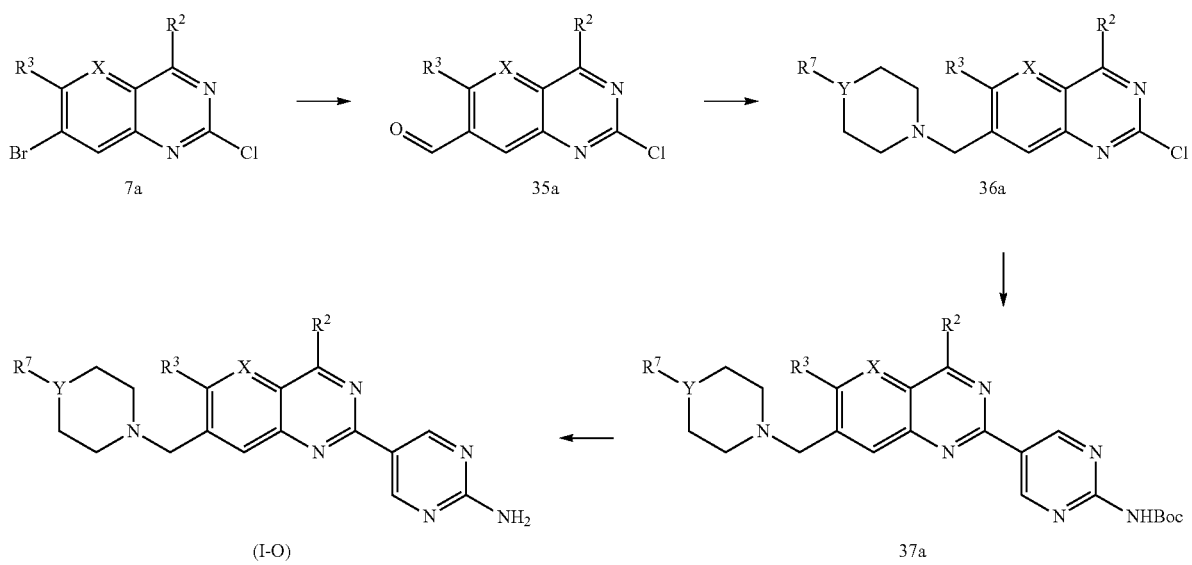

Scheme V provides the preparation of compounds of formula (I-O) from starting material compound 7a. In this Scheme compound 7a, which may be prepared as described in Schemes I-III, is reacted with an alkyl lithium reagent and DMF to provide aldehyde compound 35a. In one embodiment, the alkyl lithium reagent is n-butyl lithium. Desirably, the reaction is performed in an ether solvent such as THF at reduced temperatures such as about −78° C. to about room temperature. Compound 35a is then reacted with an optionally substituted amine in the presence of trimethyl orthoformate and a reducing agent such as sodium triacetoxyborohydride to provide compound 36a. In one embodiment, the optionally substituted amine is a primary amine. In another embodiment, the optionally substituted amine is a secondary amine 1n a further embodiment, the optionally substituted amine is an optionally substituted piperidine. In yet another embodiment, the optionally substituted amine is an optionally substituted piperazine. In still a further embodiment, the optionally substituted amine has the following structure, wherein Y and $R^7$ are defined above:

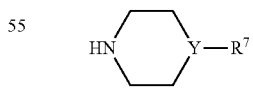

In one embodiment, Y is H,

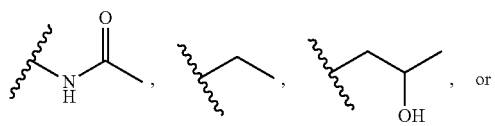

the pyrimidine substituent is then removed using reagents and conditions known to those skilled in the art. In one embodiment, the BOC group is removed using TFA. In another embodiment, the deprotection is performed in DCM at about room temperature.

As yet another example of the derivatization of the amino moiety in compound 30a or compound 31a in Scheme IV to prepare additional compounds of Formula (I), compound 30a or 31a may be converted to compound (I-N) by their initial reaction with 2,2,2,-trichloroethyl chloroformate to form the following intermediate:

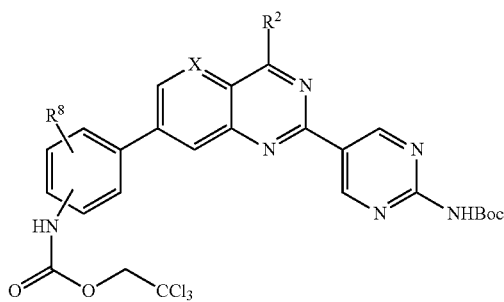

This O-(2,2,2,-trichloroethyl)carbamoyl intermediate is then reacted with an optionally substituted amine, for example in toluene in the presence of TEA at room temperature to about 110° C. In one embodiment, the optionally substituted amine is a primary amine. In another embodiment, the optionally substituted amine is a secondary amine 1n a further embodiment, the optionally substituted amine is an optionally substituted piperidine. In still another embodiment, the optionally substituted amine is morpholine. The BOC group of the pyrimidine substituent is then removed using reagents and conditions known to those skilled in the art. In one embodiment, the BOC group is removed using TFA. In another embodiment, the deprotection is performed in DCM at about room temperature.

41

-continued

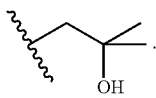

The reaction is performed in the presence of a reducing agent which may be selected by one skilled in the art and may include sodium triacetoxyborohydride, among others. In one embodiment, the reaction is performed in DCE as solvent at about room temperature.

The 2-position of compound 36a is then substituted with a tert-butoxycarbonyl)amino-pyrimidine group to provide compound 37a. In one embodiment, the 2-position of compound 36a is substituted using 2-((tert-butoxycarbonyl)amino)pyrimidin-5-yl)boronic acid. In another embodiment, the substitution is performed in the presence of a palladium catalyst such as $PdCl_2(PPh_3)_2$. In a further embodiment, the pyrimidine substitution is performed at elevated temperatures of about 90 to about 95° C. In still another embodiment, the pyrimidine substitution is performed using $Pd(PPh_3)_4$ in the presence of $K_3PO_4$. In yet a further embodiment, the pyrimidine substitution is performed using $PdCl_2(PPh_3)_2$ in the presence of $Cs_2CO_3$. In another embodiment, the reaction is carried out in a solvent system such as DMF and $H_2O$, or toluene/ethanol/$H_2O$. Finally compound 37a is N—BOC-deprotected to the corresponding amino compound. In one embodiment, the BOC-deprotection is performed using an acid such as TFA or HCl in DCM or 1,4-dioxane as solvent.

42 having the following structure, wherein Y and $R^7$ are defined above, to provide compound 36b.

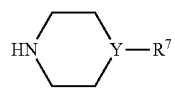

In one embodiment, Y is H,

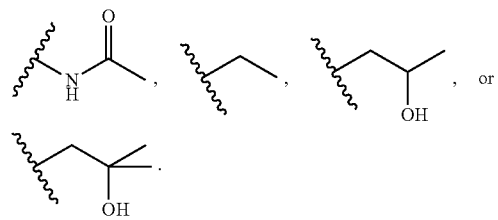

The reaction is performed in the presence of a reducing agent which may be selected by one skilled in the art and may include sodium triacetoxyborohydride, among others. The 2-position of compound 36b is then substituted with a tert-butoxycarbonyl)amino-pyrimidine group to provide compound 37b. In one embodiment, the 2-position of compound 36b is substituted using 2-((tert-butoxycarbonyl)amino)pyrimidin-5-yl)boronic acid. In another embodiment, the substi- Scheme Va

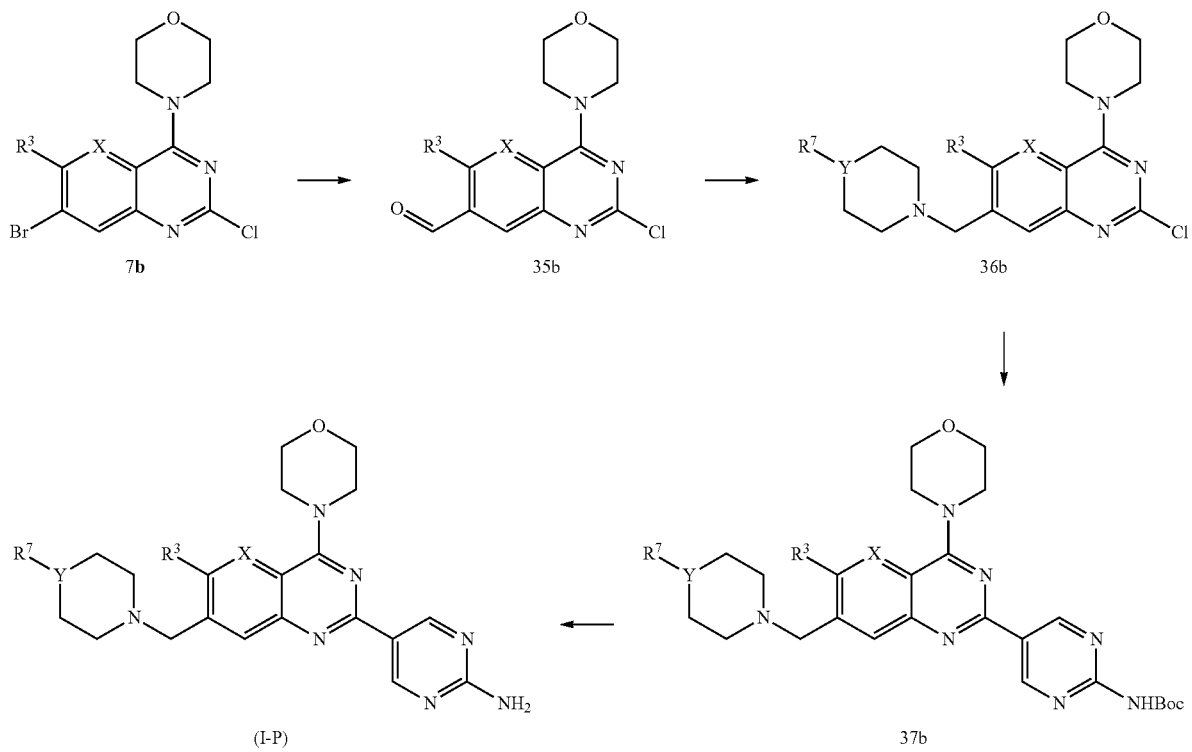

Scheme Va provides the preparation of compounds of formula (I-P) from starting material compound 7a. In this scheme, compounds 7a are prepared as described in Schemes I-III and V. Compound 35a is then reacted with an amine tution is performed in the presence of a palladium catalyst such as $PdCl_2(PPh_3)_2$. In a further embodiment, the pyrimidine substitution is performed at elevated temperatures of about 90 to about 95° C. In still another embodiment, the pyrimidine substitution is performed using Pd(PPh₃)₄ in the presence of K₃PO₄. In yet a further embodiment, the pyrimidine substitution is performed using PdCl₂(PPh₃)₂ in the presence of Cs₂CO₃. Finally compound 37b is N—BOC-deprotected to provide the corresponding amino compound. In one embodiment, the BOC-deprotection is performed using an acid such as TFA or HCl in DCM or 1,4-dioxane as solvent.

such as 1,8-bis(dimethylamino)naphthalene, at a reaction temperature of about 0° C. to room temperature. The terminal chloro group of compound 39a is then replaced with an acetate group to provide compound 40a. In one embodiment, the replacement is performed using mercuric acetate and acetic acid. In another embodiment, the replacement is performed using an excess of mercuric acetate. The nitrogen

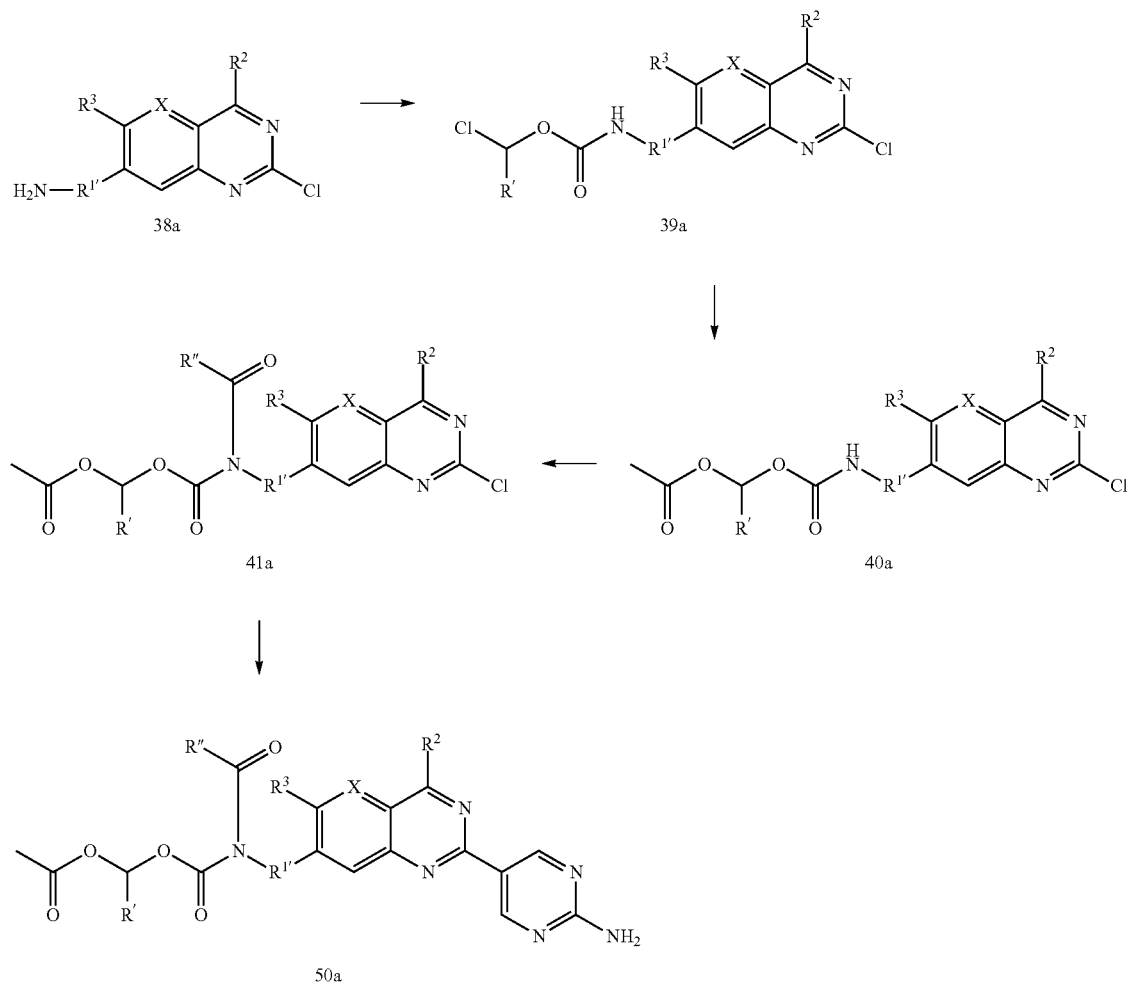

Scheme VI

Prodrugs of compounds of formula (I) may also be prepared as described above. For example, Scheme VI describes the preparation of prodrugs of formula (I). In one embodiment, prodrugs of formula (I) may be prepared using the procedures of Alexander, J. Med. Chem., 34:78-81 (1991) and International Patent Publication No. WO-2005/028473, which are hereby incorporated by reference. In another embodiment, prodrugs of formula (I), wherein R¹ is an amino substituted or amino terminated group, may be prepared. In this scheme, R¹ is R¹'—NH₂, where R¹' is a moiety derived from any of the R1 groups. Compound 38a is first reacted with a chloroalkyl chloroformate. In one embodiment, the chloroalkyl chloroformate is ClC(O)OCH(R')Cl, where R' is H or C₁ to C₆ alkyl, to provide compound 39a. In a further embodiment, R' is H or CH₃. In another embodiment, the chloroalkyl chloroformate is chloromethylchloroformate. The reaction is desirably performed in the presence of a strongly basic amine atom of the amide group of compound 40a is then substituted to form the corresponding acyl substituent in compound 41a. In one embodiment, the nitrogen atom of the amide group of compound 40a is substituted with a C(O)R" group, wherein R" is C₁ to C₆ alkyl or C₃ to C₈ cycloalkyl. In another embodiment, R" is CH₃ or cyclopropyl. In a further embodiment, compound 40a is reacted with acetic anhydride. Desirably, the reaction is performed in the presence of a base such as triethylamine and a catalyst such as N,N-dimethylpyridin-4-amine. The chloro group at the 2-position of compound 41a is then replaced with a 2-amino-pyrimidine group to provide compound 50a, i.e., a prodrug of a compound of formula (I). In one embodiment, compound 41a is reacted with 5-(4,4,5,5-tetramethyl-1,3,2-dioxaborolan-2-yl)pyrimidin-2-amine. In another embodiment, compound 41a is reacted with 5-(4,4,5,5-tetramethyl-1,3,2-dioxaborolan-2-yl)pyrimidin-2-amine in the presence of potassium phosphate tribasic and a catalyst such as Pd(PPh₃)₄ at a temperature of about 80° C.

Scheme VIa

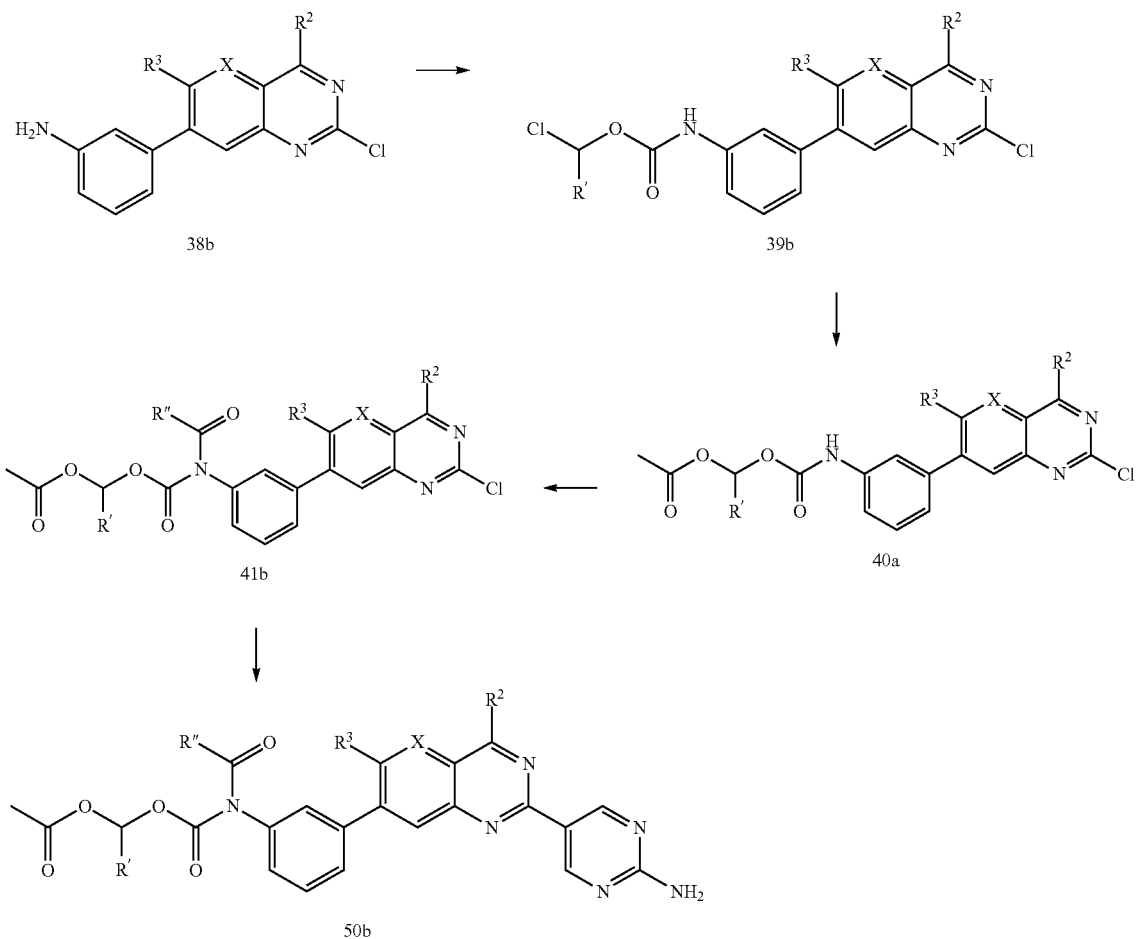

Scheme VIa also provides a route to prodrugs of formula (I) as described in Scheme VI where $R^1$ is an amino-substituted phenyl group. In one embodiment, $R^1$ is a 3-aniline group. In another embodiment, $R^1$ is a 4-aniline group. Specifically, Compound 38b is reacted with a chloroalkyl chloroformate in the presence of a strongly basic amine such as 1,8-bis(dimethylamino)naphthalene, at a reaction temperature of about 0° C. to room temperature. In one embodiment, the chloroalkyl chloroformate is ClC(O)OCH(R')Cl, where R' is H or $C_1$ to $C_6$ alkyl, to provide compound 39b. In a further embodiment, R' is H or $CH_3$. In another embodiment, the chloroalkyl chloroformate is chloromethylchloroformate. The terminal chloro group of compound 39b is then replaced with an acetate group to provide compound 40b. In one embodiment, the replacement is performed using mercuric acetate and acetic acid. The nitrogen atom of the amide group of compound 40b is then substituted to form the corresponding acyl substituent in compound 41b. In one embodiment, the nitrogen atom of the amide group of compound 40b is substituted with a C(O)R" group, wherein R" is $C_1$ to $C_6$ alkyl or $C_3$ to $C_8$ cycloalkyl, in the presence of a base such as triethylamine and a catalyst such as N,N-dimethylpyridin-4-amine. In another embodiment, R" is $CH_3$ or cyclopropyl. In a further embodiment, compound 40b is reacted with acetic anhydride. The chloro group at the 2-position of compound 41b is then replaced with a 2-amino-pyrimidine group to provide compound 50b, i.e., a prodrug of a compound of formula (I). In one embodiment, compound 41b is reacted with 5-(4,4,5,5-tetramethyl-1,3,2-dioxaborolan-2-yl)pyrimidin-2-amine 1n another embodiment, compound 41b is reacted with 5-(4,4,5,5-tetramethyl-1,3,2-dioxaborolan-2-yl)pyrimidin-2-amine in the presence of potassium phosphate tribasic and a catalyst such as $Pd(PPh_3)_4$.

Pharmaceutical compositions useful herein contain a compound of formula (I) in a pharmaceutically acceptable carrier optionally with other pharmaceutically inert or inactive ingredients. In another embodiment, a compound of formula (I) is present in a single composition. In a further embodiment, a compound of formula (I) is combined with one or more excipients and/or other therapeutic agents as described below.

The pharmaceutical compositions of the invention comprise an amount of a compound of formula (I) or a pharmaceutically acceptable salt, solvate, or prodrug thereof that is effective for regulating the PI3K/AKT/mTOR pathway in a subject. Specifically, the dosage of the compound of formula (I) to achieve a therapeutic effect will depend on the formulation, age, weight and sex of the patient and route of delivery. It is also contemplated that the treatment and dosage of the compound of formula (I) may be administered in unit dosage form and that one skilled in the art would adjust the unit dosage form accordingly to reflect the relative level of activity. The decision as to the particular dosage to be employed (and the number of times to be administered per day) is within the discretion of the ordinarily-skilled physician, and may be varied by titration of the dosage to the particular circumstances to produce the desired therapeutic effect. In one embodiment, the therapeutically effective amount is about 0.01 mg/kg to 10 mg/kg body weight. In another embodiment, the therapeutically effective amount is less than about 5 g/kg, about 500 mg/kg, about 400 mg/kg, about 300 mg/kg, about 200 mg/kg, about 100 mg/kg, about 50 mg/kg, about 25 mg/kg, about 10 mg/kg, about 1 mg/kg, about 0.5 mg/kg, about 0.25 mg/kg, about 0.1 mg/kg, about 100 µg/kg, about 75 µg/kg, about 50 µg/kg, about 25 µg/kg, about 10 µg/kg, or about 1 µg/kg. However, the therapeutically effective amount of the compound of formula (I) can be determined by the attending physician and depends on the condition treated, the compound administered, the route of delivery, the age, weight, severity of the patient's symptoms and response pattern of the patient.

The therapeutically effective amounts may be provided on regular schedule, i.e., daily, weekly, monthly, or yearly basis or on an irregular schedule with varying administration days, weeks, months, etc. Alternatively, the therapeutically effective amount to be administered may vary. In one embodiment, the therapeutically effective amount for the first dose is higher than the therapeutically effective amount for one or more of the subsequent doses. In another embodiment, the therapeutically effective amount for the first dose is lower than the therapeutically effective amount for one or more of the subsequent doses. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy will be determined according to the judgment of a health-care practitioner. The therapeutically effective amounts described herein refer to total amounts administered for a given time period; that is, if more than one compound of formula (I) or a pharmaceutically acceptable salt or prodrug thereof is administered, the therapeutically effective amounts correspond to the total amount administered.

The pharmaceutical compositions containing a compound of formula (I) may be formulated neat or with one or more pharmaceutical carriers for administration. The amount of the pharmaceutical carrier(s) is determined by the solubility and chemical nature of the compound of formula (I), chosen route of administration and standard pharmacological practice. The pharmaceutical carrier(s) may be solid or liquid and may incorporate both solid and liquid carriers. A variety of suitable liquid carriers are known and may be readily selected by one of skill in the art. Such carriers may include, e.g., dimethylsulfoxide (DMSO), saline, buffered saline, hydroxypropylcyclodextrin, and mixtures thereof. Similarly, a variety of solid carriers and excipients are known to those of skill in the art. The compounds of formula (I) may be administered by any route, taking into consideration the specific condition for which it has been selected. The compounds of formula (I) may, be delivered orally, by injection, inhalation (including orally, intranasally and intratracheally), ocularly, transdermally, intravascularly, subcutaneously, intramuscularly, sublingually, intracranially, epidurally, rectally, and vaginally, among others.

Although the compound of formula (I) may be administered alone, it may also be administered in the presence of one or more active pharmaceutical ingredient that are physiologically compatible. The carriers may be in dry or liquid form and must be pharmaceutically acceptable. Liquid pharmaceutical compositions are typically sterile solutions or suspensions. When liquid carriers are utilized for parenteral administration, they are desirably sterile liquids. Liquid carriers are typically utilized in preparing solutions, suspensions, emulsions, syrups and elixirs. In one embodiment, the compound of formula (I) is dissolved a liquid carrier. In another embodiment, the compound of formula (I) is suspended in a liquid carrier. One of skill in the art of formulations would be able to select a suitable liquid carrier, depending on the route of administration. The compound of formula (I) may alternatively be formulated in a solid carrier. In one embodiment, the composition may be compacted into a unit dose form, i.e., tablet or caplet. In another embodiment, the composition may be added to unit dose form, i.e., a capsule. In a further embodiment, the composition may be formulated for administration as a powder. The solid carrier may perform a variety of functions, i.e., may perform the functions of two or more of the excipients described below. For example, solid carrier may also act as a flavoring agent, lubricant, solubilizer, suspending agent, filler, glidant, compression aid, binder, disintegrant, or encapsulating material.

The composition may also be sub-divided to contain appropriate quantities of the compound of formula (I). For example, the unit dosage can be packaged compositions, e.g., packeted powders, vials, ampoules, prefilled syringes or sachets containing liquids.

Examples of excipients which may be combined with one or more compound of formula (I) include, without limitation, adjuvants, antioxidants, binders, buffers, coatings, coloring agents, compression aids, diluents, disintegrants, emulsifiers, emollients, encapsulating materials, fillers, flavoring agents, glidants, granulating agents, lubricants, metal chelators, osmo-regulators, pH adjustors, preservatives, solubilizers, sorbents, stabilizers, sweeteners, surfactants, suspending agents, syrups, thickening agents, or viscosity regulators. See, for example, the excipients described in the "Handbook of Pharmaceutical Excipients", $5^{th}$ Edition, Eds.: Rowe, Sheskey, and Owen, APhA Publications (Washington, D.C.), Dec. 14, 2005, which is incorporated herein by reference.

In one embodiment, the compositions may be utilized as inhalants. For this route of administration, compositions may be prepared as fluid unit doses using a compound of formula (I) and a vehicle for delivery by an atomizing spray pump or by dry powder for insufflation.

In another embodiment, the compositions may be utilized as aerosols, i.e., oral or intranasal. For this route of administration, the compositions are formulated for use in a pressurized aerosol container together with a gaseous or liquefied propellant, e.g., dichlorodifluoromethane, carbon dioxide, nitrogen, propane, and the like. Also provided is the delivery of a metered dose in one or more actuations.

In another embodiment, the compositions may be administered by a sustained delivery device. "Sustained delivery" as used herein refers to delivery of a compound of formula (I) which is delayed or otherwise controlled. Those of skill in the art know suitable sustained delivery devices. For use in such sustained delivery devices, the compound of formula (I) is formulated as described herein.

In addition to the components described above for use in the composition and the compound of formula (I), the compositions may contain one or more medications or therapeutic agents which are used to treat solid tumors. In one embodiment, the medication is a chemotherapeutic. Examples of chemotherapeutics include those recited in the "Physician's Desk Reference", $64^{th}$ Edition, Thomson Reuters, 2010, which is hereby incorporated by reference. Therapeutically effective amounts of the additional medication(s) or therapeutic agents are well known to those skilled in the art. However, it is well within the attending physician to determine the amount of other medication to be delivered.

The compounds of formula (I) and/or other medication(s) or therapeutic agent(s) may be administered in a single composition. However, the present invention is not so limited. In other embodiments, the compounds of formula (I) may be administered in one or more separate formulations from other compounds of formula (I), chemotherapeutic agents, or other agents as is desired.

Also provided herein are kits or packages of pharmaceutical formulations containing the compounds of formula (I) or compositions described herein. The kits may be organized to indicate a single formulation or combination of formulations to be taken at each desired time.

Suitably, the kit contains packaging or a container with the compound of formula (I) formulated for the desired delivery route. Suitably, the kit contains instructions on dosing and an insert regarding the active agent. Optionally, the kit may further contain instructions for monitoring circulating levels of product and materials for performing such assays including, e.g., reagents, well plates, containers, markers or labels, and the like. Such kits are readily packaged in a manner suitable for treatment of a desired indication. For example, the kit may also contain instructions for use of a spray pump or other delivery device. Other suitable components to include in such kits will be readily apparent to one of skill in the art, taking into consideration the desired indication and the delivery route.

The compounds of formula (I) or compositions described herein can be a single dose or for continuous or periodic discontinuous administration. For continuous administration, a package or kit can include the compound of formula (I) in each dosage unit (e.g., solution, lotion, tablet, pill, or other unit described above or utilized in drug delivery), and optionally instructions for administering the doses daily, weekly, or monthly, for a predetermined length of time or as prescribed. When the compound of formula (I) is to be delivered periodically in a discontinuous fashion, a package or kit can include placebos during periods when the compound of formula (I) is not delivered. When varying concentrations of a composition, of the components of the composition, or the relative ratios of the compounds of formula (I) or agents within a composition over time is desired, a package or kit may contain a sequence of dosage units which provide the desired variability.

A number of packages or kits are known in the art for dispensing pharmaceutical agents for periodic oral use. In one embodiment, the package has indicators for each period. In another embodiment, the package is a labeled blister package, dial dispenser package, or bottle.

The packaging means of a kit may itself be geared for administration, such as an inhalant, syringe, pipette, eye dropper, or other such apparatus, from which the formulation may be applied to an affected area of the body, such as the lungs, injected into a subject, or even applied to and mixed with the other components of the kit.

The compositions of these kits also may be provided in dried or lyophilized forms. When reagents or components are provided as a dried form, reconstitution generally is by the addition of a suitable solvent. It is envisioned that the solvent also may be provided in another package.

The kits of the present invention also will typically include a means for containing the vials in close confinement for commercial sale such as, e.g., injection or blow-molded plastic containers into which the desired vials are retained. Irrespective of the number or type of packages and as discussed above, the kits also may include, or be packaged with a separate instrument for assisting with the injection/administration or placement of the composition within the body of an animal. Such an instrument may be an inhalant, syringe, pipette, forcep, measuring spoon, eye dropper or any such medically approved delivery means.

In one embodiment, a kit is provided and contains a compound of formula (I). The compound of formula (I) may be in the presence or absence of one or more of the carriers or excipients described above. The kit may optionally contain instructions for administering the medication and the compound of formula (I) to a subject having a disease characterized by the dysregulation of the PI3K/AKT/mTOR pathway.

In a further embodiment, a kit is provided and contains a compound of formula (I) in a second dosage unit, and one or more of the carriers or excipients described above in a third dosage unit. The kit may optionally contain instructions for administering the medication and the compound of formula (I) to a subject having a disease characterized by the dysregulation of the PI3K/AKT/mTOR pathway.

The compounds described herein are useful in regulating conditions which are associated with the PI3K/AKT/mTOR pathway. In one embodiment, such a disease is associated with abnormal cellular proliferation. The term "abnormal cellular proliferation" refers to the uncontrolled growth of cells which are naturally present in a mammalian body. In one embodiment, a disease which is characterized by abnormal cellular proliferation is cancer, including, without limitation, cancer of the prostate, head, neck, eye, mouth, throat, esophagus, bronchus, larynx, pharynx, chest, bone, lung, colon, rectum, stomach, bladder, uterus, cervix, breast, ovaries, vagina, testicles, skin, thyroid, blood, lymph nodes, kidney, liver, intestines, pancreas, brain, central nervous system, adrenal gland, or skin or a leukemia. In one embodiment, the disease characterized by abnormal cellular proliferation is cancer of the prostate.

The compounds of formula (I) regulate activity of mTOR and of PI3K. In a further embodiment, the compounds of formula (I) regulate PI3K activity. The tested compounds of formula (I) have the ability to inhibit all four isoforms of PI3K ($\alpha$, $\beta$, $\delta$, $\gamma$) with at least two of the compounds showing selectivity for the $\alpha$ PI3K isoform. These compounds associated with selective activity for the $\alpha$ isoform may be particularly well suited for treatment of conditions associated with the PI3K isoform, including, e.g., breast and gastric cancers, colorectal tumors, glioblastomas, and prostate cancer, and lung cancers.

In another embodiment, the compounds of formula (I) regulate the pathway of the PI3K-$\beta$ isoform. In still a further embodiment, the compounds of formula (I) regulate the pathway of the PI3K-$\delta$ isoform. In yet another embodiment, the compounds of formula (I) regulate the pathway of the PI3K-$\gamma$ isoform.

The ability of compounds to inhibit the PI3K $\delta$ and PI3K $\gamma$ isoforms has been described with the ability to treat acute and chronic inflammatory disorders. See, e.g., R C Camps et al, Nat Rev Immunol., 2007, Mar. 7(3): 191-201 [PI3K delta and PI3K gamma: partners in crime in inflammation in rheumatoid arthritis and beyond?]. Other inflammatory disorders have been associated more specifically with the PI3K $\delta$ isoform, including neutrophil-associated inflammation. Models for testing the ability of compounds to reduce inflammation in inflammatory arthritis are known, e.g., as described by Camps et al, Nature Med., 2005, 11, 936-943. Camps et al (2005) also describes models useful in assessing the ability of compounds to reduce inflammation in peritonitis. Models for testing the ability of compounds to reduce inflammation and/or improve healing after myocardial infarction are described by Siragusa et al, Circ. Res. (2010), 106, 757-768. A model for testing the ability of compounds to prevent bleomycin-induced pulmonary fibrosis is described by Wei et al, Biochem Biophys Res Comm. 2010, 397: 311-317 and Brent et al, Toxicology, 2000, 147: 1-13.

The term "regulation" or variations thereof as used herein refers to the ability of a compound of formula (I) to inhibit one or more components of a biological pathway. In one embodiment, "regulation" refers to inhibition of mTOR activity. In another embodiment, "regulation" refers to inhibition of PI3K activity. In a further embodiment, regulation refers to dual inhibition of mTOR and PI3K activity.

The utility of the compounds of formula (I) can be illustrated, for example, by their activity in the in vitro tumor cell proliferation assay described below. The compounds of formula (I) exhibit an mTOR and PI3K inhibitory activity, and therefore can be utilized in order to inhibit abnormal cell growth in which mTOR plays a role. Thus, the compounds of formula (I) are effective in the treatment of disorders with which abnormal cell growth actions of mTOR and/or PI3K dysregulation are associated, such as cancer.

In one embodiment, methods for regulating the PI3K and/or mTOR pathways are provided and include administering a therapeutically effective amount of a compound of formula (I) to a patient in need thereof.

In another desirable embodiment, methods for treating a disease characterized by an abnormal cellular growth resulting from a dysregulated PI3K/mTOR pathway are provided and include administering of a therapeutically effective amount of a compound of formula (I) to a patient in need thereof.

In a further desirable embodiment, methods for treating a condition treatable by inhibiting the PI3K/AKT/mTOR pathway are provided and include administering a therapeutically effective amount of a compound of formula (I) to a patient in need thereof.

As described herein, a therapeutically effective amount of a compound when used for the treatment of cancer is an amount which may reduce the number of cancer cells, reduce tumor size, inhibit metastasis, inhibit tumor growth and/or ameliorate one or more of the symptoms of the cancer. For cancer therapy, efficacy can be measured for example, by assessing the time to disease progression and/or determining the response rate.

As described herein, a therapeutically effective amount of a compound when used for the treatment of an inflammatory disorder is an amount which may delay the onset of or reduce the severity or duration of an inflammatory response, or which mitigates one or more symptoms of an inflammatory response. For treatment of an inflammatory disorder, efficacy can be measured, for example, by a reduction in physiologic signs of inflammation (e.g., redness, swelling, heat, loss of function) or by measuring changes in the levels of cells (e.g., monocytes, macrophages and other mononuclear cells) or molecules (e.g., pro-inflammatory cytokines) associated with inflammation.

In one aspect, the compound is of formula (I) and $R^2$ is morpholine. In one embodiment, $R^2$ is morpholine substituted by one or more methyl. In a further embodiment, $R^2$ is:

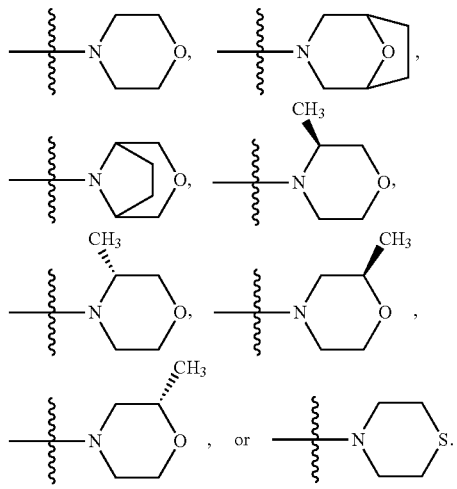

In yet another embodiment, $R^1$ is

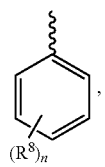

wherein n is 1 to 5; and each $R^8$ is independently selected from the group consisting of halogen, alkyl, aryl, alkylsulfonyl, alkylthio, alkylcarbonylamino, halogenated alkylcarbonylamino, alkylsulfonylamino, arylsulfonylamino, alkylaminocarbonyl, alkylaminocarbonylamino, alkylaminoalkylcarbonylamino, hydroxyalkylcarbonylamino, heteroarylcarbonylamino, heteroarylalkylcarbonylamino, heteroarylcarbonyl, heterocyclecarbonylamino, arylcarbonylamino, alkylsulfonylheterocyclecarbonyl, heterocyclecarbonyl, heterocycleaminocarbonyl, heteroarylalkylamino, hydroxyalkylamino, heterocyclealkylcarbonylamino, or cyanoalkylcarbonylamino. In still a further embodiment, the $R^1$ substituted phenyl is 3- or 4-substituted. In another embodiment, $R^8$ in the substituted phenyl is selected from the group consisting of F, $CH_3$, $C(CH_3)_2OH$, ⁓NHC(O)$CH_3$, ⁓NHC(O)$CH_2CH_3$, ⁓NHC(O)CH($CH_3$)$_2$, ⁓NHC(O)C($CH_3$)$_3$, ⁓NHC(O)$CH_2CH_2$CH($CH_3$)$_2$, ⁓N($CH_3$)C(O)$CH_3$, ⁓NHC(O)NH$CH_3$, ⁓NHSO$_2CH_3$, ⁓NHC(O)$CH_2$N($CH_3$)$_2$, ⁓NHC(O)C($CH_3$)$_2$OH, ⁓NHC(O)CH($CH_3$)OH, ⁓NHC(O)$CH_2$OH, ⁓NHC(O)CH($CH_3$)F, ⁓NHC(O)C($CH_3$)$_2$CN, ⁓NHC(O)$CH_2$CN, ⁓NHC(O)(cyclopropyl optionally substituted with CN), ⁓NHC(O)cyclobutyl, ⁓NHC(O)(cyclopentyl), ⁓NHC(O)(cyclohexyl optionally substituted with OH), ⁓NHC(O)(adamantanyl), ⁓NHC(O)(pyridinyl), ⁓NHC(O)(furanyl optionally substituted with $CH_3$), ⁓NHC(O)(tetrahydropyranyl), ⁓NHC(O)(pyrazinyl optionally substituted with $CH_3$), ⁓NHC(O)(piperazinyl optionally substituted with $CH_3$), ⁓C(O)(4-C(O)$CH_3$-piperazinyl), ⁓NHC(O)$CH_2$(piperazinyl optionally substituted with $CH_3$), ⁓C(O)(4-SO$_2CH_3$-piperazinyl), ⁓C(O)NHCH$_3$, ⁓C(O)NHCH$_2CH_2$N($CH_3$)$_2$, ⁓C(O)N($CH_3$)$_2$, ⁓C(O)NH(thiazolyl), ⁓C(O)NH(pyridinyl optionally substituted with halogen), ⁓C(O)(piperidinyl optionally substituted with CH₂CH₂OH, OH or CH₃), ⁓NHC(O)(pyridinyl optionally substituted with F or CF₃), ⁓NHC(O)(thiadiazolyl), ⁓C(O)NH(cyclopropyl), ⁓NHC(O)(phenyl optionally substituted with F), ⁓NHSO₂-(phenyl optionally substituted with F), ⁓NHC(O)CH₂(morpholinyl), ⁓NHC(O)CH₂(piperidinyl optionally substituted with OH), ⁓NHC(O)(morpholinyl), ⁓NHSO₂(cyclopropyl), piperidinyl optionally substituted with C(O)C(CH₃)₂CN, C(O)CH₂N(CH₃)₂, CH₂CH₂OH, or C(O)C(CH₃)₂OH, and ⁓SO₂CH₃. In a further embodiment, R¹ is optionally substituted heterocycle or optionally substituted heteroaryl. In still another embodiment, R¹ is substituted with 0 to 3 R⁴ groups independently selected from the group consisting of alkyl, SO₂(alkyl), alkylsulfonylamino, halogen, alkylcarbonylamino, alkylcarbonylheterocyclecarbonyl, heterocyclecarbonyl, and heteroarylaminocarbonyl. In yet a further embodiment, R¹ is

wherein Z¹ is O, S, or NR⁵; Z² is CR⁴ or N; R⁴H, alkyl, ⁓C(O)(optionally substituted heterocycle), or ⁓C(O)NH(optionally substituted heteroaryl); R⁵ is absent, H or alkyl; and p is 0 to 2. In another embodiment, R¹ is a substituted heteroaryl selected from the group consisting of pyrazole, thiophene and furan. In still a further embodiment, R¹ is a heteroaryl substituted with CH₃, ⁓C(O)(optionally substituted heterocycle), or ⁓C(O)NH(optionally substituted heteroaryl). In another embodiment, R¹ is

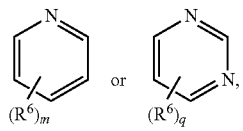

wherein m is 0 to 4; q is 0 to 3; and each R⁶ is, independently, selected from the group consisting of halogen, piperidinyl, 4-CH₃-piperidinyl, alkylsulfonyl, aminosulfonylalkyl, and alkylcarbonylamino. In a further embodiment, R¹ is selected from among pyridine and pyrimidine. In yet another embodiment, R¹ is substituted with F, Cl, 4-CH₃-piperidinyl, ⁓NHCOCH₃, ⁓NHC(O)(cyclopropyl), or ⁓SO₂CH₃. In still a further embodiment, R¹ is an optionally substituted benzo[b]oxazine. In yet another embodiment, R¹ is an optionally substituted benzo[b][1,3]oxazine or benzo[b][1,4]oxazine. In a further embodiment, R¹ is a benzo[b]oxazinone. In another embodiment, R¹ is an optionally substituted benzo[b][1,3]oxazin-2-one, benzo[b][1,3]oxazin-4-one, benzo[b][1,4]oxazin-2-one, or benzo[b][1,4]oxazin-3-one. In still a further embodiment, R¹ is optionally substituted alkyl. In yet another embodiment, R¹ is ⁓CH₂—(optionally substituted heterocycle). In another embodiment, R¹ is ⁓CH₂—(optionally substituted piperazinyl) or CH₂-(optionally substituted piperidinyl). In still another embodiment, R¹ is

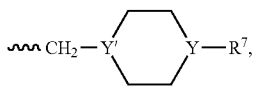

wherein Y and Y' are, independently, N or CH; and R⁷ is H, ⁓C(O)(hydroxyalkyl), ⁓C(O)(alkyl), or ⁓NHC(O)(alkyl). In a further embodiment, R⁷ is H, ⁓C(O)CH(CH₃)OH, ⁓C(O)C(CH₃)₂OH, ⁓C(O)CH₃, or ⁓NHC(O)CH₃.

In another aspect, the compound is of formula (II).

In a further aspect, the compound is of formula (III). In one embodiment, R¹ is optionally substituted heteroaryl. In another embodiment, R¹ is optionally substituted phenyl. In a further embodiment, R¹ is optionally substituted heterocycle. In still another embodiment, R¹ is optionally substituted alkyl.

In yet another aspect, the compound is of formula (IV).

In still a further aspect, the compound is of formula (I) and R¹ is optionally substituted aryl, optionally substituted heterocycle, optionally substituted heteroaryl, or optionally substituted alkyl;

R² is optionally substituted morpholine or thiomorpholine; R³ is H, F, Cl, CH₃, or CH₃O; X is CH or N; or a pharmaceutically acceptable salt, prodrug or solvate thereof.

In another aspect, the compound is of formula (I) and R¹ is optionally substituted aryl, optionally substituted heterocycle, optionally substituted heteroaryl, or optionally substituted alkyl; R² is optionally substituted morpholine or thiomorpholine; R³ is H, F, Cl, CH₃, or CH₃O; X is CH or N; or a pharmaceutically acceptable salt, prodrug or solvate thereof.

In a further aspect, any of the compounds described herein are a salt of an acid. In one embodiment, the acid salt is selected from among an acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, trifluoroacetic, and camphorsulfonic salt.

In still another aspect, a method for co-regulating PI3K and mTOR is provided and includes administering a therapeutically effective amount of one or more compound described herein to a patient in need thereof. In one embodiment, the co-regulation includes inhibiting the PI3K/AKT/mTOR pathway.

In yet a further aspect, a method for treating a condition treatable by inhibiting the PI3K/AKT/pathway is provided and includes administering a therapeutically effective amount of one or more compound described herein to a patient in need thereof.

In another aspect, a method for treating a disease characterized by an abnormal cellular proliferation resulting from a dysregulated PI3K/AKT/mTOR pathway is provided and includes administering a therapeutically effective amount of one or more compound described herein to a patient in need thereof. In one embodiment, the disease is cancer. In another embodiment, the disease is a cancer is of the prostate, head, neck, eye, mouth, throat, esophagus, bronchus, larynx, pharynx, chest, bone, lung, colon, rectum, stomach, bladder, uterus, cervix, breast, ovaries, vagina, testicles, skin, thyroid, blood, lymph nodes, kidney, liver, intestines, pancreas, brain, central nervous system, adrenal gland, or skin or a leukemia. In a further embodiment, the disease is a cancer of the prostate. In yet another embodiment, the patient has at least one solid tumor. In still another embodiment, the condition is an inflammatory disorder. In yet a further embodiment, the disease is an inflammatory disorder selected from among arthritis, pulmonary fibrosis, myocardial infarction, and peritonitis.

In still a further aspect, a pharmaceutical composition is provided and contains one or more of a compound described herein and a pharmaceutically acceptable carrier.

In another aspect, a kit is provided and includes one more compound described herein.

The following methods outline the synthesis of the compounds of Formula (I). The following examples are presented to illustrate certain embodiments of the present invention, but should not be construed as limiting the scope of this invention.

EXAMPLES

Unless otherwise stated, all the raw materials are purchased from Sigma-Aldrich, Fluorochem, Apollo Scientific and Matrix Labs and solvents from Ranchem, S.D. Fine and Merck labs. $^1$H NMR spectra were recorded on Varian 300 and 400 MHz instruments, using TMS as internal reference. The chemical shift values are quoted in δ (parts per million). Mass spectra of all the intermediates and final compounds were recorded using Agilent® LC/MSD/VL and API 2000 LC/MS instruments using a Synergi™ 2.5μ MAX-RP column (100 Å Mercury; 20×4.0 mm), a mobile phase of 0.1% formic acid in water and ACN, a flow rate of 2 mL/min, a temperature of 30° C., and a run time of 3.0 minutes. The purity of all the final compounds was detected using Agilent® HPLC 1100 & 1200 instruments and the following conditions:

Condition 1: Column: AG/C18/25-008 (Zorbax® Eclipse XDB-C18 column, 4.6×250 mm, 5μ), mobile phase: A=0.01% TFA in water; B=ACN/MeOH (1:1); gradient: 95:05; flow: 1.0 mL/min; temperature: 40° C.; run time: 12 min Condition 2: Column: AG/C18/15-001 (Zorbax® Eclipse XDB-C18 column, 4.6×150 mm, 5μ), mobile phase: A=0.01% TFA in water; B=ACN/MeOH (1:1), isocratic: 40:60, flow: 1.0 mL/min, temperature: 25° C., run time:12 min, Condition 3: Column: AG/C18/15-009 (Zorbax® Eclipse XDB-C18 column, 4.6×150 mm, 5μ), mobile phase: A=5 mM ammonium acetate in water; B: ACN, gradient: 95:05, flow: 1.0 mL/min, temperature: 40° C., run time: 12.0 min Preparation 1:
7-Bromo-2-chloro-4-morpholin-4-yl-quinazoline

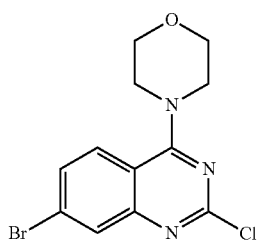 [SMILES: Clc1nc(N2CCOCC2)c2ccc(Br)cc2n1]

Step 1:
N-(3-Bromo-phenyl)-2-hydroxyimino-acetamide

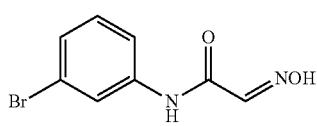

To a 3000 mL round bottom flask, 3-bromoaniline (50 g, 0.2907 mol), water (1500 mL), chloral hydrate (57.7 g, 0.3488 mol), hydroxylamine hydrochloride (64.6 g, 0.9302 mol) and sodium sulphate (250 g) were added. To this reaction mixture was slowly added concentrated HCl (76 mL). The reaction mixture was stirred at 90° C. for 2 hours. The white precipitate was formed and was collected by filtration. The white solid was dried to provide the title compound [60 g, 85%]. $^1$H NMR (300 MHz, DMSO-$d_6$): δ 12.28 (s, 1H), 10.38 (s, 1H), 8.03 (t, J=1.5 Hz, 1H), 7.62-7.65 (m, 2H), 7.29-7.31 (m, 2H). LC-MS (ESI): Calculated mass: 242.0; Observed mass [M+H]$^+$: 243.0 (RT: 0.17 min).

Step 2: 6-Bromo-1H-indole-2,3-dione

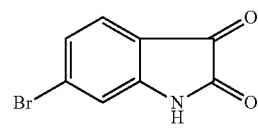

To concentrated sulfuric acid (275 mL) at 50° C. was added N-(3-bromo-phenyl)-2-hydroxyimino-acetamide (55 g, 0.2272 mol). The temperature was raised to 90° C. and maintained for 3 hours. The reaction mixture was added to ice cold water to provide a yellow precipitate. The precipitate was filtered and dried to provide the title compound as a yellow solid (50 g, 98%). This material was taken for next step without any further purification.

Step 3: 2-Amino-4-bromo-benzoic acid

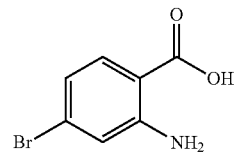

To a 500 mL round bottom flask, 6-bromo-1H-indole-2,3-dione (50 g, 0.2192 mol) and NaOH (20 g in 250 mL water) were added and the reaction vessel was cooled to 0° C. To this reaction mixture, 30% hydrogen peroxide (50 mL) was slowly added. The reaction mixture was stirred at 0° C. for 2 hours. The reaction mixture was then acidified with 2N HCl (pH 6) at 0° C. to afford the solid compound. The solid material was collected by filtration and dried to obtain the title compound (10 g, 21%). $^1$H NMR (300 MHz, DMSO-$d_6$): δ 7.59 (d, J=8.7 Hz, 1H), 6.96 (d, J=2.1 Hz, 1H), 6.65 (dd, f=8.7 Hz, f'=1.8 Hz, 1H) LC-MS (ESI): Calculated mass: 215.0; Observed mass [M+H]$^+$: 217.9. (RT: 0.83 min).

Step 4: 7-Bromo-1H-quinazoline-2,4-dione

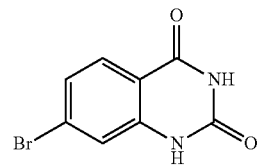

To a 250 mL round bottom flask, 2-amino-4-bromo-benzoic acid (10 g, 0.0463 mol) and urea (27.78 g, 0.4629 mol) were added. The reaction mixture was stirred at 195° C. for 3 hours. The reaction mixture was allowed to cool to 80° C. and water was added. The aqueous reaction mixture was stirred at 80° C. for 5-10 minutes then allowed to reach room temperature. The solid was filtered, dried and azeotroped with toluene to afford the title compound (10 g, 90%). This material was taken to the next step without further purification.

Step 5: 7-Bromo-2,4-dichloro-quinazoline

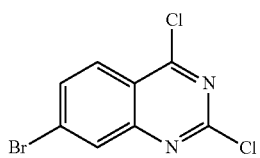 [SMILES: Clc1nc(Cl)c2ccc(Br)cc2n1]

To a 250 mL round bottom flask, 7-bromo-1H-quinazoline-2,4-dione (10 g 0.0413 mol) was added. To the same flask, POCl$_3$ (100 mL) and DIPEA (6.5 mL, 0.0413 mol) were added. The reaction mixture was maintained at 130° C. for 12 hours. The volatiles were evaporated and azeotroped with toluene to provide the crude residue. The crude residue was purified using column chromatography (60-120 silica gel, 10% ethyl acetate in hexane) to provide the title compound (7 g, 60%). $^1$H NMR (300 MHz, CDCl$_3$): δ 8.41 (s, 1H), 8.00-8.09 (m, 1H), 7.89-7.91 (m, 1H): LC-MS (ESI): Calculated mass: 275.9; Observed mass [M+H]$^+$: 276.8. (RT: 0.68 min).

Step 6: 7-Bromo-2-chloro-4-morpholin-4-yl-quinazoline

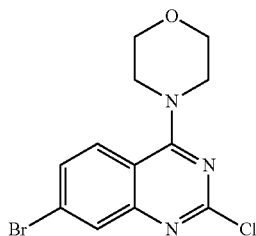 [SMILES: Clc1nc(N2CCOCC2)c2ccc(Br)cc2n1]

To an ice cold solution of 7-bromo-2,4-dichloro-quinazoline (7 g, 0.0255 mol) in dichloromethane (150 mL), morpholine (4.43 mL, 0.0509 mol) was slowly added and the reaction was continued at 0° C. for 30 minutes. The solvent was evaporated to dryness to provide the crude compound. The crude product was purified using column chromatography (60-120 silica gel, 30% ethyl acetate in hexane) to provide the title compound (7 g, 84%). $^1$H NMR (300 MHz, CDCl$_3$): δ 8.17 (d, J=7.5 Hz, 1H), 8.04 (d, J=7.5 Hz, 1H), 7.63 (d, J=8.1 Hz, 1H), 3.72-3.74 (m, 8H): LC-MS (ESI): Calculated mass: 327.0; Observed mass [M+H]$^+$: 329.8. (RT: 0.45 min).

Preparation 2: 7-Bromo-2-chloro-6-fluoro-4-morpholin-4-yl-quinazoline

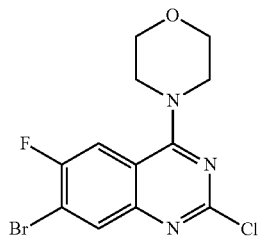 [SMILES: Fc1cc2c(N3CCOCC3)nc(Cl)nc2cc1Br]

Step 1: N-(3-Bromo-4-fluoro-phenyl)-2-hydroxy-imino-acetamide

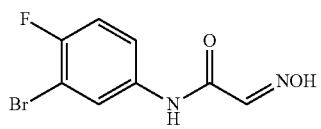

To a 500 mL round bottom flask, 3-bromo-4-fluoraniline (5 g, 0.0261 mol), water (300 mL), chloral hydrate (5.19 g, 0.0314 mol), hydroxylamine hydrochloride (5.8 g, 0.0835 mol) and sodium sulphate (25 g) were added. To this reaction mixture, concentrated HCl (7.5 mL) was slowly added. The reaction mixture was stirred at 90° C. for 3 hours. A precipitate formed and was collected by filtration. The solid was dried to provide the title compound (4.2 g, 61%). $^1$H NMR (300 MHz, DMSO-d$_6$): δ 12.28 (s, 1H), 10.51 (s, 1H), 8.12 (dd, J=2.4 Hz, J=2.7 Hz, 1H), 7.68 (m, 2H), 7.36 (t, J=8.7 Hz, 1H).

Step 2: 6-Bromo-5-fluoro-1H-indole-2,3-dione

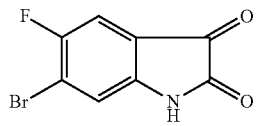

To concentrated sulfuric acid (40 mL) at 50° C. was added N-(3-bromo-4-fluoro-phenyl)-2-hydroxyimino-acetamide (4 g, 0.0152 mol). The temperature was raised to 90° C. and maintained for 3 hours. The reaction mixture was added to ice cold water to provide a precipitate. The precipitate was filtered and dried to provide the title compound (3.0 g, 80%).

Step 3: 2-Amino-4-bromo-5-fluoro-benzoic acid

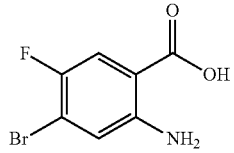

To a 100 mL round bottom flask, 6-bromo-5-fluoro-1H-indole-2,3-dione (3 g, 0.0121 mol) and 2N NaOH (15 mL) were added and cooled the reaction vessel to 0° C. To this reaction mixture, 30% hydrogen peroxide (10.5 mL) was slowly added. The reaction mixture was stirred at 0° C. for 3 hours. Subsequently, the reaction mixture was acidified with 2N HCl at 0° C. (pH 5) to afford solid compound. The solid material was collected by filtration and dried to obtain the title compound (700 mg, 25%). $^1$H NMR (300 MHz, DMSO-$d_6$): δ 7.52 (d, J=9.6 Hz, 1H), 7.09 (d, J=6.0 Hz, 1H).

Step 4: 7-Bromo-6-fluoro-1H-quinazoline-2,4-dione

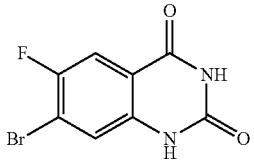

To a 100 mL round bottom flask, 2-amino-4-bromo-5-fluoro-benzoic acid (0.7 g, 2.99 mmol) and urea (1.07 g, 17.94 mmol) were added. The reaction mixture was stirred at 200° C. for 2 hours. The reaction mixture was allowed to cool to 100° C. and water was added. The aqueous reaction mixture was refluxed for 5-10 minutes and cooled to room temperature to provide the precipitate. The solid was filtered and dried to afford the title compound (400 mg, 51%). This material was taken to the next step without further purification.

Step 5: 7-Bromo-2,4-dichloro-6-fluoro-quinazoline

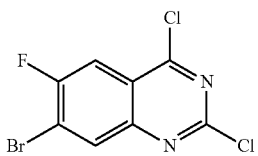 [SMILES: Fc1cc2c(Cl)nc(Cl)nc2cc1Br]

A 100 mL round bottom flask was charged with 7-bromo-6-fluoro-1H-quinazoline-2,4-dione (0.4 g 1.532 mmol). To the same flask, POCl$_3$ (15 mL) and DIPEA (0.714 mL, 0.005 mol) were added. The reaction mixture was maintained at 140° C. overnight. The volatiles were evaporated and azeotroped with toluene to provide the residue. The crude residue was purified using column chromatography (60-120 silica gel, 20% ethyl acetate in hexane) to provide the title compound (350 mg, 77%) This material was immediately taken to the next step.

Step 6: 7-Bromo-2-chloro-6-fluoro-4-morpholin-4-yl-quinazoline

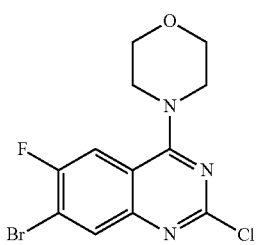 [SMILES: Fc1cc2c(N3CCOCC3)nc(Cl)nc2cc1Br]

To an ice cold solution of 7-bromo-2,4-dichloro-6-fluoro-quinazoline (0.35 g, 1.178 mmol) in dichloromethane (15 mL), morpholine (0.566 mL, 0.0066 mol) was slowly added and the reaction was continued for 20 minutes. The reaction mixture was diluted with dichloromethane and washed with water. The organic layer was dried over sodium sulphate and evaporated to provide crude solid. The crude material was purified using column chromatography (60-120 silica gel, 30% ethyl acetate in hexane) to provide the title compound (220 mg, 57%). $^1$H NMR (300 MHz, DMSO-$d_6$): δ 8.16 (d, J=6.6 Hz, 1H), 8.01 (d, J=9.6 Hz, 1H), 3.83-3.86 (m, 4H), 3.76-3.73 (m, 4H); LC-MS (ESI): Calculated mass: 345.0; Observed mass [M+H]$^+$: 347.8 (RT: 1.70 min).

Preparation 3: 4-(7-bromo-2-chloropyrido[3,2-d]pyrimidin-4-yl)morpholine

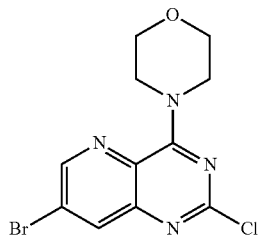 [SMILES: Clc1nc(N2CCOCC2)c2ncc(Br)cc2n1]

Step 1: 3-Amino-5-bromo-pyridine-2-carboxylic acid amide

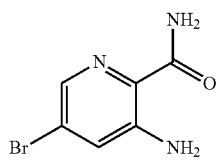

To a 100 mL round bottom flask, Raney Nickel (2.5 g) and ethanol (15 mL) were added. To the same flask, was added 5-bromo-3-nitropyridine-2-carbonitrile (5 g, 0.0219 mol). The reaction mass was stirred under hydrogen atmosphere for 14 hours at ambient temperature. The catalyst was removed by filtration. The clear filtrate was evaporated to provide the crude product. The crude material was subject to column chromatography (60-120 silica gel, 30% ethyl acetate in hexane) to provide title compound as a light yellow solid (1.1 g, 23%). $^1$H NMR (300 MHz, DMSO-$d_6$): δ 7.89 (br s, 1H), 7.79 (d, J=1.8 Hz, 1H), 7.40 (br s, 1H), 7.38 (d, J=1.8 Hz, 1H), 7.04 (br s, 2H).

Step 2: 3-Amino-5-bromo-pyridine-2-carboxylic acid

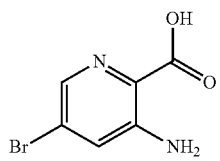

To a 100 mL round bottom flask, 3-amino-5-bromo-pyridine-2-carboxylic acid amide (1.05 g, 0.0049 mol) and aqueous sodium hydroxide solution (0.98 g in 10 mL water, 0.0245 mol) were added. The reaction mixture was stirred at reflux temperature for 5 hours. The volatiles were evaporated under reduced pressure to provide the residue. The residue was neutralized to pH 7.0, using 2N HCl at 0° C. to obtain the precipitate. The precipitate was filtered and dried to provide the title compound as light yellow solid (1 g, 95%). $^1$H NMR (300 MHz, DMSO-$d_6$): δ 7.65 (d, J=2.1 Hz, 1H), 7.20 (d, J=2.1 Hz, 1H), 7.01-7.16 (br s, 2H); LC-MS (ESI): Calculated mass: 216.0; Observed mass [M+H]$^+$: 217.0. (RT: 0.43 min).

Step 3: 7-Bromo-pyrido[2,3-d]pyrimidine-2,4-diol

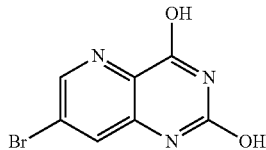 [SMILES: Oc1nc(O)c2ncc(Br)cc2n1]

To a 100 mL round bottom flask, 3-amino-5-bromo-pyridine-2-carboxylic acid (1 g, 0.0046 mol) and urea (27.8 g, 0.4629 mol) were added. The reaction mixture was stirred at 200° C. for 2.5 hours. The reaction mixture was cooled, water was added and the mixture was stirred to provide a precipitate. The precipitate was filtered and dried to provide the title compound (1 g, 91%). This material was taken to the next step without further purification.

Step 4: 7-Bromo-2,4-dichloro-pyrido[3,2-d]pyrimidine

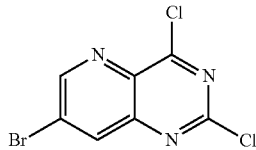

To a 100 mL round bottom flask, 7-bromo-pyrido[2,3-d]pyrimidine-2,4-diol (1 g, 0.0041 mol) was added. To the same flask, POCl$_3$ (10 mL) and DIPEA (1 mL) were added. The reaction mixture was stirred at 130° C. for 10 hours. The volatiles were evaporated and azeotroped with toluene (2×10 mL). The obtained residue was treated with ethyl acetate and filtered through a pad of Celite® reagent. The filtrate was evaporated to provide the crude title compound (0.9 g, 78% crude yield). This material was taken to the next step without further purification.

Step 5: 4-(7-bromo-2-chloropyrido[3,2-d]pyrimidin-4-yl)morpholine

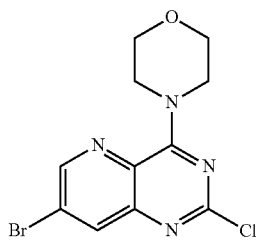 [SMILES: Clc1nc(N2CCOCC2)c2ncc(Br)cc2n1]

To an ice cold solution of crude 4-(7-bromo-2-chloropyrido[3,2-d]pyrimidin-4-yl)morpholine (2.85 g, 0.0102 mol) in dichloromethane (25 mL) at 0° C. was added morpholine (1.8 g, 0.0204 mol). The reaction was stirred at 0° C. for 30 minutes. The volatiles were evaporated and subjected to column chromatography (60-120 silica gel, 0-12% ethyl acetate in hexane) to provide the title compound as a light yellow solid (0.35 g, 26%). $^1$H NMR (300 MHz, DMSO-$d_6$): δ 8.68 (d, J=2.7 Hz, 1H), 8.19 (d, J=2.4 Hz, 1H), 3.86-3.89 (m, 8H): LC-MS (ESI): Calculated mass: 328.0; Observed mass [M+H]$^+$: 330.8. (RT: 1.5 min).

Example 1

5-(7-(3-(Methylsulfonyl)phenyl)-4-morpholinoquinazolin-2-yl)pyrimidin-2-amine (Scheme I)

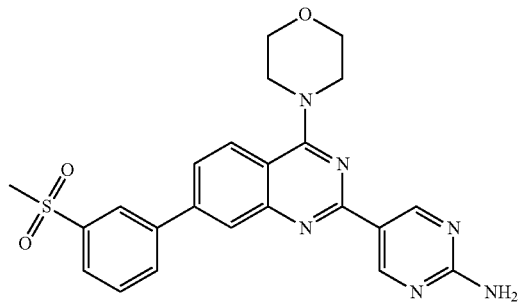 [SMILES: CS(=O)(=O)c1cccc(-c2ccc3c(N4CCOCC4)nc(-c4cnc(N)nc4)nc3c2)c1]

Step 1: 4-(2-Chloro-7-(3-(methylsulfonyl)phenyl)quinazolin-4-yl)morpholine

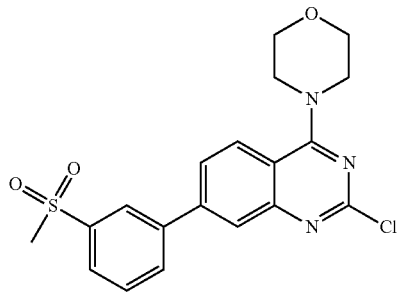 [SMILES: CS(=O)(=O)c1cccc(-c2ccc3c(N4CCOCC4)nc(Cl)nc3c2)c1]

To a 50 mL round bottom flask, 4-(7-bromo-2-chloroquinazolin-4-yl)morpholine (0.25 g, 0.0007 mol—Preparation 1), 3-methylsulfonylphenylboronic acid (0.137 g, 0.0006 mol), sodium carbonate (0.121 g, 0.00105 mol), DMF (8 mL) and water (2 mL) were added. The reaction vessel was degassed with N$_2$ for 5-10 minutes. To the same reaction mixture, Pd(PPh$_3$)$_2$Cl$_2$ (0.027 g, 0.000035 mol) was added and the mixture again degassed with N$_2$ for 5-10 minutes. The reaction mixture was stirred at 95° C. for 2 hours. The reaction mixture was cooled and water was added. The crude product was extracted with ethyl acetate. The organic layer was washed with water, brine and dried over sodium sulfate. The solvent was removed under the reduced pressure to afford the crude product. The crude product was purified by column chromatography (60-120 silica gel, 50-100% ethyl acetate in n-hexane) to provide the desired product (0.2 g, 65%). $^1$H NMR (300 MHz, CDCl$_3$): δ 8.25 (br s, 1H), 8.06-7.94 (m, 3H), 7.75-7.46 (m, 3H), 3.93 (br s, 4H), 3.91 (br s, 4H), 3.12 (s, 3H): LC-MS (ESI): Calculated mass: 403.0; Observed mass [M+H]+: 404.0 (RT=1.30 min).

Step 2: 5-(7-(3-(Methylsulfonyl)phenyl)-4-morpholinoquinazolin-2-yl)pyrimidin-2-amine

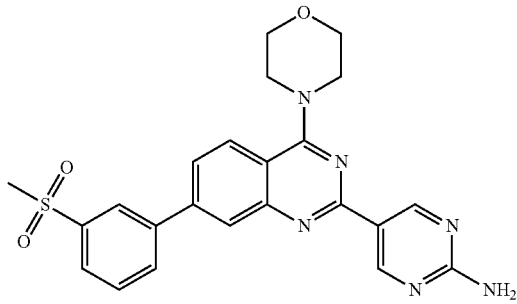 [SMILES: CS(=O)(=O)c1cccc(-c2ccc3c(N4CCOCC4)nc(-c4cnc(N)nc4)nc3c2)c1]

To a 50 mL round bottom flask, 4-(2-chloro-6-fluoro-7-(3-(methylsulfonyl)phenyl)quinazolin-4-yl)morpholine (0.06 g, 0.00015 mol), (2-aminopyrimidin-5-yl)boronic acid (0.03 g, 0.00023 mol), cesium carbonate (0.097 g, 0.0003 mol), DMF (5 mL) and water (2 mL) were added. The reaction vessel was degassed with $N_2$ for 5-10 minutes. To the same reaction mixture, Pd(PPh$_3$)$_2$Cl$_2$ (0.005 g, 0.0000075 mol) was added and again degassed with $N_2$ for 5-10 minutes. The reaction mixture was stirred at 95° C. for 2 hours. The reaction mixture was cooled and water was added. The crude product was extracted with ethyl acetate. The organic layer was washed with water, brine and dried over sodium sulfate. The solvent was removed under the reduced pressure to afford the crude product. The crude product was purified by column chromatography (60-120 silica gel, 0-5% methanol in chloroform) to provide the desired product (0.05 g, 7%). $^1$H NMR (400 MHz, DMSO-d$_6$): δ 9.22 (s, 2H), 8.36 (s, 1H), 8.25 (s, 1H), 8.22 (d, J=2.0 Hz, 1H), 8.15 (d, J=8.8 Hz, 1H), 8.01 (d, J=8.0 Hz, 1H), 7.87-7.80 (m, 2H), 7.21 (s, 2H), 3.85 (s, 8H); $^1$H NMR (400 MHz, DMSO-d$_6$+D$_2$O): δ 9.12 (s, 2H), 8.20 (s, 1H), 8.14-8.06 (m, 3H), 7.95 (d, J=7.6 Hz, 1H), 7.79 (t, J=7.2 Hz, 2H), 3.83-3.77 (m, 8H), 3.21 (s, 3H). LC-MS (ESI): Calculated mass: 462.1; Observed mass [M+H]+: 463.1 (RT=0.23 min).

Example 2

5-(6-Fluoro-7-(3-(methylsulfonyl)phenyl)-4-morpholinoquinazolin-2-yl)pyrimidin-2-amine (Scheme 1)

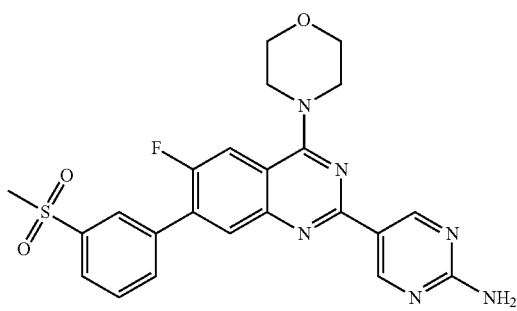 [SMILES: CS(=O)(=O)c1cccc(-c2cc3nc(-c4cnc(N)nc4)nc(N4CCOCC4)c3cc2F)c1]

Step 1: 4-(2-chloro-6-fluoro-7-(3-(methylsulfonyl)-phenyl)quinazolin-4-yl)-morpholine

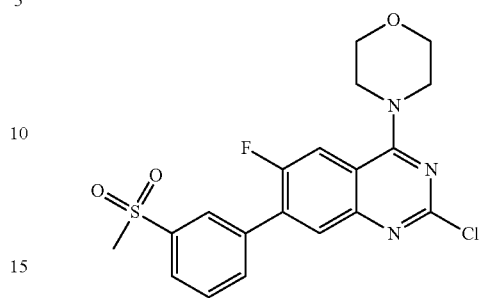

To a 50 mL round bottom flask, 4-(7-bromo-2-chloro-6-fluoroquinazolin-4-yl)morpholine (0.15 g, 0.0004 mol—Preparation 2), 3-methylsulfonylphenylboronic acid (0.078 g, 0.00039 mol), sodium carbonate (0.114 g, 0.0011 mol), DMF (6 mL) and water (2 mL) were added. The reaction vessel was degassed with $N_2$ for 5-10 minutes. To the same reaction mixture, Pd(PPh$_3$)$_2$Cl$_2$ (0.015 g, 0.000022 mol) was added and again degassed with $N_2$ for 5-10 minutes. The reaction mixture was stirred at 90° C. for 3 hours. The reaction mixture was cooled and diluted with ethyl acetate. The organic layer was washed with water, brine and dried over sodium sulfate. The solvent was removed under the reduced pressure to afford the crude product. The crude product was purified by column chromatography (60-120 silica gel, 50% ethyl acetate in n-hexane) to yield the desired product (0.12 g, 66%). $^1$H NMR (300 MHz, CDCl$_3$): δ 8.23 (d, J=1.8 Hz, 1H), 8.06-7.90 (m, 3H), 7.68 (t, J=7.8 Hz, 1H), 7.64 (d, J=11.1 Hz, 1H), 3.92 (s, 8H), 3.12 (s, 3H): LC-MS (ESI): Calculated mass: 421.0; Observed mass [M+H]+: 422.1 (RT=1.45 min).

Step 2: 5-(6-Fluoro-7-(3-(methylsulfonyl)phenyl)-4-morpholinoquinazolin-2-yl)pyrimidin-2-amine

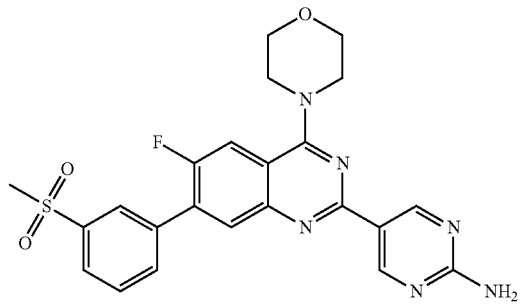 [SMILES: CS(=O)(=O)c1cccc(-c2cc3nc(-c4cnc(N)nc4)nc(N4CCOCC4)c3cc2F)c1]

To a 50 mL round bottom flask, 4-(2-chloro-6-fluoro-7-(3-(methylsulfonyl)phenyl)quinazolin-4-yl)morpholine (0.1 g, 0.0002 mol), (2-((tert-butoxycarbonyl)amino)pyrimidin-5-yl)boronic acid (0.085 g, 0.0003 mol), cesium carbonate (0.192 g, 0.0005 mol), toluene (5 mL), ethanol (5 mL) and water (2 mL) were added. The reaction vessel was degassed with $N_2$ for 5-10 minutes. To the same reaction mixture, Pd(PPh$_3$)$_2$Cl$_2$ (0.008 g, 0.000012 mol) was added and again degassed with $N_2$ for 5-10 minutes. The reaction mixture was stirred at 75° C. for 3 hours. The reaction mixture was cooled and diluted with chloroform. The organic layer was washed with water, brine and dried over sodium sulfate. The solvent was removed under the reduced pressure to afford the crude product. The crude product was purified by column chromatography (60-120 silica gel, 50% ethyl acetate in n-hexane) to yield tert-butyl (5-(6-fluoro-7-(3-(methylsulfonyl)phenyl)-4-morpholinoquinazolin-2-yl)pyrimidin-2-yl)carbamate [0.06 g, 43%]. LC-MS (ESI): Calculated mass: 580.1; Observed mass [M+H]+: 581.3 (RT=1.52 min).

To a 25 mL flask, tert-butyl (5-(6-fluoro-7-(3-(methylsulfonyl)phenyl)-4-morpholinoquinazolin-2-yl)pyrimidin-2-yl)carbamate (0.06 g, 0.0001 mol) and 1,4-dioxane (4 mL) were added. The reaction mixture was cooled to 0° C. To the flask, 4 N HCl in 1,4-dioxane (6 mL) was added. The reaction mixture was stirred at room temperature for 12 hours. The volatiles were evaporated under reduced pressure to provide the crude product. The crude product was purified by preparative HPLC (10 mM ammonium acetate in water and acetonitrile) to provide the title compound (0.01 g, 7%). $^1$H NMR (400 MHz, DMSO-$d_6$): δ 9.21 (s, 2H), 8.23 (s, 1H), 8.13-8.07 (m, 3H), 8.02 (d, J=11.2 Hz, 1H), 7.88 (t, J=8.0 Hz, 1H), 7.42 (br s, 2H), 3.96 (br s, 4H), 3.84 (br s, 4H), 3.43 (s, 3H): LC-MS (ESI): Calculated mass: 480.1; Observed mass [M+H]+: 481.1 (RT=0.30 min).

Example 3

N-(3-(2-(2-Aminopyrimidin-5-yl)-4-morpholinopyrido[3,2-d]pyrimidin-7-yl)-phenyl)acetamide
(Scheme II)

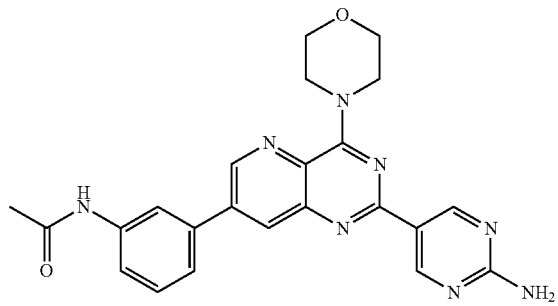 [SMILES: CC(=O)Nc1cccc(-c2cnc3c(N4CCOCC4)nc(-c4cnc(N)nc4)nc3c2)c1]

Step 1: N-(3-(2-Chloro-4-morpholinopyrido[3,2-d]pyrimidin-7-yl)phenyl)acetamide

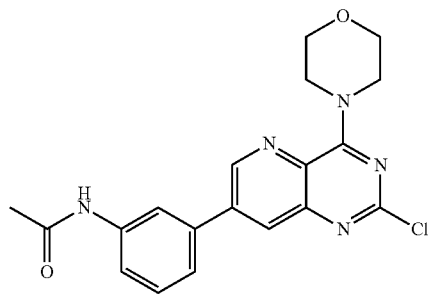 [SMILES: CC(=O)Nc1cccc(-c2cnc3c(N4CCOCC4)nc(Cl)nc3c2)c1]

To a 100 mL round bottom flask, 4-(7-bromo-2-chloropyrido[3,2-d]pyrimidin-4-yl)morpholine (1.5 g, 0.0045 mol—Preparation 3), 3-acetamidophenylboronic acid (0.769 g, 0.0043 mol), sodium carbonate (1.2 g, 0.0113 mol), toluene (30 mL), ethanol (30 mL) and water (10 mL) were added. The reaction mixture was degassed with $N_2$ for 5-10 minutes. To the same reaction mixture, Pd(PPh$_3$)$_2$Cl$_2$ (0.159 g, 0.00022 mol) was added and again degassed with $N_2$ for 5-10 minutes. The reaction mixture was stirred at 95° C. for 2 hours. The reaction mixture was cooled to room temperature and diluted with ethyl acetate. The organic layer was washed with water, brine, dried over anhydrous sodium sulfate and evaporated under reduced pressure to afford the crude product. The crude product was purified by column chromatography (60-120 silica gel, 60% ethyl acetate in hexane) to provide the title compound (1.3 g, 76%). $^1$H NMR (300 MHz, DMSO-$d_6$): δ 10.15 (s, 1H), 9.05 (d, J=2.4 Hz, 1H), 8.18 (d, J=2.4 Hz, 1H), 8.11 (s, 1H), 7.46-7.66 (m, 3H), 4.52 (br s, 4H), 3.81 (t, J=5.1 Hz, 4H), 2.09 (s, 3H): LC-MS (ESI): Calculated mass: 383.1; Observed mass [M+H]+: 383.8. (RT=1.31 min).

Step 2: tert-Butyl (5-(7-(3-acetamidophenyl)-4-morpholinopyrido[3,2-d]pyrimidin-2-yl)pyrimidin-2-yl)carbamate

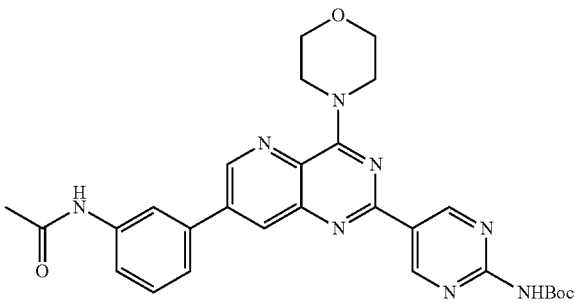 [SMILES: CC(=O)Nc1cccc(-c2cnc3c(N4CCOCC4)nc(-c4cnc(NC(=O)OC(C)(C)C)nc4)nc3c2)c1]

To a 50 mL sealed tube, N-(3-(2-chloro-4-morpholinopyrido[3,2-d]pyrimidin-7-yl)-phenyl)acetamide (1.30 g, 0.0033 mol), (2-((tert-butoxycarbonyl)amino)pyrimidin-5-yl)boronic acid (1.21 g, 0.0050 mol), potassium phosphate (K$_3$PO$_4$) (1.43 g, 0.0067 mol), DMF (35 mL) and water (9 mL) were added. The reaction mixture was degassed with $N_2$ for 5-10 minutes. To the same reaction mixture, Pd(PPh$_3$)$_4$ (0.274 g, 0.00023 mol) was added and again degassed with $N_2$ for 5-10 minutes. The reaction mixture was stirred at 105° C. for 2 hours. The reaction mass was cooled and added to ice cold water. The precipitate was obtained and was collected by filtration. The solid was dissolved in chloroform, dried over anhydrous sodium sulfate and evaporated under reduced pressure to provide the crude product. The crude product was purified by column chromatography (60-120 silica gel, 3% methanol in chloroform) to provide the title compound (1.6 g, 87.4%). NMR (300 MHz, DMSO-$d_6$): δ 10.42 (s, 1H), 10.15 (s, 1H), 9.47 (s, 1H), 9.05 (d, J=2.4 Hz, 1H), 8.29 (d, J=2.1 Hz, 1H), 8.17 (s, 1H), 7.63 (t, J=8.4 Hz, 2H), 7.49 (t, J=7.8 Hz, 1H), 4.56 (br s, 4H), 3.85 (t, J=3.9 Hz, 4H), 2.10 (s, 3H), 1.49 (s, 9H): LC-MS (ESI): Calculated mass: 542.2; Observed mass [M+H]+: 542.9. (RT=1.39 min).

Step 3: N-(3-(2-(2-Aminopyrimidin-5-yl)-4-morpholinopyrido[3,2-d]pyrimidin-7-yl)phenyl)acetamide

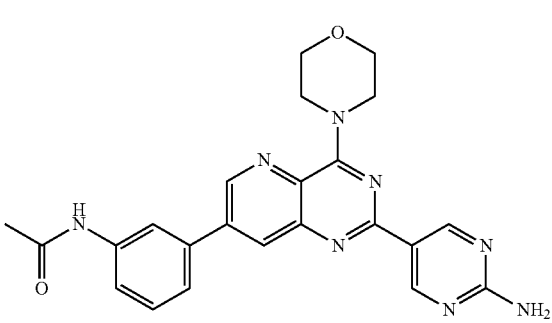 [SMILES: CC(=O)Nc1cccc(-c2cnc3c(N4CCOCC4)nc(-c4cnc(N)nc4)nc3c2)c1]

To a 250 mL round bottom flask, tert-butyl (5-(7-(3-aminophenyl)-4-morpholinopyrido[3,2-d]pyrimidin-2-yl)pyrimidin-2-yl)carbamate (1.6 g, 0.0029 mol) and DCM (160 mL) were added and the flask cooled to 0° C. To the reaction flask, trifluoroacetic acid (16 mL, 10% volume) was added at 0° C. and the reaction mixture was stirred at room temperature for 3 hours. The volatiles were evaporated under reduced pressure and methanol was added to provide a solid. The solid was collected by filtration. The solid was suspended into water and basified with saturated sodium bicarbonate solution. The reaction mixture was extracted with chloroform (3×200 mL). The organic layer was washed with water, brine, dried over anhydrous sodium sulfate and concentrated under reduced pressure to provide the crude product. The crude product was subjected to flash column chromatography using 4% methanol in chloroform. The obtained solid was washed with methanol and diethyl ether, filtered and dried under vacuum to afford the title compound as off-white solid (0.900 g, 69%). $^1$H NMR (400 MHz, DMSO-$d_6$): δ 10.18 (s, 1H), 9.22 (s, 2H), 9.02 (d, J=2.0 Hz, 1H), 8.26 (d, J=2.0 Hz, 1H), 8.19 (s, 1H), 7.67 (d, J=8.0 Hz, 1H), 7.63 (d, J=8.0 Hz, 1H), 7.54 (t, J=8.0 Hz, 1H), 7.24 (s, 2H), 4.55 (br s, 4H), 3.87 (t, J=4.4 Hz, 4H), 2.12 (s, 3H). LC-MS (ESI): Calculated mass: 442.2; Observed mass [M+H]$^+$: 443.1. (RT=0.18 min).

Example 4

4-(2-(2-Aminopyrimidin-5-yl)-4-morpholinopyrido [3,2-d]pyrimidin-7-yl)-N-cyclopropylbenzamide (Scheme III)

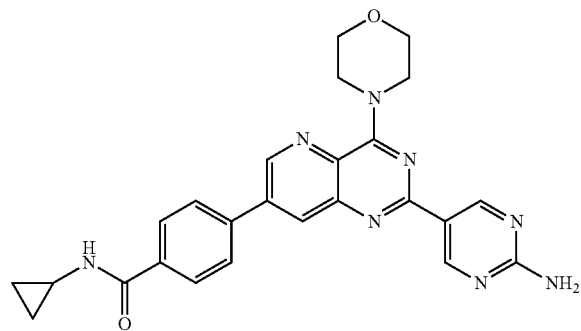 [SMILES: Nc1ncc(-c2nc(N3CCOCC3)c3ncc(-c4ccc(C(=O)NC5CC5)cc4)cc3n2)cn1]

Step 1: 4-(2-Chloro-4-morpholinopyrido[3,2-d]pyrimidin-7-yl)benzoic acid

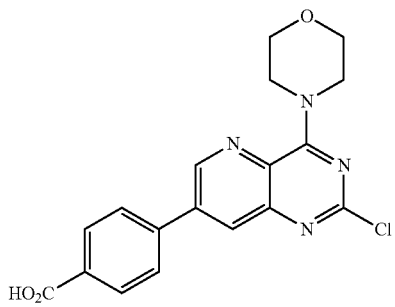 [SMILES: O=C(O)c1ccc(-c2cnc3c(N4CCOCC4)nc(Cl)nc3c2)cc1]

To a 50 mL round bottom flask, 4-(7-bromo-2-chloropyrido[3,2-d]pyrimidin-4-yl)morpholine (1.0 g, 0.0030 mol— Preparation 3), 4-carboxyphenylboronic acid (0.5 g, 0.0030 mol), sodium carbonate (0.64 g, 0.0060 mol) dioxane (60 mL), ethanol (10 mL) and water (10 mL) were added. The reaction mixture was degassed with N$_2$ for 5-10 minutes. To the same reaction mixture, Pd(PPh$_3$)$_2$Cl$_2$ (0.106 g, 0.00015 mol) was added and degassed with N$_2$ for 5-10 minutes. The reaction mixture was stirred at 90° C. for 2 hours. The volatiles were evaporated to provide a residue. The residue was stirred with water and acidified with 2 N hydrochloric acid to pH 5-6 to provide a precipitate. The precipitate was collected by filtration and dried under reduced pressure to afford the title compound (0.8 g, 71%). The compound was used in the next step without further purification. $^1$H NMR (300 MHz, DMSO-$d_6$): δ 9.18 (d, J=2.4 Hz, 1H), 8.40 (d, J=2.4 Hz, 1H), 8.10-8.03 (m, 4H), 4.58 (br s, 4H), 3.79 (t, J=4.5 Hz, 4H): LC-MS (ESI): Calculated mass: 370.0; Observed mass [M+H]$^+$: 371.1 (RT=1.37 min).

Step 2: 4-(2-Chloro-4-morpholinopyrido[3,2-d]pyrimidin-7-yl)-N-cyclopropylbenzamide

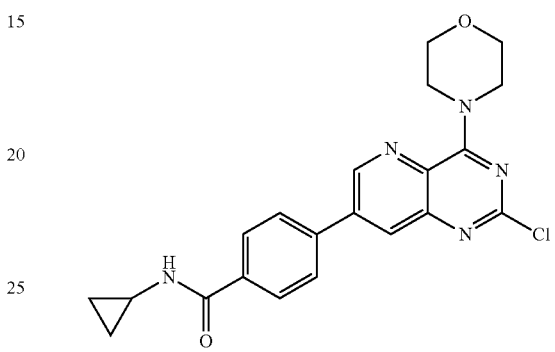

To a 50 mL round bottom flask, 4-(2-chloro-4-morpholinopyrido[3,2-d]pyrimidin-7-yl)benzoic acid (0.2 g, 0.00054 mol), cyclopropyl amine (0.046 g, 0.00081 mol) and DMF (10 mL) were added. To the same flask, HATU (0.3 g, 0.00081 mol) and TEA (0.23 mL, 0.0018 mol) were added. The reaction mixture was stirred at room temperature for 12 hours. The reaction mixture was diluted with 10% methanol in chloroform and washed with water. The organic layer was washed with brine, dried over anhydrous sodium sulfate and evaporated under reduced pressure to provide the crude product. The crude product was purified by flash column chromatography (0-1% methanol in chloroform) to provide the title compound (0.15 g, 68%). $^1$H NMR (300 MHz, DMSO-$d_6$): δ 9.21 (d, J=2.4 Hz, 1H), 8.59 (d, J=4.2 Hz, 1H), 8.42 (d, J=2.4 Hz, 1H), 7.94-8.06 (m, 4H), 4.52 (br s, 4H), 3.80 (t, J=4.8 Hz, 4H), 2.88-2.90 (m, 1H), 0.60-0.62 (m, 2H), 0.70-0.73 (m, 2H): LC-MS (ESI): Calculated mass: 409.1; Observed mass [M+H]$^+$: 410.1. (RT=1.34 min).

Step 3: tert-Butyl (5-(7-(4-(cyclopropylcarbamoyl) phenyl)-4-morpholinopyrido[3,2-d]-pyrimidin-2-yl) pyrimidin-2-yl)carbamate

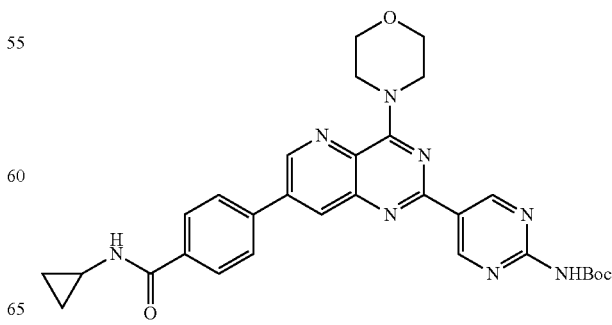

To a 50 mL sealed tube, 4-(2-chloro-4-morpholinopyrido[3,2-d]pyrimidin-7-yl)-N-cyclo-propylbenzamide (0.15 g, 0.00036 mol), (2-((tert-butoxycarbonyl)amino)pyrimidin-5-yl)boronic acid (0.113 g, 0.00047), potassium phosphate (0.155 g, 0.00072 mol), DMF (10 mL) and water (2 mL) were added. The reaction mixture was degassed with $N_2$ for 5-10 minutes. To the same reaction mixture, Pd(PPh$_3$)$_4$ (0.022 g, 0.000018 mol) was added and degassed with $N_2$ for 5-10 minutes. The reaction mixture was stirred at 95° C. for 1 hour. The reaction mass was cooled to room temperature and added ice cold water. A precipitate was obtained and the solid was collected by filtration. The solid was dissolved in chloroform, dried over anhydrous sodium sulfate and evaporated under reduced pressure to provide the crude product. The crude product was purified by flash column chromatography (2% methanol in chloroform) to provide the title compound (0.1 g, 48%). $^1$H NMR (300 MHz, DMSO-d$_6$): δ 10.41 (br s, 1H), 9.47 (s, 1H), 9.19 (d, J=1.8 Hz, 1H), 6.59 (d, J=4.2 Hz, 1H), 8.51 (d, J=1.8 Hz, 1H), 7.98-8.08 (m, 4H), 4.57 (br s, 4H), 3.83 (s, 4H), 2.88-2.89 (m, 1H), 1.48 (s, 9H), 0.73 (d, J=5.4 Hz, 2H), 0.61 (d, J=3.0 Hz, 2H): LC-MS (ESI): Calculated mass: 568.2; Observed mass [M+H]$^+$: 569.2. (RT=1.57 min).

Step 4: 4-(2-(2-Aminopyrimidin-5-yl)-4-morpholinopyrido[3,2-d]pyrimidin-7-yl)-N-cyclo-propyl benzamide

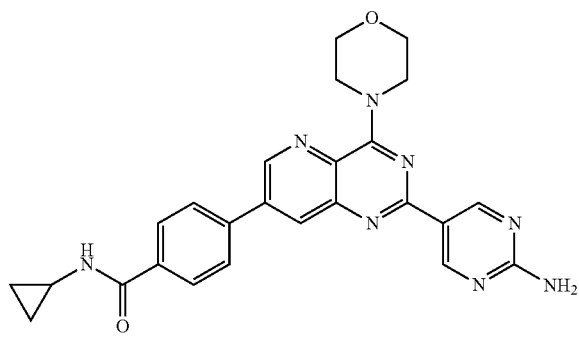 [SMILES: Nc1ncc(-c2nc(N3CCOCC3)c3ncc(-c4ccc(C(=O)NC5CC5)cc4)cc3n2)cn1]

To a 50 mL round bottom flask, tert-butyl (5-(7-(4-(cyclopropylcarbamoyl)phenyl)-4-morpholinopyrido[3,2-d]pyrimidin-2-yl)pyrimidin-2-yl)carbamate (0.1 g, 0.00018 mol) and DCM (10 mL) were added. To the same reaction flask, TFA (0.055 mL, 0.00072 mol) was added and the reaction mixture was stirred at room temperature for 12 hours. The volatiles were evaporated under reduced pressure to provide crude residue. The residue was dissolved in 10% methanol in chloroform, washed with saturated sodium bicarbonate solution, brine, dried over sodium sulfate and evaporated under reduced pressure to provide the crude product. The crude product was purified by flash column chromatography (3-4% methanol in chloroform) to provide the title compound (0.016 g, 12%). $^1$H NMR (400 MHz, DMSO-d$_6$): δ 9.19 (br s, 2H), 9.12 (d, J=1.6 Hz, 1H), 8.58 (d, J=4.0 Hz, 1H), 8.43 (d, J=1.6 Hz, 1H), 8.07 (d, J=8.4 Hz, 2H), 8.00 (d, J=8.4 Hz, 2H), 7.22 (br s, 2H), 4.52 (br s, 4H), 3.83 (s, 4H), 2.93-2.86 (m, 1H), 0.72 (d, J=5.2 Hz, 2H), 0.61 (d, J=2.4 Hz, 2H): LC-MS (ESI): Calculated mass: 468.2; Observed mass [M+H]$^+$: 469.0. (RT=0.19 min).

Example 5

(5-(2-(2-Aminopyrimidin-5-yl)-4-morpholinopyrido[3,2-d]pyrimidin-7-yl)furan-2-yl)(4-methylpiperazin-1-yl)methanone (Scheme III)

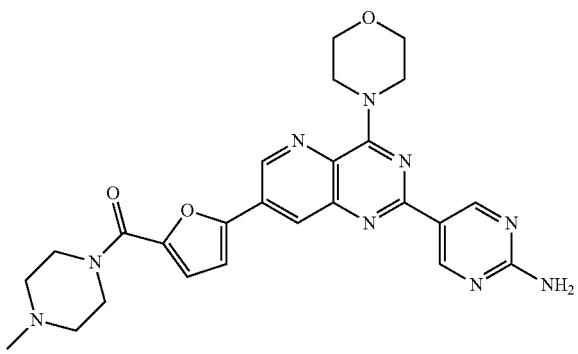 [SMILES: CN1CCN(C(=O)c2ccc(-c3cnc4c(N5CCOCC5)nc(-c5cnc(N)nc5)nc4c3)o2)CC1]

Step 1: 5-(2-Chloro-4-morpholinopyrido[3,2-d]pyrimidin-7-yl)furan-2-carbaldehyde To a 50 mL round bottom flask, 4-(7-bromo-2-chloropyrido[3,2-d]pyrimidin-4-yl)morpholine (0.5 g, 0.0015 mol—Preparation 3), 5-formyl-2-furanylboronic acid (0.21 g, 0.0015 mol), sodium carbonate (0.32 g, 0.003 mol), toluene (20 mL), ethanol (10 mL) and water (5 mL) were added. The reaction vessel was degassed with $N_2$ for 5-10 minutes. To the same reaction mixture, Pd(PPh$_3$)$_2$Cl$_2$ (0.053 g, 0.000075 mol) was added and again degassed with $N_2$ for 5-10 minutes. The reaction mixture was stirred at 95° C. for 2 hours. The reaction mixture was cooled and diluted with ethyl acetate. The organic layer was washed with water, brine and dried over sodium sulfate. The solvent was removed under reduced pressure to afford the crude product. The crude product was purified by column chromatography (60-120 silica gel, 60% ethyl acetate in n-hexane) to yield the desired product (0.38 g, 72%). $^1$H NMR (300 MHz, CDCl$_3$): δ 9.77 (s, 1H), 9.12 (d, J=2.1 Hz, 1H), 8.34 (d, J=2.1 Hz, 1H), 7.40 (d, J=3.6 Hz, 1H), 7.11 (d, J=3.6 Hz, 1H), 4.50 (br s, 4H), 3.91-3.88 (m, 4H):

LC-MS (ESI): Calculated mass: 344.0; Observed mass [M+H]⁺: 345.0 (RT=1.39 min).

Step 2: Methyl 5-(2-chloro-4-morpholinopyrido[3,2-d]pyrimidin-7-yl)furan-2-carboxylate

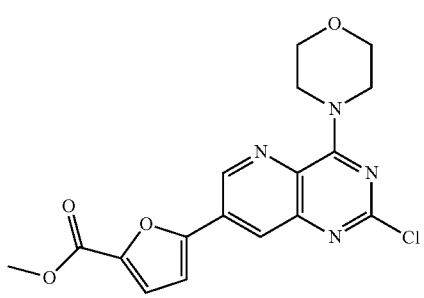 [SMILES: COC(=O)c1ccc(-c2cnc3c(N4CCOCC4)nc(Cl)nc3c2)o1]

To a 100 mL flask, 5-(2-chloro-4-morpholinopyrido[3,2-d]pyrimidin-7-yl)furan-2-carbaldehyde (0.38 g, 0.0011 mol) and methanol (30 mL) were added and the solution cooled to 0° C. To the reaction mixture, manganese (IV) oxide (0.191 g, 0.0022 mol) and sodium cyanide (0.109 g, 0.0022 mol) were added at 0° C. The reaction mixture was stirred at 0° C. for 3 hours. The reaction mixture was diluted with ethyl acetate. The organic layer was washed with water, brine, dried over anhydrous sodium sulfate and was evaporated under reduced pressure to provide methyl 5-(2-chloro-4-morpholinopyrido[3,2-d]pyrimidin-7-yl)furan-2-carboxylate as a solid (0.35 g). ¹H NMR (300 MHz, DMSO-d₆): δ 9.19 (d, J=2.1 Hz, 1H), 8.29 (d, J=2.1 Hz, 1H), 7.62 (d, J=3.6 Hz, 1H), 7.54 (d, J=3.6 Hz, 1H), 4.84-4.10 (br s, 4H), 3.87 (s, 3H), 3.81 (t, J=4.8 Hz, 4H): LC-MS (ESI): Calculated mass: 374.0; Observed mass [M+H]⁺: 375.0 (RT=1.51 min).

Step 3: 5-(2-(2-(tert-Butoxycarbonyl)amino)pyrimidin-5-yl)-4-morpholinopyrido[3,2-d]pyrimidin-7-yl)furan-2-carboxylic acid

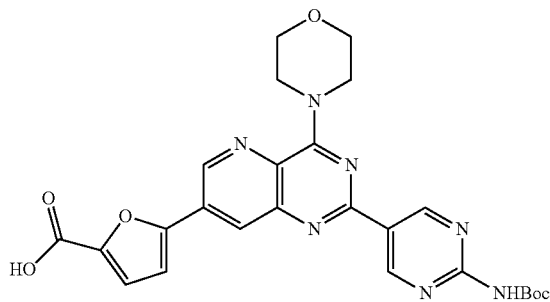 [SMILES: CC(C)(C)OC(=O)Nc1ncc(-c2nc(N3CCOCC3)c3ncc(-c4ccc(C(=O)O)o4)cc3n2)cn1]

To a 50 mL sealed tube, methyl 5-(2-chloro-4-morpholinopyrido[3,2-d]pyrimidin-7-yl)furan-2-carboxylate (0.35 g, 0.0009 mol), (2-(tert-butoxycarbonyl)amino)pyrimidin-5-yl) boronic acid (0.33 g, 0.0014 mol), potassium phosphate (0.39 g, 0.0018 mol), DMF (15 mL) and water (5 mL) were added. The reaction mixture was degassed with N₂ for 5-10 minutes. To the same reaction mixture, Pd(PPh₃)₄ (0.053 g, 0.000046 mol) was added and the mixture was degassed again with N₂ for 5-10 minutes. The reaction mixture was stirred at 95° C. for 1 hour. The reaction mixture was cooled and mixed with water. A precipitate formed which was collected by filtration. The filtered solid was purified by flash column chromatography (3% methanol in chloroform) to provide methyl 5-(2-(2-((tert-butoxycarbonyl)amino)pyrimidin-5-yl)-4-morpholinopyrido[3,2-d]pyrimidin-7-yl)furan-2-carboxylate (0.3 g). LC-MS (ESI): Calculated mass: 533.0; Observed mass: 434.1 [M-Boc+H]⁺ (RT=1.60 min).

Methyl 5-(2-(2-(tert-butoxycarbonyl)amino)pyrimidin-5-yl)-4-morpholinopyrido[3,2-d]-pyrimidin-7-yl)furan-2 carboxylate (0.3 g, 0.0006 mol) was taken into a 25 mL round bottom flask and lithium hydroxide monohydrate (0.23 g, 0.006 mol), THF (5 mL), methanol (5 mL), and water (5 mL) were added. The reaction mixture was stirred at room temperature for 3 hours. The volatiles were evaporated under reduced pressure to afford a residue. The residue was neutralized with 2N hydrochloric acid and extracted with DCM. The organic layer was washed with water and brine, dried over anhydrous sodium sulfate and evaporated to provide the title compound (0.2 g, 68%). ¹H NMR (300 MHz, DMSO-d₆): δ 10.40 (s, 1H), 9.43 (s, 1H), 9.17 (d, J=2.1 Hz, 1H), 8.39 (d, J=2.1 Hz, 1H), 7.58 (d, J=3.6 Hz, 1H), 7.41 (d, J=3.6 Hz, 1H), 4.51 (br s, 4H), 3.82 (br s, 4H), 1.48 (s, 9H): LC-MS (ESI): Calculated mass: 519.1; Observed mass [M+H]⁺: 520.0 (RT=0.99 min).

Step 4: tert-Butyl (5-(7-(5-(4-methylpiperazine-1-carbonyl)furan-2-yl)-4-morpholino-pyrido[3,2-d]pyrimidin-2-yl)pyrimidin-2-yl)carbamate

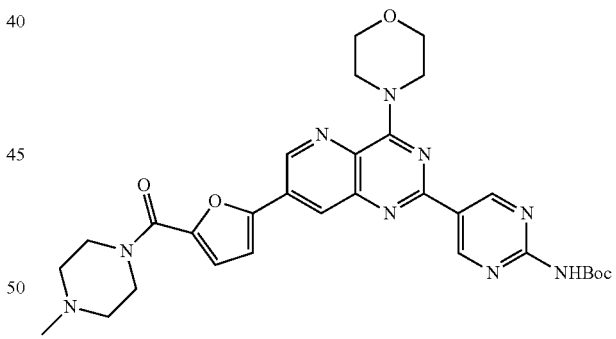

To a 25 mL flask, 5-(2-(2-(tert-butoxycarbonyl)amino)pyrimidin-5-yl)-4-morpholinopyrido[3,2-d]pyrimidin-7-yl)furan-2-carboxylic acid (0.1 g, 0.0002 mol), N-methylpiperazine (0.02 g, 0.0003 mol), HATU (0.14 g, 0.0004 mol), triethyl amine (0.055 mL, 0.0004 mol) and DMF (10 mL) were added. The reaction mixture was stirred at room temperature for 12 hours. To the reaction mixture, chloroform and water were added. The organic layer was washed with brine, dried over sodium sulfate and evaporated under reduced pressure to provide the crude product. The crude product was purified by flash column chromatography (3% methanol in chloroform) to yield the title compound (0.06 g, 52%). LC-MS (ESI): Calculated mass: 601.2; Observed mass [M-Boc+H]+: 502.2 (RT=0.11 min).

Step 5: (5-(2-(2-Aminopyrimidin-5-yl)-4-morpholinopyrido[3,2-d]pyrimidin-7-yl)furan-2-yl)(4-methylpiperazin-1-yl)-methanone

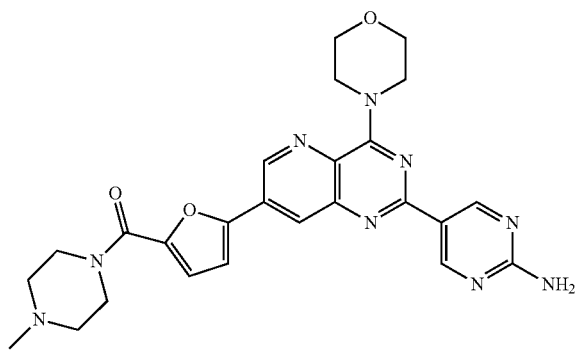 [SMILES: CN1CCN(C(=O)c2ccc(-c3cnc4c(N5CCOCC5)nc(-c5cnc(N)nc5)nc4c3)o2)CC1]

To a 25 mL flask, tert-butyl (5-(7-(5-(4-methylpiperazine-1-carbonyl)furan-2-yl)-4-morpholinopyrido[3,2-d]pyrimidin-2-yl)pyrimidin-2-yl)carbamate (0.06 g, 0.0001 mol) and DCM (10 mL) were added. To the reaction mixture, trifluoroacetic acid (0.076 mL, 0.001 mol) was added. The reaction mixture was stirred at room temperature for 3 hours. The volatiles were evaporated under reduced pressure to provide a residue. The residue was basified to pH 8.0 with saturated sodium bicarbonate solution and extracted with DCM. The organic layer was washed with water and brine, dried over sodium sulfate and evaporated to provide the crude product. The crude product was purified by preparative TLC (5% methanol in chloroform) to provide the title compound (0.01 g, 20%). $^1$H NMR (400 MHz, DMSO-d$_6$): δ 9.39 (s, 2H), 9.02 (d, J=2.4; H, 1H), 8.35 (d, J=2.0 Hz, 1H), 7.23 (d, J=3.6 Hz, 1H), 7.08 (d, J=3.6 Hz, 1H), 5.40 (br s, 2H), 4.63 (br s, 4H), 3.99 (t, J=4.8 Hz, 8H), 2.61 (t, J=4.4 Hz, 4H), 2.43 (s, 3H): LC-MS (ESI): Calculated mass: 501.2; Observed mass [M+H]+: 502.0 (RT=0.08 min).

Example 6

N-(3-(2-(2-Aminopyrimidin-5-yl)-4-morpholinoquinazolin-7-yl)phenyl)-2-hydroxy-2-methylpropanamide (Scheme IVa)

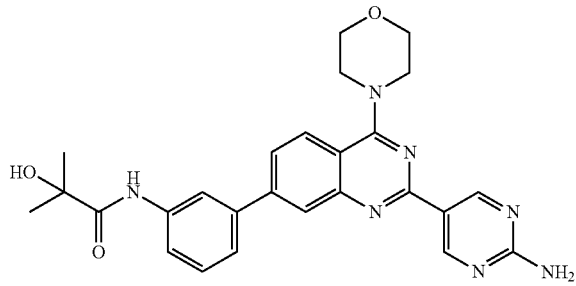 [SMILES: CC(C)(O)C(=O)Nc1cccc(-c2ccc3c(N4CCOCC4)nc(-c4cnc(N)nc4)nc3c2)c1]

Step 1: 3-(2-Chloro-4-morpholinoquinazolin-7-yl)aniline

To a 50 mL round bottom flask, 4-(7-bromo-2-chloroquinazolin-4-yl)morpholine (1.0 g, 0.0030 mol—Preparation 1), 3-aminophenylboronic acid pinacol ester (0.657 g, 0.0030 mol), sodium carbonate (0.635 g, 0.0060 mol), toluene (20 mL), ethanol (4 mL) and water (3 mL) were added. The reaction mixture was degassed with N$_2$ for 5-10 minutes. To the same reaction mixture, Pd(PPh$_3$)$_2$Cl$_2$ (0.105 g, 0.00015 mol) was added and degassed with N$_2$ for 5-10 minutes. The reaction mixture was stirred at 95° C. for 2 hours. The reaction mixture was cooled and diluted with ethyl acetate. The organic layer was washed with water, brine, dried over anhydrous sodium sulfate and evaporated under reduced pressure to afford the crude product. The crude product was purified by flash column chromatography (40% ethyl acetate in hexane) to provide the title compound (0.65 g, 62%). $^1$H NMR (400 MHz, CDCl$_3$): δ 8.00 (d, J=1.6 Hz, 1H), 7.89 (d, J=8.8 Hz, 1H), 7.66 (dd, J'=8.4 Hz, J"=1.6 Hz, 1H), 7.30 (d, J=7.6 Hz, 1H), 7.08 (d, J=8.0 Hz, 1H), 6.99 (t, J=2.0 Hz, 1H), 6.77 (dd, J'=7.6 Hz, J"=1.2 Hz, 1H), 3.90 (s, 8H), 3.84 (br s, 2H), LC-MS (ESI): Calculated mass. 340.11, Observed mass [M+H]+: 341.1 (RT=0.48 min).

Step 2: tert-Butyl (5-(7-(3-aminophenyl)-4-morpholinoquinazolin-2-yl)pyrimidin-2-yl)-carbamate In 50 mL round bottom flask, 3-(2-chloro-4-morpholinoquinazolin-7-yl)aniline (0.6 g, 0.0018 mol), (2-((tert-butoxycarbonyl)amino)pyrimidin-5-yl)boronic acid (0.506 g, 0.0022), potassium phosphate (1.08 g, 0.0054 mol), 1,4-dioxane (20 mL) and water (5 mL) were added. The reaction mixture was degassed with N$_2$ for 5-10 minutes. To the same reaction mixture, Pd (PPh$_3$)$_4$ (0.098 g, 0.00009 mol) was added and degassed with N$_2$ for 5-10 minutes. The reaction mixture was stirred at 95° C. for 2 hours. The reaction mass was cooled to room temperature and water was added. The crude product was extracted with ethyl acetate (3×100 mL). The combined organic layer was washed with brine, dried over sodium sulfate and evaporated under reduced pressure to provide the crude product. The crude product was purified by flash column chromatography (2% methanol in chloroform) to provide the title compound (0.3 g, 34%). $^1$H NMR (400 MHz, DMSO-d$_6$): δ 10.40 (s, 1H), 9.49 (s, 2H), 8.12 (d, J=8.8 Hz, 1H), 8.01 (d, J=1.6 Hz, 1H), 7.75 (dd, J'=8.8 Hz, J"=1.6 Hz, 1H), 7.20 (t, J=7.6 Hz, 1H), 7.04 (br s, 1H), 6.98 (d, J=7.6 Hz, 1H), 6.66 (d, J=8.4 Hz, 1H), 5.29 (s, 2H), 3.90 (d, J=4.4 Hz, 4H), 3.84 (d, J=4.0 Hz, 4H), 1.49 (s, 9H): LC-MS (ESI): Calculated mass. 499.2, Observed mass [M+H]$^+$: 500.4. (RT=0.78 min).

Step 3: tert-Butyl (5-(7-(3-(2-hydroxy-2-methylpropanamido)phenyl)-4-morpholinoquinazolin-2-yl)pyrimidin-2-yl)carbamate

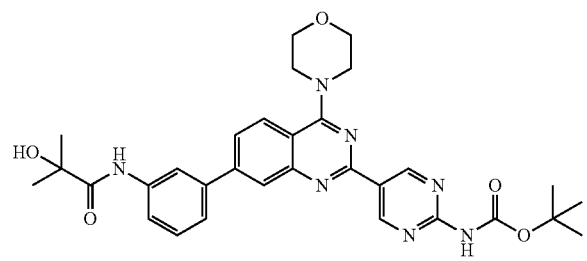 [SMILES: CC(C)(C)OC(=O)Nc1ncc(-c2nc(N3CCOCC3)c3ccc(-c4cccc(NC(=O)C(C)(C)O)c4)cc3n2)cn1]

In a 25 mL round bottom flask, tert-butyl (5-(7-(3-aminophenyl)-4-morpholinoquinazolin-2-yl)pyrimidin-2-yl) carbamate (0.1 g, 0.0002 mol), 2-hydroxy-2-methylpropanoic acid (0.052 g, 0.0005 mol) and DMF (10 mL) were added. To the flask, HATU (0.152 g, 0.0004 mol) and TEA (0.081 mL, 0.0006 mol) were added and then stirred at room temperature for 12 hours. To the reaction mixture was added water to provide a precipitate. The precipitate was collected by filtration to provide the crude product. The crude product was purified by flash column chromatography (2% methanol in chloroform) to obtain the title compound (0.06 g, 60%). LC-MS (ESI) Calculated mass. 585.2, Observed mass [M+H]$^+$: 586.1 (RT=0.83 min).

Step 4: N-(3-(2-(2-Aminopyrimidin-5-yl)-4-morpholinoquinazolin-7-yl)phenyl)-2-hydroxy-2-methylpropanamide

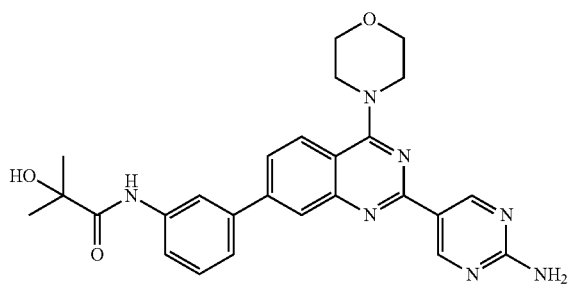 [SMILES: CC(C)(O)C(=O)Nc1cccc(-c2ccc3c(N4CCOCC4)nc(-c4cnc(N)nc4)nc3c2)c1]

In a 25 mL round bottom flask, tert-butyl (5-(7-(3-(2-hydroxy-2-methylpropanamido)phenyl)-4-morpholinoquinazolin-2-yl)pyrimidin-2-yl)carbamate (0.06 g, 0.0001 mol) and DCM (10 mL) were added. To the flask was added trifluoroacetic acid (0.5 mL) and the reaction stirred at room temperature for 5 hours. The volatiles were evaporated under reduced pressure to provide the residue. The residue was dissolved in 5% methanol in DCM and washed with saturated sodium bicarbonate. The organic layer was washed with water, brine, dried over sodium sulfate and evaporated under reduced pressure to provide the crude product. The crude product was purified by preparative HPLC (10 mM NH$_4$OAc and 1:1 MeOH:ACN) to obtain the title compound (0.007 mg, 14%). $^1$H NMR (DMSO-d$_6$, 400 MHz): δ 9.76 (s, 1H), 9.22 (s, 2H), 8.32 (s, 1H), 8.11 (d, J=8.8 Hz, 1H), 8.05 (s, 1H), 7.87 (d, J=8.0 Hz, 1H), 7.77 (d, J=7.6 Hz, 1H), 7.56 (d, J=7.6 Hz, 1H), 7.48 (t, J=8.8 Hz, 1H), 7.16 (s, 2H), 3.85 (s, 8H), 1.39 (s, 6H): LC-MS (ESI): Calculated mass. 485.2, Observed mass [M+H]$^+$: 486.2. (RT=0.11 min).

Example 7

N-(3-(2-(2-Aminopyrimidin-5-yl)-4-morpholinopyrido[3,2-d]pyrimidin-7-yl)-phenyl)cyclopropanecarboxamide (Scheme IVa)

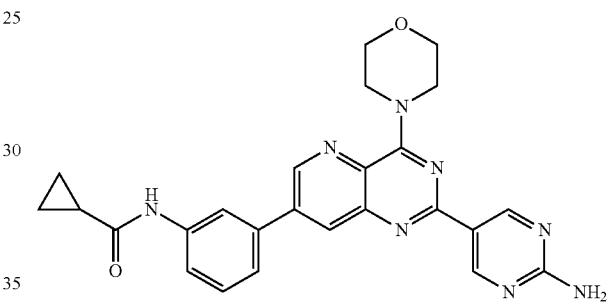

Step 1: 3-(2-chloro-4-morpholinopyrido[3,2-d]pyrimidin-7-yl)aniline

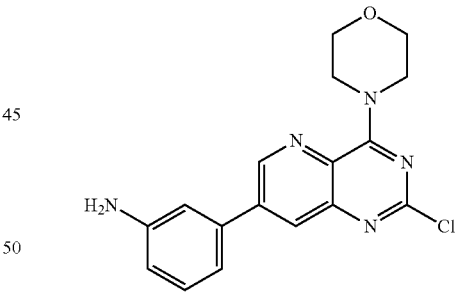

To a 100 mL round bottom flask, 4-(7-bromo-2-chloropyrido[3,2-d]pyrimidin-4-yl)morpholine (1.5 g, 0.0046 mol—Preparation 2), 3-aminophenylboronic acid (0.67 g, 0.0051 mol), sodium carbonate (0.98 g, 0.0092 mol) toluene (30 mL), ethanol (10 mL) and water (5 mL) were added. The reaction mixture was degassed with N$_2$ for 5-10 minutes. To the same reaction mixture, Pd(PPh$_3$)$_2$Cl$_2$ (0.14 g, 0.0002 mol) was added and again degassed with N$_2$ for 5-10 minutes. The reaction mixture was stirred at 90° C. for 2 hours. The reaction mixture was cooled and diluted with ethyl acetate. The organic layer was washed with water, brine, dried over anhydrous sodium sulfate and evaporated under reduced pressure to afford the crude product. The crude product was purified by column chromatography (60-120 silica gel, 60% ethyl acetate in hexane) to provide the title compound (1.1 g, 70%). $^1$H NMR (300 MHz, DMSO-d$_6$): δ 9.02 (d, J=2.1 Hz, 1H), 8.12 (d, J=2.1 Hz, 1H), 7.22 (t, J=7.8 Hz, 1H), 7.01-6.99 (m, 2H), 6.68-6.17 (m, 1H), 5.33 (br s, 2H), 4.52 (br s, 4H), 3.79 (t, J=4.8 Hz, 4H). LC-MS (ESI): Calculated mass: 341.1; Observed mass [M+H]$^+$: 342.1. (RT=0.73 min).

Step 2: tert-butyl (5-(7-(3-aminophenyl)-4-morpholinopyrido[3,2-d]pyrimidin-2-yl)pyrimidin-2-yl)carbamate

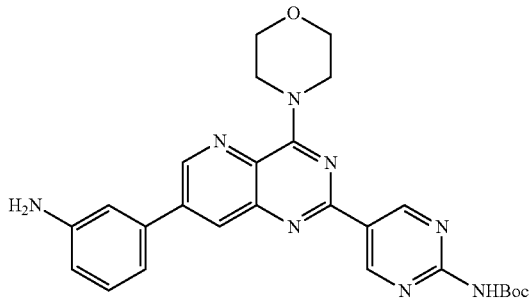 [SMILES: CC(C)(C)OC(=O)Nc1ncc(-c2nc(N3CCOCC3)c3ncc(-c4cccc(N)c4)cc3n2)cn1]

To a 50 mL sealed tube, 3-(2-chloro-4-morpholinopyrido[3,2-d]pyrimidin-7-yl)aniline (1.1 g, 0.0032 mol), (2-((tert-butoxycarbonyl)amino)pyrimidin-5-yl)boronic acid (1.15 g, 0.0048), potassium phosphate (2.04 g, 0.0096 mol), DMF (20 mL) and water (7 mL) were added. The reaction mixture was degassed with N$_2$ for 5-10 minutes. To the same reaction mixture, Pd(PPh$_3$)$_4$ (0.23 g, 0.0002 mol) was added and degassed with N$_2$ for 5-10 minutes. The reaction mixture was stirred at 105° C. for 1 hour. The reaction mass was cooled to room temperature and added ice cold water. The precipitate was obtained and the solid was collected by filtration. The solid was dissolved in chloroform, dried over anhydrous sodium sulfate and evaporated under reduced pressure to provide the crude product. The crude product was purified by column chromatography (60-120 silica gel, 2% methanol in chloroform) to provide the title compound (1.4 g, 87%). $^1$H NMR (300 MHz, DMSO-d$_6$): δ 10.42 (s, 1H), 9.47 (s, 1H), 9.02 (d, J=2.4 Hz, 1H), 8.24 (d, J=2.1 Hz, 1H), 7.23 (t, J=7.8 Hz, 1H), 7.07-7.03 (m, 2H), 6.71 (d, J=8.1 Hz, 1H), 5.33 (s, 2H), 4.55 (br s, 4H), 3.83 (t, J=4.8 Hz, 4H), 1.49 (s, 9H). LC-MS (ESI): Calculated mass: 500.2; Observed mass [M+H]$^+$: 501.1 (RT=1.09 min).

Step 3: tert-butyl (5-(7-(3-(cyclopropanecarboxamido)phenyl)-4-morpholinopyrido[3,2-d]pyrimidin-2-yl)pyrimidin-2-yl)carbamate

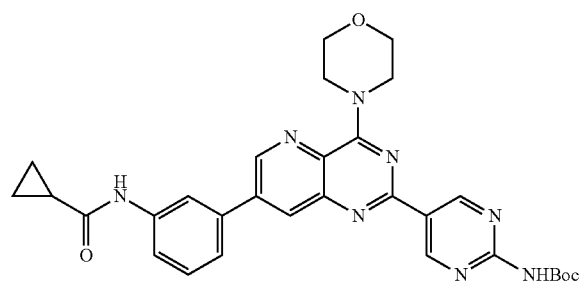 [SMILES: CC(C)(C)OC(=O)Nc1ncc(-c2nc(N3CCOCC3)c3ncc(-c4cccc(NC(=O)C5CC5)c4)cc3n2)cn1]

To a 25 mL round bottom flask, tert-butyl (5-(7-(3-aminophenyl)-4-morpholinopyrido[3,2-d]pyrimidin-2-yl)pyrimidin-2-yl)carbamate (0.2 g, 0.0004 mol), cyclopropane carboxylic acid (0.041 g, 0.00048 mol) and DMF (8 mL) were added. To the same flask, HATU (0.46 g, 0.0012 mol) and TEA (0.22 mL, 0.0016 mol) were added. The reaction mass was stirred at room temperature for 12 hours. The volatiles were evaporated to dryness under reduced pressure to provide a residue. The residue was stirred with water to provide a solid and the solid was collected by filtration. The solid was washed with diethyl ether to provide the crude product. The crude product was purified by flash column chromatography (1-2% methanol in chloroform) to afford the title compound (0.15 g, 66%). $^1$H NMR (300 MHz, DMSO-d$_6$): δ 10.42 (br s, 2H), 9.48 (s, 1H), 9.07 (d, J=2.4 Hz, 1H), 8.31 (d, J=1.8 Hz, 1H), 8.20 (s, 1H), 7.47-7.67 (m, 3H), 4.57 (br s, 4H), 3.84 (s, 4H), 1.84-1.80 (m, 1H), 1.49 (s, 9H), 0.85-0.83 (m, 4H): LC-MS (ESI): Calculated mass: 568.2; Observed mass [M+H]$^+$: 569.2 (RT=1.56 min).

Step 4: N-(3-(2-(2-aminopyrimidin-5-yl)-4-morpholinopyrido[3,2-d]pyrimidin-7-yl)phenyl)cyclopropanecarboxamide

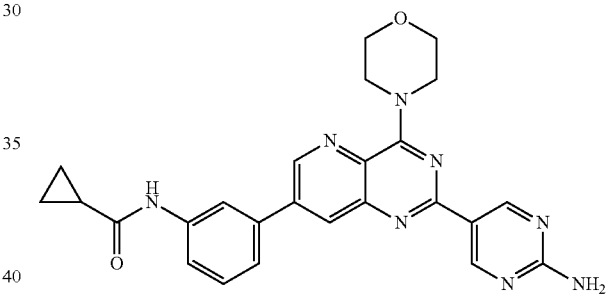

To a 50 mL round bottom flask, tert-butyl (5-(7-(3-(cyclopropanecarboxamido)phenyl)-4-morpholinopyrido[3,2-d]pyrimidin-2-yl)pyrimidin-2-yl)carbamate (0.15 g, 0.00026 mol) and DCM (10 mL) were added and then cooled to 0° C. To the same reaction flask, trifluoroacetic acid (0.12 g, 0.00104 mol) was added at 0° C. and the reaction mixture was stirred at room temperature for 12 hours. The reaction mixture was quenched with saturated sodium bicarbonate solution and extracted with 10% methanol in chloroform. The organic layer was washed with water, brine, dried over anhydrous sodium sulfate and concentrated under reduced pressure to provide the crude product. The crude product was subjected to flash column chromatography using 3-4% methanol in chloroform. The obtained solid was washed diethyl ether, filtered and dried under vacuum to afford the title compound (0.1 g, 81%). $^1$H NMR (400 MHz, DMSO-d$_6$): δ 10.44 (s, 1H), 9.23 (s, 2H), 9.04 (d, J=2.4 Hz, 1H), 8.27 (d, J=2.4 Hz, 1H), 8.23 (s, 1H), 7.68-7.50 (m, 3H), 7.24 (br s, 2H), 4.55 (br s, 4H), 3.86 (d, J=4.0 Hz, 4H), 1.85-1.83 (m, 1H), 0.87-0.85 (m, 4H): LC-MS (ESI): Calculated mass: 468.2; Observed mass [M+H]$^+$: 469.1. (RT=0.35 min).

Example 8

N-(3-(2-(2-aminopyrimidin-5-yl)-4-morpholinopyrido[3,2-d]pyrimidin-7-yl)phenyl)-4-fluorobenzenesulfonamide (Scheme IVb)

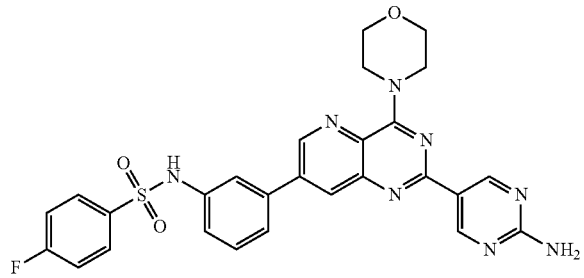 [SMILES: Nc1ncc(-c2nc(N3CCOCC3)c3ncc(-c4cccc(NS(=O)(=O)c5ccc(F)cc5)c4)cc3n2)cn1]

Step 1: tert-butyl (5-(7-(3-(4-fluorophenylsulfonamido)phenyl)-4-morpholinopyrido[3,2-d]-pyrimidin-2-yl)pyrimidin-2-yl)carbamate

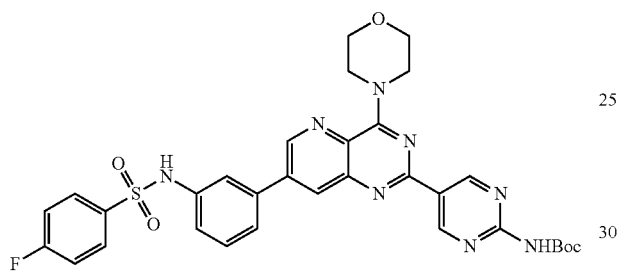

To a 25 mL flask, tert-butyl (5-(7-(3-aminophenyl)-4-morpholinopyrido[3,2-d]pyrimidin-2-yl)pyrimidin-2-yl)carbamate (Example 7, Step 2) (0.1 g, 0.0002 mol) and pyridine (4 mL) were added. To the same flask, 4-fluorobenzenesulfonyl chloride (0.038 g, 0.0002 mol) was added. The reaction mixture was stirred at room temperature for 12 hours. The reaction mixture was diluted with 10% methanol in chloroform and washed with water. The organic layer was washed with brine, dried over sodium sulfate and was evaporated to provide the crude product. The crude product was purified by flash column chromatography (3% methanol in chloroform) to obtain the title compound (0.06 g, 45%). $^1$H NMR (300 MHz, DMSO-$d_6$): δ 10.57 (s, 1H), 10.42 (s, 1H), 9.48 (s, 1H), 8.98 (d, J=2.1 Hz, 1H), 8.23 (d, J=2.1 Hz, 1H), 7.91 (dd, J'=5.1 Hz, J''=3.9 Hz, 2H), 7.65 (d, J=7.8 Hz, 1H), 7.56 (s, 1H), 7.45 (dd, J'=8.7 Hz, J''=1.5 Hz, 3H), 7.23 (d, J=7.8 Hz, 1H), 4.57 (br s, 4H), 3.83 (br s, 4H), 1.49 (s, 9H). LC-MS (ESI): Calculated mass: 658.2; Observed mass [M+H]$^+$: 658.9 (RT=1.69 min).

Step 2: N-(3-(2-(2-aminopyrimidin-5-yl)-4-morpholinopyrido[3,2-d]pyrimidin-7-yl)phenyl)-4-fluorobenzenesulfonamide

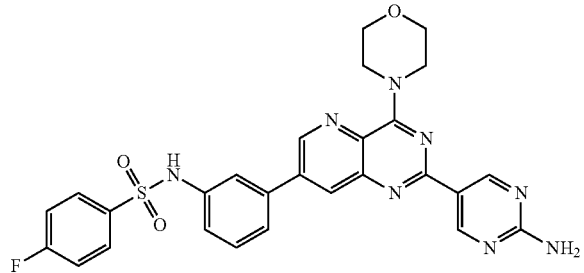 [SMILES: Nc1ncc(-c2nc(N3CCOCC3)c3ncc(-c4cccc(NS(=O)(=O)c5ccc(F)cc5)c4)cc3n2)cn1]

To a 25 mL flask, tert-butyl (5-(7-(3-(4-fluorophenylsulfonamido)phenyl)-4-morpholino-pyrido[3,2-d]pyrimidin-2-yl)pyrimidin-2-yl)carbamate (0.06 g, 0.00009 mol) and DCM (9 mL) were added. To the same reaction vessel, trifluoroacetic acid (0.5 mL) was added. The reaction mixture was stirred at room temperature for 3 hours. The volatiles were evaporated under reduced pressure to provide the residue. The residue was washed with ether and was dissolved in 10% methanol in DCM. The organic layer was basified with saturated sodium bicarbonate solution (pH 8.0). The organic layer was washed with water, brine, dried over sodium sulfate and evaporated under reduced pressure to provide the crude product. The crude product was washed with methanol and diethyl ether to provide the solid. The solid was dried under high vacuum to provide the title compound (0.031 g, 60%). $^1$H NMR (400 MHz, DMSO-$d_6$): δ 10.57 (s, 1H), 9.20 (s, 2H), 8.92 (d, J=2.4 Hz, 1H), 8.16 (d, J=2.4 Hz, 1H), 7.90-7.87 (m, 2H), 7.63 (d, J=7.6 Hz, 1H), 7.55 (br s, 1H), 7.46-7.40 (m, 3H), 7.22 (br s, 2H), 7.20 (s, 1H) 4.52 (br s, 4H), 3.84 (t, J=4.4 Hz, 4H). LC-MS (ESI): Calculated mass: 558.1; Observed mass [M+H]$^+$: 558.9 (RT=1.19 min).

Example 9

N-(3-(2-(2-Aminopyrimidin-5-yl)-4-morpholinopyrido[3,2-d]pyrimidin-7-yl)-phenyl)-2-(4-hydroxypiperidin-1-yl)acetamide (Scheme IVc)

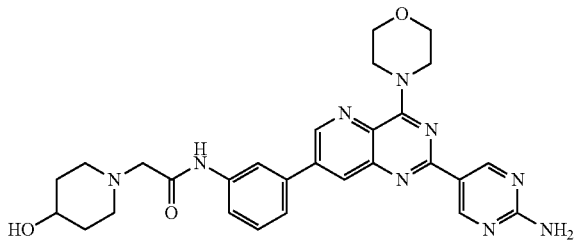 [SMILES: Nc1ncc(-c2nc(N3CCOCC3)c3ncc(-c4cccc(NC(=O)CN5CCC(O)CC5)c4)cc3n2)cn1]

Step 1: tert-Butyl (5-(7-(3-(2-chloroacetamido)phenyl)-4-morpholinopyrido[3,2-d]-pyrimidin-2-yl)pyrimidin-2-yl)carbamate

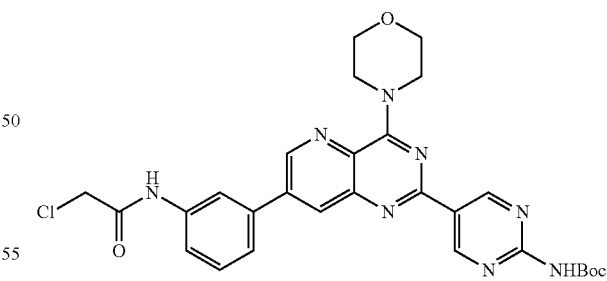

To a 25 mL round bottom flask, tert-butyl (5-(7-(3-aminophenyl)-4-morpholinopyrido[3,2-d]pyrimidin-2-yl)pyrimidin-2-yl)carbamate (Example 7, Step 2) (0.15 g, 0.0003 mol), chloroacetyl chloride (0.051 g, 0.00045 mol) and DCM (10 mL) were added and then cooled to 10° C. To the same reaction flask, triethylamine (0.12 mL, 0.0009 mol) was added. The reaction mass was stirred at room temperature for 30 minutes. The reaction mixture was diluted with DCM, washed with water and brine. The organic layer was dried over anhydrous sodium sulfate and evaporated to provide the crude product. The crude product was purified by column chromatography (60-120 silica-gel and 0-2% methanol in chloroform) to afford the title compound (0.15 g, 87%). $^1$H NMR (300 MHz, DMSO-d$_6$): δ 10.52 (s, 1H), 10.42 (s, 1H), 9.48 (s, 1H), 9.08 (d, J=1.8 Hz, 1H), 8.33 (d, J=2.1 Hz, 1H), 8.18 (s, 1H), 7.68 (t, J=4.8 Hz, 2H), 7.57 (t, J=7.8 Hz, 1H), 4.65-4.52 (br s, 4H), 4.33 (s, 2H), 3.84 (s, 4H), 1.49 (s, 9H): LC-MS (ESI): Calculated mass. 576.2, Observed mass [M+H]$^+$: 577.2 (RT=1.53 min).

Step 2: tert-butyl (5-(7-(3-(2-(4-hydroxypiperidin-1-yl)acetamido)phenyl)-4-morpholino-pyrido[3,2-d]pyrimidin-2-yl)pyrimidin-2-yl)carbamate

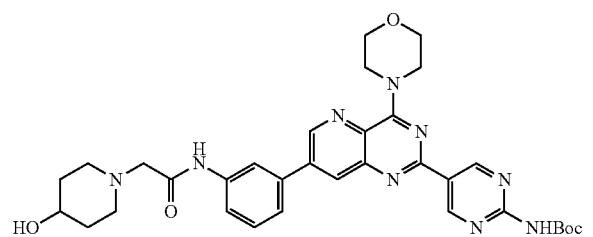 [SMILES: CC(C)(C)OC(=O)Nc1ncc(-c2nc(N3CCOCC3)c3ncc(-c4cccc(NC(=O)CN5CCC(O)CC5)c4)cc3n2)cn1]

To a 25 mL round bottom flask, 4-hydroxy piperidine (0.021 g, 0.00021 mol) and DMF (1.5 mL) were added and then cooled to 0-10° C. To the same reaction flask, potassium carbonate (0.058 g, 0.00042 mol) was added and the reaction mixture was stirred at 0-10° C. for 30 minutes. To the same flask, a solution of tert-butyl (5-(7-(3-(2-chloroacetamido)phenyl)-4-morpholinopyrido[3,2-d]pyrimidin-2-yl)pyrimidin-2-yl)carbamate (0.08 g, 0.00014 mol) in DMF (1 mL) was added and then stirred at room temperature for 12 hours. The reaction was quenched with water to provide the precipitate. The precipitate was collected by filtration to provide the title compound (0.078 g, 88%). The compound was used in the next step without purification. $^1$H NMR (300 MHz, DMSO-d$_6$): δ 10.43 (s, 1H), 9.84 (s, 1H), 9.49 (s, 1H), 9.12 (d, J=2.1 Hz, 1H), 8.38 (s, J=2.1 Hz, 1H), 8.21 (br s, 1H), 7.87 (d, J=7.8 Hz, 1H), 7.68 (d, J=7.8 Hz, 1H), 7.54 (t, J=8.1 Hz, 1H), 4.63 (d, J=3.9 Hz, 1H), 4.58 (br s, 4H), 3.84 (s, 4H), 3.51-3.49 (m, 1H), 3.28 (s, 2H), 3.13-2.75 (m, 2H), 2.29 (t, J=8.7 Hz, 2H), 1.78 (d, J=9.3 Hz, 2H), 1.58 (d, J=9.3 Hz, 2H), 1.49 (s, 9H): LCMS (ESI): Calculated. 641.3, Observed mass [M+H]$^+$: 642.2, (RT=0.22 min).

Step 3: N-(3-(2-(2-aminopyrimidin-5-yl)-4-morpholinopyrido[3,2-d]pyrimidin-7-yl)phenyl)-2-(4-hydroxypiperidin-1-yl)acetamide

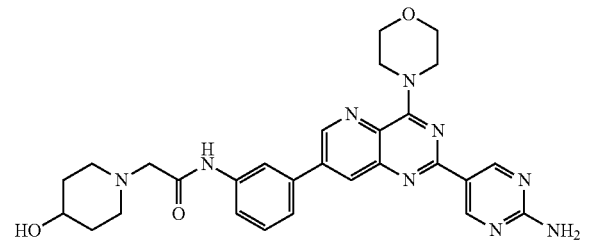

To a 25 mL round bottom flask, tert-butyl (5-(7-(3-(2-(4-hydroxypiperidin-1-yl)acetamido)phenyl)-4-morpholinopyrido[3,2-d]pyrimidin-2-1)pyrimidin-2-yl)carbamate (0.078 g, 0.00012 mol and DCM (15 mL) was added. To the same flask, TFA (0.037 mL, 0.00048 mol) was added and the reaction mixture stirred at room temperature for 12 hours. The volatiles were evaporated under reduced pressure to provide the residue. The residue was dissolved in 10% methanol in chloroform. The organic layer was washed with water, brine, dried over sodium sulfate and evaporated under reduced pressure to provide the crude product. The crude product was purified by preparative TLC (5% methanol in chloroform, 3 times eluted) to provide the title compound (0.065 g, 99%). $^1$H NMR (400 MHz, DMSO-d$_6$): δ 9.86 (s, 1H), 9.23 (s, 2H), 9.08 (d, J=1.6 Hz, 1H), 8.34 (d, J=1.6 Hz, 1H), 8.22 (s, 1H), 7.89 (d, J=8.4 Hz, 1H), 7.68 (d, J=7.6 Hz, 1H), 7.55 (t, J=8.0 Hz, 1H), 7.24 (s, 2H), 4.66 (d, J=3.6 Hz, 1H), 4.56 (br s, 4H), 3.86 (s, 4H), 3.53-3.48 (m, 1H), 3.15 (s, 2H), 2.81-2.78 (m, 2H), 2.31 (t, J=9.6 Hz, 2H), 1.80-1.78 (m, 2H), 1.60-1.55 (m, 2H): LC-MS (ESI): Calculated mass. 541.25, Observed mass [M+H]$^+$: 542.3 (RT=0.10 min).

Example 10

N-(3-(2-(2-aminopyrimidin-5-yl)-4-morpholinopyrido[3,2-d]pyrimidin-7-yl)-phenyl)morpholine-4-carboxamide (Scheme IVd)

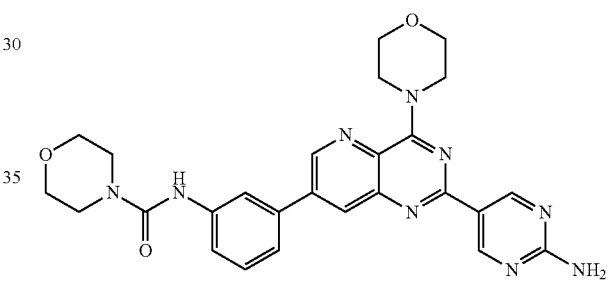

Step 1: tert-butyl (5-(7-(3-(morpholine-4-carboxamido)phenyl)-4-morpholinopyrido[3,2-d]pyrimidin-2-yl)pyrimidin-2-yl)carbamate

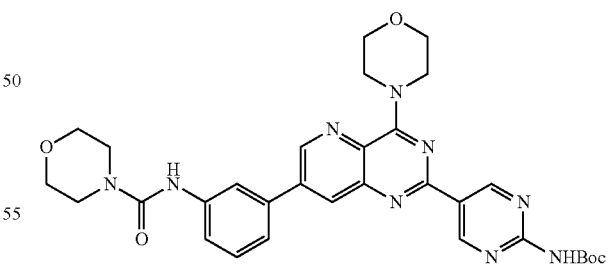

To a 25 mL round bottom flask, tert-butyl (5-(7-(3-aminophenyl)-4-morpholinopyrido[3,2-d]pyrimidin-2-yl)pyrimidin-2-yl)carbamate (Example 7, Step 2) (0.1 g, 0.0002 mol), 2,2,2,-trichloroethyl chloroformate (0.05 g, 0.00024 mol) and THF (5 mL) were added. The reaction mixture was cooled to 0° C. To the same flask, triethylamine (0.055 mL, 0.0004 mol) was added. The reaction mixture was stirred at room temperature for 30 minutes. The volatiles were removed under reduced pressure to provide crude residue. The crude residue was dissolved in chloroform. The organic layer was washed with water, brine, dried over anhydrous sodium sulfate and evaporated under reduced pressure to afford the intermediate (0.13 g, 96%) and was taken for the next step without further purification.

To a 10 mL round bottom flask, the compound immediately above (0.07 g, 0.0001 mol), morpholine (0.018 g, 0.0002 mol), triethylamine (0.07 mL, 0.0005 mol) and toluene (2 mL) were added. The reaction mixture was stirred at 110° C. for 4 hours. The volatiles were evaporated to provide a residue. The residue was dissolved in chloroform. The organic layer was washed with water, brine, dried over anhydrous sodium sulfate and evaporated under reduced pressure to afford the crude product. The crude product was purified by column chromatography (60-120 silica gel, 0-5% methanol in chloroform) followed by preparative TLC (4% methanol in chloroform) to provide the title compound (0.04 g, 63%). $^1$H, NMR (300 MHz, DMSO-$d_6$): δ 10.42 (s, 1H), 9.47 (s, 1H), 9.08 (d, J=2.1 Hz, 1H), 8.73 (s, 1H), 8.31 (d, J=2.1 Hz, 1H), 8.05 (s, 1H), 7.64 (d, J=8.4 Hz, 1H), 7.55 (d, J=7.8 Hz, 1H), 7.46 (t, J=7.8 Hz, 1H), 4.57 (br s, 4H), 3.83 (s, 4H), 3.65-3.62 (m, 4H), 3.48-3.46 (m, 4H), 1.48 (s, 9H). LC-MS (ESI): Calculated mass. 613.2, Observed mass [M+H]$^+$: 613.8, (RT=1.37 min).

Step 2: N-(3-(2-(2-aminopyrimidin-5-yl)-4-morpholinopyrido[3,2-d]pyrimidin-7-yl)phenyl)-morpholine-4-carboxamide

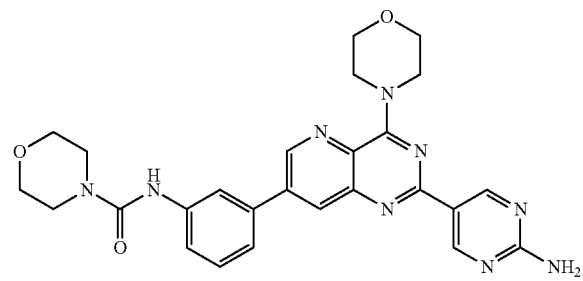 [SMILES: Nc1ncc(-c2nc(N3CCOCC3)c3ncc(-c4cccc(NC(=O)N5CCOCC5)c4)cc3n2)cn1]

To a 25 mL round bottom flask, tert-butyl (5-(7-(3-(morpholine-4-carboxamido)phenyl)-4-morpholinopyrido[3,2-d]pyrimidin-2-yl)pyrimidin-2-yl)carbamate (0.035 g, 0.00006 mol) and DCM (5 mL) were added. To the same flask, TFA (0.013 g, 0.00012 mol) was added and the mixture stirred at room temperature for 3 hours. The volatiles were evaporated under reduced pressure to provide the crude residue. The crude residue was dissolved in 10% methanol in chloroform and washed with aqueous saturated sodium bicarbonate. The organic layer was washed with water, brine, dried over anhydrous sodium sulfate and evaporated under reduced pressure to provide the crude product. The crude product was purified by preparative TLC (4% methanol in chloroform, double elution) to provide the title compound (0.015 g, 52%). $^1$H NMR (400 MHz, DMSO-$d_6$): δ 9.19 (s, 2H), 9.02 (d, J=2.4 Hz, 1H), 8.72 (s, 1H), 8.24 (d, J=2.4 Hz, 1H), 8.04 (t, J=1.6 Hz, 1H), 7.64 (d, J=8.0 Hz, 1H), 7.54 (d, J=8.0 Hz, 1H), 7.46 (t, J=8.0 Hz, 1H), 7.20 (br s, 2H), 4.52 (br s, 4H), 3.84 (t, J=4.8 Hz, 4H), 3.65 (t, J=4.4 Hz, 4H), 3.48 (t, J=4.8 Hz, 4H): LC-MS (ESI): Calculated mass. 513.2, Observed mass [M+H]$^+$: 514.2 (RT=0.19 min).

Example 11

1-(4-((2-(2-aminopyrimidin-5-yl)-4-morpholinopyrido[3,2-d]pyrimidin-7-yl)-methyl)piperazin-1-yl)-2-hydroxypropan-1-one (Scheme V)

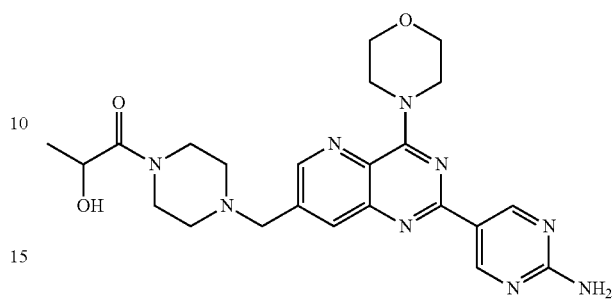

Step 1: 2-chloro-4-morpholinopyrido[3,2-d]pyrimidine-7-carbaldehyde

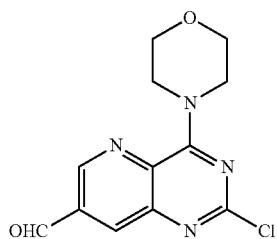 [SMILES: O=Cc1cnc2c(N3CCOCC3)nc(Cl)nc2c1]

To a 50 mL round bottom flask, 4-(7-bromo-2-chloropyrido[3,2-d]pyrimidin-4-yl)morpholine (3.0 g, 0.0091 mol—Preparation 3) and dry THF (15 mL) were added under nitrogen atmosphere and then cooled to −78° C. To the reaction flask, 2.5 M n-butyl lithium (4.4 mL, 0.0109 mol) was slowly added and the reaction mixture was stirred at −78° C. for 30 minutes. To the reaction mixture, N,N-dimethylformamide (1.27 mL, 0.0164 mol) was added and the reaction mixture allowed to warm to 0° C. The reaction mass was quenched with 10% aqueous ammonium chloride (100 mL) and extracted with ethyl acetate (3×50 mL). The combined organic layer was washed with brine, dried over anhydrous sodium sulfate and evaporated to provide the crude product. The crude product was purified by column chromatography (60-120 silica gel, 10-40% ethyl acetate) to provide the title compound as a light yellow solid (0.8 g, 31%). $^1$H NMR (300 MHz, CDCl$_3$): δ 10.24 (s, 1H), 9.11 (d, J=2.1 Hz, 1H), 8.41 (d, J=2.1 Hz, 1H), 3.91 (t, J=4.8 Hz, 8H): LC-MS (ESI): Calculated mass. 278.06, Observed mass [M+H]$^+$: 279.0 (RT=0.66 min).

Step 2: 1-(4-((2-chloro-4-morpholinopyrido[3,2-d]pyrimidin-7-yl)methyl)piperazin-1-yl)-2-hydroxypropan-1-one

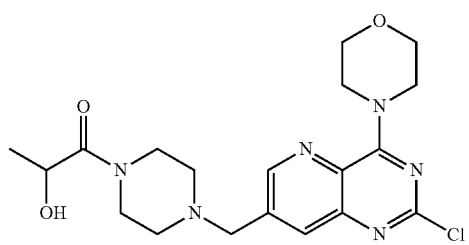 [SMILES: CC(O)C(=O)N1CCN(Cc2cnc3c(N4CCOCC4)nc(Cl)nc3c2)CC1]

In a 50 mL round bottom flask, 2-chloro-4-morpholinopyrido[3,2-d]pyrimidine-7-carbaldehyde (0.3 g, 0.0010 mol) and 1,2-dichloroethane (20 mL) were added. To the reaction flask, 2-hydroxy-1-(piperazin-1-yl)propan-1-one (0.204 g, 0.0013 mol) and trimethyl orthoformate (0.228 g, 0.0030 mol) were added and the reaction mixture stirred at room temperature for 12 hours. To the reaction mixture, sodium triacetoxyborohydride (g, 0.683 0.0020 mol) was added and stirred at room temperature for 3 hours. The reaction mixture was diluted with DCM, washed with water, brine, dried over anhydrous sodium sulfate and evaporated under reduced pressure to provide the crude product. The crude product was purified by column chromatography (60-12 silica gel, 5% methanol in chloroform) to provide the title compound (0.15 g, 33%). $^1$H NMR (300 MHz, CDCl$_3$): δ 8.62 (d, J=1.8 Hz, 1H), 7.86 (d, J=1.2 Hz, 1H), 4.72 (br s, 4H), 3.84 (t, J=9.0 Hz, 4H), 3.65 (s, 2H), 3.60-3.52 (m, 1H), 3.41 (d, J=2.7 Hz, 1H), 3.23 (s, 4H), 2.46 (d, J=3.0 Hz, 4H), 1.27 (d, J=6.6 Hz, 3H): LC-MS (ESI): Calculated mass. 420.1, Observed mass [M+H]$^+$: 421.1 (RT=0.24 min).

Step 3: 1-(4-((2-(2-aminopyrimidin-5-yl)-4-morpholinopyrido[3,2-d]pyrimidin-7-yl)methyl)piperazin-1-yl)-2-hydroxypropan-1-one

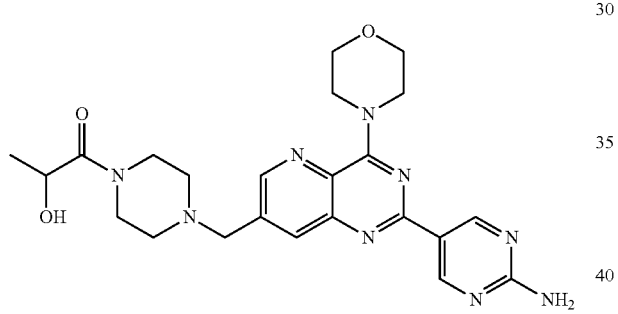

To a 25 mL round bottom flask, 1-(4-(2-chloro-4-morpholinopyrido[3,2-d]pyrimidin-7-yl)methyl)piperazin-1-yl)-2-hydroxypropan-1-one (0.1 g, 0.0002 mol), 2-aminopyrimidine-5-boronic acid (0.085 g, 0.0003 mol), cesium carbonate 0.149 g, 0.0004 mol), DMF (10 mL) and water (3 mL) were added. The reaction mixture was degassed with N$_2$ for 5-10 minutes. To the same reaction mixture, Pd(PPh$_3$)$_2$Cl$_2$ (0.008 g, 0.00001 mol) was added and degassed with N$_2$ for 5-10 minutes. The reaction mixture was stirred at 95° C. for 2 hours. The reaction mass was diluted with water and extracted with ethyl acetate (3×25 mL). The combined organic layer was washed with brine, dried over anhydrous sodium sulfate and evaporated under reduced pressure to provide the crude product. The crude product was purified by column chromatography (60-120 silica gel, 8% methanol in chloroform), followed by preparative HPLC (0.1% TFA in water and acetonitrile) to provide the title compound (0.007 g, 6%). $^1$H NMR (400 MHz, DMSO-d$_6$): δ 9.18 (s, 2H), 8.82 (s, 1H), 8.25 (s, 1H), 4.72 (br s, 4H), 4.21 (s, 2H), 3.93-3.82 (m, 10H), 3.00 (br s, 4H), 1.33 (d, J=6.4 Hz, 3H): LC-MS (ESI): Calculated mass. 479.24, Observed mass [M+H]$^+$: 480.2 (RT=0.22 min).

Example 121

((Acetyl(3-(2-(2-aminopyrimidin-5-yl)-4-morpholinopyrido[3,2-d]pyrimidin-7-yl)phenyl)carbamoyl)oxy)methyl acetate (Scheme VI) (Prodrug of Example 3)

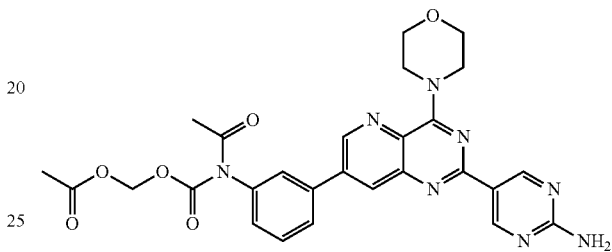

Step 1: Chloromethyl (3-(2-chloro-4-morpholinopyrido[3,2-d]pyrimidin-7-yl)phenyl)-carbamate

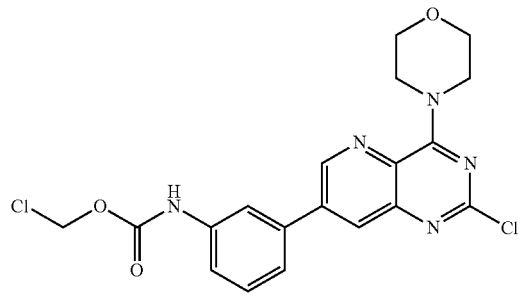 [SMILES: O=C(Nc1cccc(-c2cnc3c(N4CCOCC4)nc(Cl)nc3c2)c1)OCCl]

To a 100 mL round bottom flask, 3-(2-chloro-4-morpholinopyrido[3,2-d]pyrimidin-7-yl)aniline (1.0 g, 0.0029 mol), 1,8-bis(dimethylamino)naphthalene (0.626 g, 0.0029 mol) and chloroform (60 mL) were added. The reaction mixture was cooled in an ice bath. To the same flask was added chloromethyl chloroformate (0.377 g, 0.0029 mol) and the mixture was stirred at room temperature for 3 hours. The reaction mixture was diluted with chloroform, washed with water and brine. The organic layer was dried over anhydrous sodium sulphate and evaporated under reduced pressure to provide the title compound as a yellow solid (1.25 g, 98.4%). $^1$H NMR (400 MHz, DMSO-d$_6$): δ 10.41 (br s, 1H), 9.07 (d, J=2.0 Hz, 1H), 8.22 (d, J=2.0 Hz, 1H), 7.94 (br s, 1H), 7.62-7.51 (m, 3H), 6.01 (s, 2H), 4.98-3.98 (br s, 4H), 3.81 (t, J=4.4

Hz, 4H). LC-MS (ESI): Calculated mass: 433.07; Observed mass [M+H]+: 433.8 (RT: 1.63 min).

Step 2: (((3-(2-Chloro-4-morpholinopyrido[3,2-d]pyrimidin-7-yl)phenyl)carbamoyl)oxy)-methyl acetate

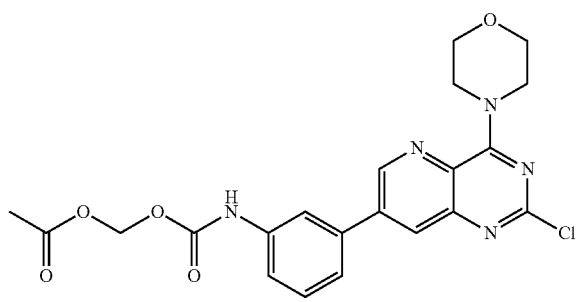 [SMILES: CC(=O)OCOC(=O)Nc1cccc(-c2cnc3c(N4CCOCC4)nc(Cl)nc3c2)c1]

To a 100 mL round bottom flask, chloromethyl(3-(2-chloro-4-morpholinopyrido[3,2-d]pyrimidin-7-yl)phenyl)carbamate (1.2 g, 0.0028 mol) and acetic acid (20 mL) were added. To the reaction mixture was added mercuric acetate (0.968 g, 0.0031 mol) and the mixture was stirred at room temperature for 4 hours. The reaction mixture was diluted with chloroform and washed with water. The organic layer was washed with brine, dried over anhydrous sodium sulphate and evaporated under reduced pressure to provide the title compound as a yellow solid (1.1 g, 87%). $^1$H NMR (400 MHz, DMSO-$d_6$): δ 10.25 (br s, 1H), 9.05 (d, J=1.6 Hz, 1H), 8.19 (d, J=1.2 Hz, 1H), 7.93 (s, 1H), 7.59-7.48 (m, 3H), 5.77 (s, 2H), 4.64-3.98 (br s, 4H), 3.81 (t, J=4.4 Hz, 4H), 2.10 (s, 3H). LC-MS (ESI): Calculated mass: 457.12; Observed mass [M+H]+: 457.9 (RT: 1.57 min).

Step 3: ((Acetyl(3-(2-chloro-4-morpholinopyrido[3,2-d]pyrimidin-7-yl)phenyl)-carbamoyl)-oxy)methyl acetate

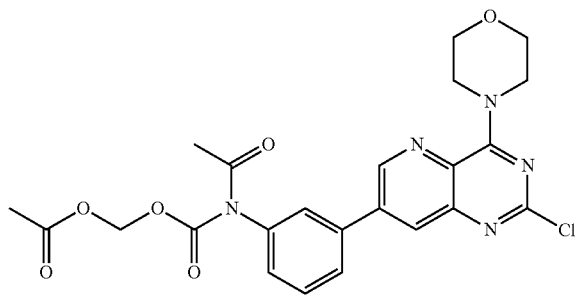 [SMILES: CC(=O)OCOC(=O)N(C(C)=O)c1cccc(-c2cnc3c(N4CCOCC4)nc(Cl)nc3c2)c1]

To a 100 mL round bottom flask, (((3-(2-chloro-4-morpholinopyrido[3,2-d]pyrimidin-7-yl)phenyl)carbamoyl)oxy)methyl acetate (1.0 g, 0.0022 mol), triethylamine (0.6 mL, 0.0044 mol) N,N-dimethylpyridin-4-amine (0.0054 g, 0.000044 mol) and DCM (25 mL) were added. To the same flask was added acetic anhydride (2.67 g, 0.0264 mol). The reaction was continued at room temperature for 18 hour. Additional acetic anhydride (1.63 g, 0.0161 mol) was then added to the reaction mixture. The reaction was further continued at room temperature for 24 hours. The reaction mixture was diluted with DCM. The organic layer was washed with water, brine, dried over anhydrous sodium sulphate and evaporated under reduced pressure to provide the title compound (0.97 g, 83%). $^1$H NMR (400 MHz, DMSO-$d_6$): δ 9.14 (d, J=2.0 Hz, 1H), 8.32 (d, J=2.0 Hz, 1H), 7.95 (d, J=8.0 Hz, 1H), 7.87 (s, 1H), 7.61 (t, J=7.6 Hz, 1H), 7.53 (dd, J'=7.6 Hz, J''=0.8 Hz, 1H), 5.66 (s, 2H), 4.65-3.97 (br s, 4H), 3.80 (t, J=4.8 Hz, 4H), 2.55 (s, 3H), 2.03 (s, 3H). LC-MS (ESI): Calculated mass: 499.13; Observed mass [M+H]+: 499.8 (RT: 1.52 min).

Step 4: ((Acetyl(3-(2-(2-aminopyrimidin-5-yl)-4-morpholinopyrido[3,2-d]pyrimidin-7-yl)-phenyl)carbamoyl)oxy)methyl acetate

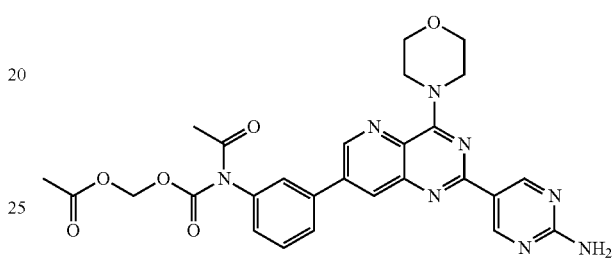

To a 50 mL sealed tube, ((acetyl(3-(2-chloro-4-morpholinopyrido[3,2-d]pyrimidin-7-yl)phenyl)carbamoyl)oxy)methyl acetate (0.96 g, 0.0019 mol), 5-(4,4,5,5-tetramethyl-1,3,2-dioxaborolan-2-yl)pyrimidin-2-amine (0.852 g, 0.0038 mol), potassium phosphate tribasic (0.81 g, 0.0038 mol), 1,4-dioxane (45 mL), and water (4 mL) were added. The reaction mixture was degassed with N$_2$ for 5-10 minutes. To the same reaction mixture, Pd(PPh$_3$)$_4$ (0.11 g, 0.000096 mol) was added and the mixture was degassed with N$_2$ for 5-10 min. The reaction mixture was stirred at 82° C. for 30 minutes. The volatiles were evaporated to provide a residue. The residue was dissolved in chloroform. The chloroform layer was washed with water, brine, dried over anhydrous sodium sulphate and evaporated under reduced pressure to provide a crude solid. The crude solid was purified by flash column chromatography (0-2% methanol in chloroform) to provide a solid. The solid was washed with methanol to provide the title compound as a light yellow solid (0.4 g, 40%). $^1$H NMR (400 MHz, DMSO-$d_6$): δ 9.18 (s, 2H), 9.08 (s, 1H), 8.35 (s, 1H), 7.98 (d, J=8.0 Hz, 1H), 7.91 (br s, 1H), 7.62 (t, J=7.6 Hz, 1H), 7.35 (d, J=7.6 Hz, 1H), 7.20 (br s, 2H), 5.68 (s, 2H), 4.52 (br s, 4H), 3.84 (t, J=4.0 Hz, 4H), 2.57 (s, 3H), 2.06 (s, 3H). LC-MS (ESI): Calculated mass: 558.20; Observed mass [M+H]+: 558.8 (RT: 0.40 min).

Examples 1 to 126

Additional compounds listed in Table 1 were prepared in a similar manner, using the methods described for Examples 1 to 11 and in the Schemes I to VI. In some cases, compounds were isolated and characterized as the trifluoroacetate or hydrochloride salt. LC-MS characterization data for Examples 1 to 126 are tabulated in Table 2. Further additional compounds of the invention are prepared in a similar manner to the methods described for the Examples 1 to 126 and in Schemes I to VI.

TABLE 1

| Ex. No. | Structure | Structure Name | Synthetic Method |
|---|---|---|---|
| 1 | 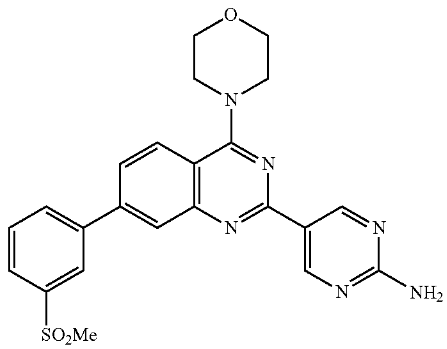 [SMILES: CS(=O)(=O)c1cccc(-c2ccc3c(N4CCOCC4)nc(-c4cnc(N)nc4)nc3c2)c1] | 5-(7-(3 (methylsulfonyl)phenyl)-4-morpholinoquinazolin-2-yl)pyrimidin-2-amine | I |
| 2 | 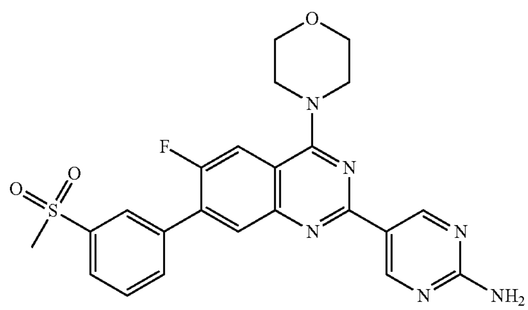 [SMILES: CS(=O)(=O)c1cccc(-c2cc3nc(-c4cnc(N)nc4)nc(N4CCOCC4)c3cc2F)c1] | 5-(6-fluoro-7-(3-(methylsulfonyl)phenyl)-4-morpholinoquinazolin-2-yl)pyrimidin-2-amine | I |
| 3 | 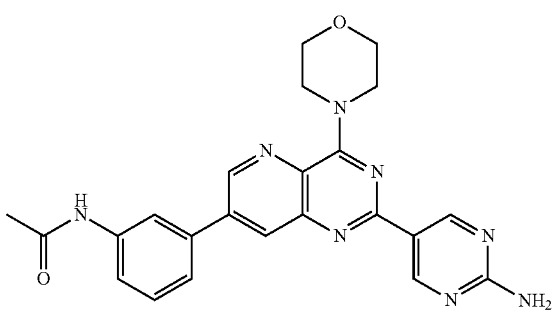 | N-(3-(2-(2-aminopyrimidin-5-yl)-4-morpholinopyrido[3,2-d]pyrimidin-7-yl)phenyl)acetamide | II |
| 4 | 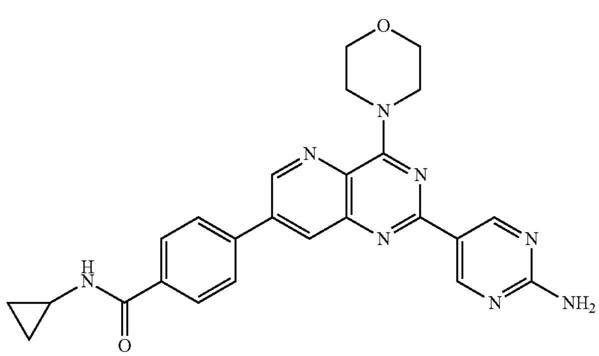 [SMILES: Nc1ncc(-c2nc(N3CCOCC3)c3ncc(-c4ccc(C(=O)NC5CC5)cc4)cc3n2)cn1] | 4-(2-(2-aminopyrimidin-5-yl)-4-morpholinopyrido[3,2-d]pyrimidin-7-yl)-N-cyclopropylbenzamide | III |

TABLE 1-continued

| Ex. No. | Structure | Structure Name | Synthetic Method |
|---|---|---|---|
| 5 | 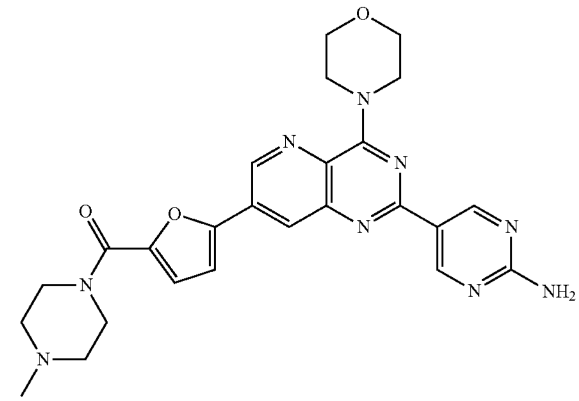 [SMILES: CN1CCN(C(=O)c2ccc(-c3cnc4c(N5CCOCC5)nc(-c5cnc(N)nc5)nc4c3)o2)CC1] | (5-(2-(2-aminopyrimidin-5-yl)-4-morpholinopyrido[3,2-d]pyrimidin-7-yl)furan-2-yl)(4-methylpiperazin-1-yl)methanone | III |
| 6 | 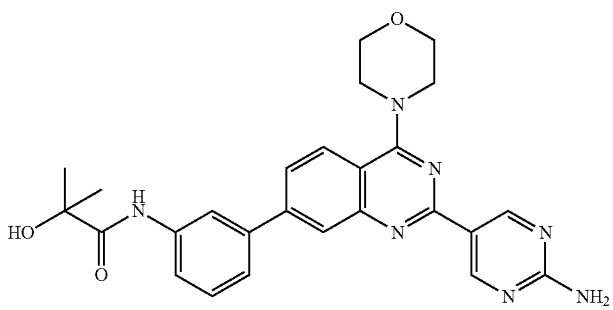 [SMILES: CC(C)(O)C(=O)Nc1cccc(-c2ccc3c(N4CCOCC4)nc(-c4cnc(N)nc4)nc3c2)c1] | N-(3-(2-(2-amino-pyrimidin-5-yl)-4-morpholinoquinazolin-7-yl)phenyl)-2-hydroxy-2-methylpropanamide | IVa |
| 7 | 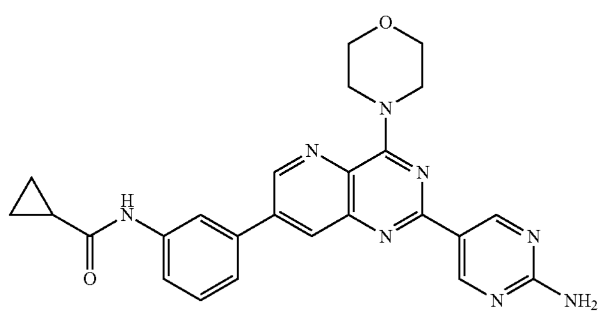 | N-(3-(2-(2-amino-pyrimidin-5-yl)-4-morpholinopyrido[3,2-d]pyrimidin-7-yl)-phenyl)cyclopropane-carboxamide | IVa |
| 8 | 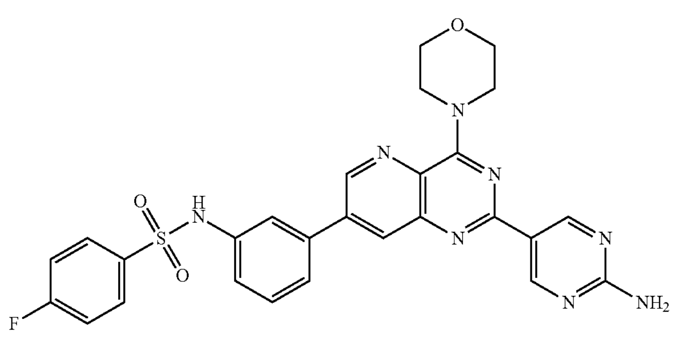 [SMILES: Nc1ncc(-c2nc(N3CCOCC3)c3ncc(-c4cccc(NS(=O)(=O)c5ccc(F)cc5)c4)cc3n2)cn1] | N-(3-(2-(2-amino-pyrimidin-5-yl)-4-morpholinopyrido[3,2-d]pyrimidin-7-yl)phenyl)-4-fluoro-benzenesulfonamide | IVb |

TABLE 1-continued

| Ex. No. | Structure | Structure Name | Synthetic Method |
|---|---|---|---|
| 9 | 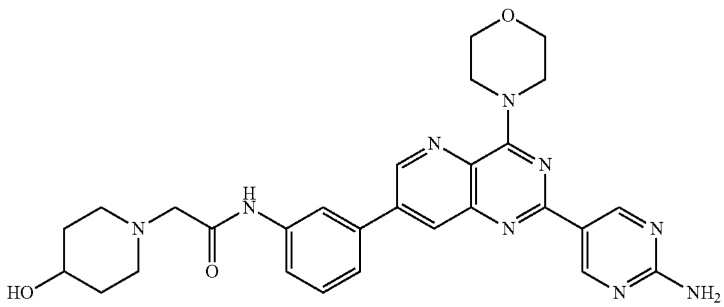 [SMILES: Nc1ncc(-c2nc(N3CCOCC3)c3ncc(-c4cccc(NC(=O)CN5CCC(O)CC5)c4)cc3n2)cn1] | N-(3-(2-(2-amino-pyrimidin-5-yl)-4-morpholinopyrido[3,2-d]-pyrimidin-7-yl)phenyl)-2-(4-hydroxypiperidin-1-yl)acetamide | IVc |
| 10 | 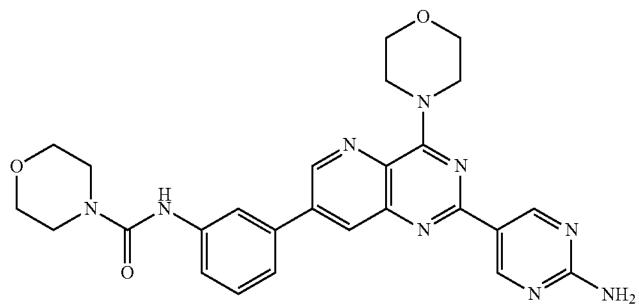 | N-(3-(2-(2-amino-pyrimidin-5-yl)-4-morpholinopyrido[3,2-d]pyrimidin-7-yl)-phenyl)morpholine-4-carboxamide | IVd |
| 11 | 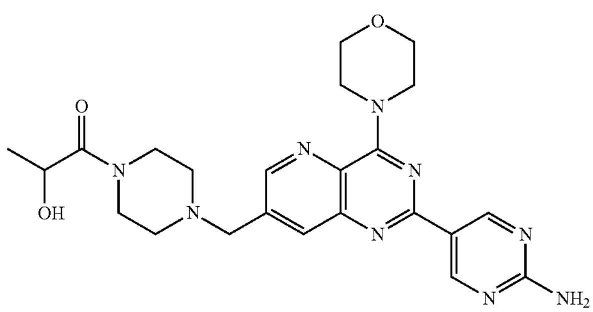 [SMILES: CC(O)C(=O)N1CCN(Cc2cnc3c(N4CCOCC4)nc(-c4cnc(N)nc4)nc3c2)CC1] | 1-(4-((2-(2-amino-pyrimidin-5-yl)-4-morpholinopyrido[3,2-d]pyrimidin-7-yl)-methyl)piperazin-1-yl)-2-hydroxypropan-1-one | V |
| 12 | 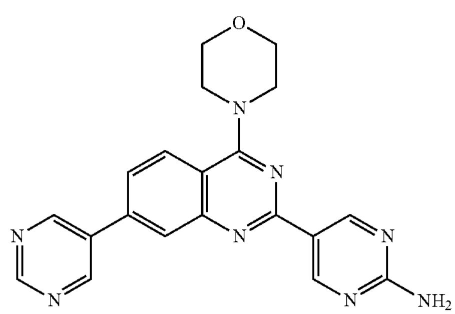 [SMILES: Nc1ncc(-c2nc(N3CCOCC3)c3ccc(-c4cncnc4)cc3n2)cn1] | 5-(4-morpholino-7-(pyrimidin-5-yl)quinazolin-2-yl)pyrimidin-2-amine | I |
| 13 | 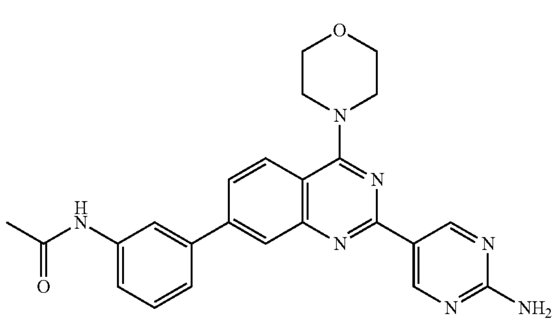 | N-(3-(2-(2-amino-pyrimidin-5-yl)-4-morpholinoquinazolin-7-yl)phenyl)acetamide | I |

TABLE 1-continued

| Ex. No. | Structure | Structure Name | Synthetic Method |
|---|---|---|---|
| 14 | 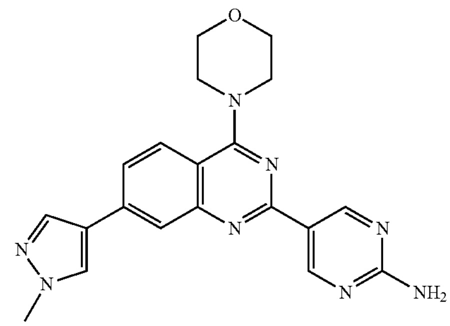 [SMILES: Cn1cc(-c2ccc3c(N4CCOCC4)nc(-c4cnc(N)nc4)nc3c2)cn1] | 5-(7-(1-methyl-1H-pyrazol-4-yl)-4-morpholinoquinazolin-2-yl)pyrimidin-2-amine | I |
| 15 | 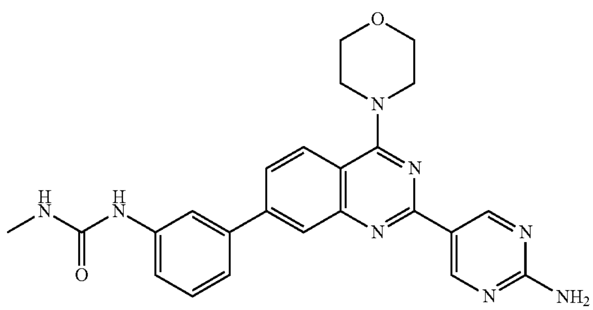 | 1-(3-(2-(2-amino-pyrimidin-5-yl)-4-morpholinoquinazolin-7-yl)phenyl)-3-methylurea | I |
| 16 | 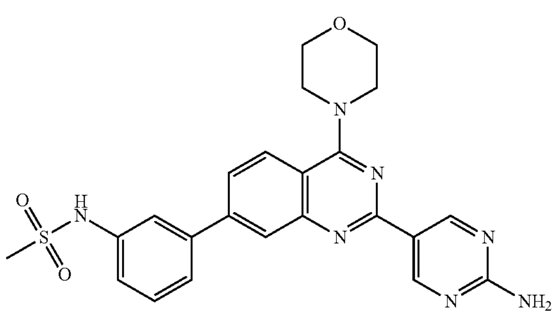 [SMILES: CS(=O)(=O)Nc1cccc(-c2ccc3c(N4CCOCC4)nc(-c4cnc(N)nc4)nc3c2)c1] | N-(3-(2-(2-amino-pyrimidin-5-yl)-4-morpholinoquinazolin-7-yl)phenyl)methane-sulfonamide | I |
| 17 | 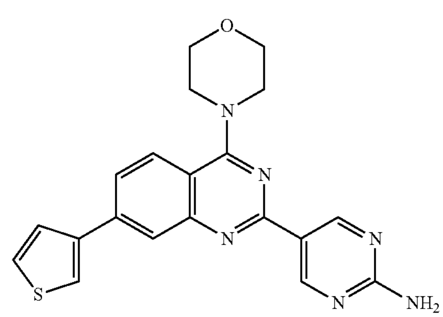 [SMILES: Nc1ncc(-c2nc(N3CCOCC3)c3ccc(-c4ccsc4)cc3n2)cn1] | 5-(4-morpholino-7-(thiophen-3-yl)-quinazolin-2-yl)-pyrimidin-2-amine | I |

TABLE 1-continued

| Ex. No. | Structure | Structure Name | Synthetic Method |
|---|---|---|---|
| 18 | 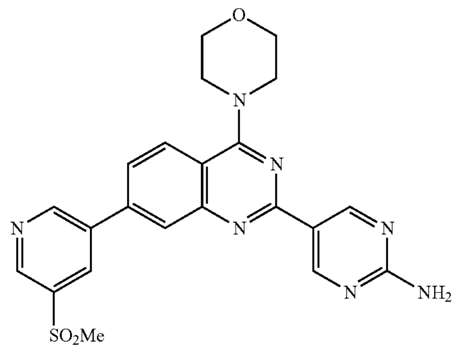 [SMILES: CS(=O)(=O)c1cncc(-c2ccc3c(N4CCOCC4)nc(-c4cnc(N)nc4)nc3c2)c1] | 5-(7-(5-(methyl-sulfonyl)pyridin-3-yl)-4-morpholinoquinazolin-2-yl)pyrimidin-2-amine | I |
| 19 | 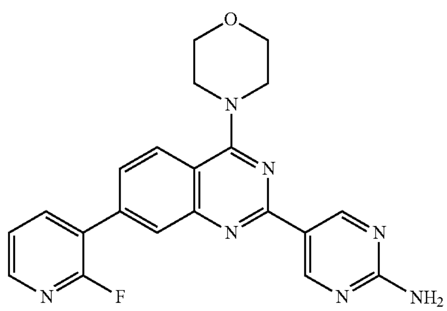 [SMILES: Nc1ncc(-c2nc(N3CCOCC3)c3ccc(-c4cccnc4F)cc3n2)cn1] | 5-(7-(2-fluoropyridin-3-yl)-4-morpholino-quinazolin-2-yl)-pyrimidin-2-amine | I |
| 20 | 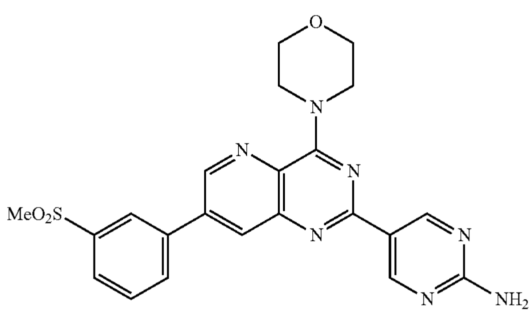 [SMILES: CS(=O)(=O)c1cccc(-c2cnc3c(N4CCOCC4)nc(-c4cnc(N)nc4)nc3c2)c1] | 5-(7-(3-(methyl-sulfonyl)phenyl)-4-morpholinopyrido[3,2-d]-pyrimidin-2-yl)pyrimidin-2-amine | II |
| 21 | 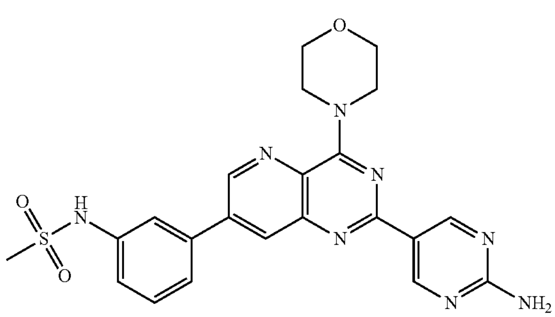 [SMILES: CS(=O)(=O)Nc1cccc(-c2cnc3c(N4CCOCC4)nc(-c4cnc(N)nc4)nc3c2)c1] | N-(3-(2-(2-amino-pyrimidin-5-yl)-4-morpholinopyrido[3,2-d]-pyrimidin-7-yl)phenyl)-methanesulfonamide | II |

TABLE 1-continued

| Ex. No. | Structure | Structure Name | Synthetic Method |
|---|---|---|---|
| 22 | 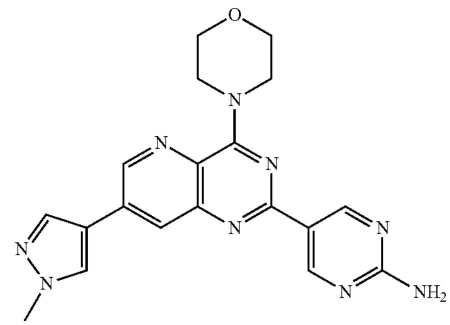 [SMILES: Cn1cc(-c2cnc3c(N4CCOCC4)nc(-c4cnc(N)nc4)nc3c2)cn1] | 5-(7-(1-methyl-1H-pyrazol-4-yl)-4-morpholinopyrido[3,2-d]-pyrimidin-2-yl)pyrimidin-2-amine | II |
| 23 | 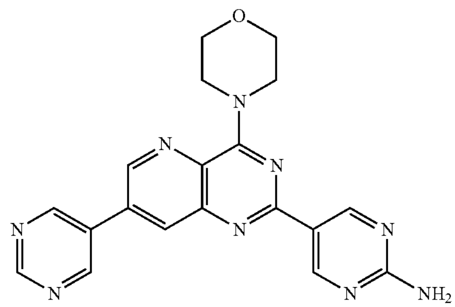 | 5-(4-morpholino-7-(pyrimidin-5-yl)-pyrido[3,2-d]pyrimidin-2-yl)pyrimidin-2-amine | II |
| 24 | 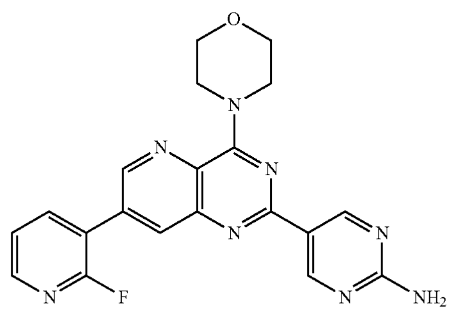 [SMILES: Nc1ncc(-c2nc(N3CCOCC3)c3ncc(-c4cccnc4F)cc3n2)cn1] | 5-(7-(2-fluoropyridin-3-yl)-4-morpholino-pyrido[3,2-d]pyrimidin-2-yl)pyrimidin-2-amine | II |
| 25 | 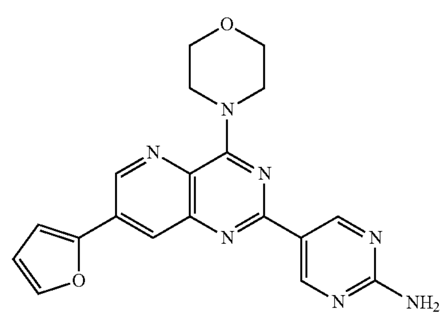 [SMILES: Nc1ncc(-c2nc(N3CCOCC3)c3ncc(-c4ccco4)cc3n2)cn1] | 5-(7-(furan-2-yl)-4-morpholinopyrido[3,2-d]-pyrimidin-2-yl)pyrimidin-2-amine | II |
| 26 | 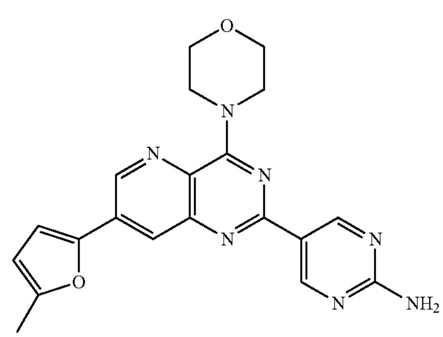 [SMILES: Cc1ccc(-c2cnc3c(N4CCOCC4)nc(-c4cnc(N)nc4)nc3c2)o1] | 5-(7-(5-methylfuran-2-yl)-4-morpholino-pyrido[3,2-d]pyrimidin-2-yl)pyrimidin-2-amine | II |

TABLE 1-continued

| Ex. No. | Structure | Structure Name | Synthetic Method |
|---|---|---|---|
| 27 | 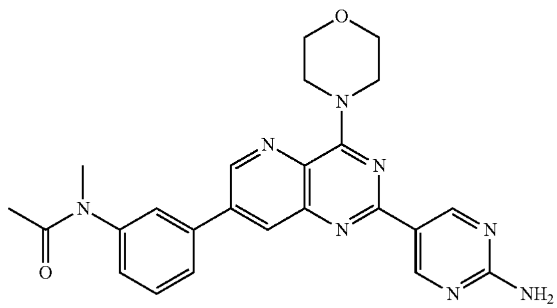 [SMILES: CC(=O)N(C)c1cccc(-c2cnc3c(N4CCOCC4)nc(-c4cnc(N)nc4)nc3c2)c1] | N-(3-(2-(2-amino-pyrimidin-5-yl)-4-morpholinopyrido[3,2-d]-pyrimidin-7-yl)phenyl)-N-methylacetamide | II |
| 28 | 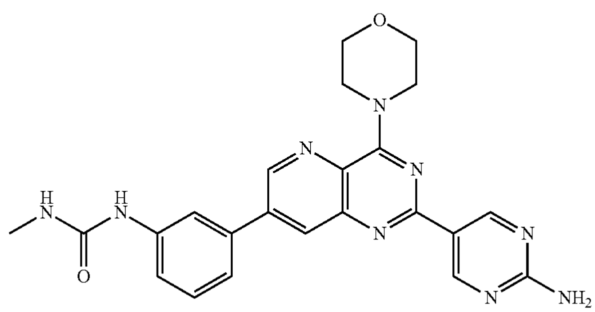 [SMILES: CNC(=O)Nc1cccc(-c2cnc3c(N4CCOCC4)nc(-c4cnc(N)nc4)nc3c2)c1] | 1-(3-(2-(2-amino-pyrimidin-5-yl)-4-morpholinopyrido[3,2-d]pyrimidin-7-yl)phenyl)-3-methylurea | II |
| 29 | 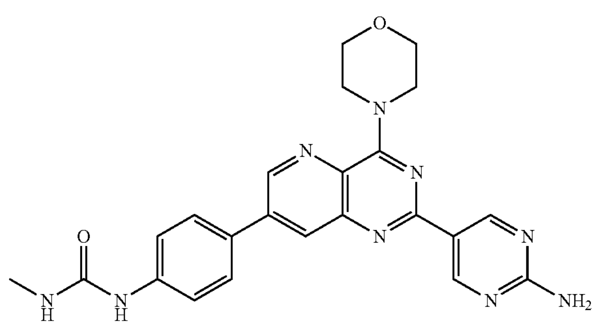 [SMILES: CNC(=O)Nc1ccc(-c2cnc3c(N4CCOCC4)nc(-c4cnc(N)nc4)nc3c2)cc1] | 1-(4-(2-(2-amino-pyrimidin-5-yl)-4-morpholinopyrido[3,2-d]pyrimidin-7-yl)phenyl)-3-methylurea | II |
| 30 | 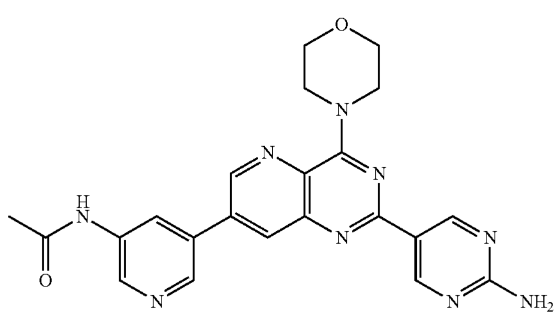 | N-(5-(2-(2-amino-pyrimidin-5-yl)-4-morpholinopyrido[3,2-d]pyrimidin-7-yl)pyridin-3-yl)acetamide | II |
| 31 | 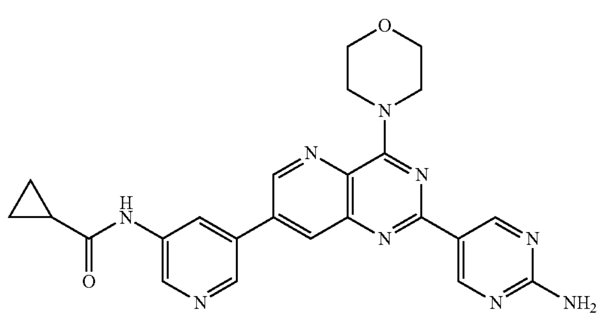 [SMILES: Nc1ncc(-c2nc(N3CCOCC3)c3ncc(-c4cncc(NC(=O)C5CC5)c4)cc3n2)cn1] | N-(5-(2-(2-amino-pyrimidin-5-yl)-4-morpholinopyrido[3,2-d]pyrimidin-7-yl)pyridin-3-yl)cyclopropane-carboxamide | II |

TABLE 1-continued

| Ex. No. | Structure | Structure Name | Synthetic Method |
|---|---|---|---|
| 32 | 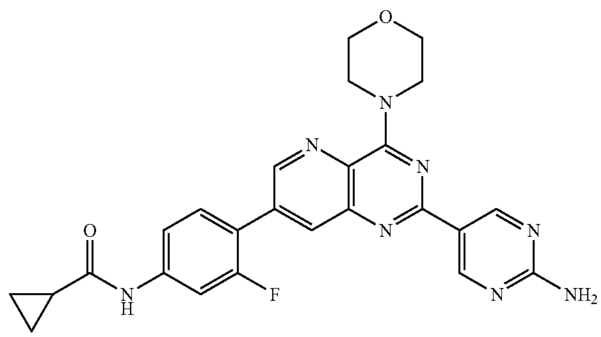 [SMILES: Nc1ncc(-c2nc(N3CCOCC3)c3ncc(-c4ccc(NC(=O)C5CC5)cc4F)cc3n2)cn1] | N-(4-(2-(2-amino-pyrimidin-5-yl)-4-morpholinopyrido[3,2-d]pyrimidin-7-yl)-3-fluorophenyl)cyclo-propanecarboxamide | II |
| 33 | 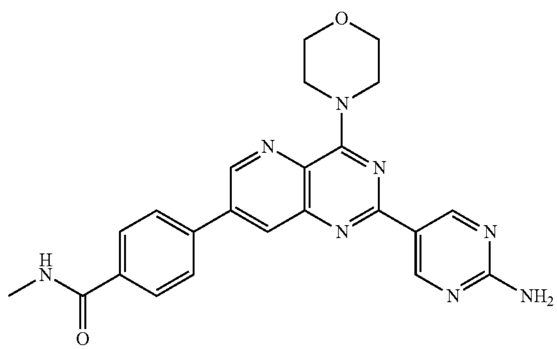 [SMILES: CNC(=O)c1ccc(-c2cnc3c(N4CCOCC4)nc(-c4cnc(N)nc4)nc3c2)cc1] | 4-(2-(2-aminopyrimidin-5-yl)-4-morpholinopyrido[3,2-d]pyrimidin-7-yl)-N-methylbenzamide | III |
| 34 | 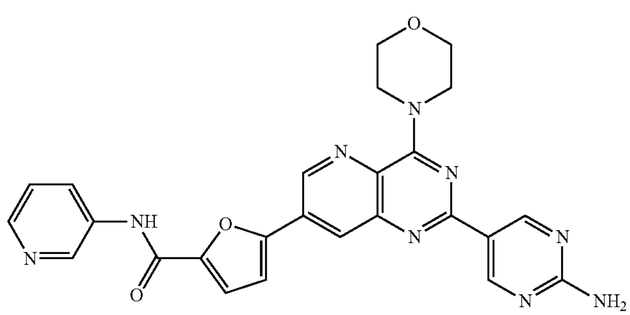 [SMILES: Nc1ncc(-c2nc(N3CCOCC3)c3ncc(-c4ccc(C(=O)Nc5cccnc5)o4)cc3n2)cn1] | 5-(2-(2-aminopyrimidin-5-yl)-4-morpholino-pyrido[3,2-d]pyrimidin-7-yl)-N-(pyridin-3-yl)furan-2-carboxamide | III |
| 35 | 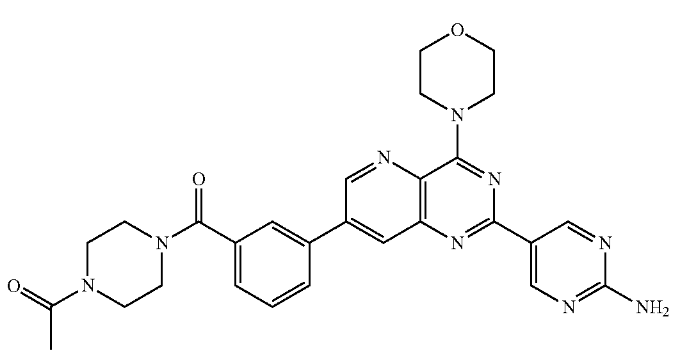 [SMILES: CC(=O)N1CCN(C(=O)c2cccc(-c3cnc4c(N5CCOCC5)nc(-c5cnc(N)nc5)nc4c3)c2)CC1] | 1-(4-(3-(2-(2-amino-pyrimidin-5-yl)-4-morpholinopyrido[3,2-d]-pyrimidin-7-yl)benzoyl)-piperazin-1-yl)ethanone | III |

TABLE 1-continued

| Ex. No. | Structure | Structure Name | Synthetic Method |
|---|---|---|---|
| 36 | 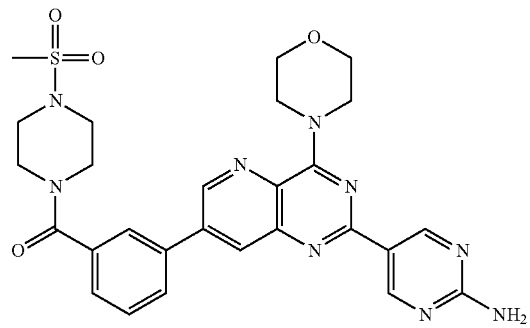 [SMILES: CS(=O)(=O)N1CCN(C(=O)c2cccc(-c3cnc4c(N5CCOCC5)nc(-c5cnc(N)nc5)nc4c3)c2)CC1] | (3-(2-(2-aminopyrimidin-5-yl)-4-morpholino-pyrido[3,2-d]pyrimidin-7-yl)phenyl)(4-(methyl-sulfonyl)piperazin-1-yl)-methanone | III |
| 37 | 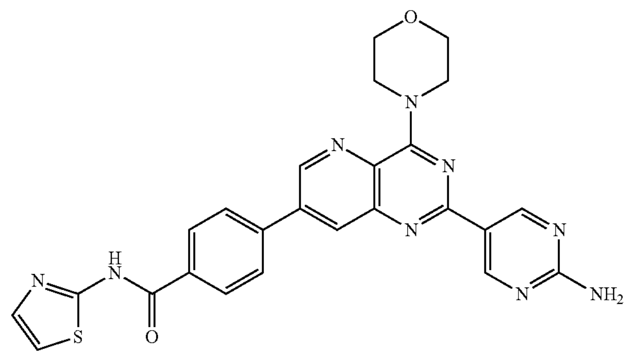 [SMILES: Nc1ncc(-c2nc(N3CCOCC3)c3ncc(-c4ccc(C(=O)Nc5nccs5)cc4)cc3n2)cn1] | 4-(2-(2-aminopyrimidin-5-yl)-4-morpholino-pyrido[3,2-d]pyrimidin-7-yl)-N-(thiazol-2-yl)-benzamide | III |
| 38 | 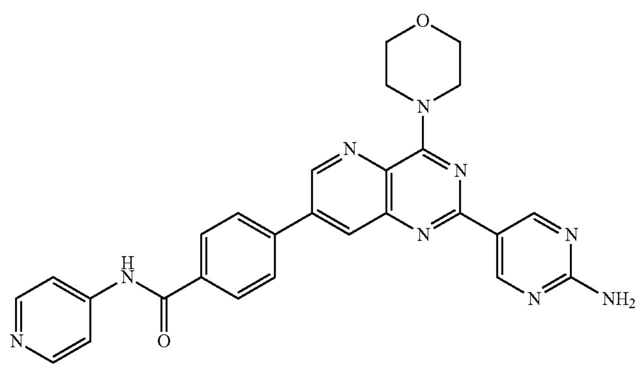 [SMILES: Nc1ncc(-c2nc(N3CCOCC3)c3ncc(-c4ccc(C(=O)Nc5ccncc5)cc4)cc3n2)cn1] | 4-(2-(2-aminopyrimidin-5-yl)-4-morpholino-pyrido[3,2-d]pyrimidin-7-yl)-N-(pyridin-4-yl)-benzamide | III |
| 39 | 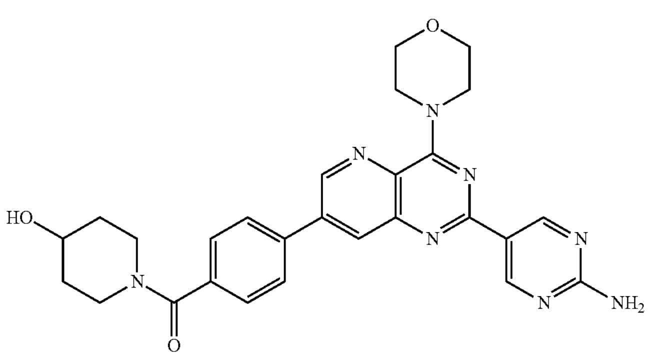 [SMILES: Nc1ncc(-c2nc(N3CCOCC3)c3ncc(-c4ccc(C(=O)N5CCC(O)CC5)cc4)cc3n2)cn1] | (4-(2-(2-aminopyrimidin-5-yl)-4-morpholino-pyrido[3,2-d]pyrimidin-7-yl)phenyl)(4-hydroxy-piperidin-1-yl)methanone | III |

TABLE 1-continued

| Ex. No. | Structure | Structure Name | Synthetic Method |
|---|---|---|---|
| 40 | 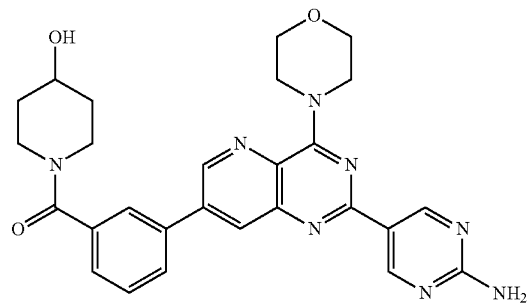 [SMILES: Nc1ncc(-c2nc(N3CCOCC3)c3ncc(-c4cccc(C(=O)N5CCC(O)CC5)c4)cc3n2)cn1] | (3-(2-(2-aminopyrimidin-5-yl)-4-morpholino-pyrido[3,2-d]pyrimidin-7-yl)phenyl)(4-hydroxy-piperidin-1-yl)methanone | III |
| 41 | 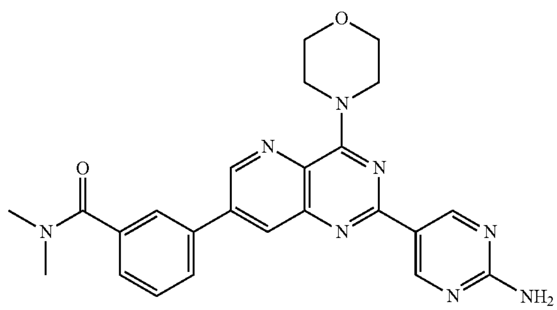 [SMILES: CN(C)C(=O)c1cccc(-c2cnc3c(N4CCOCC4)nc(-c4cnc(N)nc4)nc3c2)c1] | 3-(2-(2-aminopyrimidin-5-yl)-4-morpholinopyrido[3,2-d]pyrimidin-7-yl)-N,N-dimethylbenzamide | III |
| 42 | 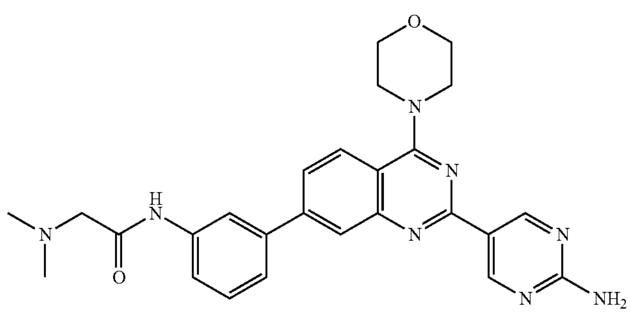 [SMILES: CN(C)CC(=O)Nc1cccc(-c2ccc3c(N4CCOCC4)nc(-c4cnc(N)nc4)nc3c2)c1] | N-(3-(2-(2-amino-pyrimidin-5-yl)-4-morpholinoquinazolin-7-yl)phenyl)-2-(dimethylamino)-acetamide | IVa |
| 43 | 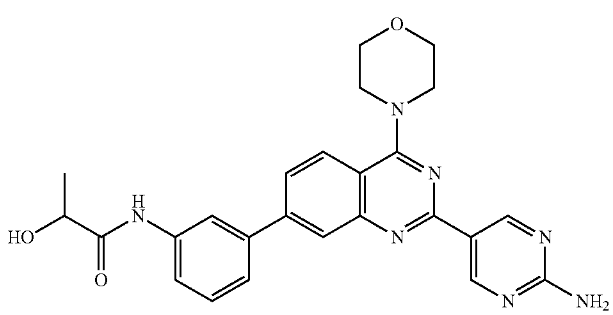 | N-(3-(2-(2-amino-pyrimidin-5-yl)-4-morpholinoquinazolin-7-yl)phenyl)-2-hydroxy-propanamide | IVa |
| 44 | 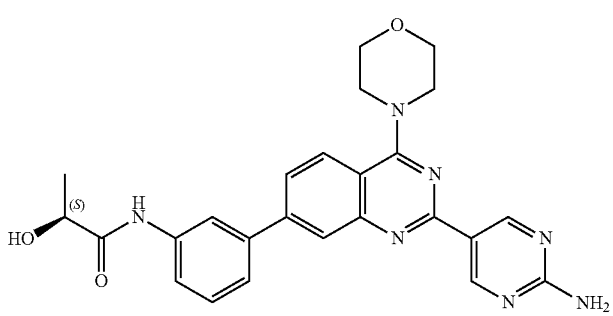 | (S)-N-(3-(2-(2-amino-pyrimidin-5-yl)-4-morpholinoquinazolin-7-yl)phenyl-2-hydroxy-propanamide | IVa |

TABLE 1-continued

| Ex. No. | Structure | Structure Name | Synthetic Method |
|---|---|---|---|
| 45 | 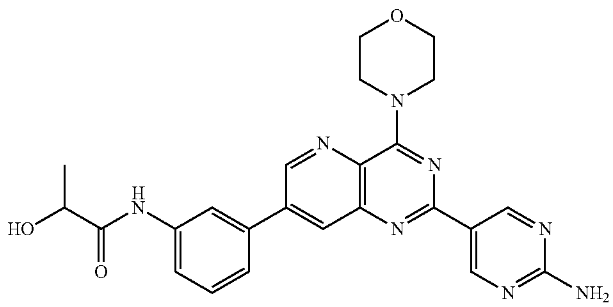 | N-(3-(2-(2-amino-pyrimidin-5-yl)-4-morpholinopyrido[3,2-d]pyrimidin-7-yl)phenyl)-2-hydroxypropanamide | IVa |
| 46 | 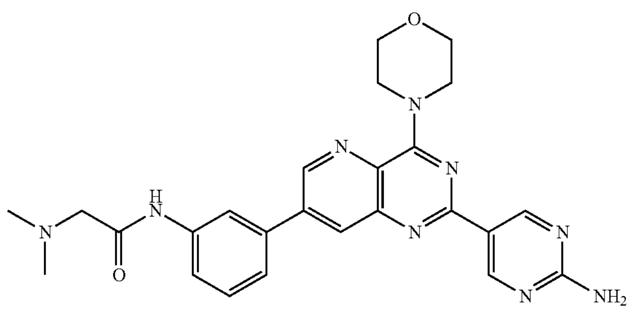 | N-(3-(2-(2-amino-pyrimidin-5-yl)-4-morpholinopyrido[3,2-d]pyrimidin-7-yl)phenyl)-2-(dimethylamino)-acetamide | IVa |
| 47 | 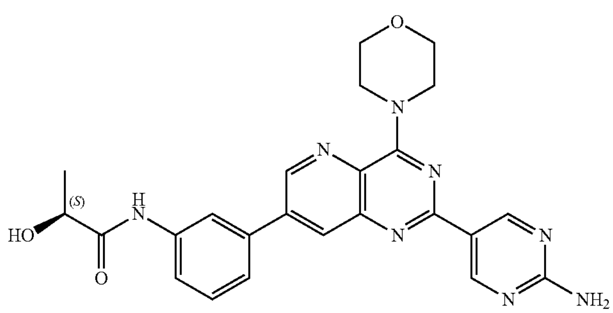 | (S)-N-(3-(2-(2-amino-pyrimidin-5-yl)-4-morpholinopyrido[3,2-d]pyrimidin-7-yl)phenyl)-2-hydroxypropanamide | IVa |
| 48 | 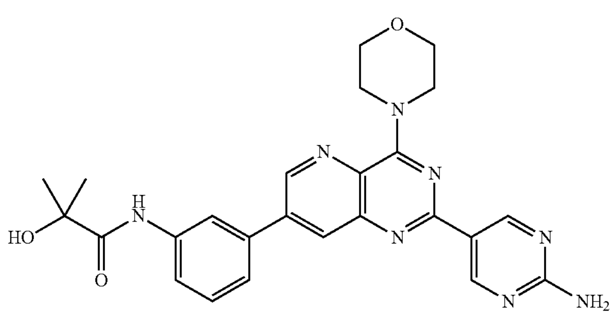 | N-(3-(2-(2-amino-pyrimidin-5-yl)-4-morpholinopyrido[3,2-d]pyrimidin-7-yl)phenyl)-2-hydroxy-2-methylpropanamide | IVa |
| 49 | 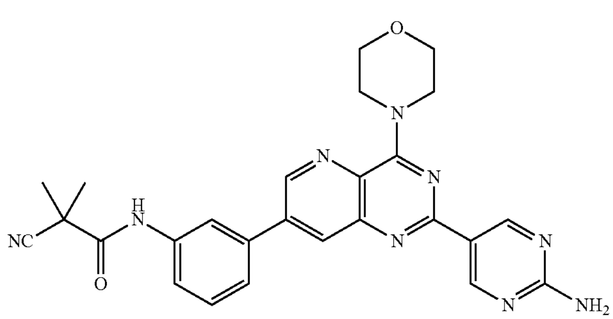 [SMILES: CC(C)(O)C(=O)Nc1cccc(-c2cnc3c(N4CCOCC4)nc(-c4cnc(N)nc4)nc3c2)c1] | N-(3-(2-(2-amino-pyrimidin-5-yl)-4-morpholinopyrido[3,2-d]pyrimidin-7-yl)phenyl)-2-cyano-2-methylpropanamide | IVa |

TABLE 1-continued

| Ex. No. | Structure | Structure Name | Synthetic Method |
|---|---|---|---|
| 50 | 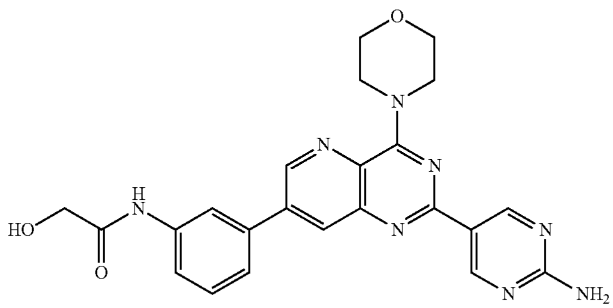 | N-(3-(2-(2-amino-pyrimidin-5-yl)-4-morpholinopyrido[3,2-d]pyrimidin-7-yl)phenyl)-2-hydroxyacetamide | IVa |
| 51 | 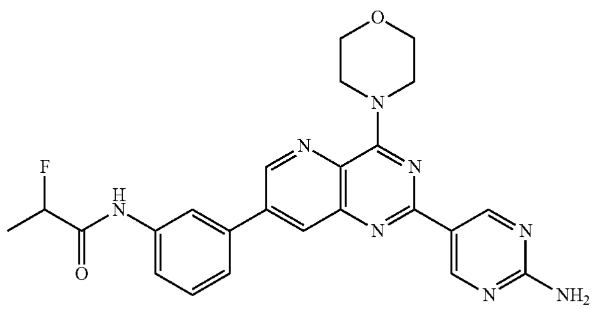 [SMILES: CC(F)C(=O)Nc1cccc(-c2cnc3c(N4CCOCC4)nc(-c4cnc(N)nc4)nc3c2)c1] | N-(3-(2-(2-amino-pyrimidin-5-yl)-4-morpholinopyrido[3,2-d]pyrimidin-7-yl)phenyl)-2-fluoropropanamide | IVa |
| 52 | 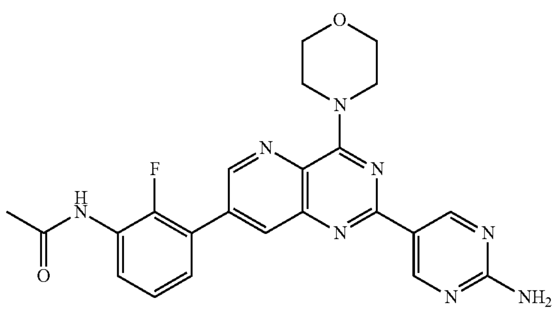 | N-(3-(2-(2-amino-pyrimidin-5-yl)-4-morpholinopyrido[3,2-d]pyrimidin-7-yl)-2-fluorophenyl)acetamide | IVa |
| 53 | 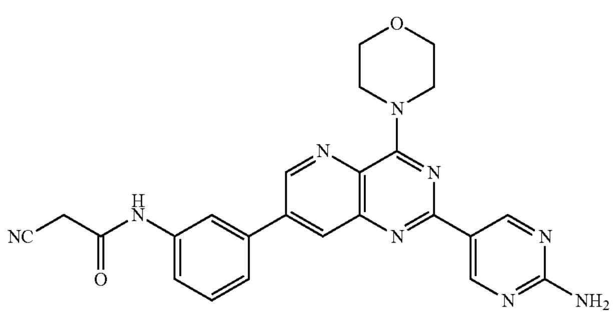 [SMILES: N#CCC(=O)Nc1cccc(-c2cnc3c(N4CCOCC4)nc(-c4cnc(N)nc4)nc3c2)c1] | N-(3-(2-(2-amino-pyrimidin-5-yl)-4-morpholinopyrido[3,2-d]pyrimidin-7-yl)phenyl)-2-cyanoacetamide | IVa |
| 54 | 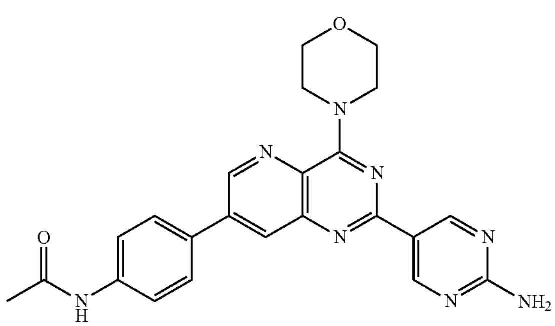 [SMILES: CC(=O)Nc1ccc(-c2cnc3c(N4CCOCC4)nc(-c4cnc(N)nc4)nc3c2)cc1] | N-(4-(2-(2-amino-pyrimidin-5-yl)-4-morpholinopyrido[3,2-d]pyrimidin-7-yl)phenyl)acetamide | IVa |

TABLE 1-continued

| Ex. No. | Structure | Structure Name | Synthetic Method |
|---|---|---|---|
| 55 | 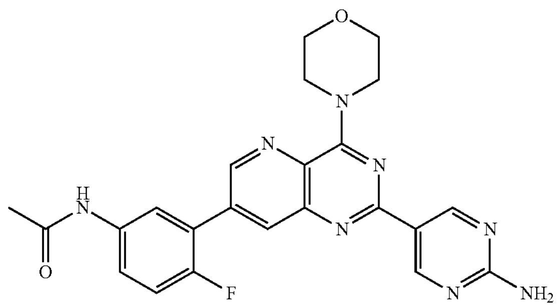 [SMILES: CC(=O)Nc1ccc(F)c(-c2cnc3c(N4CCOCC4)nc(-c4cnc(N)nc4)nc3c2)c1] | N-(3-(2-(2-amino-pyrimidin-5-yl)-4-morpholinopyrido[3,2-d]pyrimidin-7-yl)-4-fluorophenyl)acetamide | IVa |
| 56 | 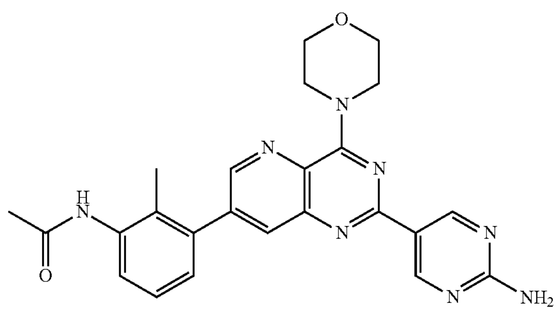 [SMILES: CC(=O)Nc1cccc(-c2cnc3c(N4CCOCC4)nc(-c4cnc(N)nc4)nc3c2)c1C] | N-(3-(2-(2-amino-pyrimidin-5-yl)-4-morpholinopyrido[3,2-d]pyrimidin-7-yl)-2-methylphenyl)acetamide | IVa |
| 57 | 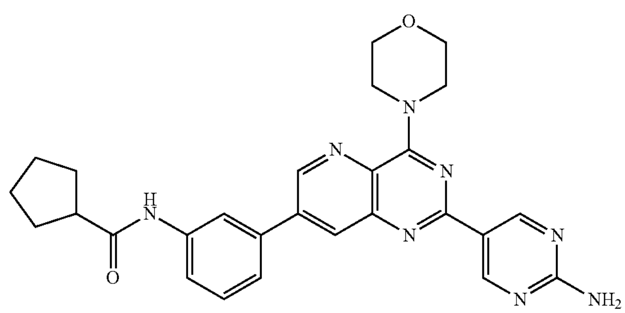 [SMILES: Nc1ncc(-c2nc(N3CCOCC3)c3ncc(-c4cccc(NC(=O)C5CCCC5)c4)cc3n2)cn1] | N-(3-(2-(2-amino-pyrimidin-5-yl)-4-morpholinopyrido[3,2-d]pyrimidin-7-yl)-phenyl)cyclopentane-carboxamide | IVa |
| 58 | 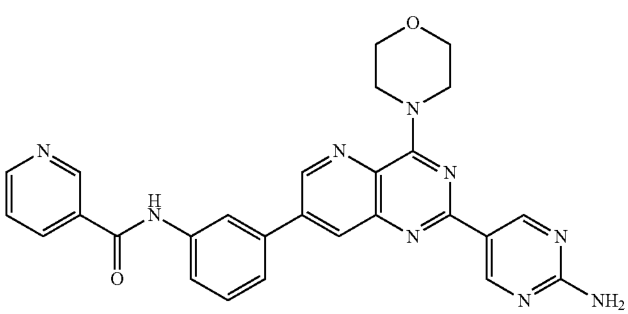 [SMILES: Nc1ncc(-c2nc(N3CCOCC3)c3ncc(-c4cccc(NC(=O)c5cccnc5)c4)cc3n2)cn1] | N-(3-(2-(2-amino-pyrimidin-5-yl)-4-morpholinopyrido[3,2-d]pyrimidin-7-yl)-phenyl)nicotinamide | IVa |
| 59 | 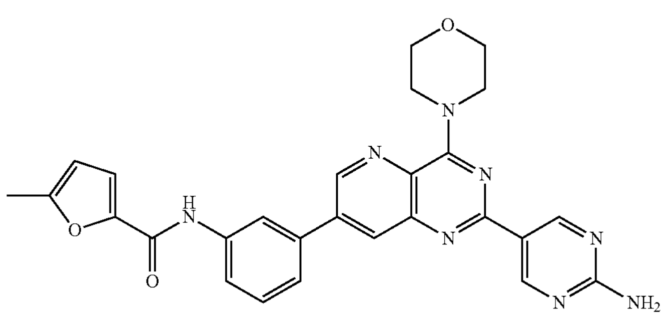 [SMILES: Cc1ccc(C(=O)Nc2cccc(-c3cnc4c(N5CCOCC5)nc(-c5cnc(N)nc5)nc4c3)c2)o1] | N-(3-(2-(2-amino-pyrimidin-5-yl)-4-morpholinopyrido[3,2-d]pyrimidin-7-yl)phenyl)-5-methylfuran-2-carboxamide | IVa |

TABLE 1-continued

| Ex. No. | Structure | Structure Name | Synthetic Method |
|---|---|---|---|
| 60 | 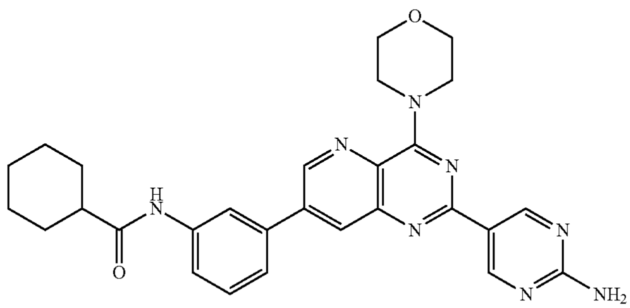 [SMILES: Nc1ncc(-c2nc(N3CCOCC3)c3ncc(-c4cccc(NC(=O)C5CCCCC5)c4)cc3n2)cn1] | N-(3-(2-(2-amino-pyrimidin-5-yl)-4-morpholinopyrido[3,2-d]pyrimidin-7-yl)-phenyl)cyclohexane-carboxamide | IVa |
| 61 | 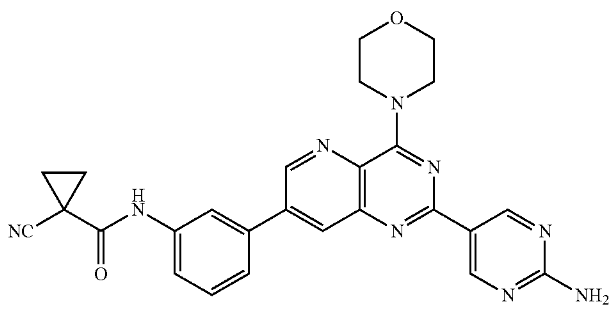 [SMILES: N#CC1(C(=O)Nc2cccc(-c3cnc4c(N5CCOCC5)nc(-c5cnc(N)nc5)nc4c3)c2)CC1] | N-(3-(2-(2-amino-pyrimidin-5-yl)-4-morpholinopyrido[3,2-d]pyrimidin-7-yl)phenyl)-1-cyanocyclopropane-carboxamide | IVa |
| 62 | 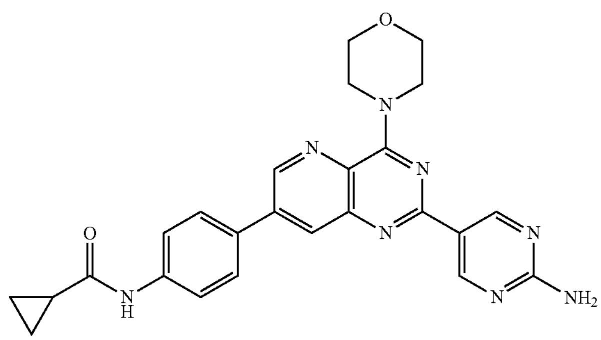 [SMILES: Nc1ncc(-c2nc(N3CCOCC3)c3ncc(-c4ccc(NC(=O)C5CC5)cc4)cc3n2)cn1] | N-(4-(2-(2-amino-pyrimidin-5-yl)-4-morpholinopyrido[3,2-d]pyrimidin-7-yl)-phenyl)cyclopropane-carboxamide | IVa |
| 63 | 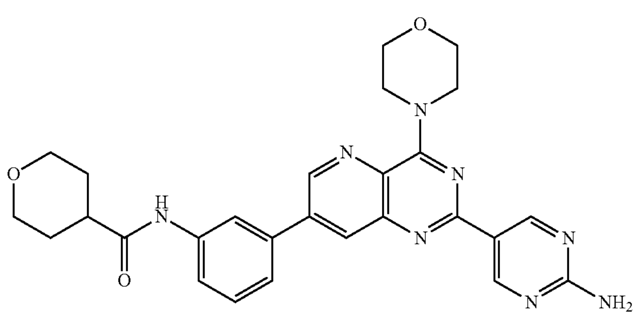 [SMILES: Nc1ncc(-c2nc(N3CCOCC3)c3ncc(-c4cccc(NC(=O)C5CCOCC5)c4)cc3n2)cn1] | N-(3-(2-(2-amino-pyrimidin-5-yl)-4-morpholinopyrido[3,2-d]pyrimidin-7-yl)-phenyl)tetrahydro-2H-pyran-4-carboxamide | IVa |
| 64 | 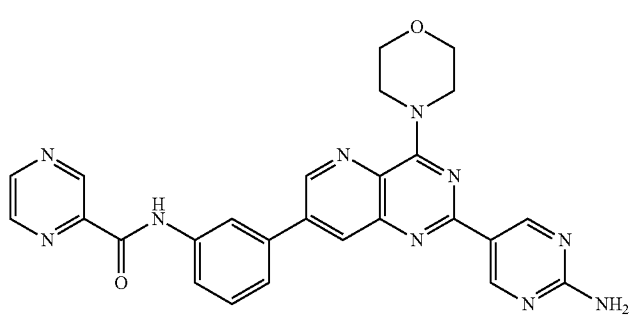 [SMILES: Nc1ncc(-c2nc(N3CCOCC3)c3ncc(-c4cccc(NC(=O)c5cnccn5)c4)cc3n2)cn1] | N-(3-(2-(2-amino-pyrimidin-5-yl)-4-morpholinopyrido[3,2-d]pyrimidin-7-yl)-phenyl)pyrazine-2-carboxamide | IVa |

TABLE 1-continued

| Ex. No. | Structure | Structure Name | Synthetic Method |
|---|---|---|---|
| 65 | 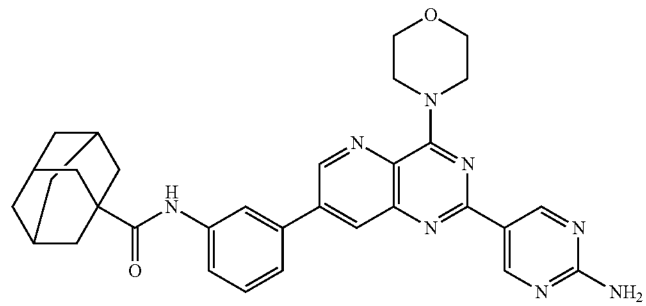 [SMILES: Nc1ncc(-c2nc(N3CCOCC3)c3ncc(-c4cccc(NC(=O)C56CC7CC(CC(C7)C5)C6)c4)cc3n2)cn1] | N-(3-(2-(2-amino-pyrimidin-5-yl)-4-morpholinopyrido[3,2-d]pyrimidin-7-yl)-phenyl)adamantane-1-carboxamide | IVa |
| 66 | 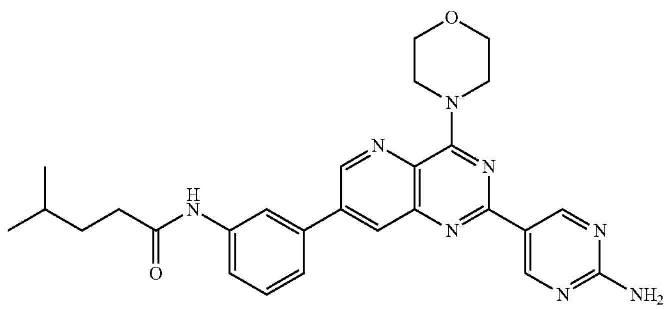 [SMILES: CC(C)CCC(=O)Nc1cccc(-c2cnc3c(N4CCOCC4)nc(-c4cnc(N)nc4)nc3c2)c1] | N-(3-(2-(2-amino-pyrimidin-5-yl)-4-morpholinopyrido[3,2-d]pyrimidin-7-yl)phenyl)-4-methylpentanamide | IVa |
| 67 | 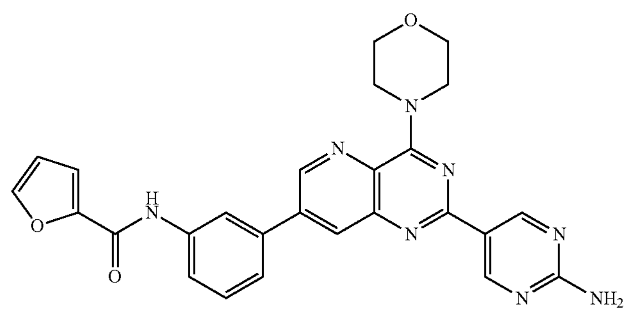 [SMILES: Nc1ncc(-c2nc(N3CCOCC3)c3ncc(-c4cccc(NC(=O)c5ccco5)c4)cc3n2)cn1] | N-(3-(2-(2-amino-pyrimidin-5-yl)-4-morpholinopyrido[3,2-d]pyrimidin-7-yl)-phenyl)furan-2-carboxamide | IVa |
| 68 | 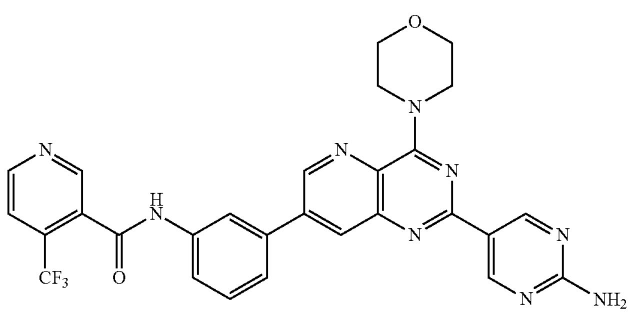 [SMILES: Nc1ncc(-c2nc(N3CCOCC3)c3ncc(-c4cccc(NC(=O)c5cnccc5C(F)(F)F)c4)cc3n2)cn1] | N-(3-(2-(2-amino-pyrimidin-5-yl)-4-morpholinopyrido[3,2-d]pyrimidin-7-yl)phenyl)-4-(trifluoromethyl)-nicotinamide | IVa |
| 69 | 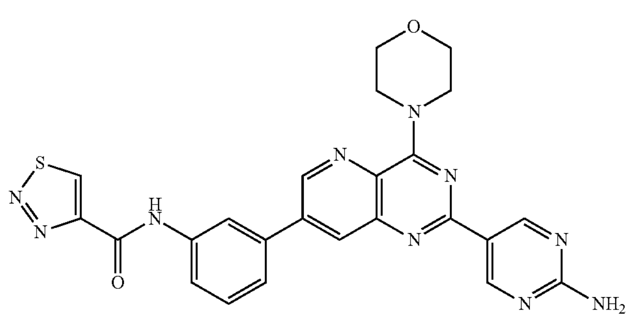 [SMILES: Nc1ncc(-c2nc(N3CCOCC3)c3ncc(-c4cccc(NC(=O)c5csnn5)c4)cc3n2)cn1] | N-(3-(2-(2-amino-pyrimidin-5-yl)-4-morpholinopyrido[3,2-d]pyrimidin-7-yl)phenyl)-1,2,3-thiadiazole-4-carboxamide | IVa |

TABLE 1-continued

| Ex. No. | Structure | Structure Name | Synthetic Method |
|---|---|---|---|
| 70 | 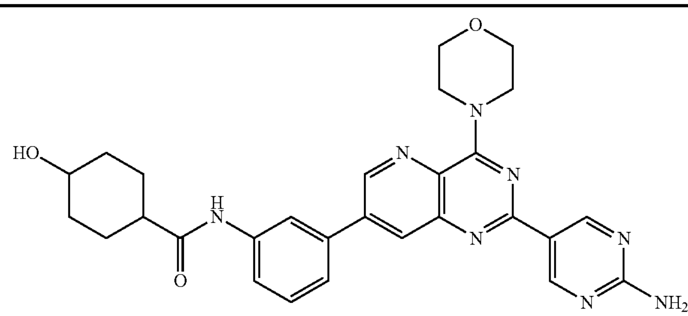 | N-(3-(2-(2-amino-pyrimidin-5-yl)-4-morpholinopyrido[3,2-d]pyrimidin-7-yl)phenyl)-4-hydroxycyclohexane-carboxamide | IVa |
| 71 | 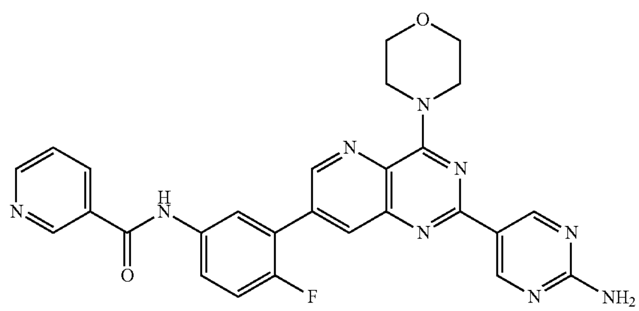 [SMILES: Nc1ncc(-c2nc(N3CCOCC3)c3ncc(-c4cc(NC(=O)c5cccnc5)ccc4F)cc3n2)cn1] | N-(3-(2-(2-amino-pyrimidin-5-yl)-4-morpholinopyrido[3,2-d]-pyrimidin-7-yl)-4-fluoro-phenyl)nicotinamide | IVa |
| 72 | 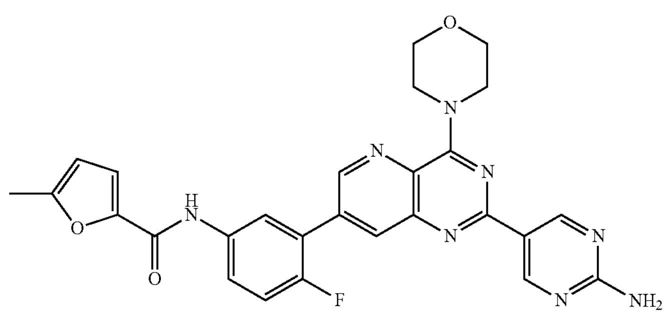 [SMILES: Cc1ccc(C(=O)Nc2ccc(F)c(-c3cnc4c(N5CCOCC5)nc(-c5cnc(N)nc5)nc4c3)c2)o1] | N-(3-(2-(2-amino-pyrimidin-5-yl)-4-morpholinopyrido[3,2-d]pyrimidin-7-yl)-4-fluorophenyl)-5-methylfuran-2-carboxamide | IVa |
| 73 | 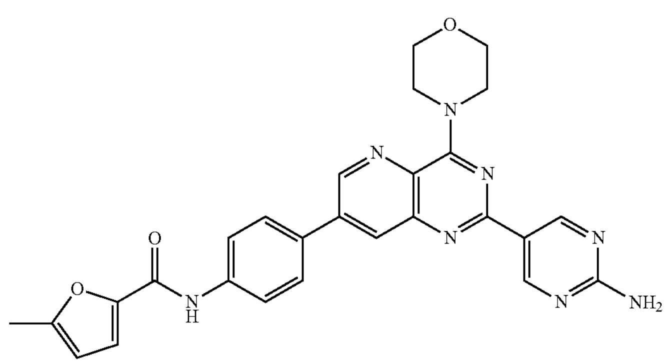 [SMILES: Cc1ccc(C(=O)Nc2ccc(-c3cnc4c(N5CCOCC5)nc(-c5cnc(N)nc5)nc4c3)cc2)o1] | N-(4-(2-(2-amino-pyrimidin-5-yl)-4-morpholinopyrido[3,2-d]pyrimidin-7-yl)phenyl)-5-methylfuran-2-carboxamide | IVa |
| 74 | 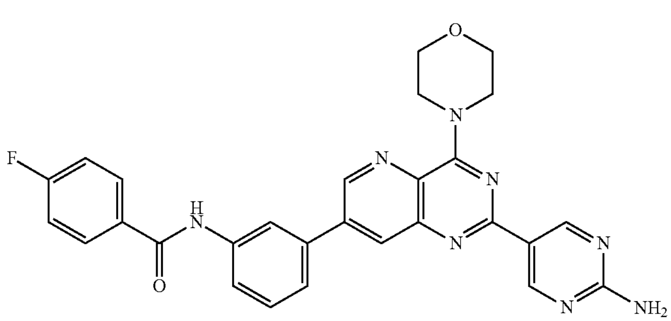 [SMILES: Nc1ncc(-c2nc(N3CCOCC3)c3ncc(-c4cccc(NC(=O)c5ccc(F)cc5)c4)cc3n2)cn1] | N-(3-(2-(2-amino-pyrimidin-5-yl)-4-morpholinopyrido[3,2-d]pyrimidin-7-yl)phenyl)-4-fluorobenzamide | IVa |

TABLE 1-continued

| Ex. No. | Structure | Structure Name | Synthetic Method |
|---|---|---|---|
| 75 | 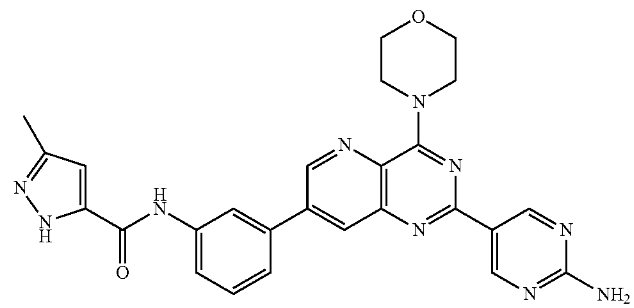 [SMILES: Cc1cc(C(=O)Nc2cccc(-c3cnc4c(N5CCOCC5)nc(-c5cnc(N)nc5)nc4c3)c2)[nH]n1] | N-(3-(2-(2-amino-pyrimidin-5-yl)-4-morpholinopyrido[3,2-d]pyrimidin-7-yl)phenyl)-3-methyl-1H-pyrazole-5-carboxamide | IVa |
| 76 | 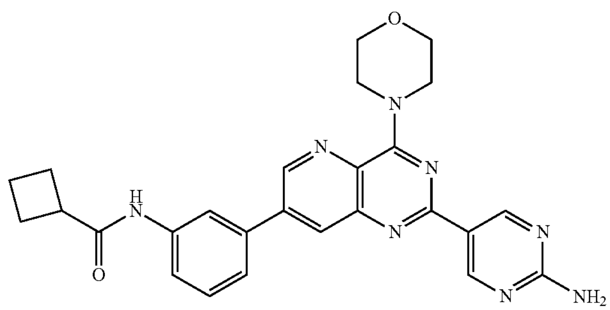 [SMILES: Nc1ncc(-c2nc(N3CCOCC3)c3ncc(-c4cccc(NC(=O)C5CCC5)c4)cc3n2)cn1] | N-(3-(2-(2-amino-pyrimidin-5-yl)-4-morpholinopyrido[3,2-d]pyrimidin-7-yl)-phenyl)cyclobutane-carboxamide | IVa |
| 77 | 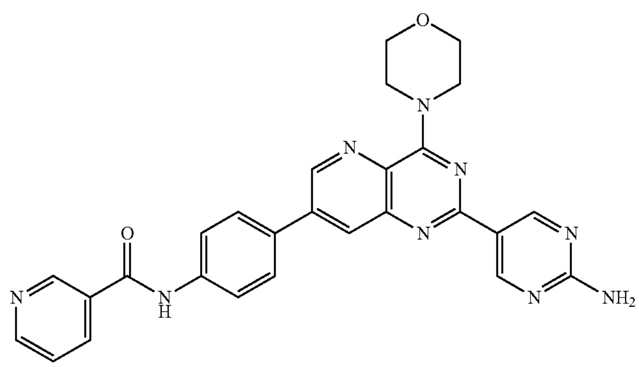 [SMILES: Nc1ncc(-c2nc(N3CCOCC3)c3ncc(-c4ccc(NC(=O)c5cccnc5)cc4)cc3n2)cn1] | N-(4-(2-(2-amino-pyrimidin-5-yl)-4-morpholinopyrido[3,2-d]pyrimidin-7-yl)-phenyl)nicotinamide | IVa |
| 78 | 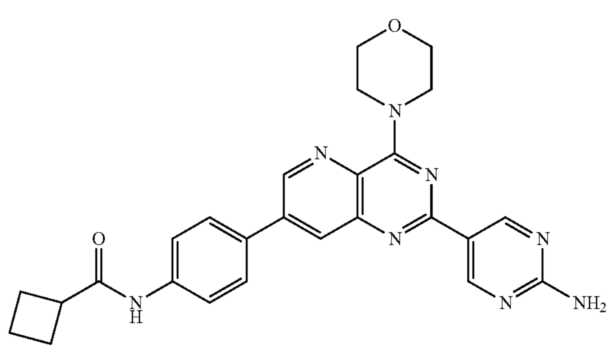 [SMILES: Nc1ncc(-c2nc(N3CCOCC3)c3ncc(-c4ccc(NC(=O)C5CCC5)cc4)cc3n2)cn1] | N-(4-(2-(2-amino-pyrimidin-5-yl)-4-morpholinopyrido[3,2-d]pyrimidin-7-yl)-phenyl)cyclobutane-carboxamide | IVa |

TABLE 1-continued

| Ex. No. | Structure | Structure Name | Synthetic Method |
|---|---|---|---|
| 79 | 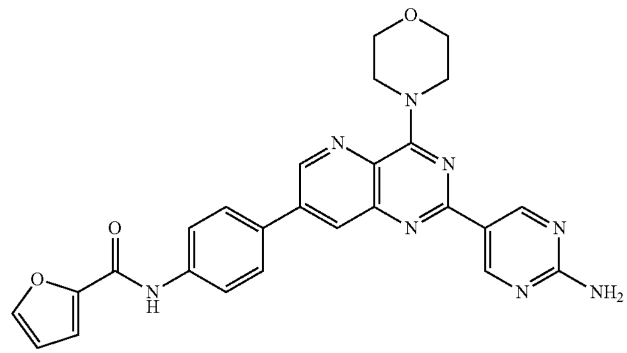 [SMILES: Nc1ncc(-c2nc(N3CCOCC3)c3ncc(-c4ccc(NC(=O)c5ccco5)cc4)cc3n2)cn1] | N-(4-(2-(2-amino-pyrimidin-5-yl)-4-morpholinopyrido[3,2-d]pyrimidin-7-yl)-phenyl)furan-2-carboxamide | IVa |
| 80 | 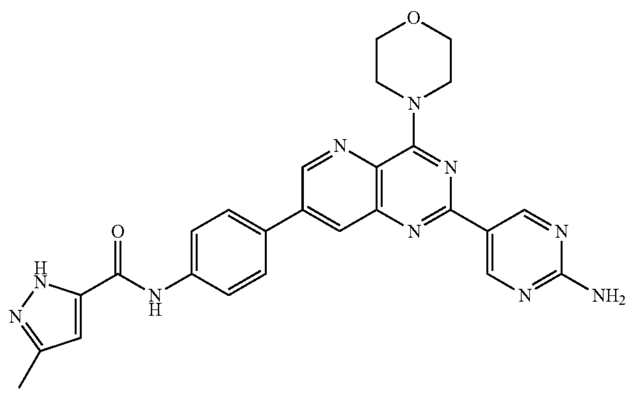 [SMILES: Cc1cc(C(=O)Nc2ccc(-c3cnc4c(N5CCOCC5)nc(-c5cnc(N)nc5)nc4c3)cc2)[nH]n1] | N-(4-(2-(2-amino-pyrimidin-5-yl)-4-morpholinopyrido[3,2-d]pyrimidin-7-yl)phenyl)-3-methyl-1H-pyrazole-5-carboxamide | IVa |
| 81 | 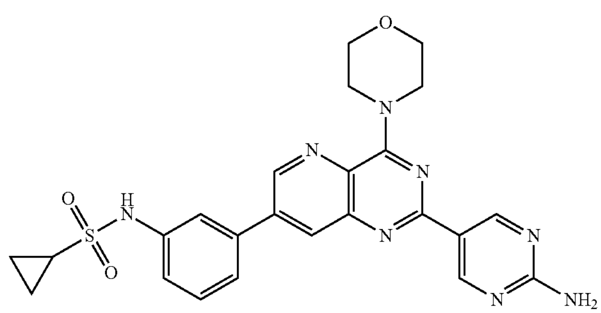 [SMILES: Nc1ncc(-c2nc(N3CCOCC3)c3ncc(-c4cccc(NS(=O)(=O)C5CC5)c4)cc3n2)cn1] | N-(3-(2-(2-amino-pyrimidin-5-yl)-4-morpholinopyrido[3,2-d]pyrimidin-7-yl)-phenyl)cyclopropane-sulfonamide | IVb |
| 82 | 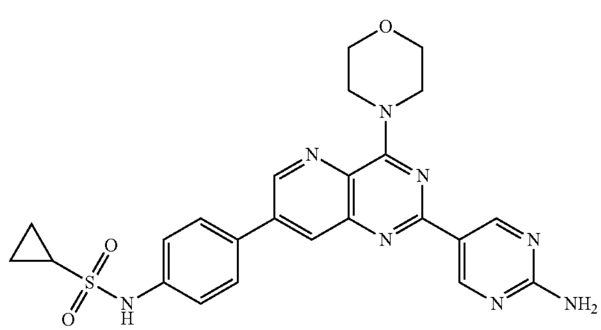 [SMILES: Nc1ncc(-c2nc(N3CCOCC3)c3ncc(-c4ccc(NS(=O)(=O)C5CC5)cc4)cc3n2)cn1] | N-(4-(2-(2-amino-pyrimidin-5-yl)-4-morpholinopyrido[3,2-d]-pyrimidin-7-yl)phenyl)-cyclopropanesulfonamide | IVb |

TABLE 1-continued

| Ex. No. | Structure | Structure Name | Synthetic Method |
|---|---|---|---|
| 83 | 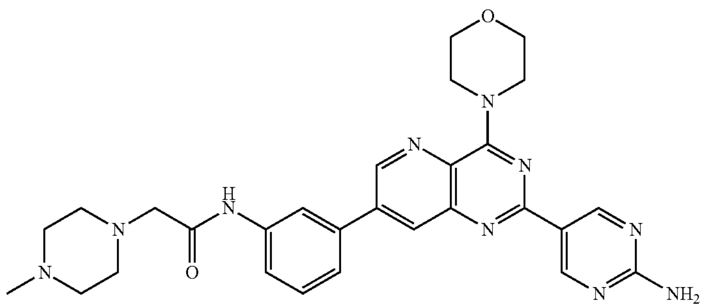 [SMILES: CN1CCN(CC(=O)Nc2cccc(-c3cnc4c(N5CCOCC5)nc(-c5cnc(N)nc5)nc4c3)c2)CC1] | N-(3-(2-(2-aminopyrimidin-5-yl)-4-morpholinopyrido[3,2-d]pyrimidin-7-yl)phenyl)-2-(4-methylpiperazin-1-yl)acetamide | IVc |
| 84 | 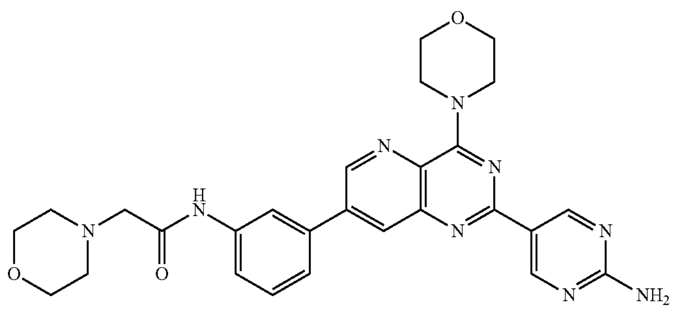 [SMILES: Nc1ncc(-c2nc(N3CCOCC3)c3ncc(-c4cccc(NC(=O)CN5CCOCC5)c4)cc3n2)cn1] | N-(3-(2-(2-aminopyrimidin-5-yl)-4-morpholinopyrido[3,2-d]pyrimidin-7-yl)phenyl)-2-morpholinoacetamide | IVc |
| 85 | 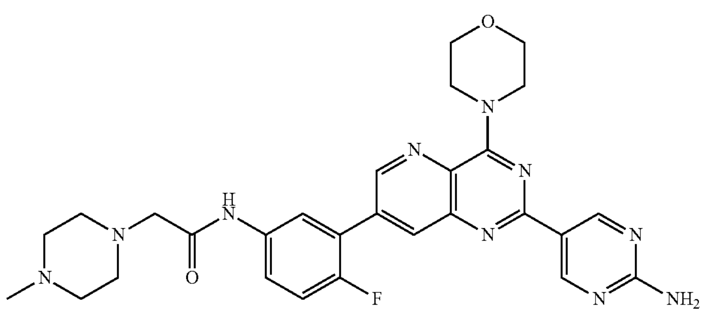 [SMILES: CN1CCN(CC(=O)Nc2ccc(F)c(-c3cnc4c(N5CCOCC5)nc(-c5cnc(N)nc5)nc4c3)c2)CC1] | N-(3-(2-(2-aminopyrimidin-5-yl)-4-morpholinopyrido[3,2-d]pyrimidin-7-yl)-4-fluorophenyl)-2-(4-methylpiperazin-1-yl)-acetamide | IVc |
| 86 | 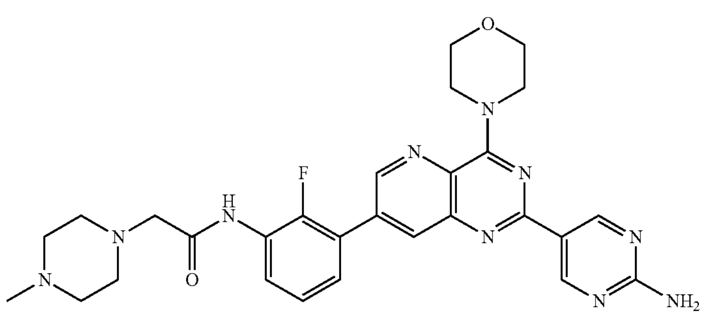 [SMILES: CN1CCN(CC(=O)Nc2cccc(-c3cnc4c(N5CCOCC5)nc(-c5cnc(N)nc5)nc4c3)c2F)CC1] | N-(3-(2-(2-amino-pyrimidin-5-yl)-4-morpholinopyrido[3,2-d]-pyrimidin-7-yl)-2-fluoro-phenyl)-2-(4-methyl-piperazin-1-yl)acetamide | IVc |
| 87 | 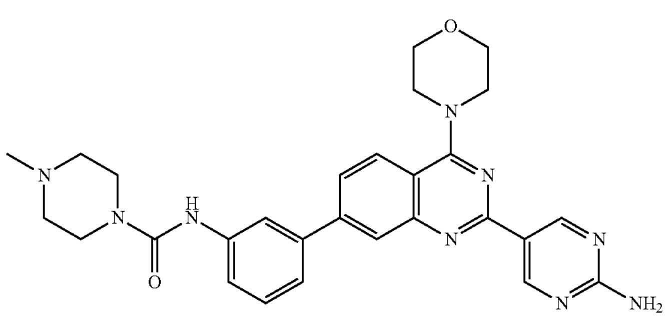 | N-(3-(2-(2-amino-pyrimidin-5-yl)-4-morpholinoquinazolin-7-yl)phenyl)-4-methyl-piperazine-1-carboxamide | IVd |

| Ex. No. | Structure | Structure Name | Synthetic Method |
|---|---|---|---|
| 88 | 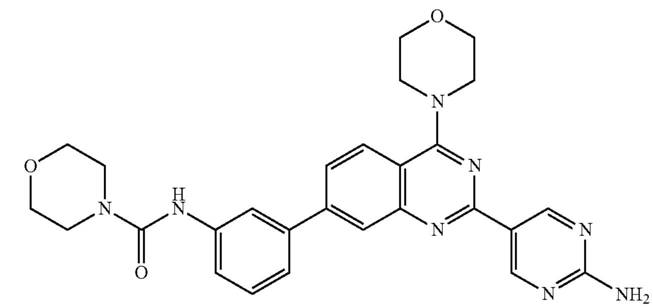 | N-(3-(2-(2-amino-pyrimidin-5-yl)-4-morpholinoquinazolin-7-yl)phenyl)morpholine-4-carboxamide | IVd |
| 89 | 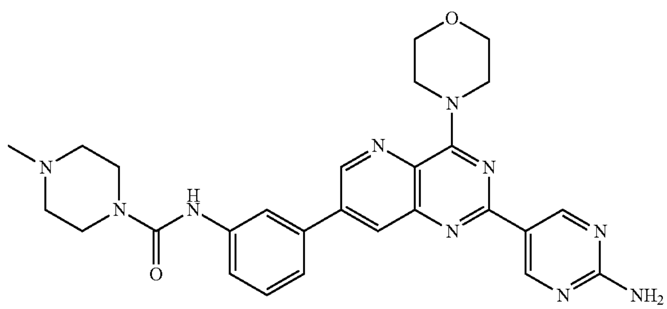 [SMILES: CN1CCN(C(=O)Nc2cccc(-c3ccc4c(N5CCOCC5)nc(-c5cnc(N)nc5)nc4c3)c2)CC1] | N-(3-(2-(2-aminopyrimidin-5-yl)-4-morpholinopyrido[3,2-d]pyrimidin-7-yl)phenyl)-4-methylpiperazine-1-carboxamide | IVd |
| 90 | 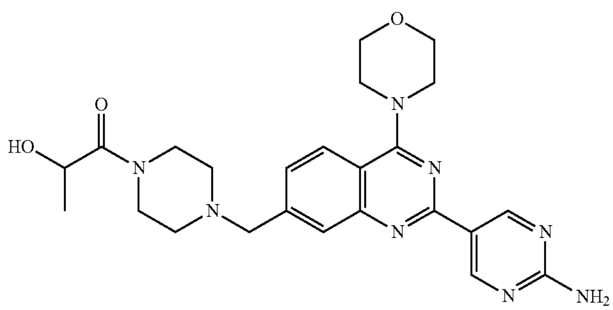 [SMILES: CC(O)C(=O)N1CCN(Cc2ccc3c(N4CCOCC4)nc(-c4cnc(N)nc4)nc3c2)CC1] | 1-(4-((2-(2-aminopyrimidin-5-yl)-4-morpholinoquinazolin-7-yl)methyl)piperazin-1-yl)-2-hydroxypropan-1-one | V |
| 91 | 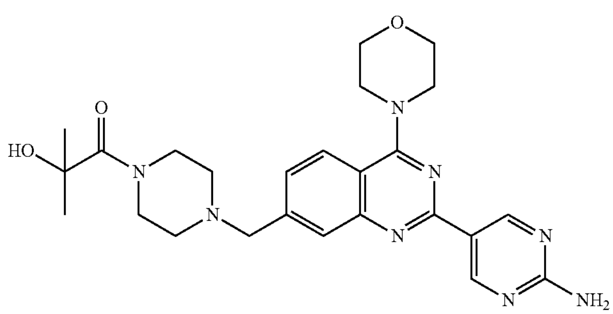 | 1-(4-((2-(2-amino-pyrimidin-5-yl)-4-morpholinoquinazolin-7-yl)methyl)piperazin-1-yl)-2-hydroxy-2-methyl-propan-1-one | V |
| 92 | 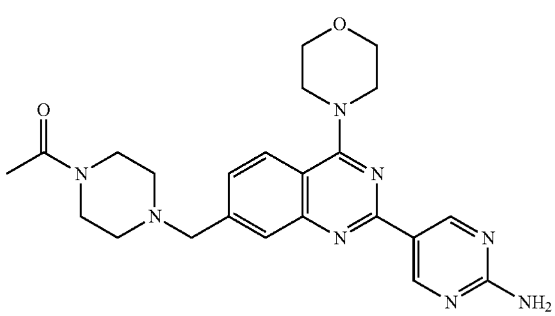 [SMILES: CC(=O)N1CCN(Cc2ccc3c(N4CCOCC4)nc(-c4cnc(N)nc4)nc3c2)CC1] | 1-(4-((2-(2-amino-pyrimidin-5-yl)-4-morpholinoquinazolin-7-yl)methyl)piperazin-1-yl)ethanone | V |

| Ex. No. | Structure | Structure Name | Synthetic Method |
|---|---|---|---|
| 93 | 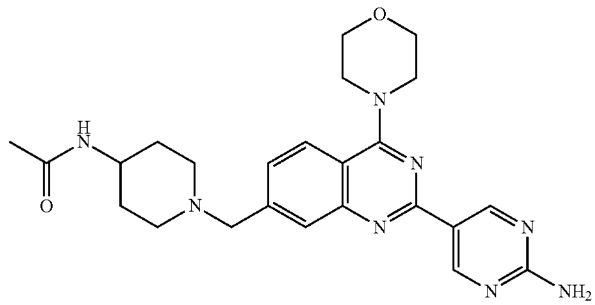 [SMILES: CC(=O)NC1CCN(Cc2ccc3c(N4CCOCC4)nc(-c4cnc(N)nc4)nc3c2)CC1] | N-(1-((2-(2-amino-pyrimidin-5-yl)-4-morpholinoquinazolin-7-yl)methyl)piperidin-4-yl)-acetamide | V |
| 94 | 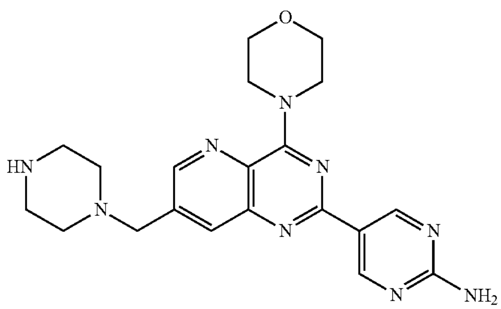 [SMILES: Nc1ncc(-c2nc(N3CCOCC3)c3ncc(CN4CCNCC4)cc3n2)cn1] | 5-(4-morpholino-7-(piperazin-1-yl-methyl)pyrido[3,2-d]-pyrimidin-2-yl)pyrimidin-2-amine | V |
| 95 | 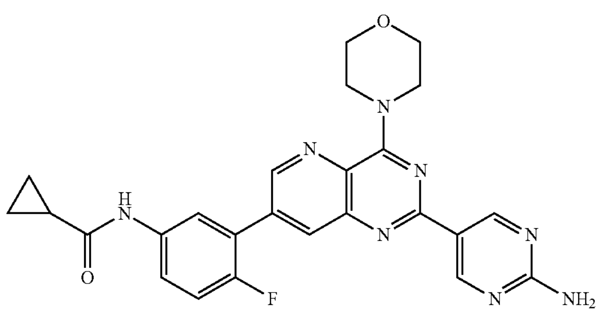 [SMILES: Nc1ncc(-c2nc(N3CCOCC3)c3ncc(-c4cc(NC(=O)C5CC5)ccc4F)cc3n2)cn1] | N-(3-(2-(2-amino-pyrimidin-5-yl)-4-morpholinopyrido[3,2-d]-pyrimidin-7-yl)-4-fluorophenyl)cyclopropane-carboxamide | II |
| 96 | 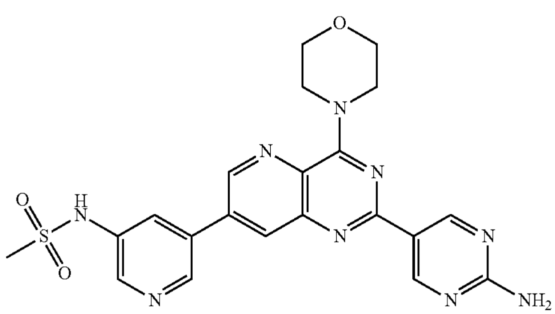 [SMILES: CS(=O)(=O)Nc1cncc(-c2cnc3c(N4CCOCC4)nc(-c4cnc(N)nc4)nc3c2)c1] | N-(5-(2-(2-amino-pyrimidin-5-yl)-4-morpholinopyrido[3,2-d]-pyrimidin-7-yl)pyridin-3-yl)methanesulfonamide | II |
| 97 | 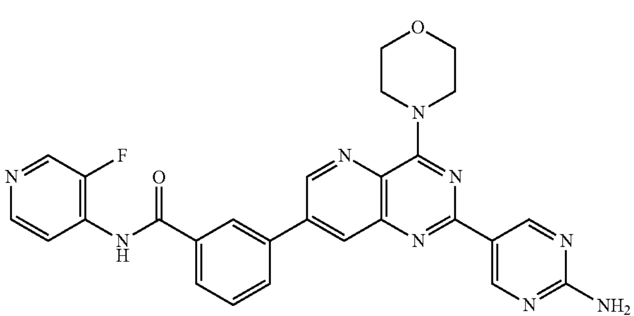 [SMILES: Nc1ncc(-c2nc(N3CCOCC3)c3ncc(-c4cccc(C(=O)Nc5ccncc5F)c4)cc3n2)cn1] | 3-(2-(2-aminopyrimidin-5-yl)-4-morpholinopyrido[3,2-d]-pyrimidin-7-yl)-N-(3-fluoropyridin-4-yl)-benzamide | III |

TABLE 1-continued

| Ex. No. | Structure | Structure Name | Synthetic Method |
|---|---|---|---|
| 98 | 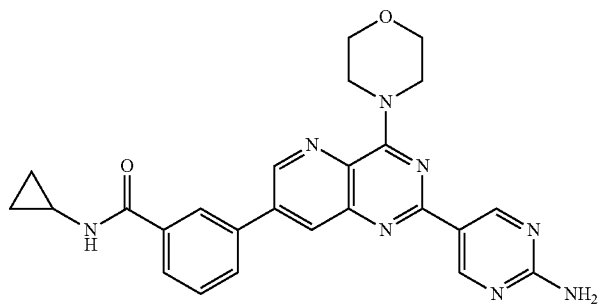 [SMILES: Nc1ncc(-c2nc(N3CCOCC3)c3ncc(-c4cccc(C(=O)NC5CC5)c4)cc3n2)cn1] | 3-(2-(2-aminopyrimidin-5-yl)-4-morpholinopyrido[3,2-d]pyrimidin-7-yl)-N-cyclopropylbenzamide | III |
| 99 | 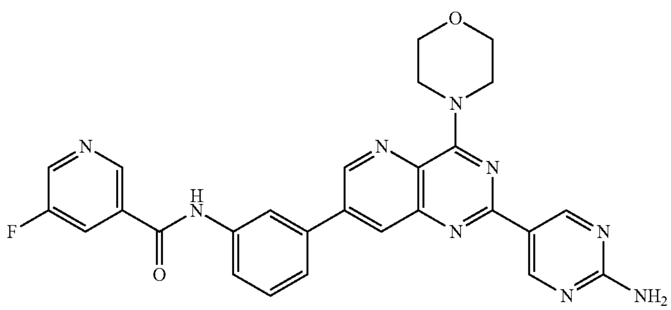 [SMILES: Nc1ncc(-c2nc(N3CCOCC3)c3ncc(-c4cccc(NC(=O)c5cncc(F)c5)c4)cc3n2)cn1] | N-(3-(2-(2-amino-pyrimidin-5-yl)-4-morpholinopyrido[3,2-d]-pyrimidin-7-yl)phenyl)-5-fluoronicotinamide | IVa |
| 100 | 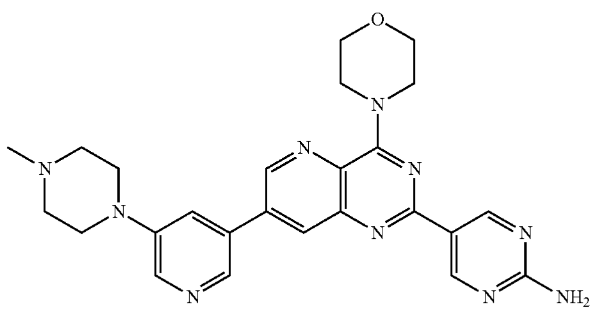 [SMILES: CN1CCN(c2cccc(-c3cnc4c(N5CCOCC5)nc(-c5cnc(N)nc5)nc4c3)c2)CC1] | 5-(7-(5-(4-methyl-piperazin-1-yl)pyridin-3-yl)-4-morpholino-pyrido[3,2-d]pyrimidin-2-yl)pyrimidin-2-amine | II |
| 101 | 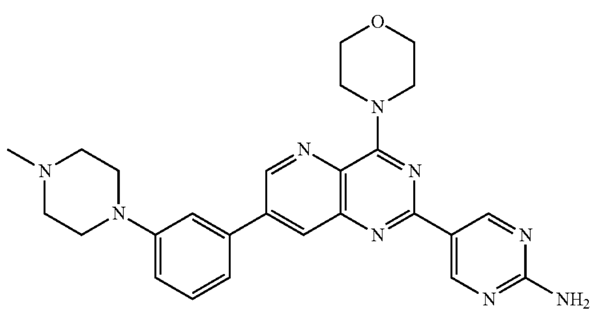 | 5-(7-(3-(4-methyl-piperazin-1-yl)phenyl)-4-morpholinopyrido[3,2-d]-pyrimidin-2-yl)pyrimidin-2-amine | II |
| 102 | 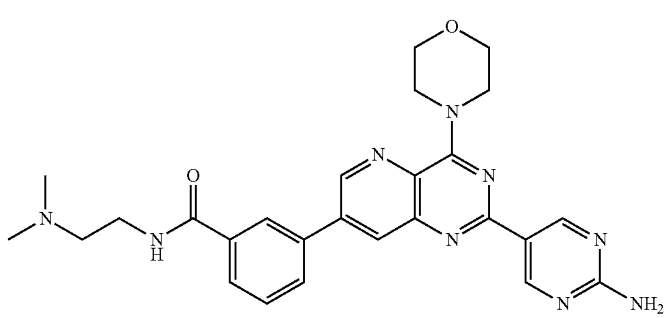 [SMILES: CN(C)CCNC(=O)c1cccc(-c2cnc3c(N4CCOCC4)nc(-c4cnc(N)nc4)nc3c2)c1] | 3-(2-(2-aminopyrimidin-5-yl)-4-morpholinopyrido[3,2-d]-pyrimidin-7-yl)-N-(2-(dimethylamino)ethyl)-benzamide | III |

TABLE 1-continued

| Ex. No. | Structure | Structure Name | Synthetic Method |
|---|---|---|---|
| 103 | 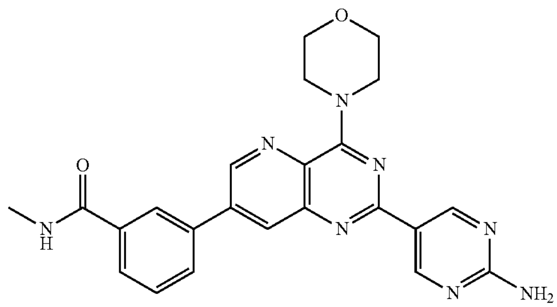 [SMILES: CNC(=O)c1cccc(-c2cnc3c(N4CCOCC4)nc(-c4cnc(N)nc4)nc3c2)c1] | 3-(2-(2-aminopyrimidin-5-yl)-4-morpholinopyrido[3,2-d]pyrimidin-7-yl)-N-methylbenzamide | III |
| 104 | 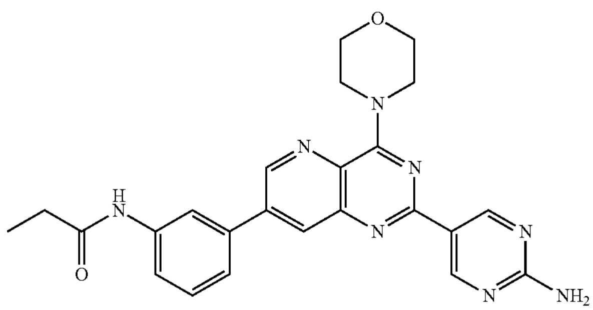 | N-(3-(2-(2-amino-pyrimidin-5-yl)-4-morpholinopyrido[3,2-d]-pyrimidin-7-yl)-phenyl)propionamide | IVa |
| 105 | 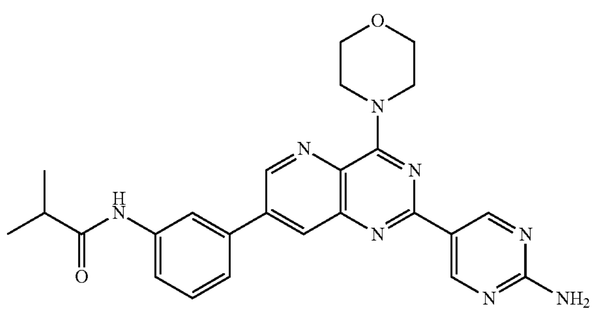 | N-(3-(2-(2-amino-pyrimidin-5-yl)-4-morpholinopyrido[3,2-d]-pyrimidin-7-yl)-phenyl)isobutyramide | IVa |
| 106 | 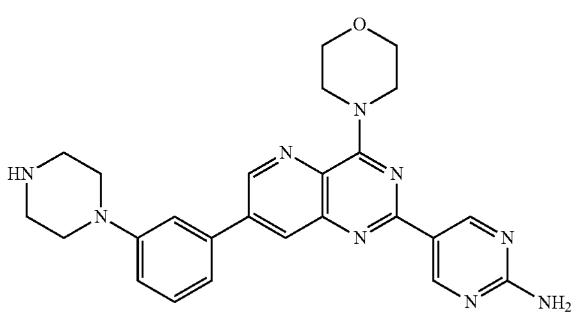 [SMILES: Nc1ncc(-c2nc(N3CCOCC3)c3ncc(-c4cccc(N5CCNCC5)c4)cc3n2)cn1] | 5-(4-morpholino-7-(3-(piperazin-1-yl)-phenyl)pyrido[3,2-d]-pyrimidin-2-yl)pyrimidin-2-amine | II |
| 107 | 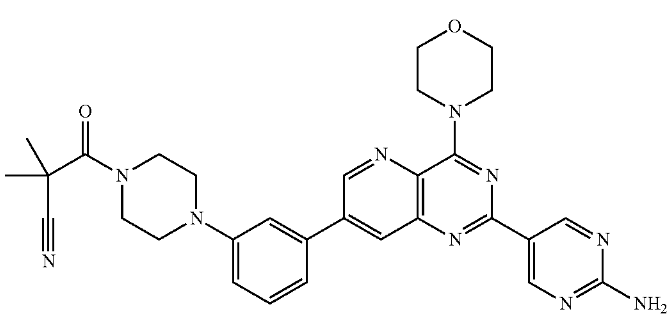 [SMILES: CC(C)(C#N)C(=O)N1CCN(c2cccc(-c3cnc4c(N5CCOCC5)nc(-c5cnc(N)nc5)nc4c3)c2)CC1] | 3-(4-(3-(2-(2-amino-pyrimidin-5-yl)-4-morpholinopyrido[3,2-d]-pyrimidin-7-yl)-phenyl)piperazin-1-yl)-2,2-dimethyl-3-oxopropanenitrile | IVa |

TABLE 1-continued

| Ex. No. | Structure | Structure Name | Synthetic Method |
|---|---|---|---|
| 108 | 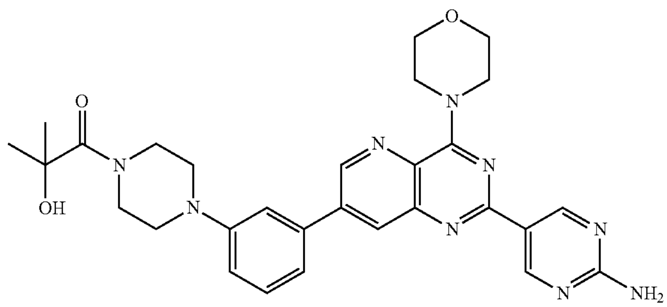 [SMILES: CC(C)(O)C(=O)N1CCN(c2cccc(-c3cnc4c(N5CCOCC5)nc(-c5cnc(N)nc5)nc4c3)c2)CC1] | 1-(4-(3-(2-(2-amino-pyrimidin-5-yl)-4-morpholinopyrido[3,2-d]pyrimidin-7-yl)-phenyl)piperazin-1-yl)-2-hydroxy-2-methylpropan-1-one | IVa |
| 109 | 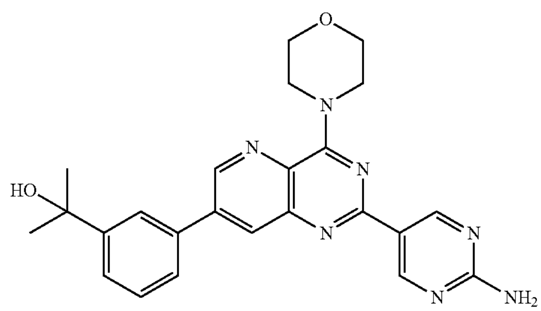 [SMILES: CC(C)(O)c1cccc(-c2cnc3c(N4CCOCC4)nc(-c4cnc(N)nc4)nc3c2)c1] | 2-(3-(2-(2-amino-pyrimidin-5-yl)-4-morpholinopyrido[3,2-d]pyrimidin-7-yl)-phenyl)propan-2-ol | III |
| 110 | 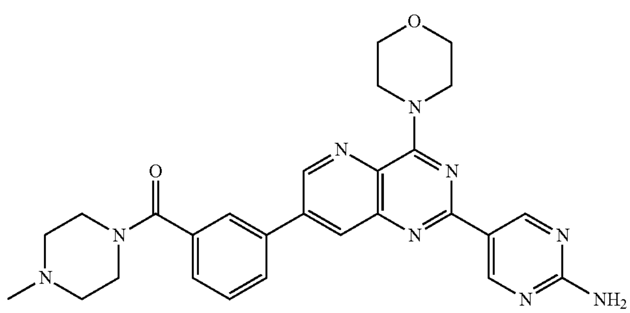 [SMILES: CN1CCN(C(=O)c2cccc(-c3cnc4c(N5CCOCC5)nc(-c5cnc(N)nc5)nc4c3)c2)CC1] | (3-(2-(2-aminopyrimidin-5-yl)-4-morpholinopyrido[3,2-d]-pyrimidin-7-yl)phenyl)(4-methylpiperazin-1-yl)-methanone | III |
| 111 | 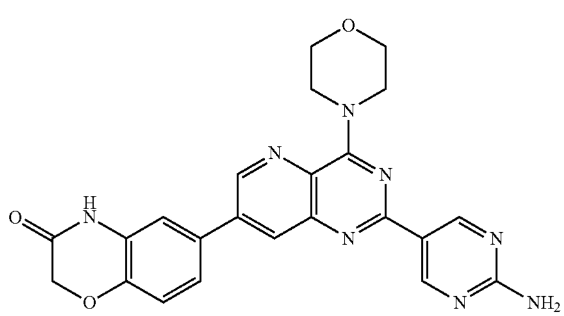 [SMILES: Nc1ncc(-c2nc(N3CCOCC3)c3ncc(-c4ccc5c(c4)NC(=O)CO5)cc3n2)cn1] | 6-(2-(2-aminopyrimidin-5-yl)-4-morpholinopyrido[3,2-d]pyrimidin-7-yl)-2H-benzo[b][1,4]oxazin-3(4H)-one | II |
| 112 | 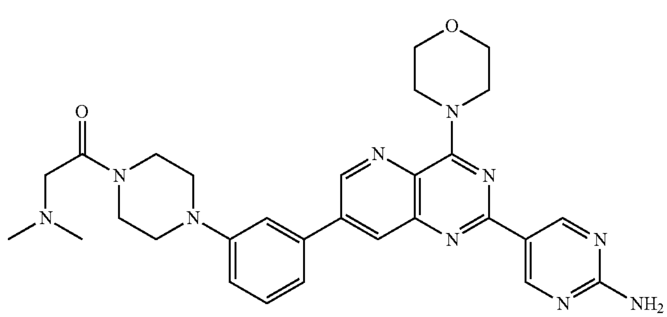 [SMILES: CN(C)CC(=O)N1CCN(c2cccc(-c3cnc4c(N5CCOCC5)nc(-c5cnc(N)nc5)nc4c3)c2)CC1] | 1-(4-(3-(2-(2-amino-pyrimidin-5-yl)-4-morpholinopyrido[3,2-d]pyrimidin-7-yl)-phenyl)piperazin-1-yl)-2-(dimethylamino)ethanone | IVa |

TABLE 1-continued

| Ex. No. | Structure | Structure Name | Synthetic Method |
|---|---|---|---|
| 113 | 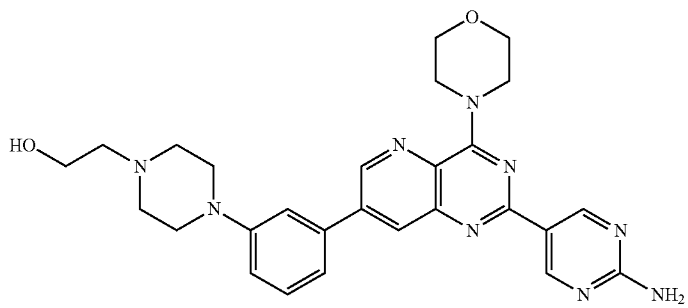 [SMILES: Nc1ncc(-c2nc(N3CCOCC3)c3ncc(-c4cccc(N5CCN(CCO)CC5)c4)cc3n2)cn1] | 2-(4-(3-(2-(2-amino-pyrimidin-5-yl)-4-morpholinopyrido[3,2-d]pyrimidin-7-yl)-phenyl)piperazin-1-yl)-ethanol | II |
| 114 | 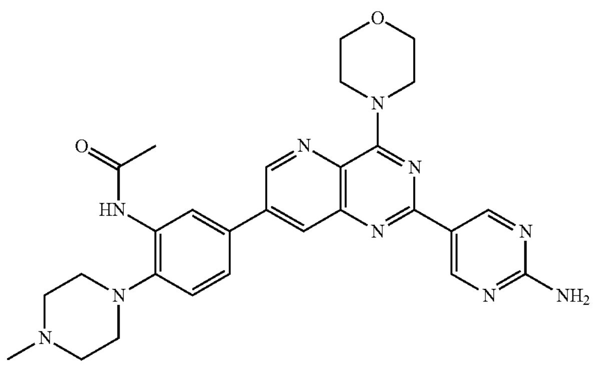 [SMILES: CC(=O)Nc1cc(-c2cnc3c(N4CCOCC4)nc(-c4cnc(N)nc4)nc3c2)ccc1N1CCN(C)CC1] | N-(5-(2-(2-amino-pyrimidin-5-yl)-4-morpholinopyrido[3,2-d]pyrimidin-7-yl)-2-(4-methylpiperazin-1-yl)-phenyl)acetamide | II |
| 115 | 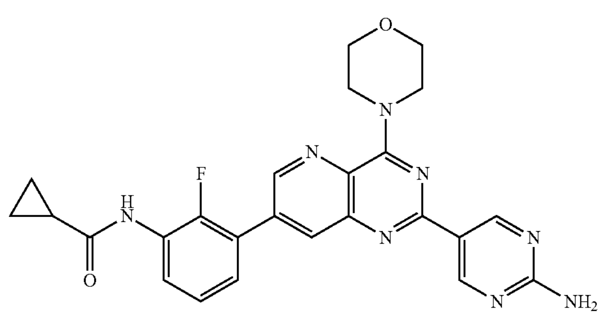 [SMILES: Nc1ncc(-c2nc(N3CCOCC3)c3ncc(-c4cccc(NC(=O)C5CC5)c4F)cc3n2)cn1] | N-(3-(2-(2-amino-pyrimidin-5-yl)-4-morpholinopyrido[3,2-d]pyrimidin-7-yl)-2-fluorophenyl)-cyclopropane-carboxamide | IVa |
| 116 | 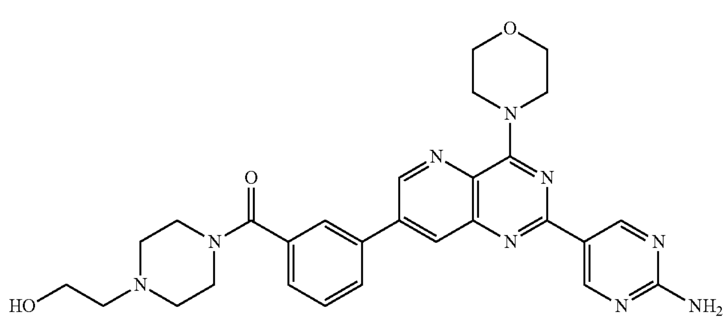 [SMILES: Nc1ncc(-c2nc(N3CCOCC3)c3ncc(-c4cccc(C(=O)N5CCN(CCO)CC5)c4)cc3n2)cn1] | (3-(2-(2-aminopyrimidin-5-yl)-4-morpholinopyrido[3,2-d]-pyrimidin-7-yl)phenyl)(4-(2-hydroxyethyl)piperazin-1-yl)methanone | III |

TABLE 1-continued

| Ex. No. | Structure | Structure Name | Synthetic Method |
|---|---|---|---|
| 117 | 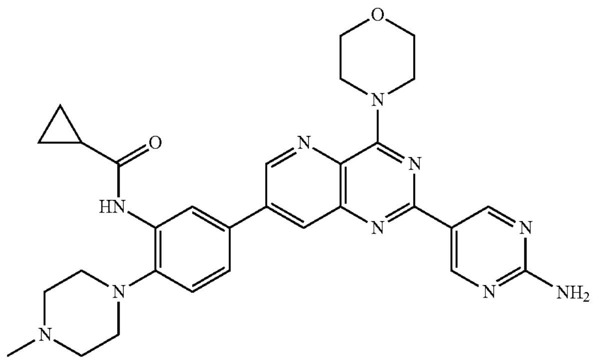 [SMILES: CN1CCN(c2ccc(-c3cnc4c(N5CCOCC5)nc(-c5cnc(N)nc5)nc4c3)cc2NC(=O)C2CC2)CC1] | N-(5-(2-(2-amino-pyrimidin-5-yl)-4-morpholinopyrido[3,2-d]pyrimidin-7-yl)-2-(4-methylpiperazin-1-yl)-phenyl)cyclopropane-carboxamide | II |
| 118 | 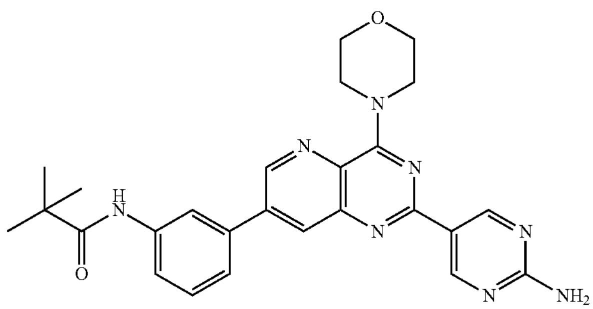 [SMILES: CC(C)(C)C(=O)Nc1cccc(-c2cnc3c(N4CCOCC4)nc(-c4cnc(N)nc4)nc3c2)c1] | N-(3-(2-(2-amino-pyrimidin-5-yl)-4-morpholinopyrido[3,2-d]pyrimidin-7-yl)-phenyl)pivalamide | IVa |
| 119 | 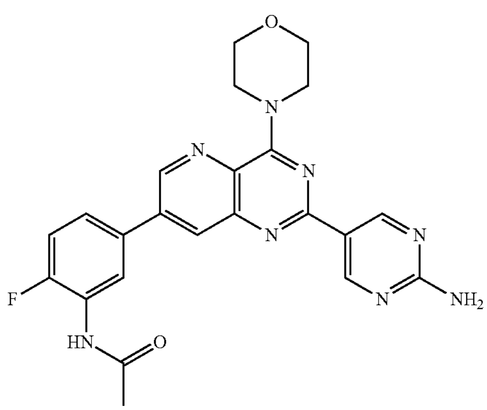 [SMILES: CC(=O)Nc1cc(-c2cnc3c(N4CCOCC4)nc(-c4cnc(N)nc4)nc3c2)ccc1F] | N-(5-(2-(2-amino-pyrimidin-5-yl)-4-morpholinopyrido[3,2-d]-pyrimidin-7-yl)-2-fluorophenyl)acetamide | II |
| 120 | 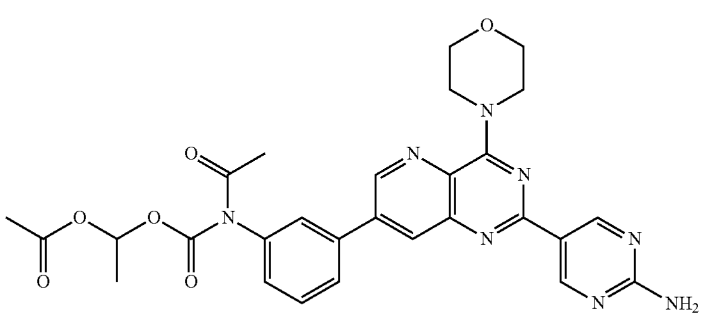 [SMILES: CC(=O)OC(C)OC(=O)N(C(C)=O)c1cccc(-c2cnc3c(N4CCOCC4)nc(-c4cnc(N)nc4)nc3c2)c1] | 1-((acetyl(3-(2-(2-amino-pyrimidin-5-yl)-4-morpholinopyrido[3,2-d]-pyrimidin-7-yl)-phenyl)carbamoyl)oxy) ethyl acetate | VI |

| Ex. No. | Structure | Structure Name | Synthetic Method |
|---|---|---|---|
| 121 | 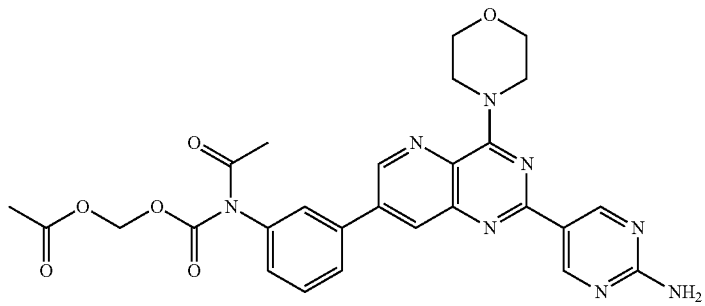 [SMILES: CC(=O)OCOC(=O)N(C(C)=O)c1cccc(-c2cnc3c(N4CCOCC4)nc(-c4cnc(N)nc4)nc3c2)c1] | ((acetyl(3-(2-(2-amino-pyrimidin-5-yl)-4-morpholinopyrido[3,2-d]-pyrimidin-7-yl)-phenyl)carbamoyl)oxy) methyl acetate | VI |
| 122 | 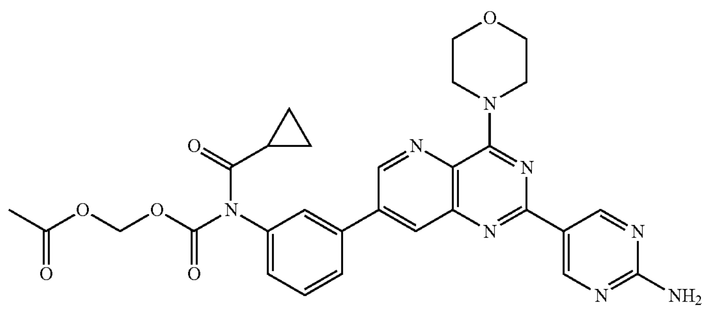 [SMILES: CC(=O)OCOC(=O)N(C(=O)C1CC1)c1cccc(-c2cnc3c(N4CCOCC4)nc(-c4cnc(N)nc4)nc3c2)c1] | (((3-(2-(2-amino-pyrimidin-5-yl)-4-morpholinopyrido[3,2-d]pyrimidin-7-yl)-phenyl)(cyclopropane-carbonyl)carbamoyl)-oxy)methyl acetate | VI |
| 123 | 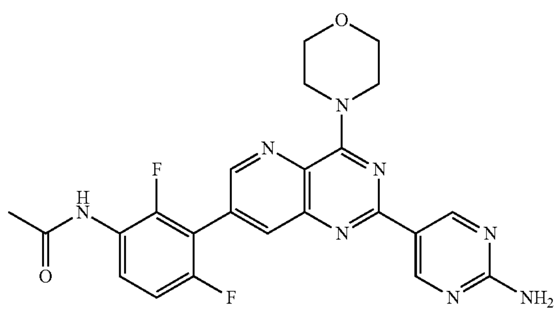 [SMILES: CC(=O)Nc1ccc(F)c(-c2cnc3c(N4CCOCC4)nc(-c4cnc(N)nc4)nc3c2)c1F] | N-(3-(2-(2-amino-pyrimidin-5-yl)-4-morpholinopyrido[3,2-d]pyrimidin-7-yl)-2,4-difluorophenyl)acetamide | IVa |
| 124 | 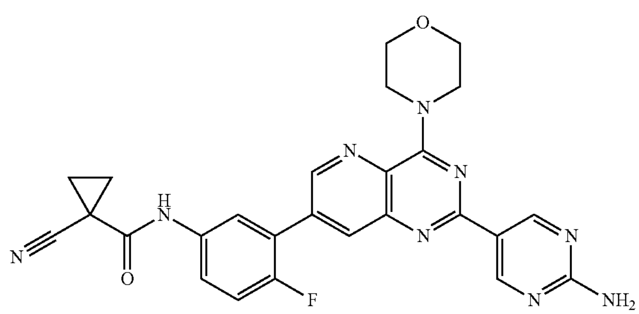 [SMILES: N#CC1(C(=O)Nc2ccc(F)c(-c3cnc4c(N5CCOCC5)nc(-c5cnc(N)nc5)nc4c3)c2)CC1] | N-(3-(2-(2-amino-pyrimidin-5-yl)-4-morpholinopyrido[3,2-d]pyrimidin-7-yl)-4-fluorophenyl)-1-cyanocyclopropane-carboxamide | IVa |
| 125 | 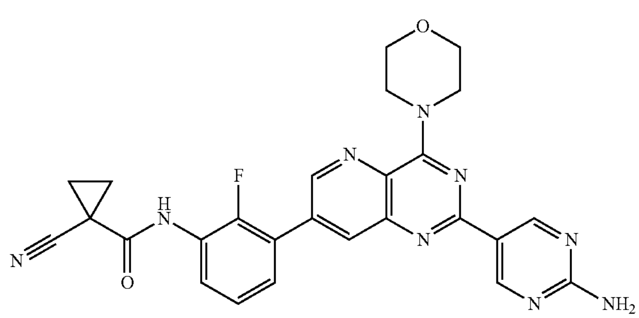 | N-(3-(2-(2-amino-pyrimidin-5-yl)-4-morpholinopyrido[3,2-d]pyrimidin-7-yl)-2-fluorophenyl)-1-cyanocyclopropane-carboxamide | IVa |

TABLE 1-continued

| Ex. No. | Structure | Structure Name | Synthetic Method |
|---|---|---|---|
| 126 | 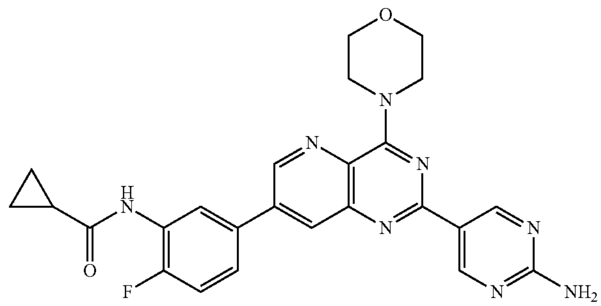 [SMILES: Nc1ncc(-c2nc(N3CCOCC3)c3ncc(-c4ccc(F)c(NC(=O)C5CC5)c4)cc3n2)cn1] | N-(5-(2-(2-amino-pyrimidin-5-yl)-4-morpholinopyrido[3,2-d]pyrimidin-7-yl)-2-fluorophenyl)-cyclopropane carboxamide | IVa |

Example 127

Biological Assays (i) PI3 Kinase Time-Resolved Fluorescence Resonance Energy Transfer (TR-FRET) Assay The ability of compounds of the invention to inhibit PI3K activity was determined in a homogeneous TR-FRET assay using a PI3K assay kit (Millipore, USA; cat #33-016) according to manufacturer's instructions. PI3-Kinases (isoforms α, β, γ and δ) catalyze the phosphorylation of phosphatidylinositol, PIP2 to PIP3 in the presence of ATP and $Mg^{2+}$. The PIP3 product is detected by displacement of biotin-PIP3 from an energy transfer complex consisting of Europium labeled anti-GST monoclonal antibody, a GST-tagged PH domain, biotinylated PIP3 and Streptavidin-APC. Excitation of Europium in the complex results in an energy transfer to the APC and a fluorescence emission at 665 nm. The PIP3 product displaces biotin-PIP3 from the complex resulting in a loss of energy transfer and thus a decrease in signal.

To test for the ability of compounds to inhibit the activity of PI3Kα (wild-type), exemplary compounds of formula (I) were dissolved in DMSO and directly distributed into 384-well plates at a volume of 0.5 µL. 14.5 µL of P110/P85α/PIP2 mixture in buffer (obtained from the Millipore kit) containing $MgCl_2$ (40 mM) and DTT (5 mM) was added to compound wells and incubated for 60 minutes at room temperature. P110/P85α was expressed in SF9 insect cells and purified nickel column extraction. Five ng of wild-type P110/P85α was used in the assay. The kinase reaction was started by the addition of ATP. The assay concentrations of both PIP2 and ATP were 10 µM. The reaction mixture was incubated for 30 minutes at room temperature and was terminated by the addition of stop mix and detection mix. Fluorescence was measured at 615 and 665 nm upon excitation at 340 nm in a Victor™ V5 fluorometer (Perkin Elmer, USA). The fluorescence emission ratio at 665 to 615 nm, proportional to the kinase activity, was plotted against the compound concentration to generate dose-response curves and $IC_{50}$ values were determined using GraphPad Prism® 5 software.

Inhibition of PI3Kα activity was observed for compounds of formula (I) as determined by this assay. See, Table 2.

The activity of PI3 kinase isoforms β, γ and δ were assayed in a similar manner to the assay protocol described above for PI3Kα, by substituting the appropriate p110/p85 isoform for the p110α/p85α. Compounds of formula (I) caused inhibition of PI3 kinase isoforms β, γ and δ as determined by these assays. For example, the compounds of Examples 3 and 21 each caused inhibition of PI3 kinase isoform β with IC50 values<500 nM. The compounds of Examples 3, 7, 21, 47, 48 and 49 each caused inhibition of PI3 kinase isoform γ with IC50 values<500 nM. The compounds of Example 3, 7, 47, 48, and 49 caused inhibition of PI3 kinase isoform δ with IC50 values<1 µM.

The activity of PI3Kα mutations H1047R and E545K were assayed in a similar manner to the assay protocol described above for PI3Kα (wild type). The compounds of formula (I) caused inhibition of PI3Kα mutations H1047R (a mutation associated with breast and gastric cancers) and E545K (a mutation associated with colorectal tumors, glioblastomas, gastric cancers, breast cancers, and lung cancers). For example, each of the compounds of Example 3, 7, 21, 47, 48 and 49 caused inhibition of each of the PI3Kα mutations H1047R and E545K with IC50 values<50 nM.

(ii) mTOR Kinase TR-FRET Assay

Compound inhibition for mTOR kinase was determined in a homogeneous TR-FRET assay using the Lance® ULight-p70 S6K (Thr 389) peptide (obtained from Perkin-Elmer). The ULight™-labeled synthetic peptide contains the amino acid residues surrounding Thr389 of human p70 S6K. The ULight-p70 S6K peptide is phosphorylated at Thr389 by mTOR. Phosphorylation motif: LGFTYVAP as substrate.

The compound dilution was carried out in 100% DMSO followed by a buffer dilution. The reaction buffer was HEPES (50 mM pH 7.5), EGTA (1 mM), $MnCl_2$ (3 mM). Test compounds at various concentrations were pre-incubated with mTOR (Millipore, USA; 5 ng) for 60 min, and then the Lance® ULight-p70 S6K (Thr 389) peptide (50 nM) was added along with ATP (20 µM). After incubating the reaction mixture for 60 minutes at room temperature, the kinase reaction was terminated by the addition of EDTA (10 mM) followed by the addition of detection mix, i.e., 1 nM Eu-labeled anti-phospho-substrate antibody (Perkin Elmer, USA). The fluorescence emission at 615 and 665 nM was measured upon excitation at 340 nM. $IC_{50}$ values were subsequently determined using a sigmoidal dose-response curve (variable slope) in GraphPad Prism® 5 software.

Compounds of formula (I) caused inhibition of mTOR kinase activity as determined by this assay. See Table 2.

(iii) In-Cell Western Assay

Cells from human prostate cancer cell line PC3 (American Type Culture Collection (ATCC), Manassas, Va. 20108 USA) were seeded at an optimal density of 22,000 cell/well in 96-well plates containing Ham's F12K medium (90 µL) and incubated overnight. The compound dilutions were carried out in 100% DMSO followed by a dilution in the medium. Test compounds were added in serial dilutions to the wells and incubated for 2 hours. The cells were washed and fixed with 4% paraformaldehyde. After incubation at room temperature for 1 hour in the dark, blocking was done for 2 hours at room temperature. Primary antibodies for pAkt(S473) (Aid phosphorylated at serine 473), pAkt(T308) (Akt phosphorylated at threonine 308) and for pS6RP (S235/236) (phosphorylated at serine 235/236) (commercially available from Cell Signaling Technology®, whose protocol was followed for the in-cell western assay, were diluted to the required concentration and added to the corresponding wells followed by overnight incubation at 4° C. Eu-labeled rabbit (PE) (Perkin-Elmer USA catalog #AD0106) secondary antibody was added and incubated for 2 hours at room temperature. Delfia® enhancement solution (cat #1244-105, Perkin Elmer USA) was subsequently added to the plate before taking the reading at 615 nm with excitation wavelength of 340 nm, after which 0.5 µg/mL of Hoechst® 33258 dye (Catalog #86140-5, Sigma) was added to the plate and fluorescence emission was read at 460 nm with 355 nm excitation, to evaluate the correction factor. $IC_{50}$ values were calculated using a sigmoidal dose-response curve fit in GraphPad Prism® v5 software. Compounds of formula (I) inhibited phosphorylation of Akt (S473), Akt(T308) and S6RP in PC3 cells, as shown in Table 2. These results indicate the ability of the tested compounds to inhibit a PI3K/Akt-pathway dependent prostate neoplasm.

In-cell Western assays for pAkt(T308) and pS6RP were also carried out in a glioma cancer cell line with a PTEN null mutation (U87MG cells), in a similar manner to the protocol described above for PC3 cells, in order to assess the ability of the compounds to inhibit the Akt-pathway in a glioma cancer cell line. The compound of Example 3 caused inhibition of pAkt(T308) and pS6RP in U87MG cells with IC50 values<500 nM. In-cell Western assays for pAkt(T308), pAkt (S473) and pS6RP are also carried out in a breast cancer cell line with PI3K mutations (PIK3CA-K111N mutation) which overexpresses HER 2 (BT474 cells) and a human ductal breast epithelial cell line with PI3K mutations (PIK3CA-H1047R mutation) (T47D cells), in a similar manner to the protocol described above for PC3 cells, in order to assess the ability of the compounds to inhibit the Akt-pathway in two breast cancer cell lines. Compounds of the invention cause inhibition of pAkt(T308), pAkt(S473) and pS6RP in U87MG, BT474 and T47D cell lines as determined by these assays.

(iv) XTT Assay for Cell Viability

Using a commercial kit from Sigma Aldrich (Catalog #X34251) and following its protocol, PC3 cells in the log phase of growth were employed and seeded at an optimal density of 1000 cell/well on to 96 well plates and incubated for 24 hours followed by the addition of compounds of formula (I) in serial dilutions. Compound dilutions were made in DMSO. The cells were incubated with the compounds of formula (I) for 96 hours and XTT tetrazolium dye (Sigma, USA) was subsequently added and incubated at 37° C. After the color formation, absorbance was measured at 465 nm in a Spectramax® Gemini spectrophotometer. $EC_{50}$ values were calculated using a sigmoidal dose response curve fit in GraphPad Prism® v5 software. The tested compounds of formula (I) which caused inhibition of PC3 cell proliferation as determined by this assay protocol are shown in Table 2.

XTT assays for cell viability were also determined in U87MG, BT474 cells and T47D cells, in a similar manner to the protocol described above. The compounds cause inhibition of U87MG, BT474 and T47D cell proliferation as determined by these assays. For example, the compounds of Examples 3 and 7 caused inhibition of U87MG, BT474 and T47D cell proliferation with IC50 values<600 nM.

(v) In Vivo Pharmacokinetic/Pharmacodynamic (PK/PD) Studies for Oncology

PC3 cells are cultured at 37° C. in a 5% $CO_2$ incubator using Hams F12 K medium. Ten million ($10^7$) cells are injected subcutaneously to the right flank region of athymic male mice (Harlan, age: 6-7 weeks, weight: about 20 g). Tumor bearing mice are randomized when the tumor volume reaches about 250 mm$^3$ and three mice are used per each time point. Test compounds of formula (I) are typically formulated in 40% HPCD in 1×PBS, pH 7.4 or in 10% Ethanol/40% Solutol/50% 50 mM aq. methanesulfonic acid and dosed orally at 50 mg/kg single dose (dose volume—10 mL/kg). Plasma and tumor samples are collected at 0 (vehicle control animals), 1, 4 and 24 hours post dosing. Blood is drawn (retro orbital) to a tube containing 0.2% EDTA for plasma collection. The tumor is excised from the mouse and immediately frozen in liquid nitrogen for PD analysis. Tumor and plasma drug concentrations are measured for PK analysis using LC-MS.

Snap frozen tumor samples are pulverized in a mortar (Belart) containing liquid nitrogen and tumor powder is stored at –80° C. until analysis. Pre coated ELISA kits (Cell Signaling Technology; pAKT (T308), CST#7135; pAKT (S473), CST#7134 and pS6RP, CST#7205) are used for PD analysis. Tumor powder is transferred to Eppendorf® tubes and lysis buffer (1 mL) is added to the powder. Protease and phosphatase inhibitors (SIGMA) and phenylmethane-sulfonylfluoride (PMSF) are added to tumor powder and mixed by vortexing followed by sonication (15 sec). Samples are kept on an ice bath for 30 minutes. Supernatant is separated after centrifugation at 10,000 rpm for 20 minutes at 4° C. Supernatant is re-centrifuged and fresh supernatant is aliquoted to different tubes. Total protein is estimated using a BCA kit (Thermo Scientific) and 50 µg total protein is loaded to each well. ELISA analysis is carried out as per manufacturer's instructions. The detection for pAKT is based on chemiluminescence and pS6RP is based on absorbance. Qualitative assessments of the suppression of pAKT (T308), pAKT (S473), and pS6RP are also carried out by standard Western blot analyses.

The compounds cause suppression of pAkt and pS6RP as measured at 1, 4 and 24 hours after a single dose of 30-50 mg/kg po.

In vivo pharmacokinetic/pharmacodynamic (PK/PD) studies were carried out in a similar manner using U87MG tumor cells (glioma cancer cell line with a PTEN null mutation) and the corresponding tumor-bearing xenograft mice, and compounds of the invention were determined to be active in this assay. For example, the compound of Examples 3 and 61 were determined to cause suppression of pAKT (T308), pAKT (S473), and pS6RP, when dosed at 50 mg/kg po.

(vi) In Vivo Efficacy Studies for Oncology (Tumor Growth Suppression)

PC3 cells were cultured at 37° C. in a 5% $CO_2$ incubator using Hams F12 K medium. Five million ($5×10^6$) cells were implanted subcutaneously to the right flank of athymic male mice (Harlan, age: 6-7 weeks, weight: about 20 g). Tumor bearing mice were randomized when the tumor volume reached about 100 mm³ Ten mice were used per group. Compounds of formula (I) were typically formulated using HPCD in PBS, pH 7.4 or in 10% Ethanol/40% Solutol/50% 50 mM aq. methanesulfonic acid and dosed orally (dose volume, 10 mL/kg). Solutions of the compounds were prepared immediately before dosing the animals. A vehicle control and a reference compound were included along with test compounds.

The tumor size was measured on alternate days using Vernier® calipers. Assuming tumors to be ellipsoid, the tumor volume was calculated using the formula:

$$V=(D\times d^2)/2$$

where:
V (mm³) is tumor volume
D is longest diameter in mm
d is shortest diameter in mm.

Changes in tumor volume (Δ volumes) for each treated (T) and control (C) group were calculated by subtracting the mean tumor volume on the first day of treatment (starting day) from the mean tumor volume on the specified observation day. These values were used to calculate a percentage growth (% T/C) using the formula:

$$\% \ T/C = (\Delta T/\Delta C) \times 100$$

where ΔT>0, or $$\% \ T/C = (\Delta T/\Delta Ti) \times 100$$

where ΔT<0 and Ti is the mean tumor volume at the start of the experiment.

Percentage tumor growth inhibition was calculated as [100–% T/C]. Percentage body weight change was calculated as [(Body weight on specified observation day–Body weight on starting day)/Body weight on starting day]×100. Compounds of the invention suppress tumor growth in this in vivo efficacy model. For example, the compound of Example 3 caused more than 40% tumor growth inhibition as measured relative to vehicle control group, after 14 days of dosing at 50 mg/kg qd po.

In vivo efficacy studies were also carried out using U87MG tumor cells, in a similar manner to the protocol described above for the PC3 tumor cell in vivo efficacy study. Compounds of the invention suppressed tumor growth in the in vivo U87MG efficacy model. For example, relative to vehicle control group after 12 to 14 days of dosing, the compound of Examples 3, 7, 61, 105 and 119 at 50 mg/kg qd po caused more than 80% tumor growth inhibition, and the compound of Example 120 at 50 mg/kg qd po caused more than 70% tumor growth inhibition. It should be noted that the compound of Example 120 is a prodrug of the compound of Example 3.

(vii) In Vivo Efficacy Studies for Inflammation

The ability of compounds of the invention to reduce inflammation is determined by using various animal models that are known in the art. Some examples are as follows:

(a) Inflammatory arthritis. The ability of compounds of the invention to reduce inflammation in inflammatory arthritis is determined by following procedures for the collagen-induced arthritis (CIA) mouse model. See, e.g., the procedure described in Camps et al., Nature Med. 2005, 11, 936-943, which is incorporated herein by reference.

(b) Pulmonary fibrosis. The ability of compounds of the invention to prevent bleomycin-induced pulmonary fibrosis in rats is determined by following the procedures described in Wei et al., Biochem. Biophys. Res. Comm. 2010, 397, 311-317 and Brent et al., Toxicology 2000, 147, 1-13, which are incorporated herein by reference.

(c) Myocardial infarction. The ability of compounds of the invention to reduce inflammation and/or improve healing after myocardial infarction is determined by following the procedures for a mouse model described in Siragusa et al., Circ. Res. 2010, 106, 757-768, which is incorporated herein by reference.

(d) Peritonitis. The ability of compounds of the invention to reduce inflammation in peritonitis is determined by following procedures for the RANTES-induced or thioglycollate-induced peritonitis mouse model, e.g., as described in Camps et al., Nature Med. 2005, 11, 936-943, which is incorporated herein by reference.

TABLE 2

LC-MS and Biological Data of Examples 1 to 126

| Ex. No. | LC-MS m/z [M+H]⁺ | LC-MS Ret. time (min) | PI3Kα | mTOR | pAkt-T308 | pAkt-S473 | pS6RP | XTT |
|---|---|---|---|---|---|---|---|---|
| 1 | 463.1 | 0.23 | B | B | F | E | E | F |
| 2 | 481.1 | 0.30 | A | B | | | F | F |
| 3 | 443.1 | 0.18 | A | A | E | E | E | E |
| 4 | 469.0 | 0.19 | A | A | | | | D |
| 5 | 502.0 | 0.08 | A | B | E | | | |
| 6 | 486.2 | 0.11 | B | B | | | | |
| 7 | 469.1 | 0.35 | A | A | E | D | E | E |
| 8 | 558.9 | 1.19 | A | A | E | | | F |
| 9 | 542.3 | 0.10 | A | A | D | | | E |
| 10 | 514.2 | 0.19 | A | A | | | | F |
| 11 | 480.2 | 0.22 | C | C | | | | |
| 12 | 387.1 | 0.22 | C | C | | | | |
| 13 | 442.0 | 0.23 | C | B | | | | F |
| 14 | 389.1 | 0.22 | C | C | | | | F |
| 15 | 457.2 | 0.23 | C | A | | | | F |
| 16 | 478.0 | 0.23 | B | A | | | | F |
| 17 | 391.0 | 0.23 | | B | | | | |
| 18 | 463.9 | 0.21 | C | C | | | | |
| 19 | 404.2 | 0.65 | G | G | | | | |
| 20 | 464.1 | 0.26 | A | A | | | E | E |
| 21 | 479.4 | 0.26 | A | A | E | E | | D |
| 22 | 389.9 | 0.12 | A | A | E | F | E | D |
| 23 | 387.9 | 0.11 | A | B | | E | F | G |
| 24 | 404.8 | 0.25 | A | B | E | F | E | E |
| 25 | 376.0 | 0.16 | A | A | | | | E |
| 26 | 390.1 | 0.17 | A | B | | | | F |
| 27 | 457.1 | 0.21 | B | B | | | | |
| 28 | 458.1 | 0.14 | A | B | | | | F |
| 29 | 458.1 | 0.14 | A | A | E | | | E |
| 30 | 443.9 | 0.11 | A | C | | | | |
| 31 | 470.1 | 0.17 | A | A | E | | | D |
| 32 | 487.1 | 0.58 | A | B | | | | |
| 33 | 442.9 | 0.14 | A | A | E | | | E |
| 34 | 495.9 | 0.12 | A | A | | | | E |
| 35 | 540.1 | 0.12 | A | B | | | | F |
| 36 | 575.9 | 0.21 | A | | | | | |
| 37 | 512.1 | 0.51 | | | | | | |
| 38 | 506.0 | 0.15 | A | B | | | | G |
| 39 | 513.2 | 0.13 | | | | | | F |
| 40 | 513.1 | 0.11 | | | | | | E |
| 41 | 457.2 | 0.18 | A | B | | | | |
| 42 | 485.2 | 0.56 | C | B | | | | |
| 43 | 472.1 | 0.11 | C | A | | | | |
| 44 | 472.1 | 0.12 | B | C | | | | |
| 45 | 473.1 | 0.12 | A | A | F | | E | D |
| 46 | 486.1 | 0.10 | A | A | | F | | E |
| 47 | 473.2 | 0.68 | A | A | D | | | E |
| 48 | 487.1 | 0.70 | A | A | E | | | E |
| 49 | 496.2 | 0.46 | A | A | E | D | D | D |
| 50 | 459.0 | 0.14 | A | A | F | | | E |
| 51 | 475.2 | 0.33 | A | A | | | | E |

TABLE 2-continued

LC-MS and Biological Data of Examples 1 to 126

| Ex. No. | LC-MS m/z [M + H]+ | LC-MS Ret. time (min) | PI3Kα | mTOR | pAkt-T308 | pAkt-S473 | pS6RP | XTT |
|---|---|---|---|---|---|---|---|---|
| 52 | 461.1 | 0.19 | A | A | D | D | D | D |
| 53 | 468.1 | 0.20 | A | A | E | | | E |
| 54 | 443.1 | 0.15 | A | A | D | | | E |
| 55 | 461.0 | 0.22 | A | B | | | | E |
| 56 | 457.1 | 0.14 | A | B | E | | | E |
| 57 | 497.2 | 0.80 | A | A | E | | | F |
| 58 | 506.1 | 0.19 | A | A | D | | | E |
| 59 | 509.0 | 0.61 | A | A | E | D | D | E |
| 60 | 511.1 | 1.21 | A | B | | | | F |
| 61 | 494.1 | 0.40 | A | A | D | E | D | E |
| 62 | 469.0 | 0.27 | A | B | | | | |
| 63 | 513.0 | 0.23 | A | A | | | | |
| 64 | 506.9 | 0.34 | A | | E | | | |
| 65 | 563.2 | 1.58 | A | C | | | | F |
| 66 | 499.1 | 1.25 | A | A | F | | | E |
| 67 | 495.0 | 0.39 | A | A | E | | | E |
| 68 | 574.0 | 0.63 | A | A | D | | | E |
| 69 | 513.1 | 0.39 | A | | | | | |
| 70 | 527.2 | 0.21 | A | A | E | | | E |
| 71 | 523.9 | 0.29 | A | A | | | | |
| 72 | 527.0 | 1.00 | A | | | | | |
| 73 | 509.2 | 0.67 | A | | | | | |
| 74 | 523.2 | 1.27 | A | | | | | |
| 75 | 509.2 | 0.30 | A | A | | | | |
| 76 | 483.0 | 0.50 | A | A | D | | | E |
| 77 | 506.1 | 0.20 | A | A | | | | E |
| 78 | 483.2 | 0.46 | A | | | | | |
| 79 | 495.0 | 0.34 | A | | | | | |
| 80 | 509.0 | 0.16 | | | | | | G |
| 81 | 505.0 | 0.33 | A | A | D | | | E |
| 82 | 505.0 | 0.14 | A | A | D | | | E |
| 83 | 541.2 | 0.09 | A | B | | | | E |
| 84 | 528.2 | 0.10 | A | A | E | | | E |
| 85 | 559.2 | 0.11 | A | A | E | | | E |
| 86 | 559.2 | 0.10 | A | B | F | | | |
| 87 | 526.2 | 0.09 | A | C | | | | |
| 88 | 513.4 | 0.64 | B | B | | | | |
| 89 | 527.2 | 0.09 | A | A | | | | F |
| 90 | 478.9 | 0.10 | C | C | | | | |
| 91 | 493.6 | 0.09 | C | C | | | | |
| 92 | 448.9 | 0.09 | C | C | | | | |
| 93 | 463.5 | 0.10 | C | C | | | | |
| 94 | 408.2 | 0.21 | B | C | | | | |
| 95 | 487.0 | 0.45 | A | B | D | E | | E |
| 96 | 480.1 | 0.14 | A | A | | | | |
| 97 | 524.0 | 0.17 | A | A | | | | E |
| 98 | 469.3 | 0.22 | A | A | | | | E |
| 99 | 523.9 | 0.38 | A | A | | | | E |
| 100 | 485.2 | 0.09 | A | B | | | | F |
| 101 | 484.2 | 0.10 | A | B | | | | E |
| 102 | 500.0 | 0.09 | A | B | | | | E |
| 103 | 443.0 | 0.14 | A | B | D | | D | D |
| 104 | 457.2 | 0.25 | A | A | D | | | E |
| 105 | 471.2 | 0.38 | A | A | F | | | E |
| 106 | 470.2 | 0.10 | A | B | | | | F |
| 107 | 565.2 | 1.05 | A | | | | | |
| 108 | 556.2 | 0.33 | A | A | | | | E |
| 109 | 444.2 | 0.11 | A | B | F | | | E |
| 110 | 512.2 | 0.09 | | B | | | | E |
| 111 | 457.0 | 0.20 | A | B | | | | E |
| 112 | 554.9 | 0.10 | A | A | | | | |
| 113 | 514.2 | 0.11 | A | A | | | | F |
| 114 | 541.2 | 0.09 | A | A | | | | E |
| 115 | 487.0 | 0.42 | A | A | | | | |
| 116 | 542.2 | 0.10 | A | C | | | | F |
| 117 | 567.3 | 0.10 | A | A | | | | E |
| 118 | 485.0 | 0.66 | A | A | F | F | F | |
| 119 | 461.1 | 0.19 | A | A | D | E | D | D |
| 120 | 573.0 | 0.61 | | | | | | |
| 121 | 558.9 | 0.36 | | | | | | |
| 122 | 584.9 | 0.80 | | | | | | |
| 123 | 479.2 | 0.26 | A | B | | | | E |
| 124 | 512.1 | 0.61 | A | B | | | | G |
| 125 | 512.4 | 0.46 | A | A | | | | E |
| 126 | 487.3 | 0.36 | | | | | | |

Activities (nM):
A: $IC_{50} < 50$;
B: $IC_{50} = 50\text{-}200$;
C: $IC_{50} = 201\text{-}10{,}000$;
D: $IC_{50} < 100$;
E: $IC_{50} = 100\text{-}500$;
F: $IC_{50} = 501\text{-}5000$;
G: $IC_{50} > 1000$.

All publications cited in this specification and priority applications including U.S. Provisional Patent Application No. 61/678,694, filed Aug. 2, 2012, are incorporated herein by reference. While the invention has been described with reference to particular embodiments, it will be appreciated that modifications can be made without departing from the spirit of the invention. Such modifications are intended to fall within the scope of the appended claims.

What is claimed is:

1. A compound of formula (I):

$$\text{(I)}$$

wherein:
R[1] is a substituted phenyl of the structure:

wherein:
n is 1 to 5;
each R[8] is independently selected from the group consisting of halogen, alkyl, aryl, alkylsulfonyl, alkylthio, alkylcarbonylamino, halogenated alkylcarbonylamino, alkylsulfonylamino, arylsulfonylamino, alkylaminocarbonyl, alkylaminocarbonylamino, alkylaminoalkylcarbonylamino, hydroxyalkylcarbonylamino, heteroarylcarbonylamino, heteroarylalkylcarbonylamino, heteroarylcarbonyl, heterocyclecarbonylamino, arylcarbonylamino, alkylsulfonylheterocyclecarbonyl, heterocyclecarbonyl, heterocycleaminocarbonyl, heteroarylalkylamino, hydroxyalkylamino, heterocyclealkylcarbo-
nylamino, or cyanoalkylcarbonylamino;
$R^2$ is optionally substituted morpholine or thiomorpho-
line;
$R^3$ is H, F, Cl, $CH_3$, or $CH_3O$;
X is CH or N;
or a pharmaceutically acceptable salt, solvate, or pro-
drug thereof.

2. The compound of claim 1, wherein $R^2$ is morpholine.

3. The compound of claim 1, which is of formulae (II), (III), or (IV):

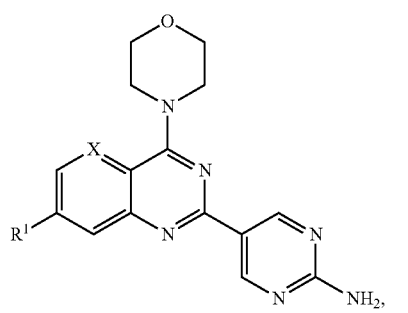

(II)

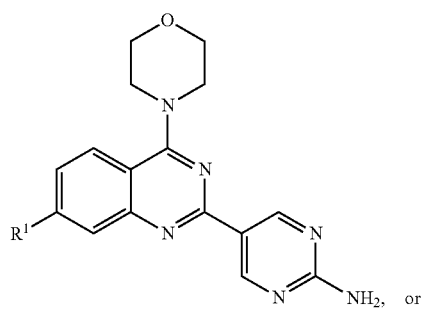

(III)

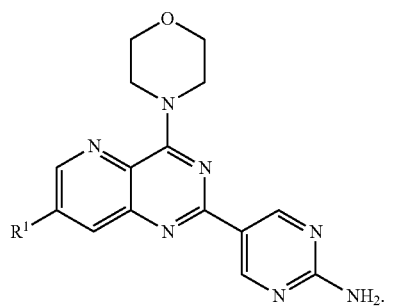

(IV)

4. The compound selected from the group consisting of:
5-(7-(3 (methylsulfonyl)phenyl)-4-morpholinoquinazo-
lin-2-yl)pyrimidin-2-amine;
5-(6-fluoro-7-(3-(methylsulfonyl)phenyl)-4-morpholino-
quinazolin-2-yl)pyrimidin-2-amine;
N-(3-(2-(2-aminopyrimidin-5-yl)-4-morpholinopyrido[3,
2-d]-pyrimidin-7-yl)phenyl)acetamide;
4-(2-(2-aminopyrimidin-5-yl)-4-morpholinopyrido[3,2-
d]pyrimidin-7-yl)-N-cyclopropylbenzamide;
(5-(2-(2-aminopyrimidin-5-yl)-4-morpholinopyrido[3,2-
d]pyrimidin-7-yl)furan-2-yl)(4-methylpiperazin-1-yl)
methanone;
N-(3-(2-(2-aminopyrimidin-5-yl)-4-morpholinoquinazo-
lin-7-yl)phenyl)-2-hydroxy-2-methylpropanamide;
N-(3-(2-(2-aminopyrimidin-5-yl)-4-morpholinopyrido[3,
2-d]pyrimidin-7-yl)phenyl)cyclopropanecarboxamide;
N-(3-(2-(2-aminopyrimidin-5-yl)-4-morpholinopyrido[3,
2-d]pyrimidin-7-yl)phenyl)-4-fluorobenzenesulfona-
mide;
N-(3-(2-(2-aminopyrimidin-5-yl)-4-morpholinopyrido[3,
2-d]-pyrimidin-7-yl)phenyl)-2-(4-hydroxypiperidin-1-
yl)acetamide;
N-(3-(2-(2-aminopyrimidin-5-yl)-4-morpholinopyrido[3,
2-d]pyrimidin-7-yl)phenyl)morpholine-4-carboxam-
ide;
1-(4-((2-(2-aminopyrimidin-5-yl)-4-morpholinopyrido[3,
2-d]pyrimidin-7-yl)methyl)piperazin-1-yl)-2-hydrox-
ypropan-1-one;
5-(4-morpholino-7-(pyrimidin-5-yl)quinazolin-2-yl)pyri-
midin-2-amine;
N-(3-(2-(2-aminopyrimidin-5-yl)-4-morpholinoquinazo-
lin-7-yl)phenyl)acetamide;
5-(7-(1-methyl-1H-pyrazol-4-yl)-4-morpholinoquinazo-
lin-2-yl)pyrimidin-2-amine;
1-(3-(2-(2-aminopyrimidin-5-yl)-4-morpholinoquinazo-
lin-7-yl)phenyl)-3-methylurea;
N-(3-(2-(2-aminopyrimidin-5-yl)-4-morpholinoquinazo-
lin-7-yl)phenyl)methanesulfonamide;
5-(4-morpholino-7-(thiophen-3-yl)quinazolin-2-yl)pyri-
midin-2-amine;
5-(7-(5-(methylsulfonyl)pyridin-3-yl)-4-morpholino-
quinazolin-2-yl)pyrimidin-2-amine;
5-(7-(2-fluoropyridin-3-yl)-4-morpholinoquinazolin-2-
yl)pyrimidin-2-amine;
5-(7-(3-(methylsulfonyl)phenyl)-4-morpholinopyrido[3,
2-d]-pyrimidin-2-yl)pyrimidin-2-amine;
N-(3-(2-(2-aminopyrimidin-5-yl)-4-morpholinopyrido[3,
2-d]-pyrimidin-7-yl)phenyl)methanesulfonamide;
5-(7-(1-methyl-1H-pyrazol-4-yl)-4-morpholinopyrido[3,
2-d]-pyrimidin-2-yl)pyrimidin-2-amine;
5-(4-morpholino-7-(pyrimidin-5-yl)pyrido[3,2-d]pyrimi-
din-2-yl)pyrimidin-2-amine;
5-(7-(2-fluoropyridin-3-yl)-4-morpholinopyrido[3,2-d]-
pyrimidin-2-yl)pyrimidin-2-amine;
5-(7-(furan-2-yl)-4-morpholinopyrido[3,2-d]pyrimidin-2-
yl)pyrimidin-2-amine
5-(7-(5-methylfuran-2-yl)-4-morpholinopyrido[3,2-d]-
pyrimidin-2-yl)pyrimidin-2-amine;
N-(3-(2-(2-aminopyrimidin-5-yl)-4-morpholinopyrido[3,
2-d]-pyrimidin-7-yl)phenyl)-N-methylacetamide;
1-(3-(2-(2-aminopyrimidin-5-yl)-4-morpholinopyrido[3,
2-d]pyrimidin-7-yl)phenyl)-3-methylurea;
1-(4-(2-(2-aminopyrimidin-5-yl)-4-morpholinopyrido[3,
2-d]pyrimidin-7-yl)phenyl)-3-methylurea;
N-(5-(2-(2-aminopyrimidin-5-yl)-4-morpholinopyrido[3,
2-d]pyrimidin-7-yl)pyridin-3-yl)acetamide;
N-(5-(2-(2-aminopyrimidin-5-yl)-4-morpholinopyrido[3,
2-d]pyrimidin-7-yl)pyridin-3-yl)cyclopropanecarboxa-
mide;
N-(4-(2-(2-aminopyrimidin-5-yl)-4-morpholinopyrido[3,
2-d]pyrimidin-7-yl)-3-fluorophenyl)cyclopropanecar-
boxamide;
4-(2-(2-aminopyrimidin-5-yl)-4-morpholinopyrido[3,2-
d]pyrimidin-7-yl)-N-methylbenzamide;
5-(2-(2-aminopyrimidin-5-yl)-4-morpholinopyrido[3,2-
d]pyrimidin-7-yl)-N-(pyridin-3-yl)furan-2-carboxam-
ide;
1-(4-(3-(2-(2-aminopyrimidin-5-yl)-4-morpholinopyrido
[3,2-d]pyrimidin-7-yl)benzoyl)piperazin-1-yl)etha-
none;
(3-(2-(2-aminopyrimidin-5-yl)-4-morpholinopyrido[3,2-
d]pyrimidin-7-yl)phenyl)(4-(methylsulfonyl)piperazin-
1-yl)-methanone;

4-(2-(2-aminopyrimidin-5-yl)-4-morpholinopyrido[3,2-d]pyrimidin-7-yl)-N-(thiazol-2-yl)benzamide;
4-(2-(2-aminopyrimidin-5-yl)-4-morpholinopyrido[3,2-d]pyrimidin-7-yl)-N-(pyridin-4-yl)benzamide;
(4-(2-(2-aminopyrimidin-5-yl)-4-morpholinopyrido[3,2-d]pyrimidin-7-yl)phenyl)(4-hydroxypiperidin-1-yl)methanone;
(3-(2-(2-aminopyrimidin-5-yl)-4-morpholinopyrido[3,2-d]pyrimidin-7-yl)phenyl)(4-hydroxypiperidin-1-yl)methanone;
3-(2-(2-aminopyrimidin-5-yl)-4-morpholinopyrido[3,2-d]pyrimidin-7-yl)-N,N-dimethylbenzamide;
N-(3-(2-(2-aminopyrimidin-5-yl)-4-morpholinoquinazolin-7-yl)phenyl)-2-(dimethylamino)acetamide;
N-(3-(2-(2-aminopyrimidin-5-yl)-4-morpholinoquinazolin-7-yl)phenyl)-2-hydroxypropanamide;
(S)—N-(3-(2-(2-aminopyrimidin-5-yl)-4-morpholinoquinazolin-7-yl)phenyl)-2-hydroxypropanamide;
N-(3-(2-(2-aminopyrimidin-5-yl)-4-morpholinopyrido[3,2-d]pyrimidin-7-yl)phenyl)-2-hydroxypropanamide;
N-(3-(2-(2-aminopyrimidin-5-yl)-4-morpholinopyrido[3,2-d]pyrimidin-7-yl)phenyl)-2-(dimethylamino)acetamide;
(S)—N-(3-(2-(2-aminopyrimidin-5-yl)-4-morpholinopyrido[3,2-d]pyrimidin-7-yl)phenyl)-2-hydroxypropanamide;
N-(3-(2-(2-aminopyrimidin-5-yl)-4-morpholinopyrido[3,2-d]pyrimidin-7-yl)phenyl)-2-hydroxy-2-methylpropanamide;
N-(3-(2-(2-aminopyrimidin-5-yl)-4-morpholinopyrido[3,2-d]pyrimidin-7-yl)phenyl)-2-cyano-2-methylpropanamide;
N-(3-(2-(2-aminopyrimidin-5-yl)-4-morpholinopyrido[3,2-d]pyrimidin-7-yl)phenyl)-2-hydroxyacetamide;
N-(3-(2-(2-aminopyrimidin-5-yl)-4-morpholinopyrido[3,2-d]pyrimidin-7-yl)phenyl)-2-fluoropropanamide;
N-(3-(2-(2-aminopyrimidin-5-yl)-4-morpholinopyrido[3,2-d]pyrimidin-7-yl)-2-fluorophenyl)acetamide;
N-(3-(2-(2-aminopyrimidin-5-yl)-4-morpholinopyrido[3,2-d]pyrimidin-7-yl)phenyl)-2-cyanoacetamide;
N-(4-(2-(2-aminopyrimidin-5-yl)-4-morpholinopyrido[3,2-d]pyrimidin-7-yl)phenyl)acetamide;
N-(3-(2-(2-aminopyrimidin-5-yl)-4-morpholinopyrido[3,2-d]pyrimidin-7-yl)-4-fluorophenyl)acetamide;
N-(3-(2-(2-aminopyrimidin-5-yl)-4-morpholinopyrido[3,2-d]pyrimidin-7-yl)-2-methylphenyl)acetamide;
N-(3-(2-(2-aminopyrimidin-5-yl)-4-morpholinopyrido[3,2-d]pyrimidin-7-yl)phenyl)cyclopentanecarboxamide;
N-(3-(2-(2-aminopyrimidin-5-yl)-4-morpholinopyrido[3,2-d]pyrimidin-7-yl)phenyl)nicotinamide;
N-(3-(2-(2-aminopyrimidin-5-yl)-4-morpholinopyrido[3,2-d]pyrimidin-7-yl)phenyl)-5-methylfuran-2-carboxamide;
N-(3-(2-(2-aminopyrimidin-5-yl)-4-morpholinopyrido[3,2-d]pyrimidin-7-yl)phenyl)cyclohexanecarboxamide;
N-(3-(2-(2-aminopyrimidin-5-yl)-4-morpholinopyrido[3,2-d]pyrimidin-7-yl)phenyl)-1-cyanocyclopropanecarboxamide;
N-(4-(2-(2-aminopyrimidin-5-yl)-4-morpholinopyrido[3,2-d]pyrimidin-7-yl)phenyl)cyclopropanecarboxamide;
N-(3-(2-(2-aminopyrimidin-5-yl)-4-morpholinopyrido[3,2-d]pyrimidin-7-yl)phenyl)tetrahydro-2H-pyran-4-carboxamide;
N-(3-(2-(2-aminopyrimidin-5-yl)-4-morpholinopyrido[3,2-d]pyrimidin-7-yl)phenyl)pyrazine-2-carboxamide;
N-(3-(2-(2-aminopyrimidin-5-yl)-4-morpholinopyrido[3,2-d]pyrimidin-7-yl)phenyl)adamantane-1-carboxamide;
N-(3-(2-(2-aminopyrimidin-5-yl)-4-morpholinopyrido[3,2-d]pyrimidin-7-yl)phenyl)-4-methylpentanamide;
N-(3-(2-(2-aminopyrimidin-5-yl)-4-morpholinopyrido[3,2-d]pyrimidin-7-yl)phenyl)furan-2-carboxamide;
N-(3-(2-(2-aminopyrimidin-5-yl)-4-morpholinopyrido[3,2-d]pyrimidin-7-yl)phenyl)-4-(trifluoromethyl)nicotinamide;
N-(3-(2-(2-aminopyrimidin-5-yl)-4-morpholinopyrido[3,2-d]pyrimidin-7-yl)phenyl)-1,2,3-thiadiazole-4-carboxamide;
N-(3-(2-(2-aminopyrimidin-5-yl)-4-morpholinopyrido[3,2-d]pyrimidin-7-yl)phenyl)-4-hydroxycyclohexanecarboxamide;
N-(3-(2-(2-aminopyrimidin-5-yl)-4-morpholinopyrido[3,2-d]-pyrimidin-7-yl)-4-fluorophenyl)nicotinamide;
N-(3-(2-(2-aminopyrimidin-5-yl)-4-morpholinopyrido[3,2-d]pyrimidin-7-yl)-4-fluorophenyl)-5-methylfuran-2-carboxamide;
N-(4-(2-(2-aminopyrimidin-5-yl)-4-morpholinopyrido[3,2-d]pyrimidin-7-yl)phenyl)-5-methylfuran-2-carboxamide;
N-(3-(2-(2-aminopyrimidin-5-yl)-4-morpholinopyrido[3,2-d]pyrimidin-7-yl)phenyl)-4-fluorobenzamide;
N-(3-(2-(2-aminopyrimidin-5-yl)-4-morpholinopyrido[3,2-d]pyrimidin-7-yl)phenyl)-3-methyl-1H-pyrazole-5-carboxamide;
N-(3-(2-(2-aminopyrimidin-5-yl)-4-morpholinopyrido[3,2-d]pyrimidin-7-yl)phenyl)cyclobutanecarboxamide;
N-(4-(2-(2-aminopyrimidin-5-yl)-4-morpholinopyrido[3,2-d]pyrimidin-7-yl)phenyl)nicotinamide;
N-(4-(2-(2-aminopyrimidin-5-yl)-4-morpholinopyrido[3,2-d]pyrimidin-7-yl)phenyl)cyclobutanecarboxamide;
N-(4-(2-(2-aminopyrimidin-5-yl)-4-morpholinopyrido[3,2-d]pyrimidin-7-yl)phenyl)furan-2-carboxamide;
N-(4-(2-(2-aminopyrimidin-5-yl)-4-morpholinopyrido[3,2-d]pyrimidin-7-yl)phenyl)-3-methyl-1H-pyrazole-5-carboxamide;
N-(3-(2-(2-aminopyrimidin-5-yl)-4-morpholinopyrido[3,2-d]pyrimidin-7-yl)phenyl)cyclopropanesulfonamide;
N-(4-(2-(2-aminopyrimidin-5-yl)-4-morpholinopyrido[3,2-d]pyrimidin-7-yl)phenyl)cyclopropanesulfonamide;
N-(3-(2-(2-aminopyrimidin-5-yl)-4-morpholinopyrido[3,2-d]pyrimidin-7-yl)phenyl)-2-(4-methylpiperazin-1-yl)acetamide;
N-(3-(2-(2-aminopyrimidin-5-yl)-4-morpholinopyrido[3,2-d]pyrimidin-7-yl)phenyl)-2-morpholinoacetamide;
N-(3-(2-(2-aminopyrimidin-5-yl)-4-morpholinopyrido[3,2-d]pyrimidin-7-yl)-4-fluorophenyl)-2-(4-methylpiperazin-1-yl)-acetamide;
N-(3-(2-(2-aminopyrimidin-5-yl)-4-morpholinopyrido[3,2-d]-pyrimidin-7-yl)-2-fluorophenyl)-2-(4-methylpiperazin-1-yl)acetamide;
N-(3-(2-(2-aminopyrimidin-5-yl)-4-morpholinoquinazolin-7-yl)phenyl)-4-methylpiperazine-1-carboxamide;
N-(3-(2-(2-aminopyrimidin-5-yl)-4-morpholinoquinazolin-7-yl)phenyl)morpholine-4-carboxamide;
N-(3-(2-(2-aminopyrimidin-5-yl)-4-morpholinopyrido[3,2-d]pyrimidin-7-yl)phenyl)-4-methylpiperazine-1-carboxamide;
1-(4-((2-(2-aminopyrimidin-5-yl)-4-morpholinoquinazolin-7-yl)methyl)piperazin-1-yl)-2-hydroxypropan-1-one;

1-(4-((2-(2-aminopyrimidin-5-yl)-4-morpholinoquinazo-lin-7-yl)methyl)piperazin-1-yl)-2-hydroxy-2-methyl-propan-1-one;
1-(4-((2-(2-aminopyrimidin-5-yl)-4-morpholinoquinazo-lin-7-yl)methyl)piperazin-1-yl)ethanone;
N-(1-((2-(2-aminopyrimidin-5-yl)-4-morpholinoquinazo-lin-7-yl)methyl)piperidin-4-yl)acetamide;
5-(4-morpholino-7-(piperazin-1-ylmethyl)pyrido[3,2-d]pyrimidin-2-yl)pyrimidin-2-amine;
N-(3-(2-(2-aminopyrimidin-5-yl)-4-morpholinopyrido[3,2-d]-pyrimidin-7-yl)-4-fluorophenyl)cyclopropanecar-boxamide;
N-(5-(2-(2-aminopyrimidin-5-yl)-4-morpholinopyrido[3,2-d]-pyrimidin-7-yl)pyridin-3-yl)methanesulfonamide;
3-(2-(2-aminopyrimidin-5-yl)-4-morpholinopyrido[3,2-d]-pyrimidin-7-yl)-N-(3-fluoropyridin-4-yl)benza-mide;
3-(2-(2-aminopyrimidin-5-yl)-4-morpholinopyrido[3,2-d]-pyrimidin-7-yl)-N-cyclopropylbenzamide;
N-(3-(2-(2-aminopyrimidin-5-yl)-4-morpholinopyrido[3,2-d]-pyrimidin-7-yl)phenyl)-5-fluoronicotinamide;
5-(7-(5-(4-methylpiperazin-1-yl)pyridin-3-yl)-4-mor-pholino-pyrido[3,2-d]pyrimidin-2-yl)pyrimidin-2-amine;
5-(7-(3-(4-methylpiperazin-1-yl)phenyl)-4-morpholino-pyrido[3,2-d]pyrimidin-2-yl)pyrimidin-2-amine;
3-(2-(2-aminopyrimidin-5-yl)-4-morpholinopyrido[3,2-d]-pyrimidin-7-yl)-N-(2-(dimethylamino)ethyl)benza-mide;
3-(2-(2-aminopyrimidin-5-yl)-4-morpholinopyrido[3,2-d]-pyrimidin-7-yl)-N-methylbenzamide;
N-(3-(2-(2-aminopyrimidin-5-yl)-4-morpholinopyrido[3,2-d]-pyrimidin-7-yl)phenyl)propionamide;
N-(3-(2-(2-aminopyrimidin-5-yl)-4-morpholinopyrido[3,2-d]-pyrimidin-7-yl)phenyl)isobutyramide;
5-(4-morpholino-7-(3-(piperazin-1-yl)phenyl)pyrido[3,2-d]-pyrimidin-2-yl)pyrimidin-2-amine;
3-(4-(3-(2-(2-aminopyrimidin-5-yl)-4-morpholinopyrido[3,2-d]pyrimidin-7-yl)phenyl)piperazin-1-yl)-2,2-dim-ethyl-3-oxopropanenitrile;
1-(4-(3-(2-(2-aminopyrimidin-5-yl)-4-morpholinopyrido[3,2-d]pyrimidin-7-yl)phenyl)piperazin-1-yl)-2-hy-droxy-2-methylpropan-1-one;
2-(3-(2-(2-aminopyrimidin-5-yl)-4-morpholinopyrido[3,2-d]pyrimidin-7-yl)phenyl)propan-2-ol;
(3-(2-(2-aminopyrimidin-5-yl)-4-morpholinopyrido[3,2-d]-pyrimidin-7-yl)phenyl)(4-methylpiperazin-1-yl)methanone;
6-(2-(2-aminopyrimidin-5-yl)-4-morpholinopyrido[3,2-d]pyrimidin-7-yl)-2H-benzo[b][1,4]oxazin-3(4H)-one;
1-(4-(3-(2-(2-aminopyrimidin-5-yl)-4-morpholinopyrido[3,2-d]pyrimidin-7-yl)phenyl)piperazin-1-yl)-2-(dim-ethylamino)-ethanone;
2-(4-(3-(2-(2-aminopyrimidin-5-yl)-4-morpholinopyrido[3,2-d]pyrimidin-7-yl)phenyl)piperazin-1-yl)ethanol;
N-(5-(2-(2-aminopyrimidin-5-yl)-4-morpholinopyrido[3,2-d]pyrimidin-7-yl)-2-(4-methylpiperazin-1-yl)phe-nyl)acetamide;
N-(3-(2-(2-aminopyrimidin-5-yl)-4-morpholinopyrido[3,2-d]pyrimidin-7-yl)-2-fluorophenyl)cyclopropanecar-boxamide;
(3-(2-(2-aminopyrimidin-5-yl)-4-morpholinopyrido[3,2-d]-pyrimidin-7-yl)phenyl)(4-(2-hydroxyethyl)piper-azin-1-yl)-methanone;
N-(5-(2-(2-aminopyrimidin-5-yl)-4-morpholinopyrido[3,2-d]pyrimidin-7-yl)-2-(4-methylpiperazin-1-yl)phe-nyl)cyclopropane-carboxamide;
N-(3-(2-(2-aminopyrimidin-5-yl)-4-morpholinopyrido[3,2-d]pyrimidin-7-yl)phenyl)pivalamide;
N-(5-(2-(2-aminopyrimidin-5-yl)-4-morpholinopyrido[3,2-d]-pyrimidin-7-yl)-2-fluorophenyl)acetamide;
N-(3-(2-(2-aminopyrimidin-5-yl)-4-morpholinopyrido[3,2-d]pyrimidin-7-yl)-2,4-difluorophenyl)acetamide;
N-(3-(2-(2-aminopyrimidin-5-yl)-4-morpholinopyrido[3,2-d]pyrimidin-7-yl)-4-fluorophenyl)-1-cyanocyclopro-pane-carboxamide;
N-(3-(2-(2-aminopyrimidin-5-yl)-4-morpholinopyrido[3,2-d]pyrimidin-7-yl)-2-fluorophenyl)-1-cyanocyclopro-pane-carboxamide; and
N-(5-(2-(2-aminopyrimidin-5-yl)-4-morpholinopyrido[3,2-d]pyrimidin-7-yl)-2-fluorophenyl)cyclopropanecar-boxamide;
or a pharmaceutically acceptable salt, solvate, or prodrug thereof.

5. The compound of claim 1 which is a prodrug of formula (I).

6. The compound of claim 5, wherein the prodrug is a diester.

7. The compound of claim 4 which is a prodrug.

8. The compound of claim 7, wherein the prodrug is a diester.

9. The compound of claim 1, which is selected from the group consisting of:
1-((acetyl(3-(2-(2-aminopyrimidin-5-yl)-4-morpholino-pyrido[3,2-d]pyrimidin-7-yl)phenyl)carbamoyl)oxy)ethyl acetate;
((acetyl(3-(2-(2-aminopyrimidin-5-yl)-4-morpholinopy-rido[3,2-d]pyrimidin-7-yl)-phenyl)carbamoyl)oxy)me-thyl acetate; and
(((3-(2-(2-aminopyrimidin-5-yl)-4-morpholinopyrido[3,2-d]pyrimidin-7-yl)phenyl)(cyclopropanecarbonyl)car-bamoyl)oxy)-methyl acetate.

10. A pharmaceutical composition comprising the compound of claim 1 and a pharmaceutically acceptable carrier.

11. A pharmaceutical composition comprising the compound of claim 4 and a pharmaceutically acceptable carrier.

12. A method for co-regulating PI3K and mTOR, said method comprising administering a therapeutically effective amount of the compound of claim 1 to a patient in need thereof.

13. A method for treating a condition treatable by inhibiting the PI3K/AKT/pathway, said method comprising administering a therapeutically effective amount of the compound of claim 1 to a patient in need thereof.

14. A method for treating a disease characterized by an abnormal cellular proliferation resulting from a dysregulated PI3K/AKT/mTOR pathway, said method comprising administering of a therapeutically effective amount of the compound of claim 1 to a patient in need thereof.

15. The method of claim 14, wherein said disease is cancer.

16. The method of claim 14, wherein said condition is an inflammatory disorder.

17. A method for co-regulating PI3K and mTOR, said method comprising administering a therapeutically effective amount of the compound of claim 4 to a patient in need thereof.

18. A method for treating a condition treatable by inhibiting the PI3K/AKT/pathway, said method comprising administering a therapeutically effective amount of the compound of claim 4 to a patient in need thereof.

19. A method for treating a disease characterized by an abnormal cellular proliferation resulting from a dysregulated PI3K/AKT/mTOR pathway, said method comprising administering of a therapeutically effective amount of the compound of claim 10 to a patient in need thereof.

20. The method of claim 19, wherein said disease is cancer.

21. The method of claim 18, wherein said condition is an inflammatory disorder.

* * * * *